United States Patent [19]
Oku et al.

[11] Patent Number: 6,008,230
[45] Date of Patent: Dec. 28, 1999

[54] QUINOLINE COMPOUNDS AS $H^+$-ATPASES

[75] Inventors: Teruo Oku, Tsukuba; Yoshio Kawai, Kawasaki; Shigeki Satoh, Tsukuba; Hitoshi Yamazaki, Tsukuba; Natsuko Kayakiri, Tsukuba; Yasuharu Urano, Tsukuba; Kousei Yoshihara, Tsuchiura; Noriko Yoshida, Tsukuba, all of Japan

[73] Assignee: Fujisawa Pharmaceutical Co., Ltd., Osaka, Japan

[21] Appl. No.: 09/051,093

[22] PCT Filed: Oct. 15, 1996

[86] PCT No.: PCT/JP96/02981

§ 371 Date: Apr. 14, 1998

§ 102(e) Date: Apr. 14, 1998

[87] PCT Pub. No.: WO97/14681

PCT Pub. Date: Apr. 24, 1996

[30] Foreign Application Priority Data

Oct. 16, 1995 [GB] United Kingdom .................. 9521102
Aug. 21, 1996 [AU] Australia ........................ PO 1811

[51] Int. Cl.⁶ .............. C07D 215/40; C07D 401/12; A61K 31/47
[52] U.S. Cl. .................. 514/311; 514/313; 514/314; 546/169; 546/171
[58] Field of Search ............... 546/159, 160, 546/167, 169, 171; 544/128, 363; 514/235.2, 255, 311, 313, 314

[56] References Cited

U.S. PATENT DOCUMENTS

| | | | |
|---|---|---|---|
| 4,147,694 | 4/1979 | Erickson | 546/169 |
| 4,632,696 | 12/1986 | Hagen et al. | 71/94 |
| 4,715,889 | 12/1987 | Hagen et al. | 71/94 |
| 4,797,148 | 1/1989 | Hagen et al. | 71/94 |
| 5,500,423 | 3/1996 | Glamkowski et al. | 514/228.2 |
| 5,534,530 | 7/1996 | Frehel et al. | 514/361 |
| 5,563,162 | 10/1996 | Oku et al. | 514/311 |
| 5,574,042 | 11/1996 | Oku et al. | 514/300 |
| 5,708,173 | 1/1998 | Oku et al. | 546/153 |
| 5,750,699 | 5/1998 | Oku et al. | 546/121 |
| 5,804,588 | 9/1998 | Dyke et al. | 514/314 |

FOREIGN PATENT DOCUMENTS

| | | |
|---|---|---|
| 441036 | 8/1991 | European Pat. Off. . |
| 1458332 | 1/1967 | France . |
| 2010280 | 9/1970 | Germany . |

OTHER PUBLICATIONS

Tszin et al., Chem. Abstract 83:79198r, 1975.
Derwent Abstract 96–318905, 1996.
Desneves et al., Chem. Abstract 126:84117, 1996.
Palmans et al., Chem. Abstract 124:8183, 1995.
Biniecki et al., Chem. Abstract 88:37590, 1978.
Pagani et al., Chem. Abstract 75:60353, 1971.
Werbel et al., Chem. Abstract 36031, 1968.

*Primary Examiner*—Mukund J. Shah
*Assistant Examiner*—Deepak R. Rao
*Attorney, Agent, or Firm*—Oblon, Spivak, McClelland, Maier & Neustadt, P.C.

[57] ABSTRACT

This invention relates to a quinoline compound of the formula:

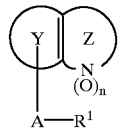

wherein
$R^1$ is a pyridyl group or aryl, each of which may be substituted with suitable substituent(s),
A is —COHN— or —NHCO—,
n is an integer of 0 or 1, and

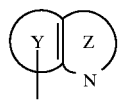

is a group of the formula:

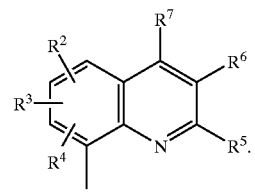

In which
$R^2$, $R^3$, $R^4$, $R^5$, $R^6$ and $R^7$ are as defined,
and pharmaceutically acceptable salt thereof, to processes for preparation thereof, to a pharmaceutical composition comprising the same, and to a method for the prevention and/or the treatment of bone diseases caused by abnormal bone metabolism in human being or animals.

9 Claims, No Drawings

QUINOLINE COMPOUNDS AS H⁺-ATPASES

This application is a 371 of PCT/JP96/02981 filed Oct. 15, 1996.

TECHNICAL FIELD

This invention relates to new heterocyclic compounds and pharmaceutically acceptable salts thereof.

More particularly, it relates to new heterocyclic compounds and pharmaceutically acceptable salts thereof which have inhibitory activities of vacuolar type $H^+$-adenosine triphosphatases ($H^+$-ATPases), especially osteoclast $H^+$-ATPase, and inhibitory activities of bone resorption, and therefore are useful for the prevention and/or the treatment of bone diseases caused by abnormal bone metabolism in human being or animals as the inhibitors of bone resorption or the inhibitors of bone metastasis.

And further, the present invention relates to processes for the preparation of said compounds, to a pharmaceutical composition comprising the same and to a method for the prevention and/or the treatment of above-mentioned diseases in human being or animals, and to a use of said compounds and pharmaceutically acceptable salts thereof for the prevention and/or the treatment of above-mentioned diseases in human being or animals.

BACKGROUND ART

Some heterocyclic compounds have been known as described in, for example, J. Chem. Soc. Pak. (1995), 17(4), 232–6; J. Am. Chem. Soc. (1994), 116(24), 11014–19; or Chem. Pharm. Bull. (1990), 38(10), 2841–6. However, it is not known that said compounds have inhibitory activities of vacuolar type $H^+$-ATPases or inhibitory activities of bone resorption.

DISCLOSURE OF THE INVENTION

The object heterocyclic compounds of this invention are new and can be represented by the following general formula [I]:

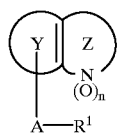
[I]

wherein $R^1$ is a heterocyclic group or aryl, each of which may be substituted with suitable substituent(s), A is —COHN— or —NHCO—, n is an integer of 0 or 1,

is a group of the formula:

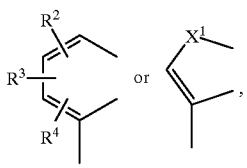

in which $R^2$ is hydrogen, halogen, lower alkyl, lower alkoxy or halo (lower) alkyl, $R^3$ is hydrogen, halogen, lower alkyl, lower alkoxy or halo(lower)alkyl, $R^4$ is hydrogen, halogen, lower alkyl, lower alkoxy or halo(lower)alkyl, and $x^1$ is O, S or NH,

is a group of the formula:

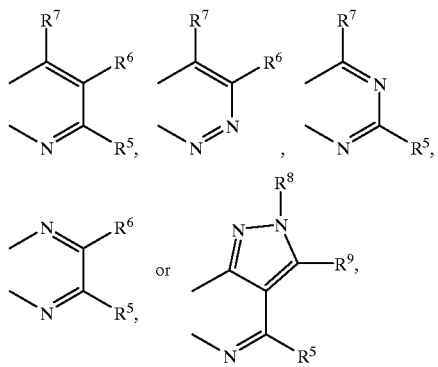

in which $R^5$ is hydrogen or lower alkyl, $R^8$ and $R^9$ are each lower alkyl, $R^6$ is hydrogen, halogen, cyano, amino, lower alkyl, substituted lower alkyl, lower alkenyl, substituted lower alkenyl, lower alkynyl, substituted lower alkynyl, lower alkylthio, lower alkylsulfinyl, lower alkylsulfonyl, a heterocyclicthio group, acyl, acylamino, aryl, substituted aryl or a heterocyclic group, and $R^7$ is hydrogen, halogen, lower alkyl, substituted lower alkyl, lower alkenyl, substituted lower alkenyl, azido, amino, substituted amino, hydrazino, substituted hydrazino, semicarbazido, substituted semicarbazido, thiosemicarbazido, substituted thiosemicarbazido, hydroxy, substituted hydroxy, mercapto, substituted mercapto, acyl or a substituted or unsubstituted heterocyclic group, or $R^6$ and $R^7$ are taken together to form a group of the formula:

[structures shown]

in which
$R^{10}$ is hydrogen or lower alkyl,
$R^{11}$ is hydrogen, acyl or lower alkyl optionally substituted with a substituent selected from the group consisting of a heterocyclic group and lower alkoxy,
$R^{12}$ is hydroxy, and
$R^{15}$ is O or N—$R^{16}$, in which $R^{16}$ is hydrogen or acyl,
provided that $R^1$ is 2,6-dichlorophenyl when $R^6$ and $R^7$ are each hydrogen.

The object compound [I] or its salt can be prepared by processes as illustrated in the following reaction schemes.

Process 1

[II]
or its reactive derivative
at the amino group
or a salt thereof $R^1$—COOH [III]
or its reactive derivative
at the carboxy group
or a salt thereof

→

[Ia]
or its salt

Process 2

[IV]
or its reactive derivative
at the carboxy group
or a salt thereof $R^1$—NH$_2$ [V]
or its reactive derivative
at the amino group
or a salt thereof

→

[Ib]
or its salt

Process 3

[Ic]
or its reactive derivative
at the carboxy group
or a salt thereof

NH$R^{13}R^{14}$ [VI]
or its reactive derivative
at the amino group
or a salt thereof

→

[Id]
or its salt

Process 4

[Ie]
or its salt $R_c^7$—H [VII]
or its salt

→

[If]
or its salt

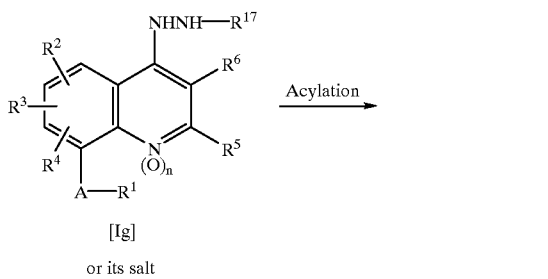

Process 5

Acylation

[Ig]
or its salt

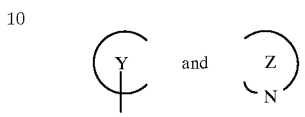

[Ih]
or its salt

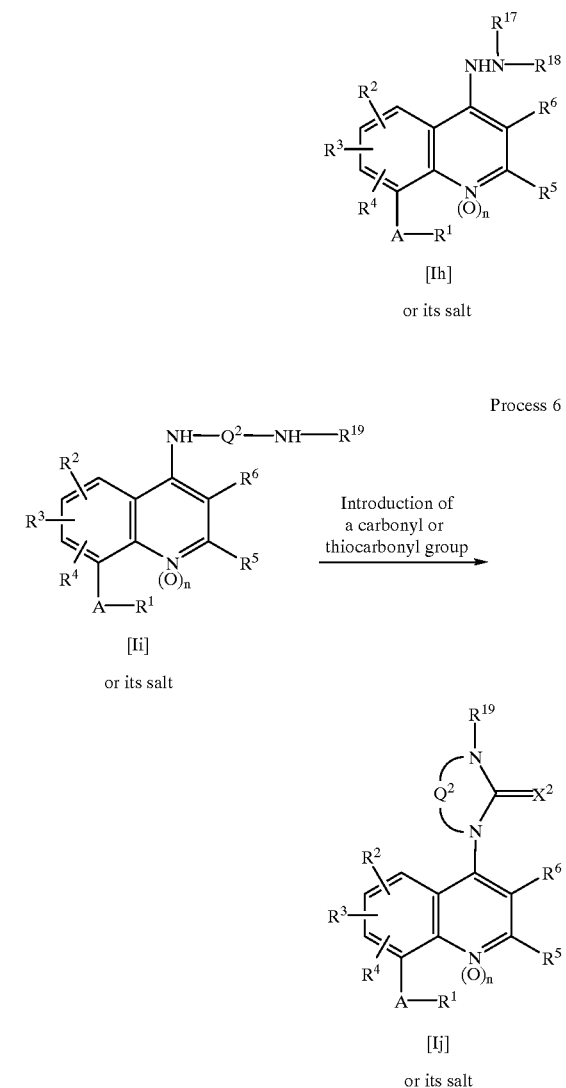

Process 6

Introduction of a carbonyl or thiocarbonyl group

[Ii]
or its salt

[Ij]
or its salt wherein
$R^{13}$ is hydrogen or lower alkyl optionally substituted with a substituent selected from the group consisting of hydroxy and lower alkoxy, and
$R^{14}$ is hydrogen; aryl optionally substituted with halo(lower) alkyl; or lower alkyl optionally substituted with substituent(s) selected from the group consisting of hydroxy, lower alkoxy and a heterocyclic group; or
$R^{13}$ and $R^{14}$ are taken together with the attached nitrogen atom to form a heterocyclic group optionally substituted with lower alkyl,
$Q^1$ is lower alkylene,
$R_b^7$ is halogen, $R_c^7$ is substituted amino, hydrazino, substituted hydrazino or a substituted or unsubstituted N-containing heterocyclic-N-yl group,
$R^{17}$ is hydrogen or lower alkyl,
$R^{18}$ is acyl,
$R^{19}$ is hydrogen or lower alkyl,
$Q^2$ is lower alkylene,
$X^2$ is O or S, and
$R^1, R^2, R^3, R^5, R^6, n, A,$ $$\left(\begin{array}{c}Y\end{array}\right) \text{ and } \left(\begin{array}{c}Z\\N\end{array}\right)$$

are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

In this respect, the term "lower" in lower alkenyl moiety or lower alkynyl moiety in the various definitions is intended to mean a group having 2 to 6 carbon atoms.

In this respect, the term "lower" in lower alkenoyl moiety, lower alkynoyl moiety and cyclo(lower)alkyl moiety in the various definitions is intended to mean a group having 3 to 6 carbon atoms.

Suitable "heterocyclic group" and all heterocyclic moieties in the various definitions mentioned in this specification and claims such as in the terms "heterocyclic(lower) alkyl", "heterocycliccarbonyl", "heterocyclicthio", etc., may include saturated or unsaturated, monocyclic or polycyclic one containing at least one hetero atom such as nitrogen atom, oxygen atom or sulfur atom, preferably N, O and/or S containing heterocyclic group, in which preferable ones may be morpholinyl, piperazinyl, pyridyl, dihydropyridyl, tetrahydropyridyl, pyrimidinyl, hexahydropyrimidinyl, piperidyl, thienyl, furyl, oxazolyl, oxazolidinyl, isoxazolyl, thiazolyl, thiazolinyl, oxadiazolyl, thiadiazolyl, triazolyl, tetrazolyl, imidazolyl, pyrrolidinyl, pyrrolyl, oxiranyl, tetrahydrofuryl, piperonyl, indolyl, quinolyl, isoquinolyl, benzimidazolyl, benzimidazolidinyl, imidazolinyl, imidazolidinyl, pyrazolyl, pyrazolidinyl, imidazo[4,5-b] pyridyl, or the like.

Suitable "aryl" and aryl moiety in the term "aryloxy" may be phenyl, naphthyl, fluorenyl, phenyl substituted with lower alkyl [e.g. tolyl, xylyl, mesityl, cumenyl, di(tert-butyl) phenyl, etc.] and the like, in which preferable one is phenyl, naphthyl and tolyl.

Suitable "halogen" may be fluorine, chlorine, bromine and iodine.

Suitable "lower alkoxy" and lower alkoxy moiety in the term "lower alkoxy(lower)alkyl" may be straight or branched one such as methoxy, ethoxy, propoxy, isopropoxy, butoxy, isobutoxy, tert-butoxy, pentyloxy, hexyloxy or the like, in which preferable one is $C_1$–$C_4$ alkoxy such as methoxy, ethoxy or isopropoxy.

Suitable "lower alkyl" and all lower alkyl moieties in the various definitions mentioned in this specification and claims such as in the terms "heterocyclic(lower)alkyl", "hydroxy(lower)alkyl", "lower alkoxy(lower)alkyl", "lower alkylthio" "lower alkylsulfinyl", "lower alkylsulfonyl", "lower alkylamino", etc., may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "lower alkenyl" may be vinyl, allyl, 1-propenyl, methylpropenyl, butenyl, pentenyl or the like.

Suitable "lower alkynyl" may be ethynyl, propynyl, butynyl, pentynyl, hexynyl or the like.

Suitable "acyl" and acyl moiety in the terms "acylamino", "acyl(lower)alkyl" and "acyloxy" may be lower alkanoyl [e.g. formyl, acetyl, propionyl, butyryl, isobutyryl, valeryl, isovaleryl, pivaloyl, hexanoyl, 3,3-dimethylbutyryl, etc.], hydroxy(lower)alkanoyl [e.g. glycoloyl, lactoyl, 3-hydroxypropionyl, hydroxybutyryl, 3-hydroxy-3-methylbutyryl, etc.], lower alkanoyloxy(lower)alkanoyl [e.g. acetyloxyacetyl, acetyloxypropionyl, etc.], lower alkoxy(lower)alkanoyl [e.g. methoxyacetyl, methoxypropionyl, ethoxyacetyl, etc.], lower alkanoylamino(lower)alkanoyl [e.g. acetylaminoacetyl, acetylaminopropionyl, etc.], lower alkylamino(lower)alkanoyl [e.g. methylaminoacetyl, dimethylaminoacetyl, dimethylaminopropionyl, etc.], halo(lower)alkanoyl [e.g. chloroacetyl, trifluoroacetyl, etc.], carboxy(lower)alkanoyl [e.g. carboxyacetyl, carboxypropionyl, carboxybutyryl, etc.], ar(lower)alkanoyl [e.g. phenylacetyl, phenylpropionyl, etc.], heterocyclic(lower)alkanoyl [e.g. thienylacetyl, imidazolylacetyl, pyridylacetyl, pyridylpropionyl, etc.], lower alkenoyl [e.g. acryloyl, methacryloyl, crotonoyl, isocrotonoyl, etc.], ar(lower)alkenoyl [e.g. cinnamoyl, etc.], cyclo(lower)alkylcarbonyl [e.g. cyclopropylcarbonyl, cyclobutylcarbonyl, cyclopentylcarbonyl, cyclohexylcarbonyl, etc.], carboxy, esterified carboxy such as lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], etc., heterocycliccarbonyl which may be substituted with substituent [e.g. furoyl, thenoyl, pyridylcarbonyl, imidazolylcarbonyl, morpholinocarbonyl, piperidinocarbonyl, 1-methylimidazolylcarbonyl, 4-methyl-1-piperazinylcarbonyl, 4-ethyl-1-piperazinylcarbonyl, dimethylaminopiperidinocarbonyl, 4-methylcarbonyl-1-piperazinylcarbonyl, 4-acetyl-1-piperazinylcarbonyl, 4-phenyl-1-piperazinylcarbonyl, chlorothenoyl, 1,2,3,6-tetrahydropyridylcarbonyl, pyrrolidinylcarbonyl, indolylcarbonyl, etc.], aroyl which may be substituted with substituent(s) [e.g. benzoyl, naphthoyl, methoxybenzoyl, dichlorobenzoyl, trifluoromethylbenzoyl, etc.], oxamoyl, substituted or unsubstituted carbamoyl such as carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], N-(lower alkoxy)-N-(lower alkyl)carbamoyl [e.g. N-methoxy-N-methylcarbamoyl, N-methoxy-N-ethylcarbamoyl, etc.], carboxy(lower)alkylcarbamoyl [e.g. carboxymethylcarbamoyl, carboxyethylcarbamoyl, etc.], esterified carboxy(lower)alkylcarbamoyl, for example, lower alkoxycarbonyl(lower)alkylcarbamoyl [e.g. methoxycarbonylmethylcarbamoyl, ethoxycarbonylmethylcarbamoyl, ethoxycarbonylethylcarbamoyl, etc.], hydroxy(lower)alkylcarbamoyl [e.g. hydroxyethylcarbamoyl, hydroxypropylcarbamoyl, di(hydroxyethyl)carbamoyl, dihydroxypropylcarbamoyl, 1,1-dimethyl-2-hydroxyethylcarbamoyl, etc.], lower alkoxy(lower)alkylcarbamoyl [e.g. methoxyethylcarbamoyl, methoxypropylcarbamoyl, di(methoxyethyl)carbamoyl, etc.], N-[lower alkoxy(lower)alkyl]-N-(lower alkyl)carbamoyl [e.g. N-methoxymethyl-N-methylcarbamoyl, N-methoxyethyl-N-methylcarbamoyl, N-methoxyethyl-N-ethylcarbamoyl, etc.], carbamoyl(lower)alkylcarbamoyl [e.g. carbamoylmethylcarbamoyl, carbamoylethylcarbamoyl, etc.], substituted or unsubstituted arylcarbamoyl, для example, arylcarbamoyl [e.g. phenylcarbamoyl, tolylcarbamoyl, xylylcarbamoyl, naphthylcarbamoyl, ethylphenylcarbamoyl, etc.], halo(lower)alkyl-arylcarbamoyl [e.g. trifluoromethylphenylcarbamoyl, etc.], etc., heterocycliccarbamoyl [e.g. pyridylcarbamoyl, imidazolylcarbamoyl, pyrazolylcarbamoyl, etc.], substituted or unsubstituted heterocyclic(lower)alkylcarbamoyl, for example, heterocyclic(lower)alkylcarbamoyl [e.g. pyridylmethylcarbamoyl, pyridylethylcarbamoyl, oxadiazolylmethylcarbamoyl, furylmethylcarbamoyl, thienylmethylcarbamoyl, tetrahydrofurylmethylcarbamoyl, piperonylmethylcarbamoyl, indolylethylcarbamoyl, imidazolylethylcarbamoyl, etc.], lower alkylheterocyclic(lower)alkylcarbamoyl [e.g. methylpyridylmethylcarbamoyl, methyloxadiazolylmethylcarbamoyl, etc.], etc., etc., lower alkylsulfonyl [e.g. methylsulfonyl, ethylsulfonyl, propylsulfonyl, etc.], arylsulfonyl [e.g. phenylsulfonyl, tolylsulfonyl, etc.], heterocyclicsulfonyl which may be substituted with substituent(s) [e.g. pyridylsulfonyl, thienylsulfonyl, fulylsulfonyl, thiazolylsulfonyl, 2-acetamido-4-methyl-5-thiazolylsulfonyl, etc.], ar(lower)alkylsulfonyl [e.g. benzylsulfonyl, phenethylsulfonyl, etc.), ar(lower)alkenylsulfonyl [e.g. styrylsulfonyl, cinnamylsulfonyl, etc.], or the like.

Suitable "halo(lower)alkyl" may be chloromethyl, bromoethyl, dichloromethyl, difluoromethyl, trifluoromethyl, or the like.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one is methylene.

Suitable "ar(lower)alkyl" may be benzyl, phenethyl, benzhydryl, trityl, naphthylmethyl or the like.

Suitable substituents in the term "a heterocyclic group or aryl, each of which may be substituted with suitable substituent(s)" for $R^1$ may be halogen; hydroxy; lower alkyl; lower alkoxy; halo(lower)alkyl; nitro; amino optionally substituted with lower alkyl or acyl [more preferably, lower alkanoyl, etc.]; aryl; acyl [more preferably, carboxy, lower alkoxycarbonyl, lower alkylcarbamoyl, etc.]; a heterocyclic group optionally substituted with lower alkyl; or the like, in which preferable ones are halogen, lower alkyl, lower alkoxy, halo(lower)alkyl or nitro. Preferably, the "a heterocyclic group or aryl" for $R^1$ is substituted with one or two substituent(s) mentioned above. In case that $R^1$ is phenyl, preferable position(s) of these substituents may be 2 and/or 6 position(s) of the phenyl group.

Suitable substituents of lower alkyl in the term "substituted lower alkyl"90 may be aryl, nitro, halogen, cyano, hydroxy, lower alkoxy, lower alkylthio, aryloxy, acyloxy, acyl, hydroxyimino, amino, lower alkylamino, N-[lower alkoxy(lower)alkyl]-N-(lower alkyl)amino, N-[hydroxy(lower)alkyl]-N-(lower alkyl)amino, a substituted or unsubstituted heterocyclic group, heterocyclicthio or the like.

Suitable substituents of lower alkenyl in the term "substituted lower alkenyl" may be acyl or the like.

Suitable substituents of lower alkynyl in the term "substituted lower alkynyl" may be lower alkyl, hydroxy, a heterocyclic group or the like.

Suitable substituents of aryl in the term "substituted aryl" may be amino, acylamino, lower alkoxy, a heterocyclic group, or the like.

Suitable substituents of amino in the term "substituted amino" may be lower alkyl, ar(lower)alkyl, hydroxy(lower)alkyl, lower alkoxy(lower)alkyl, amino(lower)alkyl, lower alkylamino(lower)alkyl, heterocyclic(lower)alkyl, lower alkoxy, aryl, substituted aryl, N-acyl-N-(lower alkyl)amino (lower)alkyl, acyl, a substituted or unsubstituted heterocyclic group or the like.

Suitable substituents of hydroxy in the term "substituted hydroxy" may be lower alkyl, lower alkoxy(lower)alkyl, ar(lower)alkyl, heterocyclic(lower)alkyl, acyl(lower)alkyl, lower alkenyl, aryl, substituted aryl, acyl, ar(lower)alkenyl [e.g. styryl, cinnamyl, etc.], a substituted or unsubstituted heterocyclic group, aryloxy(lower)alkyl [e.g. phenoxymethyl, phenoxyethyl, etc.], phthalimido(lower)alkyl [e.g. phthalimidomethyl, etc.], or the like.

Suitable substituents of mercapto in the term "substituted mercapto" may be acyl(lower)alkyl, substituted or unsubstituted heterocyclic group or the like.

Suitable substituents of a heterocyclic group in the terms "substituted or unsubstituted heterocyclic group" or "substituted or unsubstituted N-containing heterocyclic-N-yl group" may be halogen, lower alkyl, lower alkylamino (lower)alkyl, lower alkylthio, oxo, thioxo, hydroxy, aryl, ar(lower)alkyl, a heterocyclic group or the like.

Suitable substituents of hydrazino in the term "substituted hydrazino" may be lower alkyl, lower alkylidene [e.g. isopropylidene, etc.], hydroxy(lower)alkyl, lower alkoxy (lower)alkyl, acyl or the like.

Suitable substituents of semicarbazido or thiosemicarbazido in the terms "substituted semicarbazido" or "substituted thiosemicarbazido" may be lower alkyl, aryl or the like.

Suitable "heterocyclic group" formed by $R^{13}$, $R^{14}$ and the attached nitrogen atom may be morpholino, thiomorpholino, pyrrolidin-1-yl, piperidino, 1,2,3,6-tetrahydropyridin-1-yl, piperazin-1-yl, or the like.

Suitable "N-containing heterocyclic-N-yl group" may be morpholino, thiomorpholino, pyrrolidin-1-yl, piperidino, 1,2,3,6-tetrahydropyridin-1-yl, piperazin-1-yl, imidazol-1-yl, imidazolin-1-yl, imidazolidin-1-yl, benzimidazol-1-yl, benzimidazolidin-1-yl, pyrazol-1-yl, pyrazolidin-1-yl, hexahydropyrimidin-1-yl or the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] to [Ij] in the Processes 1 to 6, it is to be noted that those compounds are included within the scope of the compound [I], and accordingly the suitable examples of the salts of these compounds are to be referred to those as exemplified for the object compound [I].

Preferred embodiments of the object compound [I] are as follows:

$R^1$ is a heterocyclic group or aryl, each of which is substituted with substituent(s) selected from the group consisting of halogen, lower alkyl, lower alkoxy, imidazolyl optionally substituted with lower alkyl, hydroxy, nitro, amino, acylamino, halo(lower)alkyl and acyl [more preferably phenyl substituted with one or two halogen(s), phenyl substituted with nitro, phenyl substituted with halo(lower)alkyl and pyridyl substituted with one or two halogen(s)], n is an integer of 0 or 1, A is —COHN— or —NHCO—,

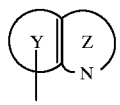

is a group of the formula:

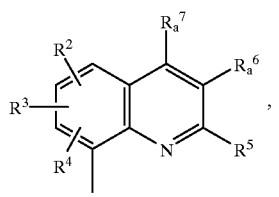

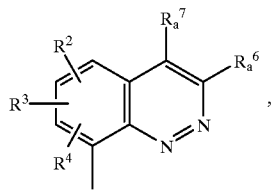

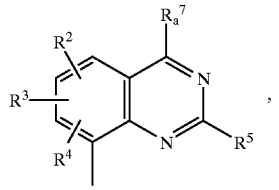

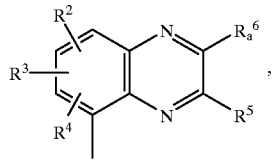

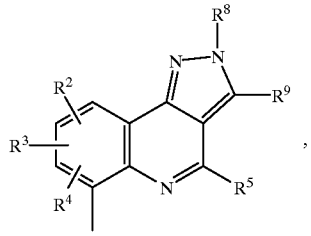

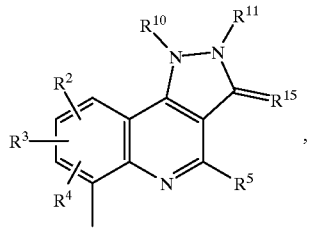

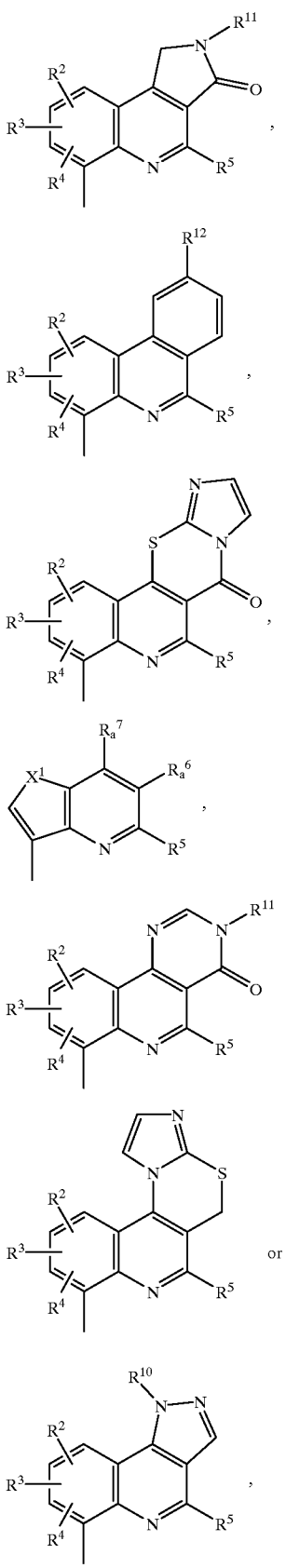

wherein
R² is hydrogen, halogen, lower alkyl, lower alkoxy or halo (lower) alkyl,
R³ is hydrogen, halogen, lower alkyl, lower alkoxy or halo (lower) alkyl,
R⁴ is hydrogen, halogen, lower alkyl, lower alkoxy or halo(lower)alkyl,
R⁵ is hydrogen or lower alkyl,
$R_a^6$ is hydrogen, halogen, cyano, amino, lower alkyl, substituted lower alkyl [more preferably, lower alkyl substituted with substituent(s) selected from the group consisting of aryl, nitro, halogen, hydroxy, lower alkoxy, lower alkylthio, aryloxy, acyloxy (e.g. lower alkanoyloxy, lower alkylcarbamoyloxy, etc.), acyl (e.g. carboxy, lower alkoxycarbonyl, carbamoyl, lower alkylcarbamoyl, etc.), hydroxyamino, a heterocyclic group (e.g. imidazolyl, benzimidazolyl, morpholinyl, etc.) and heterocyclicthio (e.g. imidazolylthio, pyridylthio, etc.)], lower alkenyl, substituted lower alkenyl [more preferably, lower alkenyl substituted with acyl (e.g. carboxy, lower alkoxycarbonyl, carbamoyl, lower alkylcarbamoyl, etc.)], lower alkynyl, substituted lower alkynyl [more preferably, lower alkynyl substituted with substituent(s) selected from the group consisting of lower alkyl, hydroxy and a heterocyclic group (e.g. pyridyl, etc.)], lower alkylthio, lower alkylsulfinyl, lower alkylsulfonyl, a heterocyclicthio group (e.g. pyridylthio, etc.), acyl [more preferably, lower alkanoyl, carboxy, lower alkoxycarbonyl, carbamoyl, lower alkylcarbamoyl, N-(lower alkoxy)-N-(lower alkyl) carbamoyl or heterocycliccarbonyl (e.g. morpholinocarbonyl, piperidinocarbonyl, etc.)], acylamino [more preferably, lower alkanoylamino or lower alkoxycarbonylamino], aryl, substituted aryl [more preferably, aryl substituted with amino] or a heterocyclic group [more preferably, pyridyl],
$R_a^7$ is hydrogen, halogen, lower alkyl, substituted lower alkyl [more preferably, lower alkyl substituted with substituent(s) selected from the group consisting of halogen, cyano, hydroxy, lower alkoxy, acyloxy (e.g. lower alkanoyloxy, etc.), acyl (e.g. carboxy, lower alkoxycarbonyl, carbamoyl, lower alkylcarbamoyl, heterocyclic-(lower)alkylcarbamoyl (e.g. pyridyl(lower) alkylcarbamoyl, etc.), hydroxy(lower)alkylcarbamoyl, N-[lower alkoxy(lower)alkyl]-N-(lower alkyl)carbamoyl, substituted or unsubstituted arylcarbamoyl (e.g. phenylcarbamoyl, halo(lower)alkylphenylcarbamoyl, etc.), substituted or unsubstituted heterocyclicarbonyl (e.g. morpholinocarbonyl, piperidinocarbonyl, lower alkyl piperazinylcarbonyl, etc.), etc.), amino, lower alkylamino, N-[lower alkoxy(lower)alkyl]-N-(lower alkyl)amino, N-[hydroxy(lower)alkyl]-N-(lower alkyl) amino, a substituted or unsubstituted heterocyclic group (e.g. imidazolyl optionally substituted with lower alkyl, lower alkylthio or phenyl; benzimidazolyl; morpholinyl; pyridyl; imidazolinyl optionally substituted with lower alkyl; imidazolidinyl optionally substituted with lower alkyl and/or oxo; etc.) and heterocyclicthio (e.g. imidazolylthio, pyridylthio, etc.)], lower alkenyl, substituted lower alkenyl [more preferably, lower alkenyl substituted with acyl (e.g. carboxy, lower alkoxycarbonyl, carbamoyl, lower alkylcarbamoyl, etc.)], azido, amino, substituted amino [more preferably, amino substituted with substituent(s) selected from the group consisting of lower alkyl, lower alkoxy, lower alkoxy(lower)alkyl, hydroxy(lower)alkyl, ar(lower)alkyl (e.g. benzyl, phenethyl, etc.), amino(lower)alkyl, lower alkylamino (lower)alkyl, heterocyclic(lower)alkyl (e.g. pyridyl (lower)alkyl, etc.), aryl (e.g. phenyl, tolyl, etc.), substituted aryl (e.g. phenyl substituted with amino, phenyl substituted with pyridylcarbonylamino, etc.), N-acyl-N-(lower alkyl)amino(lower)alkyl (e.g. N-pyridylcarbonyl-N-(lower alkyl)amino(lower)alkyl, N-imidazolylcarbonyl-N-(lower alkyl)amino(lower) alkyl, N-pyridylcarbamoyl-N-(lower alkyl)amino(lower) alkyl, etc.), acyl (e.g. lower alkanoyl, etc.) and a substituted or unsubstituted heterocyclic group (e.g. pyrazolyl, imidazolyl, triazolyl, morpholino, piperazinyl optionally substituted with lower alkyl, oxazolidinyl optionally substituted with oxo, pyrrolidinyl optionally substituted with oxo, etc.)], hydrazino, substituted hydrazino [more preferably, hydrazino substituted with substituent(s) selected from the group consisting of lower alkyl, lower alkylidene, hydroxy(lower)alkyl, lower alkoxy(lower) alkyl and acyl (e.g. lower alkanoyl, halo (lower) alkanoyl, cyclo(lower)alkylcarbonyl, carboxy, lower alkoxycarbonyl, carboxy(lower)alkanoyl, hydroxy(lower) alkanoyl, lower alkanoyloxy(lower)alkanoyl, lower alkoxy(lower)alkanoyl, lower alkanoylamino(lower) alkanoyl, lower alkylamino(lower)alkanoyl, oxamoyl, lower alkenoyl, lower alkylsulfonyl, arylsulfonyl, thienylsulfonyl, thiazolylsulfonyl optionally substituted with lower alkyl and/or lower alkanoylamino, ar(lower) alkylsulfonyl, ar(lower)alkenylsulfonyl, aroyl optionally substituted with lower alkoxy or halo (lower) alkyl, ar (lower) alkenoyl, thienyl(lower)alkanoyl, imidazolyl (lower)alkanoyl, pyridyl(lower)alkanoyl, thienylcarbonyl, furoyl, imidazolylcarbonyl optionally substituted with lower alkyl, pyridylcarbonyl, etc.)], semicarbazido, substituted semicarbazido [more preferably, semicarbazido substituted with lower alkyl or phenyl], thiosemicarbazido, substituted thiosemicarbazido [more preferably, thiosemicarbazido substituted with lower alkyl or phenyl], hydroxy, substituted hydroxy [more preferably, hydroxy substituted with a substituent selected from the group consisting of lower alkyl, lower alkoxy(lower)alkyl, ar(lower)alkyl, heterocyclic(lower) alkyl (e.g. furyl(lower)alkyl, pyridyl(lower)alkyl, benzimidazolyl(lower)alkyl, etc.), acyl(lower)alkyl (e.g. carboxy(lower)alkyl, lower alkoxycarbonyl(lower)alkyl, carbamoyl(lower)alkyl, lower alkylcarbamoyl(lower) alkyl, etc.), lower alkenyl, aryl, substituted aryl (e.g. phenyl substituted with lower alkoxy, phenyl substituted with imidazolyl), acyl (e.g. dichlorobenzoyl, etc.), ar(lower)alkenyl (e.g. styryl, cinnamyl, etc.), a substituted or unsubstituted heterocyclic group (e.g. pyridyl, benzimidazolyl, pyridyl substituted with halogen, pyridyl substituted with lower alkyl, pyridyl substituted with lower alkylamino(lower)alkyl, etc.), aryloxy(lower)alkyl and phthalimido(lower)alkyl], mercapto, substituted mercapto [more preferably, mercapto substituted with a substituent selected from the group consisting of acyl(lower) alkyl (e.g. carboxy(lower)alkyl, lower alkoxycarbonyl (lower)alkyl, carbamoyl(lower)alkyl, lower alkylcarbamoyl(lower)alkyl, heterocyclic(lower) alkylcarbamoyl(lower)alkyl (e.g. pyridyl(lower) alkylcarbamoyl(lower)alkyl, etc.), etc.) and a substituted or unsubstituted heterocyclic group (e.g. imidazolyl, pyridyl, lower alkylimidazolyl, imidazo[4,5-b]-pyridyl, pyrimidinyl, benzimidazolyl, thiazolyl, thiazolinyl, thiadiazolyl optionally substituted with lower alkyl, tetrazolyl optionally substituted with lower alkyl, triazolyl optionally substituted with lower alkyl, etc.)], acyl [more preferably, lower alkanoyl, carboxy, lower alkoxycarbonyl, carbamoyl or lower alkylcarbamoyl] or a substituted or unsubstituted heterocyclic group [more preferably, imidazolyl optionally substituted with lower alkyl or lower alkylcarbamoyl; benzimidazolyl optionally substituted with pyridyl; dihydropyridyl optionally substituted with oxo; morpholino; piperidino;

piperazinyl optionally substituted with lower alkyl; pyrazolyl optionally substituted with hydroxy; indolyl optionally substituted with hydroxy; triazolyl; imidazolidinyl optionally substituted with lower alkyl, ar(lower)alkyl, oxo and/or thioxo; hexahydropyrimidinyl optionally substituted with lower alkyl, ar(lower)alkyl, oxo and/or thioxo; benzimidazolidinyl optionally substituted with lower alkyl, ar(lower) alkyl, oxo and/or thioxo; or pyrazolidinyl optionally substituted with lower alkyl, ar(lower)alkyl, oxo and/or thioxo], $R^8$ is lower alkyl, $R^9$ is lower alkyl, $R^{10}$ is hydrogen or lower alkyl, $R^{11}$ is hydrogen, acyl [more preferably, lower alkanoyl or lower alkoxycarbonyl] or lower alkyl optionally substituted with a substituent selected from the group consisting of a heterocyclic group (e.g. pyridyl, etc.) and lower alkoxy, $R^{12}$ is hydroxy, $R^{15}$ is O or N—$R^{16}$, in which $R^{16}$ is hydrogen or acyl (more preferably lower alkanoyl), and $x^1$ is O, S or NH.

The processes for preparing the object compound [I] are explained in detail in the following.

Process 1

The object compound [Ia] or its salt can be prepared by reacting a compound [II] or its reactive derivative at the amino group or a salt thereof with a compound [III] or its reactive derivative at the carboxy group or a salt thereof.

Suitable reactive derivative at the amino group of the compound [II] may be a silyl derivative formed by the reaction of the compound [II] with a silyl compound such as bis(trimethylsilyl)acetamide or mono(trimethylsilyl) acetamide, or the like.

Suitable salts of the compound [II] and its reactive derivative can be referred to the ones as exemplified for the compound [I].

Suitable reactive derivative at the carboxy group of the compound [III] may include an acid halide, an acid anhydride, an activated amide, an activated ester, and the like.

Suitable examples of the reactive derivatives may be an acid chloride; an acid azide; a mixed acid anhydride with an acid such as dialkylphosphoric acid, sulfuric acid, aliphatic carboxylic acid or aromatic carboxylic acid; a symmetrical acid anhydride; an activated amide with imidazole; or an activated ester [e.g. p-nitrophenyl ester, etc.]. These reactive derivatives can optionally be selected from them according to the kind of the compound [III) to be used.

Suitable salts of the compound [III] and its reactive derivative can be referred to the ones as exemplified for the compound [I].

The reaction is usually carried out in a conventional solvent, such as methylene chloride, chloroform, ethylene chloride, pyridine, dioxane, tetrahydrofuran, N,N-dimethylformamide, or the like.

In case that the compound [III] is used in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

Process 2

The object compound [Ib] or its salt can be prepared by reacting a compound [IV] or its reactive derivative at the carboxy group or a salt thereof with a compound [V] or its reactive derivative at the amino group or a salt thereof.

Suitable salts of the compounds [IV] and [V] and their reactive derivatives can be referred to the ones as exemplified for the compound [I].

This reaction can be carried out in substantially the same manner as Process 1, and therefore the reaction mode and reaction condition of this reaction are to be referred to those explained in Process 1.

Process 3

The object compound [Id] or its salt can be prepared by reacting a compound [Ic] or its reactive derivative at the carboxy group or a salt thereof with a compound [VI] or its reactive derivative at the amino group or a salt thereof.

Suitable salts of the compound [VI] and its reactive derivative can be referred to the ones as exemplified for the compound [I].

This reaction can be carried out in substantially the same manner as Process 1, and therefore the reaction mode and reaction condition of this reaction are to be referred to those explained in Process 1.

Process 4

The object compound [If] or its salt can be prepared by reacting a compound [Ie] or its salt with a compound [VII] or its salt.

Suitable salts of the compound [VII] may be the same as those exemplified for the compound [I].

This reaction is usually carried out in a conventional solvent such as tetrahydrofuran, dioxane, N,N-dimethylformamide, N-methylpyrrolidone, or the like.

The reaction temperature is not critical, and the reaction is usually carried out under warming or heating.

Process 5

The object compound [Ih] or its salt can be prepared by acylating a compound [Ig] or its salt.

The acylation is carried out in the presence of an acylating agent.

Suitable acylating agents are the corresponding carboxylic acid or sulfonic acid compounds, which are represented by the formula: $R^{18}$—OH wherein $R^{18}$ is acyl, and reactive derivatives thereof, and the corresponding isocyanate or isothiocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as p-nitrophenyl ester and N-hydroxysuccinimide ester. The kind of such reactive derivatives can be selected depending on the kind of acyl group to be introduced.

The reaction is usually carried out in a conventional solvent, such as methylene chloride, chloroform, pyridine, dioxane, tetrahydrofuran, N,N-dimethylformamide, or the like. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as 1-ethyl-3-(3-dimethylaminopropyl)carbodiimide, N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

Process 6

The object compound [Ij] can be prepared by subjecting a compound [Ii] or its salt to introduction reaction of a carbonyl or thiocarbonyl group.

This reaction is carried out in the presence of reagent which introduces a carbonyl or thiocarbonyl group such as phosgene, haloformate compound [e.g. ethyl chloroformate, trichloromethyl chloroformate, etc.], 1,1'-carbonyldiimidazole, 1,1'-thiocarbonyldiimidazole, or the like.

This reaction is usually carried out in a solvent such as dioxane, tetrahydrofuran, benzene, toluene, chloroform, methylene chloride, N,N-dimethylformamide or any other organic solvent which does not adversely influence the reaction.

The reaction temperature is not critical and the reaction is usually carried out under cooling to heating.

The object compound [I] and the starting compounds can also be prepared by the methods of Preparations and Examples mentioned below or similar manners thereto or conventional manners.

The compound obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scope of this invention.

The compound of the formula [I] and its salt can be in the form of a solvate, which is included within the scope of the present invention. The solvate preferably includes a hydrate and an ethanolate.

The object compound [I] and pharmaceutically acceptable salts thereof have inhibitory activities of vacuolar type $H^+$-ATPases, especially osteoclast $H^+$-ATPase, and inhibitory activities of bone resorption, and therefore are useful for the prevention and/or the treatment of bone diseases caused by abnormal bone metabolism such as osteoporosis (especially, postmenopausal osteoporosis); hypercalcemia; hyperparathyroidism; Paget's bone diseases; osteolysis; hypercalcemia of malignancy with or without bone metastasis; rheumatoid arthritis; periodontitis; osteoarthritis; ostealgia; osteopenia; cancer cachexia; malignant tumor; or the like in human being or animals as the inhibitors of bone resorption or the inhibitors of bone metastasis.

Further, it is expected that the object compound [I] and pharmaceutically acceptable salts thereof of the present invention are useful for the prevention and/or the treatment of tumors, especially those related to renal cancer, melanoma, colon cancer, lung cancer and leukemia; viral conditions (e.g. those involving Semliki Forest, Vesicular Stomatitis, Newcastle Disease, Influenza A and B, HIV viruses); ulcers (e.g. chronic gastritis and peptic ulcer induced by *Helicobacter pylori*); autoimmune diseases; transplantation; hypercholesterolemic and atherosclerotic diseases; AIDS; Alzheimer's disease; angiogenic diseases such as diabetic retinopathy, psoriasis and solid tumors; or the like in human being or animals, and useful for regulating male fertility in human being or animals.

In order to illustrate the usefulness of the object compound [I], the pharmacological test data of some representative compounds of the compound [I] are shown in the following.

Test 1 (Inhibition of vacuolar type $H^+$-ATPase proton transport):

Test Method (a) Preparation of microsomes from mouse peritoneal macrophages

Seven-week-old male ddY mice were injected intraperitoneally with 2 ml of 3% thioglycolate medium. After 3–5 days, the mice were decapitated, and the peritoneal macrophages were obtained by peritoneal lavage with 5–6 ml of Hanks' balanced salt solution (HBSS). The cells were washed twice with cold HBSS. Vesicles were prepared from the cells, homogenized in a Douncee homogenizer (20 strokes) in 10 ml of 250 mM sucrose, 5 mM Tris, 1 mM EGTA, 1 mM $KHCO_3$ and 1 mM dithiothreitol, pH 7.0, at 4° C. After an initial centrifugation (1000× g for 5 minutes), the supernatant was centrifuged 6000× g for 15 minutes) to remove mitochondria and lysosomes. The supernatant was centrifuged at 42000× g for 30 minutes, and microsomal pellet was collected and stored at −80° C.

(b) Measurement of proton transport

Proton transport was assayed with a dual-wavelength spectrophotometer by monitering uptake of acridine orange (Reference 540 nm, Measurement 492 nm) [H. C. Blair, J. Cell. Biol., 102, 1164 (1986)] with aliquot of membrane vesicles suspended in 300 ml of assay buffer containing 150 mM KCl, 10 mM bis-tris-propane, 2 mM $MgCl_2$, 10 mM acridine orange, 1 mM valinomycin, 10 mg/ml oligomycin and test compounds (concentration: $1\times10^{-6}$M), pH 7.0. The reaction was initiated by addition of 1 mM ATP. Results were expressed as the percent of control.

Test Results

| Test Compound (Example No.) | Inhibition (%) of vacuolar type $H^+$-ATPase proton transport |
| --- | --- |
| 5 | 100 |
| 28 (dihydrochloride) | 94 |
| 52 (hydrochloride) | 100 |
| 71-(2) | 93 |
| 85-(2) (free) | 97 |

Test 2 (Bone organ culture)

Test Method

Calvariae from Wistar rats were excised and cultured in wells of 12-well culture plates containing 2 ml of Dulbecco's modified minimum essential medium supplemented with 10% fetal bovine serum and $10^{-8}$M human parathyroid hormone fragment (1–34) [PTH] in the presence of the test compound (concentration $1\times10^{-6}$M). In control dishes, PTH was not added. Control and PTH control were exposed to an equivalent concentration of the vehicle. Six days later, the concentration of calcium ([Ca]) in the medium was measured by methylxylenol blue method and the percentage of inhibition of PTH-induced bone resorption was calculated according to following formula $$\text{Inhibition (\%)} = \frac{C_P - C_D}{C_P - C_0} \times 100$$

Cp: [Ca] in PTH control dishes
CD: [Ca] in the test compound dishes
$C_0$: [Ca] in control dishes Test Results

| Test Compound (Example No.) | Inhibition (%) of PTH-induced bone resorption |
| --- | --- |
| 5 | 98 |
| 28 (dihydrochloride) | 100 |
| 52 (hydrochloride) | 100 |
| 71-(2) | 100 |
| 85-(2) (free) | 100 |

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral such as intravenous, intramuscular, subcutaneous or intraarticular, external such as topical, enteral, intrarectal, transvaginal, inhalant, ophthalmic, nasal or hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for preventing and/or treating the above-mentioned diseases. In general, amounts between 0.1 mg/body and about 1,000 mg/body may be administered per day.

EXAMPLES

The following Preparations and Examples are given for the purpose of illustrating this invention.

Preparation 1

To a stirred mixture of 8-nitro-4-methylquinoline (250 mg), ferric chloride hexahydrate (7.18 mg) and activated carbon (38 mg) in methanol was added hydrazine monohydrate (266 mg) at 65° C., and the mixture was stirred for 1 hour at the same temperature. Insoluble material was filtered off, and the filtrate was concentrated in vacuo The mixture was dissolved in ethyl acetate, washed with brine, dried over magnesium sulfate and evaporated in vacuo to give 8-amino-4-methylquinoline (208.8 mg).

mp: 76–77° C. NMR ($CDCl_3$, $\delta$): 2.65 (3H, s), 4.99 (2H, br s), 6.92 (1H, d, J=8 Hz), 7.20 (1H, d, J=4 Hz), 7.25–7.50 (2H, m), 8.62 (1H, d, J=4 Hz)

Preparation 2

(1) A mixture of 3-acetyl-1,4-dihydro-8-nitro-4-oxoquinoline (500 mg) and phosphoryl chloride was heated at 115° C. for 15 minutes. After cooling, the mixture was poured into ice water and extracted with ethyl acetate. The organic layer was washed with saturated sodium bicarbonate solution and brine, dried over magnesium sulfate and evaporated in vacuo to give 3-acetyl-4-chloro-8-nitroquinoline (485 mg).

NMR (CDCl$_3$, δ): 2.80 (3H, s), 7.81 (1H, t, J=8 Hz), 8.15 (1H, d, J=8 Hz), 8.61 (1H, d, J=8 Hz), 9.08 (1H, s)

(2) To a solution of 3-acetyl-4-chloro-8-nitroquinoline (339 mg) in dichloromethane was added 28% solution of sodium methoxide in methanol (0.52 mg) under ice-cooling, and the mixture was stirred for 30 minutes at ambient temperature. The mixture was diluted with ethyl acetate, washed with water and brine, dried over magnesium sulfate and evaporated in vacuo. The residue was purified by column chromatography on silica gel (ethyl acetate:n-hexane, 2:3, v/v) to give 3-acetyl-4-methoxy-8-nitroquinoline (239.3 mg).

mp: 100–105° C. NMR (CDCl$_3$, δ): 2.77 (3H, s), 4.13 (3H, S), 7.68 (1H, t, J=8 Hz), 8.11 (1H, d, J=8 Hz), 8.48 (1H, d, J=8 Hz), 9.18 (1H, s)

(3) A mixture of 3-acetyl-4-methoxy-8-nitroquinoline (230 mg), ammonium chloride (30 mg) and iron (313 mg) in ethanol (3 ml) and water (0.8 ml) was refluxed for 2 hours. Insoluble material was filtered off and the filtrate was concentrated in vacuo. The residue was dissolved in ethyl acetate, and the solution was washed with saturated sodium bicarbonate solution and brine, dried over magnesium sulfate and evaporated in vacuo to give 3-acetyl-8-amino-4-methoxyquinoline (175.7 mg).

mp: 76–77° C. NMR (CDCl$_3$, δ): 2.76 (3H, s), 4.07 (3H, s), 5.01 (2H, br s), 7.00 (1H, d, J=8 Hz), 7.38 (1H, t, J=8 Hz), 7.49 (1H, d, J=8 Hz), 8.95 (1H, s)

Preparation 3

4-Chloro-3-ethoxycarbonyl-8-nitroquinoline was obtained from 3-ethoxycarbonyl-1,4-dihydro-8-nitro-4-oxoquinoline according to a similar manner to that of Preparation 2-(1).

mp: 81–83° C. NMR (CDCl$_3$, δ): 1.47 (3H, t, J=7 Hz), 4.52 (2H, q, J=7 Hz), 7.80 (1H, t, J=8 Hz), 8.14 (1H, d, J=8 Hz), 8.65 (1H, d, J=8 Hz), 9.33 (1H, s)

Preparation 4

4-Ethoxy-3-ethoxycarbonyl-8-nitroquinoline was obtained by reacting 4-chloro-3-ethoxycarbonyl-8-nitroquinoline with sodium ethoxide according to a similar manner to that of Preparation 2-(2).

NMR (CDCl$_3$, δ): 1.45 (3H, t, J=7 Hz), 1.55 (3H, t, J=7 Hz), 4.39 (2H, q, J=7 Hz), 4.48 (2H, q, J=7 Hz), 7.65 (1H, t, J=8 Hz), 8.10 (1H, d, J=8 Hz), 8.51 (1H, d, J=8 Hz), 9.27 (1H, s)

Preparation 5

A mixture of 4-chloro-3-ethoxycarbonyl-8-nitroquinoline (199 mg), dimethylamine hydrochloride (63.6 mg) and triethylamine (78.9 mg) in dioxane was refluxed for 3 hours. After cooling, the mixture was diluted with ethyl acetate, washed with water, dried over magnesium sulfate and evaporated in vacuo. The residue was purified by column chromatography on silica gel (ethyl acetate:n-hexane, 1:2, v/v) to give 4-dimethylamino-3-ethoxycarbonyl-8-nitroquinoline (122 mg).

mp: 76–77° C. NMR (CDCl$_3$, δ): 1.43 (3H, t, J=7 Hz), 3.14 (6H, s), 4.45 (2H, q, J=7 Hz), 7.55 (1H, d, J=8 Hz), 7.97 (1H, t, J=8 Hz), 8.35 (1H, d, J=8 Hz), 8.99 (1H, s)

Preparation 6

(1) To a stirred mixture of 1,4-dihydro-4-oxo-8-nitroquinoline (10 g) in dimethylformamide (100 ml) was dropwise added N-bromosuccinimide (9.83 g) over the period of 2 minutes under ice-cooling, and the mixture was stirred for 30 minutes at 4° C. Water was added thereto under ice-cooling, and the mixture was stirred for 1 hour. The resulting precipitate was collected by filtration, and the residue was washed with water and hot ethanol to give 3-bromo-1,4-dihydro-8-nitro-4-oxoquinoline (12.12 g).

mp: 279–282° C. NMR (DMSO-d$_6$, δ): 7.57 (1H, t, J=7.5 Hz), 8.34 (1H, s), 8.60 (1H, d, J=7.5 Hz), 8.68 (1H, d, J=7.5 Hz)

(2) 3-Bromo-4-chloro-8-nitroquinoline was obtained according to a similar manner to that of Preparation 2-(1).

mp: 135–136° C. NMR (CDCl$_3$, δ): 7.76 (1H, t, J=7.5 Hz), 8.09 (1H, d, J=7.5 Hz), 8.49 (1H, d, J=7.5 Hz), 9.07 (1H, s)

Preparation 7

(1) To a mixture of diethyl malonate (368 mg) and N-methylpyrrolidone was added potassium tert-butoxide (246 mg) at 0° C., and the mixture was stirred for 30 minutes at ambient temperature. To a mixture was added 3-bromo-4-chloro-8-nitroquinoline (300 mg), and the mixture was stirred for 30 minutes at ambient temperature and for 30 minutes at 50° C. The mixture was poured into saturated ammonium chloride solution and extracted with ethyl acetate. The organic layer was washed with water and brine, dried over magnesium sulfate and evaporated in vacuo to give 4-[bis(ethoxycarbonyl)methyl]-3-bromo-8-nitroquinoline (315.6 mg).

mp: 94–95° C. NMR (CDCl$_3$, δ): 1.23 (6H, t, J=7 Hz), 4.15–4.35 (4H, m), 5.79 (1H, s), 7.65 (1H, t, J=8 Hz), 8.00 (1H, d, J=8 Hz), 8.25 (1H, d, J=8 Hz), 9.13 (1H, s)

(2) A mixture of 4-[bis(ethoxycarbonyl)methyl]-3-bromo-8-nitroquinoline (316 mg), lithium chloride (65.1 mg), water (13.8 mg) in dimethyl sulfoxide was stirred for 20 minutes at 130° C. The mixture was partitioned between ethyl acetate and water, and the organic layer was washed with brine, dried over magnesium sulfate and evaporated in vacuo to give 3-bromo-4-ethoxycarbonylmethyl-8-nitroquinoline (236.8 mg).

mp: 163–164° C. NMR (CDCl$_3$, δ): 1.24 (3H, t, J=7 Hz), 4.19 (2H, q, J=7 Hz), 4.35 (2H, s), 7.70 (1H, t, J=8 Hz), 8.02 (1H, d, J=8 Hz), 8.19 (1H, d, J=8 Hz), 9.11 (1H, s)

Preparation 8

(1) To a solution of 4-hydroxy-8-nitroquinoline (200 mg) and allyl bromide (140 mg) in dimethylformamide (2 ml) was added potassium carbonate (290 mg) at 0° C., and the mixture was stirred for 6 hours at 50° C. The mixture was diluted with dichloromethane and washed with water, dried over magnesium sulfate and evaporated in vacuo. The residue was dissolved into hot ethyl acetate (2 ml), and the solution was stirred at ambient temperature. The resulting precipitate was collected by filtration to give 4-allyloxy-8-nitroquinoline (120 mg).

mp: 127° C. NMR (CDCl$_3$, δ): 4.81 (2H, d, J=7 Hz), 5.43 (1H, d, J=10 Hz), 5.53 (1H, d, J=15 Hz), 6.05–6.22 (1H, m), 6.85 (1H, d, J=5 Hz), 7.54 (1H, t, J=7.5 Hz), 8.00 (1H, d, J=7.5 Hz), 8.46 (1H, d, J=7.5 Hz), 8.87 (1H, d, J=7.5 Hz)

(2) A mixture of 4-allyloxy-8-nitroquinoline (110 mg) and iron (268 mg) in acetic acid (0.4 ml) and ethanol (1.6 ml) was refluxed for 1 hour. Insoluble material was filtered off and the filtrate was concentrated in vacuo. The residue was dissolved in dichloromethane, and the solution was washed with saturated sodium bicarbonate solution and water, dried over magnesium sulfate and evaporated in vacuo. The residue was purified by flash chromatography (ethyl acetate-n-hexane) to give 8-amino-4-allyloxyquinoline (87 mg).

NMR (CDCl$_3$, δ): 4.74 (2H, d, J=5 Hz), 4.90 (2H, br s), 5.37 (1H, d, J=11 Hz), 5.51 (1H, d, J=17 Hz), 6.05–6.21 (1H, m), 6.70 (1H, d, J=4 Hz), 6.92 (1H, d, J=7.5 Hz), 7.29 (1H, t, J=7.5 Hz), 7.54 (1H, d, J=7.5 Hz), 8.59 (1H, d, J=7.5 Hz)

Preparation 9

(1) 4-Benzyloxy-8-nitroquinoline was obtained by reacting 4-hydroxy-8-nitroquinoline with benzyl bromide according to a similar manner to that of Preparation 8-(1).

mp: 162.3° C. NMR (CDCl$_3$, δ): 5.32 (2H, s), 6.92 (1H, d, J=5 Hz), 7.35–7.54 (5H, m), 7.55 (1H, t, J=7.5 Hz), 8.00 (1H, d, J=7.5 Hz), 8.46 (1H, d, J=7.5 Hz), 8.86 (1H, d, J=7.5 Hz)

(2) 8-Amino-4-benzyloxyquinoline was obtained according to a similar manner to that of Preparation 8-(2).

mp: 114.8° C. NMR (CDCl$_3$, δ): 4.91 (2H, br s), 5.26 (2H, s), 6.77 (1H, d, J=5 Hz), 6.93 (1H, d, J=7.5 Hz), 7.21–7.54 (6H, m), 7.58 (1H, d, J=7.5 Hz), 8.59 (1H, d, J=5 Hz)

Preparation 10

(1) 4-Ethoxycarbonylmethoxy-8-nitroquinoline was obtained by reacting 4-hydroxy-8-nitroquinoline with ethyl bromoacetate according to a similar manner to that of Preparation 8-(1).

mp: 108.4° C. NMR (CDCl$_3$, δ): 1.31 (3H, t, J=7.5 Hz), 4.31 (2H, q, J=7.5 Hz), 4.88 (2H, s), 6.74 (1H, d, J=5 Hz), 7.60 (1H, t, J=7.5 Hz), 8.04 (1H, d, J=7.5 Hz), 8.53 (1H, d, J=7.5 Hz), 8.89 (1H, d, J=7.5 Hz)

(2) A mixture of 4-ethoxycarbonylmethoxy-8-nitroquinoline (404 mg) and 10% palladium on carbon in ethanol (5 ml) and dioxane (5 ml) was stirred for 5 hours at ambient temperature under hydrogen atmosphere. Insoluble material was filtered off and the filtrate was concentrated in vacuo. The residue was pulverized with diethyl ether to give 8-amino-4-(ethoxycarbonylmethoxy)quinoline (234 mg).

mp: 94° C. NMR (CDCl$_3$, δ): 1.30 (3H, t, J=7.5 Hz), 4.30 (2H, q, J=7.5 Hz), 4.82 (2H, s), 4.92 (2H, br s), 6.58 (1H, d, J=5 Hz), 6.94 (1H, d, J=7.5 Hz), 7.30 (1H, t, J=7.5 Hz), 7.60 (1H, d, J=7.5 Hz), 8.60 (1H, d, J=5 Hz)

Preparation 11

(1) A solution of 4-allyloxy-8-nitroquinoline (3.72 g) in biphenyl (2.59 g) and diphenyl ether (7.4 g) was heated at 200° C. for 10 minutes. After cooling, n-hexane (40 ml) was added thereto, and the mixture was warmed at 90° C. After cooling, the resulting precipitate was collected by filtration to give 3-allyl-1,4-dihydro-8-nitro-4-oxoquinoline (3.13 g).

mp: 242.3° C. NMR (CDCl$_3$, δ): 3.36 (2H, br d, J=7 Hz), 5.12–5.25 (2H, m), 5.90–6.08 (1H, m), 7.43 (1H, t, j=7.5 Hz), 7.65 (1H, d, J=6 Hz), 8.65 (1H, d, J=7.5 Hz), 8.83 (1H, d, J=7.5 Hz), 11.08 (1H, br s)

(2) 4-Chloro-8-nitro-3-allylquinoline was obtained according to a similar manner to that of Preparation 2-(1).

mp: 64–66° C. NMR (CDCl$_3$, δ): 3.77 (2H, d, J=8 Hz), 5.10–5.30 (2H, m), 6.00 (1H, m), 7.71 (1H, t, J=8 Hz), 8.03 (1H, d, J=8 Hz), 8.19 (1H, d, J=8 Hz), 8.89 (1H, s)

(3) 4-Dimethylamino-8-nitro-3-(1-propenyl)quinoline was obtained by reacting 4-chloro-8-nitro-3-allylquinoline with dimethylamine hydrochloride according to a similar manner to that of Preparation 5.

mp: 121–123° C. NMR (CDCl$_3$, δ): 2.00 (3H, d, J=7 Hz), 6.21 (1H, dq, J=7, 15 Hz), 6.63 (1H, d, J=15 Hz), 7.49 (1H, t, J=8 Hz), 7.87 (1H, d, j=8 Hz), 8.26 (1H, d, J=8 Hz), 8.91 (1H, s)

(4) 8-Amino-4-dimethylamino-3-propylquinoline was obtained from 4-dimethylamino-8-nitro-3-(1-propenyl)quinoline according to a similar manner to that of Preparation 10-(2).

NMR (CDCl$_3$, δ): 1.01 (3H, t, J=7 Hz), 1.65 (2H, m), 2.76 (2H, m), 3.04 (6H, s), 4.90 (2H, br s), 6.84 (1H, d, J=8 Hz), 7.25 (1H, t, J=8 Hz), 7.38 (1H, d, J=8 Hz), 8.51 (1H, s)

Preparation 12

(1) To a stirred mixture of 4-hydroxy-8-nitroquinoline (5.0 g), 2,6-lutidine (4.23 g) and dimethylaminopyridine (321 mg) was dropwise added a solution of trifluoromethanesulfonic anhydride (8.16 g) in dichloromethane (100 ml) over the period of 30 minutes under ice-cooling, and the mixture was stirred for 2 hours at the same temperature and for 1 hour at ambient temperature. To the mixture was added saturated ammonium chloride solution and extracted with dichloromethane. The organic layer was washed with water and brine, dried over magnesium sulfate and evaporated in vacuo. The residue was purified by flash chromatography (dichloromethane-n-hexane) to give 8-nitro-4-(trifluoromethanesulfonyloxy)quinoline (6.17 g).

mp: 108° C. NMR (CDCl$_3$, δ): 7.58 (1H, d, J=4 Hz), 7.80 (1H, t, J=7.5 Hz), 8.15 (1H, d, J=7.5 Hz), 8.30 (1H, d, J=7.5 Hz), 9.14 (1H, d, J=4 Hz)

(2) A mixture of 8-nitro-4-(trifluoromethanesulfonyloxy) quinoline (6.0 g), tri-n-butyl(vinyl)tin (6.49 g), tetrakis (triphenylphosphine)palladium(0) (1.08 g) and lithium chloride (2.37 g) in dioxane (120 ml) was refluxed for 1.5 hours. The mixture was concentrated in vacuo, and ethyl acetate (200 ml) was added to the residue. The mixture was stirred for 1 hour, and insoluble material was filtered off. The residue was purified by flash chromatography (ethyl acetate-n-hexane) to give 8-nitro-4-vinylquinoline (2.39 g).

mp: 134° C. NMR (CDCl$_3$, δ): 5.76 (1H, d, J=11 Hz), 6.04 (1H, d, J=18 Hz), 7.40 (1H, dd, J=18, 11 Hz), 7.60 (1H, d, J=4 Hz), 7.65 (1H, t, J=7.5 Hz), 8.00 (1H, d, J=7.5 Hz), 8.30 (1H, d, J=7.5 Hz), 9.02 (1H, d, J=4 Hz)

Preparation 13

A mixture of 8-amino-3-bromoquinoline (200 mg) and sodium thiomethoxide (109 mg) in N,N-dimethylformamide (2 ml) was stirred at ambient temperature for 2 days. After diluted with ethyl acetate, the resulting mixture was washed with water and brine, dried over anhydrous sodium sulfate, and evaporated in vacuo. The residue was purified by chromatography on silica gel (n-hexane-ethyl acetate) to give 8-amino-3-methylthioquinoline (113 mg) as an oil.

NMR (CDCl$_3$, δ): 2.60 (3H, s), 4.86–4.99 (2H, m), 6.86 (1H, d, J=8 Hz), 7.05 (1H, d, J=8 Hz), 7.31 (1H, t, J=8 Hz), 7.83 (1H, s), 8.65 (1H, s)

Preparation 14

A mixture of 8-nitro-3-bromoquinoline (300 mg), tri-n-butyl(vinyl)tin (491 mg) and tetrakis(triphenylphosphine) palladium(0) (28 mg) in dimethoxyethane (6 ml) was refluxed for 1 hour. The mixture was concentrated in vacuo, and the residue was purified by column chromatography on silica gel (n-hexane-toluene) to give 8-nitro-3-vinylquinoline (127 mg).

mp: 116–117° C. NMR (CDCl$_3$, δ): 5.59 (1H, d, J=12 Hz), 6.05 (1H, d, J=17 Hz), 6.90 (1H, dd, J=12, 17 Hz), 7.62 (1H, t, j=8 Hz), 8.02 (2H, d, J=8 Hz), 8.17 (1H, s), 9.19 (1H, s)

Preparation 15

8-Nitro-3-(1-pentynyl)quinoline was obtained from 3-bromo-8-nitroquinoline and tri-n-butyl(1-pentynyl)tin according to a similar manner to that of Preparation 14.

mp: 71–73° C. NMR (CDCl$_3$, δ): 1.10 (3H, t, J=7 Hz), 1.63–1.78 (2H, m), 2.49 (2H, t, J=7 Hz), 7.62 (1H, t, J=8 Hz), 7.88 (1H, d, J=8 Hz), 8.02 (1H, d, J=8 Hz), 8.25 (1H, s), 9.00 (1H, s)

Preparation 16

(1) A mixture of 3-bromo-8-nitroquinoline (253 mg), phenylboric acid (159 mg), tetrakis(triphenylphosphine) palladium(0) (23 mg) and aqueous 2M sodium carbonate solution (2.5 ml) in 1,2-dimethoxyethane (3.5 ml) was refluxed for 4 hours. To the mixture was added phenylboric acid (122 mg), and the mixture was additionally refluxed for 3 hours. The resulting mixture, after diluted with ethyl acetate, was washed with aqueous 3° sodium bicarbonate solution and brine, dried over anhydrous sodium sulfate, and evaporated in vacuo. The residue was purified by chromatography on silica gel (n-hexane-ethyl acetate) and the obtained oil was crystallized from diethyl ether to give 8-nitro-3-phenylquinoline (104 mg).

mp: 112–114° C. NMR (CDCl$_3$, δ): 7.46–7.61 (3H, m), 7.67 (1H, t, J=8 Hz), 7.72 (2H, d, J=8 Hz), 8.07 (1H, d, J=8 Hz), 8.11 (1H, d, J=8 Hz), 8.40 (1H, s), 9.35 (1H, s)

(2) 8-Amino-3-phenylquinoline was obtained according to a similar manner to that of Preparation 1.

mp: 64–66° C. NMR (CDCl$_3$, δ): 4.42–5.07 (2H, m), 6.93 (1H, d, J=8 Hz), 7.23 (1H, t, J=8 Hz), 7.38 (1H, t, J=8 Hz), 7.44 (1H, d, J=8 Hz), 7.50 (1H, d, J=8 Hz), 7.53 (1H, d, J=8 Hz), 7.71 (2H, d, J=8 Hz), 8.21 (1H, s), 9.02 (1H, s)

Preparation 17

(1) 4-[Bis(ethoxycarbonyl)methyl]-8-nitroquinazoline was obtained by reacting 4-chloro-8-nitroquinazoline with diethyl malonate according to a similar manner to that of Preparation 7-(1).

mp: 157–159° C. NMR (CDCl$_3$, δ): 1.28–1.40 (6H, m), 4.28 (2H, q, J=7 Hz), 4.36 (2H, q, J=7 Hz), 7.39 (1H, t, J=8 Hz), 7.83 (1H, d, J=8 Hz), 7.87 (1H, d, J=8 Hz), 7.95 (1H, s)

(2) 4-(Ethoxycarbonylmethyl)-8-nitroquinazoline was obtained according to a similar manner to that of Preparation 7-(2).

mp: 162–164° C. NMR (CDCl$_3$, δ): 1.33 (3H, t, J=7 Hz), 4.23 (2H, q, J=7 Hz), 5.57 (2H, s), 7.41 (1H, t, J=8 Hz), 7.80–7.93 (3H, m)

Preparation 18

A mixture of 3-acetyl-4-chloro-8-nitroquinoline (140 mg) and methylhydrazine (77.2 mg) in ethylene chloride was refluxed for 30 minutes. The mixture was concentrated in vacuo, and the residue was purified by column chromatography on silica gel (methanol-dichloroethane) to give 2,3-dimethyl-6-nitro-2H-pyrazolo[4,3-c]quinoline (61.2 mg).

mp: 235–236° C. NMR (CDCl$_3$, δ): 2.70 (3H, s), 4.49 (3H, s), 7.73 (1H, t, J=8 Hz), 7.97 (1H, d, J=8 Hz), 8.56 (1H, d, J=8 Hz), 9.22 (1H, s)

Preparation 19

(1) 3-Formyl-8-nitroquinoline was obtained from 8-nitro-3-vinylquinoline according to a similar manner to that of Example 29.

NMR (CDCl$_3$, δ): 7.78 (1H, t, J=8 Hz), 8.20 (1H, d, J=8 Hz), 8.26 (1H, d, J=8 Hz), 8.76 (1H, s), 9.52 (1H, s), 10.32 (1H, s)

(2) A mixture of 3-formyl-8-nitroquinoline (65 mg) and ethyl (triphenylphosphoranilidene)acetate (123 mg) in dichloromethane (3 ml) was stirred for 2 hours at ambient temperature. The mixture was concentrated in vacuo, and the residue was purified by column chromatography on silica gel (ethyl acetate-n-hexane) to give 3-((E)-2-ethoxycarbonylvinyl)-8-nitroquinoline (92 mg).

NMR (CDCl$_3$, δ): 1.39 (3H, t, J=7 Hz), 4.33 (2H, q, J=7 Hz), 6.71 (1H, d, J=16 Hz), 7.68 (1H, t, J=8 Hz), 7.84 (1H, d, J=16 Hz), 8.09 (2H, d, J=8 Hz), 8.32 (1H, d, J=2 Hz), 9.24 (1H, d, J=2 Hz)

Preparation 20

A mixture of 4-methyl-8-nitroquinoline (2.80 g) and selenium(IV) oxide (1.82 g) in ethanol (45 ml) was refluxed for 4 hours. The mixture was treated with active charcoal and filtered through Celite pad. The filtrate was concentrated in vacuo to afford a brown solid. This residue was dissolved in a mixture of methanol (10 ml) and tetrahydrofuran (10 ml) and cooled in an ice bath. To this solution was added sodium borohydride (170 mg) and stirred at the same temperature for half an hour. To this mixture was added saturated ammonium chloride solution and extracted with methylene chloride. The organic layer was dried over anhydrous magnesium sulfate and evaporated under reduced pressure. The residue was purified by a flash chromatography on silica gel using methylene chloride then 3% methanol in methylene chloride as the eluent to give a solid. This solid was solidified with diethyl ether to afford 4-hydroxymethyl-8-nitroquinoline (665 mg) as a brown solid.

mp: 148° C. NMR (CDCl$_3$-CD$_3$OD, δ): 5.18 (2H, s), 7.64 (1H, t, J=7.5 Hz), 7.72 (1H, d, J=4 Hz), 8.02 (1H, d, J=7.5 Hz), 8.21 (1H, d, j=7.5 Hz), 8.98 (1H, d, J=4 Hz)

Preparation 21

A mixture of 3-bromo-8-nitroquinoline (300 mg), trimethylsilylacetylene (140 mg), palladium (II) chloride (38 mg), catalytic amount of copper (I) iodide, triethylamine (3 ml) and triphenylphosphine (113 mg) in acetonitrile (3 ml) was stirred for 3 hours at ambient temperature. The mixture was diluted with diethyl ether, and insoluble material was filtered off. The filtrate was concentrated in vacuo, and the residue was purified by column chromatography on silica gel (n-hexane-ethyl acetate) to give 8-nitro-3-(trimethylsilylethynyl)quinoline (210 mg).

NMR (CDCl$_3$, δ): 0.30 (9H, s), 7.26 (1H, s), 7.63 (1H, t, J=8 Hz), 7.99 (1H, d, J=8 Hz), 8.03 (1H, d, J=8 Hz), 8.32 (1H, s), 9.03 (1H, s)

Preparation 22

The following compounds were obtained according to a similar manner to that of Preparation 21.

(1) 8-Nitro-3-[(2-pyridyl)ethynyl]quinoline (from 3-bromo-8-nitroquinoline and 2-ethynylpyridine)

mp: 185–187° c NMR (CDCl$_3$, δ): 7.33 (1H, m), 7.62 (1H, d, J=8 Hz), 7.70 (1H, d, J=8 Hz), 7.77 (1H, t, J=8 Hz), 8.03 (1H, d, J=8 Hz), 8.08 (1H, d, J=8 Hz), 8.48 (1H, s), 8.68 (1H, d, J=8 Hz), 9.19 (1H, s)

(2) 3-(3-Hydroxy-3-methyl-1-butynyl)-8-nitroquinoline (from 3-bromo-8-nitroquinoline and 3-hydroxy-3-methyl-1-butyne)

mp: 120–121° C. NMR (CDCl$_3$, δ): 1.68 (6H, s), 2.13 (1H, s), 7.63 (1H, t, J=8 Hz), 7.98 (1H, d, J=8 Hz), 8.03 (1H, d, J=8 Hz), 8.30 (1H, s), 9.00 (1H, s)

Preparation 23

(1) A mixture of 4-chloro-3-ethoxycarbonyl-8-nitroquinoline (500 mg) and tert-butoxycarbonylhydrazine (283 mg) in dioxane was refluxed for 1 hour. The mixture was concentrated in vacuo to give 2-tert-butoxycarbonyl-2,3-dihydro-6-nitro-1H-pyrazolo[4,3-c]quinolin-3-one (458 mg).

mp: >250° C. NMR (DMSO-d$_6$, δ): 1.56 (9H, s), 7.71 (1H, t, J=8 Hz), 8.41 (1H, s), 8.53 (1H, d, J=8 Hz), 8.58 (1H, d, J=8 Hz)

(2) To a mixture of 2-tert-butoxycarbonyl-2,3-dihydro-6-nitro-1H-pyrazolo[4,3-c]quinolin-3-one (450 mg) and potassium carbonate (565 mg) in dimethylformamide was added methyl iodide (580 mg), and the mixture was stirred for 2 hours at 60° C. The mixture was poured into water and extracted with ethyl acetate. The organic layer was washed with brine, dried over magnesium sulfate and evaporated in vacuo. The residue was purified by column chromatography on silica gel (dichloromethane-ethyl acetate) to give 2-tert-butoxycarbonyl-2,3-dihydro-1-methyl-6-nitro-1H-pyrazolo[4,3-c]quinolin-3-one (114 mg).

mp: >250° C. NMR (DMSO-d$_6$, δ): 1.60 (9H, s), 3.82 (3H, s), 7.89 (1H, d, J=8 Hz), 8.42 (1H, d, J=8 Hz), 8.67 (1H, d, J=8 Hz), 9.09 (1H, s)

(3) 6-Amino-2-tert-butoxycarbonyl-2,3-dihydro-1-methyl-1H-pyrazolo[4,3-c]quinolin-3-one was obtained according to a similar manner to that of Preparation 10-(2).

mp: >250° C. NMR (CDCl$_3$-CD$_3$OD, δ): 1.62 (9H, s), 4.40 (3H, s), 7.04 (1H, d, J=8 Hz), 7.45 (1H, t, J=8 Hz), 7.66 (1H, d, J=8 Hz), 8.82 (1H, s)

Preparation 24

The following compounds were obtained according to a similar manner to that of Preparation 2-(3).

(1) 8-Amino-4-chloro-3-ethoxycarbonylquinoline mp: 112–113° C. NMR (CDCl$_3$, δ): 1.46 (3H, t, J=7 Hz), 4.50 (2H, q, J=7 Hz), 5.05 (2H, br s), 7.03 (1H, d, J=8 Hz), 7.47 (1H, t, J=8 Hz), 7.68 (1H, d, J=8 Hz), 9.02 (1H, s)

(2) 8-Amino-4-ethoxy-3-ethoxycarbonylquinoline

NMR (CDCl$_3$, δ): 1.45 (3H, t, J=7 Hz), 1.53 (3H, t, J=7 Hz), 4.29 (2H, q, J=7 Hz), 4.45 (2H, q, J=7 Hz), 4.98 (2H, br s), 6.99 (1H, d, J=8 Hz), 7.35 (1H, t, J=8 Hz), 7.56 (1H, d, J=8 Hz), 9.05 (1H, s)

(3) 8-Amino-4-dimethylamino-3-ethoxycarbonylquinoline

NMR (CDCl$_3$, δ): 1.43 (3H, t, J=7 Hz), 3.09 (6H, s), 4.44 (2H, q, J=7 Hz), 4.96 (2H, br s), 6.91 (1H, d, J=8 Hz), 7.29 (1H, t, J=8 Hz), 7.44 (1H, d, J=8 Hz), 8.77 (1H, s)

(4) 8-Amino-3-bromo-4-chloroquinoline mp: 130–131° C. NMR (DMSO-d$_6$, δ): 5.02 (2H, br s), 6.95 (1H, d, J=8 Hz), 7.42 (1H, t, J=8 Hz), 7.50 (1H, d, J=8 Hz), 8.75 (1H, s)

(5) 8-Amino-3-bromo-4-(ethoxycarbonylmethyl)quinoline mp: 139–140° C. NMR (CDCl$_3$, δ): 1.22 (3H, t, J=7 Hz), 4.17 (2H, q, J=7 Hz), 4.26 (2H, s), 5.03 (2H, br s), 6.93 (1H, d, J=8 Hz), 7.22 (1H, d, J=8 Hz), 7.37 (1H, t, J=8 Hz), 8.79 (1H, s)

(6) 8-Amino-4-chloro-3-allylquinoline mp: 111–112° C. NMR (CDCl$_3$, δ): 3.70 (2H, d, J=7 Hz), 5.01 (2H, br s), 5.00–5.20 (2H, m), 6.02 (1H, m), 6.92 (1H, d, J=8 Hz), 7.40 (1H, t, J=8 Hz), 7.53 (1H, d, J=8 Hz), 8.56 (1H, s)

(7) 8-Amino-4-vinylquinoline

NMR (CDCl$_3$, δ): 5.01 (2H, br s), 5.60 (1H, d, J=11 Hz), 5.93 (1H, d, J=17 Hz), 6.91 (1H, d, J=7.5 Hz), 7.27–7.54 (4H, m), 8.80 (1H, d, J=4 Hz)

(8) 8-Amino-3-vinylquinoline

NMR (CDCl$_3$, δ): 4.84–5.03 (2H, m), 5.43 (1H, d, J=12 Hz), 5.97 (1H, d, J=17 Hz), 6.80–6.93 (2H, m), 7.15 (1H, d, J=8 Hz), 7.32 (1H, t, J=8 Hz), 8.00 (1H, s), 8.88 (1H, s)

(9) 8-Amino-3-(1-pentynyl)quinoline mp: 75–76° C. NMR (CDCl$_3$, δ): 1.09 (3H, t, J=7 Hz), 1.62–1.76 (2H, m), 2.45 (2H, t, J=7 Hz), 4.86–5.02 (2H, m), 6.89 (1H, d, J=8 Hz), 7.08 (1H, d, J=8 Hz), 7.31 (1H, t, J=8 Hz), 8.08 (1H, d, J=2 Hz), 8.71 (1H, d, J=2 Hz)

(10) 8-Amino-3-[(2-pyridyl)ethynyl]quinoline mp: 105–107° C. NMR (CDCl$_3$, δ): 4.92–5.03 (2H, m), 6.95 (1H, d, J=8 Hz), 7.14 (1H, d, J=8 Hz), 7.25–7.32 (1H, m), 7.38 (1H, t, J=8 Hz), 7.60 (1H, d, J=8 Hz), 7.73 (1H, t, J=8 Hz), 8.31 (1H, s), 8.67 (1H, m), 8.89 (1H, s)

(11) 8-Amino-3-(3-hydroxy-3-methyl-1-butynyl)quinoline mp: 130–131° C. NMR (CDCl$_3$, δ): 1.67 (6H, s), 2.24 (1H, s), 4.90–5.00 (2H, m), 6.92 (1H, d, J=8 Hz), 7.10 (1H, d, J=8 Hz), 7.33 (1H, t, J=8 Hz), 8.12 (1H, s), 8.72 (1H, s)

(12) 8-Amino-4-(ethoxycarbonylmethyl)quinazoline mp: 132–134° C.

(13) 6-Amino-2,3-dimethyl-2H-pyrazolo[4,3-c]quinoline mp: 214–215° C. NMR (CDCl$_3$, δ): 2.65 (3H, s), 4.41 (3H, s), 5.11 (2H, br s), 7.00 (1H, d, J=8 Hz), 7.42 (1H, t, J=8 Hz), 7.67 (1H, d, J=8 Hz), 8.94 (1H, s)

(14) 8-Amino-3-((E)-2-ethoxycarbonylvinyl)quinoline

NMR (CDCl$_3$, δ): 1.38 (3H, t, J=7 Hz), 4.30 (2H, q, J=7 Hz), 4.90–5.02 (2H, m), 6.63 (1H, d, J=15 Hz), 6.95 (1H, d, J=8 Hz), 7.18 (1H, d, J=8 Hz), 7.38 (1H, t, J=8 Hz), 7.81 (1H, d, J=15 Hz), 8.15 (1H, d, J=2 Hz), 8.91 (1H, d, J=2 Hz)

(15) 8-Amino-4-hydroxymethylquinoline

NMR (DMSO-d$_6$, δ): 4.95 (2H, d, J=6 Hz), 5.50 (1H, t, J=6 Hz), 5.93 (2H, br s), 6.85 (1H, d, J=7.5 Hz), 7.04 (1H, d, J=7.5 Hz), 7.28 (1H, t, J=7.5 Hz), 7.54 (1H, d, J=4 Hz), 8.69 (1H, d, J=4 Hz)

(16) 8-Amino-1,4-dihydro-4-oxoquinoline

NMR (CDCl$_3$-CD$_3$OD, δ): 3.35 (2H, m), 6.30 (1H, d, J=6 Hz), 6.99 (1H, d, J=7.5 Hz), 7.18 (1H, t, J=7.5 Hz), 7.64–7.83 (2H, m)

(17) 8-Amino-3-(trimethylsilylethynyl)quinoline mp: 78–80° C. NMR (CDCl$_3$, δ): 0.30 (9H, s), 4.88–5.01 (2H, m), 6.92 (1H, d, J=8 Hz), 6.99 (1H, d, J=8 Hz), 7.33 (1H, t, J=8 Hz), 8.15 (1H, s), 8.73 (1H, s)

Preparation 25

A mixture of 8-amino-4-chloro-3-ethoxycarbonylquinoline (45 mg), triethylamine (0.026 ml) and 10%o palladium on carbon (15 mg) in dioxane was stirred for 7 hours at ambient temperature under 3 atmospheric pressure of hydrogen. Insoluble material was filtered off and the filtrate was concentrated in vacuo. The residue was purified by column chromatography on silica gel (ethyl acetate-dichloromethane) to give 8-amino-3-ethoxycarbonylquinoline (24.5 mg).

mp: 95–96° C. NMR (CDCl$_3$, δ): 1.46 (3H, t, J=7 Hz), 4.47 (2H, q, J=7 Hz), 5.04 (2H, br s), 7.02 (1H, d, J=8 Hz), 7.25 (1H, d, J=8 Hz), 7.40 (1H, t, J=8 Hz), 8.74 (1H, s), 9.28 (1H, s)

Example 1

A mixture of 8-amino-6-methoxyquinoline (121 mg), 2,6-dichlorobenzoyl chloride (175 mg) and triethylamine (91.4 mg) in ethylene chloride (3 ml) was refluxed for 3 hours. After cooling, the mixture was diluted with ethyl acetate, washed with water, saturated sodium bicarbonate solution and brine, dried over magnesium sulfate and evaporated in vacuo. The residue was purified by column chromatography on silica gel (ethyl acetate:n-hexane, 1:2, v/v) to give 8-(2,6-dichlorobenzoylamino)-6-methoxyquinoline (164.5 mg).

mp: 180–182° C. NMR (CDCl$_3$, δ): 3.97 (3H, s), 6.88 (1H, s), 7.30–7.50 (4H, m), 8.06 (1H, d, J=8 Hz), 8.60 (1H, m), 8.70 (1H, s)

its hydrochloride mp: 236–244° C. NMR (DMSO-d$_6$, δ): 3.93 (3H, s), 7.22 (1H, s), 7.40–7.70 (4H, m), 8.34 (1H, d, J=8 Hz), 8.43 (1H, s), 8.73 (1H, d, J=8 Hz)

Example 2

The following compounds were obtained according to a similar manner to that of Example 1.

(1) 8-(2,6-Dichlorobenzoylamino)-7-methylquinoline mp: 200–201° C. NMR (DNSO-d$_6$, δ): 2.57 (3H, s), 7.40–7.60 (5H, m), 7.87 (1H, d, J=8 Hz), 8.37 (1H, d, J=8 Hz), 8.91 (1H, m)

its hydrochloride mp: 235–247° C. NMR (DMSO-d$_6$, δ): 2.58 (3H, s), 7.40–7.70 (5H, m), 7.91 (1H, d, J=8 Hz), 8.46 (1H, d, J=8 Hz), 8.95 (1H, d, J=5 Hz)

(2) 8-(2,6-Dichlorobenzoylamino)-4-methylquinoline mp: 231–232° C. NMR (CDCl$_3$, δ): 2.72 (3H, s), 7.45–7.60 (4H, m), 7.68 (1H, t, J=8 Hz), 7.89 (1H, d, J=8 Hz), 8.70–8.75 (2H, m)

its hydrochloride mp: 230–231° C. NMR (DMSO-d$_6$, δ): 2.74 (3H, s), 7.45–7.65 (4H, m), 7.70 (1H, t, j=8 Hz), 7.92 (1H, d, J=8 Hz), 8.74 (1H, d, J=8 Hz), 8.77 (1H, d, J=6 Hz)

(3) 4-Chloro-8-(2,6-dichlorobenzoylamino)quinoline mp: 215–217° C. NMR (CDCl$_3$, δ): 7.30–7.50 (3H, m), 7.56 (1H, d, J=5 Hz), 7.72 (1H, t, J=8 Hz), 7.99 (1H, d, J=8 Hz), 8.64 (1H, d, J=5 Hz), 9.03 (1H, d, J=8 Hz)

(4) 8-(2,6-Dichlorobenzoylamino)-4-methoxyquinoline mp: 236–237° C. NMR (CDCl$_3$, δ): 4.07 (3H, s), 6.79 (1H, d, J=6 Hz), 7.30–7.50 (3H, m), 7.57 (1H, t, J=8 Hz), 7.94 (1H, d, J=8 Hz), 8.62 (1H, d, J=6 Hz), 8.95 (1H, s)

its hydrochloride mp: 197–199° C. NMR (CDCl$_3$-CD$_3$OD, δ): 4.34 (3H, s), 7.21 (1H, d, J=7 Hz), 7.30–7.50 (3H, m), 7.87 (1H, t, J=8 Hz), 8.19 (1H, d, J=8 Hz), 8.92 (1H, d, J=7 Hz), 9.14 (1H, d, J=8 Hz)

(5) 8-(2,6-Dichlorobenzoylamino)-3-methylquinoline mp: 219–220° C. NMR (CDCl$_3$, δ): 2.53 (3H, s), 7.30–7.50 (3H, m), 7.53 (1H, d, J=8 Hz), 7.58 (1H, t, J=8 Hz), 7.96 (1H, s), 8.63 (1H, s), 8.89 (1H, d, J=8 Hz)

its hydrochloride mp: 242–256° C. NMR (DMSO-d$_6$, δ): 2.52 (3H, s), 7.40–7.80 (5H, m), 8.22 (1H, s), 8.45 (1H, d, J=8 Hz), 8.77 (1H, s)

(6) 3-Acetyl-8-(2,6-dichlorobenzoylamino)-4-methoxyquinoline mp: 179–180° C. NMR (CDCl$_3$, δ): 2.77 (3H, s), 4.12 (3H, s), 7.30–7.50 (3H, m), 7.68 (1H, t, J=8 Hz), 7.96 (1H, d, J=8 Hz), 8.97 (1H, s), 9.05 (1H, d, j=8 Hz)

its hydrochloride mp: 143–148° C. (dec.) NMR (CDCl$_3$, δ): 2.79 (3H, s), 4.25 (3H, s), 7.30–7.50 (3H, m), 7.87 (1H, t, J=8 Hz), 8.18 (1H, d, J=8 Hz), 9.03 (1H, s), 9.24 (1H, d, J=8 Hz)

(7) 8-(2,6-Dichlorobenzoylamino)-3-ethoxycarbonylquinoline mp: 199–200° C. NMR (DMSO-d$_6$, δ): 1.40 (3H, t, J=7 Hz), 4.43 (2H, q, J=7 Hz), 7.50–7.60 (3H, m), 7.78 (1H, t, J=8 Hz), 8.03 (1H, d, J=8 Hz), 8.85 (1H, d, J=8 Hz), 9.07 (1H, s), 9.29 (1H, s)

(8) 8-(2,6-Dichlorobenzoylamino)-4-ethoxy-3-ethoxycarbonylquinoline mp: 155–156° C. NMR (CDCl$_3$, δ): 1.45 (3H, t, J=7 Hz), 1.56 (3H, t, J=7 Hz), 4.34 (2H, q, J=7 Hz), 4.47 (2H, q, J=7 Hz), 7.30–7.50 (3H, m), 7.65 (1H, t, J=8 Hz), 8.03 (1H, d, J=8 Hz), 9.04 (1H, d, J=8 Hz), 9.07 (1H, s)

its hydrochloride mp: 220–222° C. NMR (CDCl$_3$, δ): 1.45 (3H, t, J=7 Hz), 1.62 (3H, t, J=7 Hz), 4.48 (2H, q, J=7 Hz), 4.63 (2H, q, J=7 Hz), 7.30–7.50 (3H, m), 7.88 (1H, t, J=8 Hz), 8.26 (1H, d, J=8 Hz), 9.18 (1H, s), 9.26 (1H, d, J=8 Hz)

(9) 8-(2,6-Dichlorobenzoylamino)-4-dimethylamino-3-ethoxycarbonylquinoline mp: 163–165° C. NMR (CDCl$_3$, δ): 1.42 (3H, t, J=7 Hz), 3.13 (6H, s), 4.43 (2H, q, J=7 Hz), 7.30–7.50 (3H, m), 7.57 (1H, t, J=8 Hz), 7.89 (1H, d, J=8 Hz), 8.75 (1H, s), 8.95 (1H, d, J=8 Hz)

its hydrochloride mp: 200–202° C. NMR (CDCl$_3$, δ): 1.43 (3H, t, J=7 Hz), 4.42 (2H, q, J=7 Hz), 7.30–7.50 (3H, m), 7.72 (1H, t, J=8 Hz), 8.01 (1H, d, J=8 Hz), 8.83 (1H, s), 8.99 (1H, d, J=8 Hz)

(10) 3-Bromo-4-chloro-8-(2,6-dichlorobenzoylamino)quinoline mp: 240–242° C. NMR (CDCl$_3$, δ): 7.30–7.50 (3H, m), 7.75 (1H, t, J=8 Hz), 8.00 (1H, d, J=8 Hz), 8.81 (1H, s), 9.04 (1H, d, J=8 Hz), 9.87 (1H, s)

(11) 3-Bromo-8-(2,6-dichlorobenzoylamino)-4-(ethoxycarbonylmethyl)quinoline mp: 166–168° C. NMR (CDCl$_3$, δ): 1.23 (3H, t, J=7 Hz), 4.18 (2H, q, J=7 Hz), 4.31 (2H, s), 7.30–7.50 (3H, m), 7.60–7.75 (2H, m), 8.82 (1H, s), 8.98 (1H, d, J=8 Hz)

(12) 8-(2,6-Dichlorobenzoylamino)-4-allyloxyquinoline mp: 199–243.2° C. NMR (CDCl$_3$, δ): 4.78 (2H, d, J=7 Hz), 5.39 (2H, d, J=10 Hz), 5.51 (1H, d, J=15 Hz), 6.07–6.23 (1H, m), 6.77 (2H, d, J=5 Hz), 7.26–7.42 (3H, m), 7.55 (9H, t, J=7.5 Hz), 7.97 (1H, d, J=7.5 Hz), 8.57 (1H, d, J=7.5 Hz), 8.95 (1H, d, J=7.5 Hz)

(13) 4-Benzyloxy-8-(2,6-dichlorobenzoylamino)-quinoline mp: 192.8° C. NMR (CDCl$_3$, δ): 5.31 (2H, s), 6.84 (1H, d, J=5 Hz), 7.25–7.52 (8H, m), 7.55 (1H, t, J=7.5 Hz), 8.00 (1H, d, J=7.5 Hz), 8.56 (1H, d, J=5 Hz), 8.94 (1H, d, J=7.5 Hz)

(14) 8-(2,6-Dichlorobenzoylamino)-4-a(ethoxycarbonylmethoxy)quinoline mp: 134° C. NMR (CDCl$_3$, δ): 1.32 (3H, t, J=7.5 Hz), 4.30 (2H, q, J=7.5 Hz), 4.85 (2H, d), 6.65 (1H, d, J=6 Hz), 7.30–7.42 (3H, z), 7.60 (1H, t, J=7.5 Hz), 8.04 (1H, d, J=7.5 Hz), 8.59 (1H, d, J=5 Hz), 8.97 (1H, d, J=7.5 Hz)

(15) 8-(2,6-Dichlorobenzoylamino)-4-dimethylamino-3-propylquinoline hydrochloride mp: 195–200° C. NMR (DMSO-d$_6$, δ): 0.95 (3H, t, J=7 Hz), 1.58 (2H, m), 2.83 (2H, m), 3.19 (6H, s, 7.50–7.70 (4H, s), 7.98 (1H, d, J=78 Hz), 8.56 (1H, d, J=8 Hz), 8.60 (1H, s)

(16) 4-Chloro-8-(2,6-dichlorobenzoylamino)-3-allylquinoline mp: 127–128° C. NMR (CDCl$_3$, δ): 3.72 (2H, d, J=7 Hz), 5.00–5.20 (2H, m), 6.00 (1H, m), 7.30–7.50 (3H, m), 7.69 (1H, t, J=8 Hz), 7.98 (1H, d, J=8 Hz), 8.58 (1H, s), 8.96 (1H, d, J=8 Hz)

(17) 8-(2,6-Dichlorobenzoylamino)-4-vinylquinoline mp: 210.2° C. NMR (CDCl$_3$, δ): 5.70 (1H, d, J=11 Hz), 6.00 (1H, d, J=18 Hz), 7.27–7.50 (4H, m), 7.54 (1H, d, J=4 Hz), 7.64 (1H, t, J=7.5 Hz), 7.85 (1H, d, J=7.5 Hz), 8.72 (1H, d, J=4 Hz), 8.97 (1H, d, J=7.5 Hz)

(18) 8-(2,6-Dichlorobenzoylamino)-3-methylthioquinoline mp: 206–207° C. NMR (CDCl$_3$, δ): 2.61 (3H, s), 7.31–7.45 (3H, m), 7.51 (1H, d, J=8 Hz), 7.61 (1H, t, J=8 Hz), 7.92 (1H, s), 8.68 (1H, s), 8.90 (1H, d, J=8 Hz)

(19) 8-(2,6-Dichlorobenzoylamino)-3-vinylquinoline mp: 178–180° C. NMR (CDCl$_3$, δ): 5.48 (1H, d, J=12 Hz), 6.00 (1H, d, J=17 Hz), 6.88 (1H, dd, J=12, 17 Hz), 7.34–7.46 (3H, m), 7.56–7.46 (2H, m), 8.12 (1H, s), 8.86 (1H, s), 8.94 (1H, d, J=8 Hz), 10.00 (1H, br s)

(20) 8-(2,6-Dichlorobenzoylamino)-3-(1-pentynyl)quinoline mp: 153–154° C. NMR (CDCl$_3$, δ): 1.10 (3H, t, J=7 Hz), 1.62–1.77 (2H, m), 2.47 (2H, t, J=7 Hz), 7.30–7.47 (3H, m), 7.53 (1H, d, J=8 Hz), 7.62 (1H, t, J=8 Hz), 8.20 (1H, s), 8.72 (1H, s), 8.93 (1H, d, J=8 Hz)

its hydrochloride mp: 145–147° C. NMR (CDCl$_3$, δ): 1.09 (3H, t, J=7 Hz), 1.62–1.76 (2H, m), 2.49 (2H, t, J=7 Hz), 7.31–7.44 (3H, m), 7.78 (1H, d, J=8 Hz), 7.90 (1H, t, J=8 Hz), 8.69 (1H, s), 8.90 (1H, s), 9.21 (1H, d, J=8 Hz)

its methanesulfonate mp: 139–140° C. NMR (CDCl$_3$, δ): 1.08 (3H, t, J=7 Hz), 1.63–1.76 (2H, m), 2.49 (3H, t, J=7 Hz), 2.53 (3H, s), 7.33–7.46 (3H, m), 7.83 (1H, d, J=8 Hz), 7.92 (1H, t, J=8 Hz), 8.71 (1H, s), 8.95 (1H, d, J=8 Hz), 9.19 (1H, s)

(21) 8-(2,6-Dichlorobenzoylamino)-3-phenylquinoline mp: 190–192° C. NMR (CDCl$_3$, δ): 7.30–7.46 (4H, m), 7.54 (2H, t, J=8 Hz), 7.60–7.76 (4H, m), 8.34 (1H, s), 8.96 (1H, m), 9.04 (1H, s), 10.06 (1H, br s)

(22) 8-(2,6-Dichlorobenzoylamino)-3-[(2-pyridyl)ethynyl]quinoline hydrochloride mp: 196–197° C. NMR (DMSO-d$_6$, δ): 7.46–7.62 (4H, m), 7.72–7.82 (2H, m), 7.86 (1H, d, J=8 Hz), 7.96 (1H, t, J=8 Hz), 8.66 (1H, d, J=6 Hz), 8.76–8.82 (2H, m), 9.06 (1H, s), 10.94 (1H, s)

(23) 8-(2,6-Dichlorobenzoylamino)-3-(3-hydroxy-3-methyl-1-butynyl)quinoline mp: 216–217° C. NMR (CDCl$_3$, δ): 1.66 (6H, s), 2.08 (1H, s), 7.30–7.44 (3H, m), 7.54 (1H, d, J=8 Hz), 7.64 (1H, t, J=8 Hz), 8.24 (1H, s), 8.74 (1H, s), 8.96 (1H, d, J=8 Hz), 9.90 (1H, br s)

(24) 5-(2,6-Dichlorobenzoylamino)-2,3-dimethylquinoxaline mp: 252–254° C. NMR (CDCl$_3$, δ): 2.70 (3H, s), 2.75 (3H, s), 7.30–7.48 (3H, m), 7.68–7.80 (2H, m), 8.89 (1H, m), 9.71 (1H, br s)

(25) 5-(2,6-Dichlorobenzoylamino)quinoxaline mp: 200–201° C. NMR (CDCl$_3$, δ): 7.30–7.47 (3H, m), 7.80–7.95 (2H, m), 8.72 (1H, s), 8.93 (1H, s), 9.01 (1H, d, J=7 Hz), 9.71 (1H, br s)

(26) 8-(2,6-Dichlorobenzoylamino)-4-(ethoxycarbonylmethyl)quinazoline mp: 193–195° C. NMR (CDCl$_3$, δ): 1.32 (3H, t, J=7 Hz), 4.21 (2H, q, J=7 Hz), 5.50 (1H, s), 7.27–7.50 (5H, m), 7.71 (1H, s), 8.87 (1H, d, J=8 Hz), 9.41 (1H, br s)

(27) 8-(2,6-Dichlorobenzoylamino)-2-methylquinoline mp: 181–182° C. NMR (CDCl$_3$, δ): 2.70 (3H, s), 7.25–7.48 (4H, m), 7.50–7.60 (2H, m), 8.05 (1H, d, J=9 Hz), 8.92 (1H, t, J=5 Hz), 10.09 (1H, br s)

(28) 8-(2,6-Dichlorobenzoylamino)quinoline mp: 223–224° C. NMR (CDCl$_3$, δ): 7.30–7.50 (4H, m), 7.55–7.68 (2H, m), 8.20 (1H, d, J=8 Hz), 8.78 (1H, d, J=4H$_{Hz}$), 8.98 (1H, d, J=8 Hz)

(29) 8-(2,6-Dichlorobenzoylamino)-4-methoxyquinazoline mp: 214–215° C. NMR (CDCl$_3$, δ): 4.20 (3H, s), 7.30–7.45 (3H, m), 7.62 (1H, t, J=8 Hz), 7.89 (1H, d, J=8 Hz), 8.72 (1H, s), 9.07 (1H, d, J=8 Hz), 9.66 (1H, br s)

(30) 3-Bromo-8-(2,6-dichlorobenzoylamino)quinoline mp: 223–225° C. NMR (CDCl$_3$, δ): 7.30–7.45 (3H, m), 7.52 (1H, d, J=8 Hz), 7.65 (1H, t, J=8 Hz), 8.34 (1H, s), 8.77 (1H, s), 8.97 (1H, d, J=8 Hz), 9.33 (1H, br s)

(31) 6-(2,6-Dichlorobenzoylamino)-2,3-dimethyl-2H-pyrazolo[4,3-c]quinoline mp: >250° C. NMR (DMSO-d$_6$, δ): 2.62 (3H, s), 4.43 (3H, s), 7.45–7.65 (3H, m), 7.78 (1H, t, J=8 Hz), 8.34 (1H, d, J=8 Hz), 8.80 (1H, d, J=8 Hz), 9.17 (1H, s)

its hydrochloride mp: >250° C. NMR (DMSO-d$_6$, δ): 2.63 (3H, s), 4.45 (3H, s), 7.50–7.70 (3H, m), 7.80 (1H, t, J=8 Hz), 8.36 (1H, d, J=8 Hz), 8.78 (1H, d, J=8 Hz), 9.22 (1H, s)

(32) 8-(2,6-Dichlorobenzoylamino)-4-(2-methylphenylamino)-3-(1-oxobutyl)quinoline mp: 208–210° C. NMR (CDCl$_3$, δ): 1.06 (3H, t, J=7 Hz), 1.83 (2H, m), 2.37 (3H, s), 3.09 (2H, t, J=7 Hz), 6.99 (1H, d, J=7 Hz), 7.05–7.25 (4H, m), 7.30–7.45 (4H, m), 8.85 (1H, d, J=7 Hz), 9.04 (1H, s)

(33) 3-(2,6-Dichlorobenzoylamino)-thieno[3,2-b]pyridine hydrochloride mp: 205–232° C. NMR (DMSO-d$_6$, δ): 7.45–7.57 (4H, m), 8.50–8.60 (2H, m), 8.70 (1H, d, J=4 Hz)

(34) 8-(2,6-Dichlorobenzoylamino)-3-((E)-2-ethoxycarbonylvinyl)quinoline mp: 186–188° C. NMR (CDCl$_3$, δ): 1.38 (3H, t, J=7 Hz), 4.32 (2H, q, J=7 Hz), 6.64 (1H, d, J=17 Hz), 7.34–7.46 (3H, m), 7.60–7.72 (2H, m), 4 (1H, d, J=17 Hz), 8.26 (1H, s), 8.94 (1H, s), 9.00 (1H, d, J=8 Hz), 9.94 (1H, br s)

(35) 4-Chloro-8-(2,6-dichlorobenzoylamino)-3-ethoxycarbonylquinoline mp: 129.4° C. NMR (CDCl$_3$, δ): 1.44 (3H, t, J=7.5 Hz), 4.48 (2H, q, J=7.5 Hz), 7.30–7.46 (3H, m), 7.76 (1H, t, J=7.5 Hz), 8.15 (1H, d, J=7.5 Hz), 9.06 (1H, s), 9.10 (1H, d, J=7.5 Hz)

(36) 8-(2,6-Dichlorobenzoylamino)-3-(trimethylsilylethynyl)quinoline mp: 201–202° C. NMR (CDCl$_3$, δ): 0.30 (9H, s), 7.31–7.43 (3H, m), 7.53 (1H, d, J=8 Hz), 7.62 (1H, t, J=8 Hz), 8.28 (1H, s), 8.75 (1H, s), 8.97 (1H, d, J=8 Hz)

(37) 2-tert-Butoxycarbonyl-6-(2,6-dichlorobenzoylamino)-2,3-dihydro-1-methyl-1H-pyrazolo[4,3-c]quinolin-3-one mp: >250° C. NMR (CDCl$_3$, δ): 1.68 (9H, s), 3.78 (3H, s), 7.30–7.50 (3H, m), 7.74 (1H, d, J=8 Hz), 7.89 (1H, d, J=8 Hz), 9.00 (1H, s), 9.17 (1H, d, J=8 Hz)

Example 3

(1) A mixture of 8-amino-4-hydroxymethylquinoline (85 mg), 2,6-dichlorobenzoyl chloride (225 mg) and triethylamine (198 mg) in ethylene chloride (1.5 ml) was stirred at 80° C. overnight. After cooling, the mixture was diluted with dichloromethane, washed with brine, dried over magnesium sulfate and evaporated in vacuo to give 4-(2,6-dichlorobenzoyloxymethyl)-8-(2,6-dichlorobenzoylamino) quinoline (116 mg).

mp: 237° C. (dec.) NMR (DMSO-d$_6$, δ): 6.00 (2H, S), 7.46–7.65 (6H, m), 7.74 (1H, t, J=7.5 Hz), 7.78 (1H, d, J=4 Hz), 7.95 (1H, d, J=7.5 Hz), 8.76 (1H, d, J=7.5 Hz), 8.92 (1H, d, J=4 Hz)

(2) A mixture of 4-(2,6-dichlorobenzoyloxymethyl)-8-(2,6-dichlorobenzoylamino)quinoline (100 mg), 1N sodium hydroxide solution (0.4 ml) in ethanol (2 ml) and dioxane (1 ml) was refluxed for 5 hours. After cooling, the mixture was diluted with dichloromethane, washed with saturated sodium bicarbonate solution, dried over magnesium sulfate and evaporated in vacuo. The residue was purified by flash chromatography (ethyl acetate-n-hexane) to give 8-(2,6-dichlorobenzoylamino)-4-hydroxymethylquinoline (20 mg).

mp: 234.8–239.0° C. NMR (CDCl$_3$-CD$_3$OD, δ): 5.16 (2H, s), 7.30–7.46 (3H, m), 7.57–7.71 (3H, m), 8.75 (1H, d, J=5 Hz), 8.92 (1H, d, J=7.5 Hz)

its hydrochloride mp: 222–228° C. NMR (CDCl$_3$-CD$_3$OD, δ): 5.34 (2H, s), 7.35–7.47 (3H, m), 7.87–7.98 (2H, m), 8.18 (1H, d, J=7 Hz), 8.94–9.06 (2H, m)

Example 4

(1) A mixture of 8-amino-4-hydroxyquinoline (300 mg), 2,6-dichlorobenzoyl chloride (432 mg), triethylamine (569 mg) and catalytic amount of dimethylaminopyridine in dimethylacetamide (3 ml) was stirred for 1 hour under ice-cooling. To the mixture was added water (3 ml) and the resulting precipitate was collected by filtration. The residue was suspended in hot ethanol (10 ml) with stirring. The resulting precipitate was collected by filtration, and the residue was purified by flash chromatography (ethyl acetate-dichloromethane) to give 8-amino-4-(2,6-dichlorobenzoyloxy)quinoline (240 mg).

NMR (CDCl$_3$, δ): 5.03 (2H, br s), 6.95 (1H, d, J=7.5 Hz), 7.30–7.52 (6H, m), 8.79 (1H, d, J=5 Hz)

(2) A mixture of 8-amino-4-(2,6-dichlorobenzoyloxy) quinoline (210 mg), 2,6-dichlorobenzoyl chloride (145 mg) and triethylamine (191 mg) in ethylene chloride (3 ml) was stirred for 24 hours at 70° C. The mixture was diluted with dichloromethane, washed with water, dried over magnesium sulfate and evaporated in vacuo. The residue was washed with diethyl ether to give 4-(2,6-dichlorobenzoyloxy)-8-(2,6-dichlorobenzoylamino)quinoline (290 mg).

mp: 248° C. NMR (CDCl$_3$, δ): 7.30–7.50 (6H, m), 7.58 (1H, d, J=4 Hz), 7.66 (1H, t, J=7.5 Hz), 7.94 (1H, d, J=7.5 Hz), 8.84 (1H, d, J=4 Hz), 9.03 (1H, d, J=7.5 Hz)

(3) 8-(2,6-Dichlorobenzoylamino)-1,4-dihydro-4-oxoquinoline was obtained according to a similar manner to that of Example 3-(2).

mp: 342° C. NMR (DMSO-d$_6$, δ): 5.95–6.27 (1H, m), 7.31–7.46 (2H, m), 7.49–7.70 (3H, m), 7.88–8.09 (2H, m), 8.12 (1H, br s)

Example 5

To a solution of 8-(2,6-dichlorobenzoylamino)-3-(trimethylsilylethynyl)quinoline (150 mg) in tetrahydrofuran (3 ml) was added 1M solution of tetrabutylammonium fluoride in tetrahydrofuran (0.04 ml) under ice-cooling, and the mixture was stirred for 2 hours at the same temperature. The mixture was diluted with dichloromethane, washed with water and brine, dried over magnesium sulfate and evaporated in vacuo. The residue was purified by column chromatography on silica gel (ethyl acetate:n-hexane, 1:4, v/v) to give 8-(2,6-dichlorobenzoylamino)-3-ethynylquinoline (111 mg).

mp: 219–220° C. NMR (CDCl$_3$, δ): 3.30 (1H, s), 7.30–7.46 (3H, m), 7.56 (1H, d, J=8 Hz), 7.66 (1H, t, J=8 Hz), 8.32 (1H, s), 8.80 (1H, s), 9.00 (1H, d, J=8 Hz), 9.92 (1H, br s)

Example 6

To a solution of 2-tert-butoxycarbonyl-6-(2,6-dichlorobenzoylamino)-2,3-dihydro-1-methyl-1H-pyrazolo[4,3-c]quinolin-3-one (30 mg) in methanol (1 ml) was added 4M solution of hydrogen chloride in ethyl acetate (1 ml) at ambient temperature, and the mixture was stirred for 1 hour at the same temperature. The mixture was concentrated in vacuo, and the residue was crystallized from ethanol-ethyl acetate to give 6-(2,6-dichlorobenzoylamino)-2,3-dihydro-1-methyl-1H-pyrazolo[4,3-c]quinolin-3-one hydrochloride (17.9 mg).

mp: >250° C. NMR (DMSO-d$_6$, δ): 4.30 (3H, s), 7.50–7.70 (3H, m), 7.78 (1H, t, J=8 Hz), 8.32 (1H, d, J=8 Hz), 8.76 (1H, d, J=8 Hz), 9.13 (1H, s)

Example 7

A mixture of 6-(2,6-dichlorobenzoylamino)-2,3-dihydro-1-methyl-1H-pyrazolo[4,3-c]quinolin-3-one hydrochloride (85 mg), 4-chloromethylpyridine hydrochloride (40 mg) and potassium carbonate (111 mg) in dimethylformamide (1 ml) was stirred for 3 hours at ambient temperature. The mixture was partitioned between ethyl acetate and water. The organic layer was washed with brine, dried over magnesium sulfate and evaporated in vacuo. The residue was purified by column chromatography on silica gel to give 6-(2,6-dichlorobenzoylamino)-2,3-dihydro-1-methyl-2-(pyridin-4-ylmethyl)-1H-pyrazolo[4,3-c]quinolin-3-one.

The obtained compound was dissolved in a solution of hydrogen chloride in methanol, and the mixture was concentrated in vacuo to give 6-(2,6-dichlorobenzoylamino)-2,3-dihydro-1-methyl-2-(pyridin-4-ylmethyl)-1H-pyrazolo[4,3-c]quinolin-3-one dihydrochloride (83 mg).

mp: 226–234° C. NMR (DMSO-d$_6$, δ): 4.33 (3H, s), 5.83 (2H, s), 7.48–7.65 (3H, m), 7.80 (1H, t, J=8 Hz), 8.18 (2H, d, J=6 Hz), 8.32 (1H, d, J=8 Hz), 8.81 (1H, d, J=8 Hz), 8.93 (2H, d, J=6 Hz), 9.18 (1H, s)

Example 8

A mixture of 4-chloro-8-(2,6-dichlorobenzoylamino) quinoline (100 mg) and 2-methoxyethylamine (314 mg) in N-methylpyrrolidone (1 ml) was heated at 120° C. overnight. Water (3 ml) was added thereto under ice-cooling, and the mixture was stirred for 1 hour. The resulting precipitate was collected by filtration, and the residue was purified by preparative thin layer chromatography (methanoldichloromethane) to give 8-(2,6-dichlorobenzoylamino)-4-(2-methoxyethylamino)quinoline (65 mg).

mp: 166° c NMR (CDCl$_3$, δ): 3.43–3.53 (2H, m), 3.44 (3H, s), 3.71 (2H, t, J=6 Hz), 5.44 (1H, br t, J=6 Hz), 6.45 (1H, d, J=5 Hz), 7.25–7.40 (3H, m), 7.42–7.55 (2H, m), 8.40 (1H, d, J=5 Hz), 8.89 (1H, d, J=7.5 Hz)

Example 9

The following compounds were obtained according to a similar manner to that of Example 8.

(1) 8-(2,6-Dichlorobenzoylamino)-4-(imidazol-1-yl)quinoline mp: 236° C. NMR (CDCl$_3$, δ): 7.31–7.46 (6H, m), 7.60 (1H, d, J=7.5 Hz), 7.70 (1H, t, J=7.5 Hz), 7.88 (1H, s), 8.86 (1H, d, J=4 Hz), 9.08 (1H, d, J=7.5 Hz)

its hydrochloride mp: 238–241° C. NMR (DMSO-d$_6$, δ): 7.46–7.63 (4H, m), 7.81 (1H, t, J=8 Hz), 8.00 (1H, d, J=4 Hz), 8.07 (1H, s), 8.26 (1H, s), 8.85 (1H, d, J=8 Hz), 9.14 (1H, d, J=4 Hz), 9.69 (1H, s)

(2) 4-(1H-Benzimidazol-1-yl)-8-(2,6-dichlorobenzoylamino)quinoline mp: 244.0° C. NMR (CDCl$_3$, δ): 7.23 (1H, d, J=8 Hz), 7.29–7.46 (6H, m), 7.56 (1H, d, J=5 Hz), 7.66 (1H, t, J=7.5 Hz), 7.96 (1H, d, J=7.5 Hz), 8.19 (1H, s), 8.94 (1H, d, J=5 Hz), 9.08 (1H, d, J=7.5 Hz)

(3) 8-(2,6-Dichlorobenzoylamino)-4-[2-(dimethylamino) ethylamino]quinoline mp: 171° C. NMR (CDCl$_3$, δ): 2.29 (6H, s), 2.69 (2H, t, J=7.5 Hz), 3.23–3.34 (2H, m), 5.97 (1H, m), 6.40 (1H, d, J=5 Hz), 7.24–7.40 (3H, m), 7.47 (1H, t, J=7.5 Hz), 7.54 (1H, d, J=7.5 Hz), 8.47 (1H, d, J=5 Hz), 8.88 (1H, d, J=7.5 Hz)

(4) 8-(2,6-Dichlorobenzoylamino)-4-(imidazol-1-yl)-3-(1-propenyl)quinoline hydrochloride (from 3-allyl-4-chloro-8-(2,6-dichlorobenzoylamino)quinoline and imidazole)

mp: 220–229° C. NMR (DMSO-d$_6$, δ): 1.88 (3H, d, J=6 Hz), 6.07 (1H, d, J=15 Hz), 6.83 (1H, m), 7.06 (1H, d, J=8 Hz), 7.45–7.60 (3H, m), 7.73 (1H, t, J=8 Hz), 7.95–8.05 (2H, m), 8.73 (1H, d, J=8 Hz), 9.27 (1H, s), 9.37 (1H, s)

(5) 8-(2,6-Dichlorobenzoylamino)-3-ethoxycarbonyl-4-(imidazol-1-yl)quinoline mp: 219–220° C. NMR (CDCl$_3$, δ): 1.17 (3H, t, J=7 Hz), 4.23 (2H, q, J=7 Hz), 7.18 (1H, s), 7.25–7.50 (5H, m), 7.66 (1H, s), 7.71 (1H, t, J=8 Hz), 9.13 (1H, d, J=8 Hz), 9.29 (1H, s)

its hydrochloride mp: 219–221° C. (dec.) NMR (DMSO-d$_6$, δ): 1.14 (3H, t, J=7 Hz), 4.22 (2H, q, J=7 Hz), 7.32 (1H, d, J=8 Hz), 7.45–7.65 (3H, m), 7.88 (1H, t, J=8 Hz), 8.00 (1H, s), 8.08 (1H, s), 8.92 (1H, d, J=8 Hz), 9.41 (1H, s), 9.45 (1H, s)

(6) 8-(2,6-Dichlorobenzoylamino)-3-ethoxycarbonyl-4-[(pyridin-2-ylmethyl)amino]quinoline dihydrochloride mp: >250° C. NMR (DMSO-d$_6$, δ): 1.31 (3H, t, j=7 Hz), 4.34 (2H, q, J=7 Hz), 5.32 (2H, br s), 7.40–7.70 (5H, m), 7.75 (1H, t, J=8 Hz), 8.03 (1H, t, J=8 Hz), 8.52 (1H, d, J=8 Hz), 8.62 (1H, d, J=8 Hz), 8.70 (1H, d, J=5 Hz), 8.85 (1H, s)

(7) 8-(2,6-Dichlorobenzoylamino)-3-ethoxycarbonyl-4-morpholinoquinoline mp: 186–187° C. NMR (CDCl$_3$, δ): 1.44 (3H, t, J=7 Hz), 3.37 (4H, m), 3.97 (4H, m), 4.47 (2H, q, J=7 Hz), 7.30–7.50 (3H, m), 7.61 (1H, t, J=8 Hz), 7.91 (1H, d, J=8 Hz), 8.75 (1H, s), 8.98 (1H, d, J=8 Hz)

its hydrochloride mp: 178–181° C. NMR (DMSO-d$_6$, δ): 1.37 (3H, t, J=8 Hz), 3.28 (4H, m), 3.87 (4H, m), 4.41 (2H, q, J=7 Hz), 7.40–7.60 (3H, m), 7.70 (1H, t, J=8 Hz), 8.00 (1H, d, J=8 Hz), 8.74 (1H, d, J=8 Hz), 8.77 (1H, s)

(8) 8-(2,6-Dichlorobenzoylamino)-3-ethoxycarbonyl-4-(4-methylpiperazin-1-yl)quinoline mp: 177–178° C. NMR (CDCl$_3$, δ): 1.41 (3H, t, J=7 Hz), 2.43 (3H, s), 2.69 (4H, m), 3.39 (4H, m), 4.44 (2H, q, J=7 Hz), 7.30–7.50 (3H, m), 7.59 (1H, t, J=8 Hz), 7.89 (1H, d, J=8 Hz), 8.71 (1H, s), 8.95 (1H, d, J=8 Hz)

its hydrochloride mp: 156–162° C. NMR (DMSO-d$_6$, δ): 1.40 (3H, t, J=7 Hz), 2.90 (3H, s), 3.40–3.60 (8H, m), 4.43 (2H, q, J=7 Hz), 7.40–7.60 (3H, m), 7.74 (1H, t, J=8 Hz), 7.97 (1H, d, J=8 Hz), 8.78 (1H, d, J=8 Hz), 8.83 (1H, s)
(9) 3-Bromo-8-(2,6-dichlorobenzoylamino)-4-(imidazol-1-yl)quinoline mp: 220–221° C. NMR (DMSO-d$_6$, δ): 7.06 (1H, d, J=8 Hz), 7.30 (1H, s), 7.45–7.60 (3H, m), 7.77 (1H, t, J=8 Hz), 8.02 (1H, s), 8.79 (1H, d, J=8 Hz), 9.20 (1H, s)
its hydrochloride mp: 234–236° C. NMR (DMSO-d$_6$, δ): 7.22 (1H, d, J=8 Hz), 7.45–7.60 (3H, m), 7.81 (1H, t, J=8 Hz), 7.95 (1H, s), 8.02 (1H, s), 8.83 (1H, d, J=8 Hz), 9.25 (1H, s), 9.28 (1H, s)
(10) 3-Bromo-8-(2,6-dichlorobenzoylamino)-4-(4-methylpiperazin-1-yl)quinoline mp: 152–153° C. NMR (CDCl$_3$, δ): 2.43 (3H, s), 2.67 (4H, m), 3.50 (4H, m), 7.30–7.50 (3H, m), 7.59 (1H, t, J=8 Hz), 7.93 (1H, d, J=8 Hz), 8.67 (1H, s), 8.92 (1H, d, J=8 Hz)
its dihydrochloride mp: >250° C. NMR (DMSO-d$_6$, δ): 2.91 (3H, s), 3.35–4.40 (8H, br m), 7.45–7.60 (3H, m), 7.74 (1H, t, J=8 Hz), 8.03 (1H, m), 8.73 (1H, d, J=8 Hz), 8.87 (1H, s)

Example 10

A mixture of 4-chloro-8-(2,6-dichlorobenzoylamino)quinoline (130 mg) and 2-methoxyethylamine (210 mg) in dimethylformamide (1.5 ml) was heated for 5 hours at 100° C. The mixture was concentrated in vacuo, and the residue was purified by preparative thin layer chromatography to give 8-(2,6-dichlorobenzoylamino)-4-dimethylaminoquinoline (94 mg).

mp: 215–216° C. NMR (CDCl$_3$, δ): 3.06 (6H, s), 6.77 (1H, d, J=5 Hz), 7.26–7.52 (3H, m), 7.50 (1H, t, J=7.5 Hz), 7.79 (1H, d, J=7.5 Hz), 8.48 (1H, d, J=5 Hz), 8.89 (1H, d, J=7.5 Hz)

Example 11

8-(2,6-Dichlorobenzoylamino)-4-phenoxyquinoline was obtained by reacting 4-chloro-8-(2,6-dichlorobenzoylamino)quinoline with sodium phenoxide according to a similar manner to that of Preparation 2-(2).

mp: 170.4° C. NMR (CDCl$_3$, δ): 6.60 (1H, d, J=5 Hz), 7.14–7.53 (8H, m), 7.65 (1H, t, J=7.5 Hz), 8.11 (1H, d, J=7.5 Hz), 8.51 (1H, d, J=5 Hz), 9.01 (1H, d, J=7.5 Hz)

Example 12

(1) A mixture of 8-(2,6-dichlorobenzoylamino)-3-methylquinoline (108 mg), N-bromosuccinimide (69.6 mg) and 2,2'-azobis(2,4-dimethyl-4-methoxyvaleronitrile) (10.1 mg) in dichloromethane and carbon tetrachloride was refluxed for 2 hours. After cooling, the mixture was diluted with ethyl acetate, washed with water, saturated sodium bicarbonate solution and brine, dried over magnesium sulfate and evaporated in vacuo to give a residue containing 3-bromomethyl-8-(2,6-dichlorobenzoylamino)quinoline. The residue was dissolved in dimethylformamide, and acetic acid (27.5 mg) and potassium carbonate (63.2 mg) were added thereto. After stirring for 3 hours at ambient temperature, the mixture was poured into water and extracted with ethyl acetate. The organic layer was washed with brine, dried over magnesium sulfate and evaporated in vacuo. The residue was purified by column chromatography on silica gel (ethyl acetate-dichloromethane) to give 3-acetoxymethyl-8-(2,6-dichlorobenzoylamino)quinoline (48.4 mg).

mp: 199–201° C. NMR (CDCl$_3$, δ): 2.12 (3H, s), 5.30 (2H, s), 7.30–7.50 (3H, m), 7.50–7.70 (2H, m), 8.19 (1H, s), 8.78 (1H, s), 8.98 (1H, d, J=8 Hz)

(2) A mixture of 3-acetoxymethyl-8-(2,6-dichlorobenzoylamino)quinoline (25.9 mg), 1N sodium hydroxide solution (0.24 ml) in dioxane and dimethylformamide (4 drops) was stirred for 2 hours at ambient temperature. The mixture was poured into water and extracted with ethyl acetate. The organic layer was washed with brine, dried over magnesium sulfate and evaporated in vacuo. The residue was recrystallized from ethyl acetate-n-hexane to give 8-(2,6-dichlorobenzoylamino)-3-hydroxymethylquinoline (20 mg).

mp: 224–226° C. NMR (CDCl$_3$, δ): 1.92 (1H, t, J=7 Hz), 4.95 (1H, d, J=7 Hz), 7.30–7.50 (3H, m), 7.50–7.70 (2H, m), 8.18 (1H, s), 8.79 (1H, s), 8.96 (1H, d, J=8 Hz)
its hydrochloride mp: 217° C. NMR (DMSO-d$_6$, δ): 4.75 (2H, s), 7.49–7.61 (3H, m), 7.65 (1H, t, J=8 Hz), 7.78 (1H, d, J=8 Hz), 8.31 (1H, s), 8.68 (1H, d, J=8 Hz), 8.85 (1H, s)

(3) To a solution of 8-(2,6-dichlorobenzoylamino)-3-hydroxymethylquinoline (300 mg) in tetrahydrofuran were added carbon tetrabromide (573 mg) and triphenylphosphine (453 mg), and the mixture was stirred for 30 minutes at ambient temperature. Insoluble material was filtered off, and the filtrate was evaporated in vacuo. The residue was purified by column chromatography on silica gel (dichloromethane) to give 3-bromomethyl-8-(2,6-dichlorobenzoylamino)quinoline (253.4 mg).

mp: 223–224° C. NMR (CDCl$_3$, δ): 4.66 (2H, s), 7.30–7.50 (3H, m), 7.59 (1H, d, J=8 Hz), 7.66 (1H, t, J=8 Hz), 8.18 (1H, s), 8.81 (1H, s), 8.98 (1H, d, J=8 Hz)

(4) 8-(2,6-Dichlorobenzoylamino)-3-methoxymethylquinoline was obtained by reacting 3-bromomethyl-8-(2,6-dichlorobenzoylamino)quinoline with sodium methoxide according to a similar manner to that of Preparation 2-(2).

mp: 163° C. NMR (CDCl$_3$, δ): 3.47 (3H, s), 4.67 (2H, s), 7.30–7.50 (3H, m), 7.50–7.70 (2H, m), 8.15 (1H, s), 8.76 (1H, s), 8.96 (1H, d, J=8 Hz)
its hydrochloride mp: 159–166° C. NMR (DMSO-d$_6$, δ): 3.37 (3H, s), 4.67 (2H, s), 7.40–7.60 (3H, m), 7.67 (1H, t, J=8 Hz), 7.79 (1H, d, J=8 Hz), 8.36 (1H, s), 8.70 (1H, d, J=8 Hz), 8.85 (1H, s)

(5) To a solution of 3-bromomethyl-8-(2,6-dichlorobenzoylamino)quinoline (120 mg) and phenol (30.3 mg) in dimethylformamide was added potassium tert-butoxide (72.2 mg), and the mixture was stirred for 1 hour at ambient temperature. The mixture was poured into saturated ammonium chloride solution and extracted with ethyl acetate. The organic layer was washed with brine, dried over magnesium sulfate and evaporated in vacuo. The residue was purified by column chromatography on silica gel (ethyl acetate-n-hexane) to give 8-(2,6-dichlorobenzoylamino)-3-phenoxymethylquinoline (87.1 mg).

mp: 157° C. NMR (CDCl$_3$, δ): 5.28 (2H, s), 6.90–7.10 (3H, m), 7.25–7.50 (5H, m), 7.55–7.70 (2H, m), 8.26 (1H, s), 8.86 (1H, s), 9.98 (1H, d, J=8 Hz)
its hydrochloride mp: 164–171° C. NMR (DMSO-d$_6$, δ): 4.59 (2H, s), 6.18 (1H, t, J=8 Hz), 6.20–6.30 (2H, m), 6.45–6.55 (2H, m), 6.60–6.80 (3H, m), 7.00 (1H, t, J=8 Hz), 7.14 (1H, d, J=8 Hz), 7.90 (1H, d, J=8 Hz), 8.29 (1H, s)

Example 13

A mixture of 8-(2,6-dichlorobenzoylamino)-3-hydroxymethylquinoline (100 mg) and thionyl chloride (1 ml) in dichloromethane (1 ml) was stirred for 2 hours at ambient temperature. After concentration, the residue was dissolved in N,N-dimethylformamide (1 ml) and to the solution was added 2-mercaptoimidazole (32 mg) and potassium carbonate (60 mg). The mixture was stirred for 3 hours at ambient temperature. The resulting mixture was poured into cold water, and extracted with ethyl acetate. The organic layer was washed with aqueous saturated sodium bicarbonate solution and brine, dried over anhydrous sodium sulfate, and evaporated in vacuo. The residue was purified by column chromatography on silica gel with dichloromethane:methanol (20:1) as eluent to give an oil. The obtained oil was treated with 10% methanolic hydrogen chloride and evaporated in vacuo. The resulting oil was crystallized from ethyl acetate to give 8-(2,6-dichlorobenzoylamino)-3-[(imidazol-2-yl)thiomethyl]quinoline hydrochloride (102 mg).

mp: >250° C. NMR (CDCl$_3$, δ): 4.79 (2H, s), 7.48–7.61 (3H, m), 7.63–7.72 (4H, m), 8.20 (1H, s), 8.71 (1H, dd, J=15, 8 Hz), 8.83 (1H, s)

Example 14

A mixture of 8-(2,6-dichlorobenzoylamino)-3-methylquinoline (250 mg), N-bromosuccinimide (175 mg) and 2,2'-azobis(2,4-dimethyl-4-methoxyvaleronitrile) (23.3 mg) in dichloromethane was refluxed for 2 hours. After cooling, the mixture was diluted with ethyl acetate, washed with water, saturated sodium bicarbonate solution and brine, dried over magnesium sulfate and evaporated in vacuo. The residue was purified by column chromatography on silica gel (dichloromethane) to give 5-bromo-8-(2,6-dichlorobenzoylamino)-3-methylquinoline (54.2 mg).

mp: 238–239° C. NMR (CDCl$_3$, δ): 2.49 (3H, s), 7.30–7.50 (3H, m), 7.85 (1H, d, J=8 Hz), 8.31 (1H, s), 8.64 (1H, s), 8.78 (1H, d, J=8 Hz)

Example 15

A mixture of 8-(2,6-dichlorobenzoylamino)-3-methylquinoline (104 mg), N-bromosuccinimide (67.1 mg) and 2,2'-azobis(2,4-dimethyl-4-methoxyvaleronitrile) (20.1 mg) in carbon tetrachloride (3 ml) was refluxed for 2 hours. After cooling, the mixture was washed with water, saturated sodium bicarbonate solution and brine, dried over magnesium sulfate and evaporated in vacuo to give a residue containing 3-bromomethyl-8-(2,6-dichlorobenzoylamino)quinoline. The residue was dissolved in ethylene chloride, and imidazole (64.1 mg) was added thereto. After stirring for 2.5 hours at 60° C., the mixture was washed with water and brine, dried over magnesium sulfate and evaporated in vacuo. The residue was purified by column chromatography on silica gel (ethyl acetate-dichloromethane) to give 8-(2,6-dichlorobenzoylamino)-3-(imidazol-1-ylmethyl)quinoline (36.2 mg).

mp: 177–179° C. NMR (CDCl$_3$, δ): 5.34 (2H, s), 6.94 (1H, s), 8.98 (1H, d, J=8 Hz), 7.15 (1H, s), 7.30–7.50 (3H, m), 7.55 (1H, d, J=8 Hz), 7.6–7.7 (2H, m), 7.90 (1H, s), 8.63 (1H, s)

Example 16

To a solution of 3-acetyl-8-(2,6-dichlorobenzoylamino)-4-methoxyquinoline (115 mg) in tetrahydrofuran was added sodium borohydride (16.8 mg) at 0° C., and the mixture was stirred for 30 minutes at the same temperature. The mixture was poured into water and extracted with ethyl acetate. The organic layer was washed with brine, dried over magnesium sulfate and evaporated in vacuo to give 8-(2,6-dichlorobenzoylamino)-3-(1-hydroxyethyl)-4-methoxyquinoline (85.1 mg).

To a solution of the obtained compound (75 mg) in ethyl acetate was added 4N solution of hydrogen chloride in ethyl acetate (0.25 ml), and the solvent was removed in vacuo to give 8-(2,6-dichlorobenzoylamino)-3-(1-hydroxyethyl)-4-methoxyquinoline hydrochloride (70 mg).

mp: >210° C. (dec.) NMR (CDCl$_3$, δ): 1.61 (3H, br s), 4.32 (3H, s), 5.54 (1H, br s), 7.30–7.50 (4H, m), 8.07 (1H, d, J=8 Hz), 9.16 (1H, d, J=8 Hz), 9.43 (1H, br s)

Example 17

To 0.9M solution of methylmagnesium bromide in tetrahydrofuran (1.8 ml) was dropwise added a solution of 8-(2,6-dichlorobenzoylamino)-3-ethoxycarbonylquinoline (100 mg) in dry tetrahydrofuran (4 ml) at 4° C., and the mixture was stirred for 30 minutes at the same temperature. To the mixture was added saturated ammonium chloride solution and extracted with ethyl acetate. The organic layer was washed with brine, dried over magnesium sulfate and evaporated in vacuo. The residue was purified by column chromatography on silica gel (ethyl acetate-n-hexane) to give 8-(2,6-dichlorobenzoylamino)-3-(1-hydroxy-1-methylethyl)quinoline (55.1 mg).

mp: 187–189° C. NMR (CDCl$_3$, δ): 1.70 (6H, s), 1.89 (1H, s), 7.30–7.50 (3H, m), 7.50–7.70 (2H, m), 8.27 (1H, s), 8.90–9.00 (2H, m)

Example 18

A mixture of 8-(2,6-dichlorobenzoylamino)-3-ethoxycarbonylquinoline (300 mg), 1N sodium hydroxide solution (1.95 ml) in tetrahydrofuran (10 ml) was stirred for 6 hours at 50° C. The mixture was concentrated in vacuo, and water was added to the residue. The solution was washed with diethyl ether, and the aqueous layer was adjusted to pH 3 with 1N hydrochloric acid. The resulting precipitate was collected by filtration and washed with water to give 3-carboxy-8-(2,6-dichlorobenzoylamino)quinoline (251.1 mg).

mp: >250° C. NMR (DMSO-d$_6$, δ): 7.40–7.60 (3H, m), 7.76 (1H, t, J=8 Hz), 8.00 (1H, d, J=8 Hz), 8.81 (1H, d, J=8 Hz), 9.02 (1H, s), 9.29 (1H, 5)

Example 19

To a solution of 3-carboxy-8-(2,6-dichlorobenzoylamino) quinoline (121 mg) in dichloromethane were dropwise added oxalyl chloride (170 mg) and dimethylformamide (1 drop), and the mixture was stirred for 1 hour at ambient temperature. The mixture was concentrated in vacuo, and the residue was dissolved in dry tetrahydrofuran (3 ml). To the solution was added conc. ammonia solution (5 ml) with stirring, and the mixture was stirred for 1 hour at ambient temperature. The mixture was diluted with ethyl is acetate, washed with brine, dried over magnesium sulfate and evaporated in vacuo. The residue was recrystallized from ethyl acetate-n-hexane to give 3-carbamoyl-8-(2,6-dichlorobenzoylamino)quinoline (97.9 mg).

mp: >250° C. NMR (DMSO-d$_6$, δ):7.40–7.60 (3H, m), 7.70–7.80 (2H, overlapping), 7.74 (1H, t, J=8 Hz), 7.88 (1H, d, J=8 Hz), 8.38 (1H, br s), 8.80 (1H, d, J=8 Hz), 8.91 (1H, s), 9.28 (1H, s)

Example 20

8-(2,6-Dichlorobenzoylamino)-3-(morpholinocarbonyl) quinoline was obtained from 3-carboxy-8-(2,6-dichlorobenzoylamino)quinoline and morpholine according to a similar manner to that of Example 19.

mp: 204–205° C. NMR (CDCl$_3$, δ): 3.40–4.00 (8H, m), 7.30–7.50 (3H, m), 7.65 (1H, d, J=8 Hz), 7.70 (1H, t, J=8 Hz), 8.27 (1H, s), 8.84 (1H, s), 9.06 (1H, d, J=8 Hz)

Example 21

To a solution of 8-(2,6-dichlorobenzoylamino)-4-ethoxy-3-ethoxycarbonylquinoline (179 mg) in tetrahydrofuran was added lithium borohydride (22.5 mg), and the mixture was stirred for 4 hours at 50° C. To the mixture was dropwise added saturated ammonium chloride solution and extracted with ethyl acetate. The organic layer was washed with saturated sodium bicarbonate solution and brine, dried over magnesium sulfate and evaporated in vacuo. The residue was purified by column chromatography on silica gel (ethyl acetate-n-hexane) to give 8-(2,6-dichlorobenzoylamino)-4-ethoxy-3-hydroxymethylquinoline (55.9 mg).

To a solution of the obtained compound (50 mg) in ethyl acetate was added 4N solution of hydrogen chloride in ethyl acetate (0.15 ml), and the resulting precipitate was collected by filtration to give 8-(2,6-dichlorobenzoylamino)-4-ethoxy-3-hydroxymethylquinoline hydrochloride (47 mg).

mp: >250° C. NMR (CDCl$_3$, δ): 1.63 (3H, t, J=7 Hz), 4.77 (2H, q, J=7 Hz), 4.96 (2H, s), 7.30–7.50 (3H, m), 8.15 (1H, d, J=8 Hz), 9.09 (1H, d, J=8 Hz), 9.14 (1H, s)

Example 22

(1) 3-Carboxy-8-(2,6-dichlorobenzoylamino)-4-ethoxyquinoline was obtained from 8-(2,6-dichlorobenzoylamino)-4-ethoxy-3-ethoxycarbonylquinoline according to a similar manner to that of Example 18.

mp: 207–208° C. NMR (CDCl$_3$, δ): 1.60 (3H, t, J=7 Hz), 4.46 (2H, q, J=7 Hz), 7.30–7.50 (3H, m), 7.70 (1H, t, J=8 Hz), 7.96 (1H, d, J=8 Hz), 9.09 (1H, d, J=8 Hz), 9.25 (1H, s)

(2) To a solution of 3-carboxy-8-(2,6-dichlorobenzoylamino)-4-ethoxyquinoline (153 mg) in dimethylformamide were added 1-ethyl-3-(3-dimethylaminopropyl)carbodiimide hydrochloride (109 mg) and 1-hydroxybenzotriazole (76.5 mg), and the mixture was stirred for 2 hours at ambient temperature. To the mixture was added conc. ammonia solution (0.2 ml) with stirring, and the mixture was stirred for 6 hours at ambient temperature. The mixture was poured into water and extracted with ethyl acetate. The organic layer was washed with saturated ammonium chloride solution, saturated sodium bicarbonate solution and brine, dried over magnesium sulfate and evaporated in vacuo. The residue was crystallized from ethanol to give 3-carbamoyl-8-(2,6-dichlorobenzoylamino)-4-ethoxyquinoline (128.3 mg).

mp: 242–245° C. NMR (DMSO-d$_6$, δ): 1.44 (3H, t, J=7 Hz), 4.38 (2H, q, J=7 Hz), 7.40–7.60 (3H, m), 7.69 (1H, t, J=8 Hz), 7.85 (1H, s), 8.00 (1H, d, J=8 Hz), 8.10 (1H, s), 8.75 (1H, d, J=8 Hz), 8.80 (1H, s)

(3) To a solution of 3-carbamoyl-8-(2,6-dichlorobenzoylamino)-4-ethoxyquinoline (122 mg) in dimethylformamide was added thionyl chloride (53.9 mg), and the mixture was stirred for 30 minutes at ambient temperature. The mixture was poured into saturated sodium bicarbonate solution and extracted with ethyl acetate. The organic layer was washed with brine, dried over magnesium sulfate and evaporated in vacuo. The residue was purified by column chromatography on silica gel (ethyl acetate-n-hexane) to give 3-cyano-8-(2,6-dichlorobenzoylamino)-4-ethoxyquinoline (89.9 mg).

mp: 200–201° C. NMR (CDCl$_3$, δ): 1.63 (3H, t, J=7 Hz), 4.92 (2H, q, J=7 Hz), 7.30–7.45 (3H, m), 7.66 (1H, t, J=8 Hz), 8.00 (1H, d, J=8 Hz), 8.66 (1H, s), 9.08 (1H, d, J=8 Hz), 9.81 (1H, s)

its hydrochloride mp: 191–193° C. NMR (CDCl$_3$-CD$_3$OD, δ): 1.63 (3H, t, J=7 Hz), 4.92 (2H, q, J=7 Hz), 7.30–7.50 (3H, m), 7.66 (1H, t, J=8 Hz), 8.00 (1H, d, J=8 Hz), 8.66 (1H, s), 9.06 (1H, d, J=8 Hz)

Example 23

8-(2,6-Dichlorobenzoylamino)-4-dimethylamino-3-hydroxymethylquinoline hydrochloride was obtained from 8-(2,6-dichlorobenzoylamino)-3-ethoxycarbonyl-4-dimethylaminoquinoline according to a similar manner to that of Example 21.

mp: 124–156° C. NMR (CDCl$_3$, δ): 3.46 (6H, s), 4.88 (2H, s), 7.30–7.50 (3H, m), 7.66 (1H, t, J=8 Hz), 7.87 (1H, d, J=8 Hz), 8.80–8.90 (2H, m)

Example 24

(1) 3-Carboxy-8-(2,6-dichlorobenzoylamino)-4-dimethylaminoquinoline was obtained from 8-(2,6-dichlorobenzoylamino)-3-ethoxycarbonyl-4-dimethylaminoquinoline according to a similar manner to that of Example 18.

mp: 160–163° C. NMR (DMSO-d$_6$, δ): 3.10 (6H, s), 7.40–7.60 (4H, m), 7.98 (1H, d, J=8 Hz), 8.72 (1H, d, j=8 Hz), 8.76 (1H, s)

(2) 3-Carbamoyl-8-(2,6-dichlorobenzoylamino)-4-dimethylaminoquinoline was obtained according to a similar manner to that of Example 22-(2).

mp: 222–223° C. NMR (DMSO-d$_6$, δ): 3.06 (6H, s), 7.40–7.65 (4H, m), 7.71 (1H, br s), 7.92 (1H, d, J=8 Hz), 8.03 (1H, br s), 8.53 (1H, s), 8.67 (1H, d, J=8 Hz)

(3) 3-Cyano-8-(2,6-dichlorobenzoylamino)-4-dimethylaminoquinoline was obtained according to a similar manner to that of Example 22-(3).

mp: 227–228° C. NMR(DMSO-d$_6$, δ): 3.39 (6H, s), 7.40–7.70 (4H, m), 7.93 (1H, d, J=8 Hz), 8.64 (1H, s), 8.73 (1H, d, J=8 Hz)

its hydrochloride mp: 219–223° C. NMR (DMSO-d$_6$, δ): 3.40 (6H, s), 7.40–7.70 (4H, m), 7.93 (1H, d, J=8 Hz), 8.65 (1H, s), 8.73 (1H, d, J=8 Hz)

Example 25

To a solution of 3-bromo-4-chloro-8-(2,6-dichlorobenzoylamino)quinoline (120 mg) in N-methylpyrrolidone were added 2-mercaptoimidazole (33.5 mg) and potassium carbonate (50.1 mg), and the mixture was stirred for 40 minutes at ambient temperature, for 1 hour at 40° C., for 1 hour at 80° C. and for 1 hour at 90° C. To the mixture was added water, and the resulting precipitate was collected by filtration and washed with water and ethanol to give 3-bromo-8-(2,6-dichlorobenzoylamino)-4-(imidazol-2-ylthio)quinoline (88.0 mg).

mp: 249–251° C. NMR (DMSO-d$_6$, δ): 6.93 (1H, br s), 7.18 (1H, br s), 7.45–7.60 (3H, m), 7.70 (1H, t, J=8 Hz), 8.07 (1H, d, J=8 Hz), 8.71 (1H, d, J=8 Hz), 9.03 (1H, s)

its hydrochloride mp: 240–242° C. NMR (DMSO-d$_6$, δ): 7.45–7.60 (5H, m), 7.80 (1H, t, J=8 Hz), 8.10 (1H, d, J=8 Hz), 8.79 (1H, d, J=8 Hz), 9.10 (1H, s)

Example 26

(1) 4-Carboxymethyl-3-bromo-8-(2,6-dichlorobenzoylamino)quinoline was obtained from 3-bromo-8-(2,6-dichlorobenzoylamino)-4-(ethoxycarbonylmethyl)quinoline according to a similar manner to that of Example 18.

mp: >250° C. NMR (CDCl$_3$, δ): 4.33 (2H, s), 7.30–7.50 (3H, m), 7.69 (1H, t, J=8 Hz), 7.74 (1H, d, J=8 Hz), 8.84 (1H, s), 8.99 (1H, d, J=8 Hz)

(2) To a mixture of dimethylformamide (17.4 mg) and dichloromethane was added oxalyl chloride (27.7 mg), and the mixture was stirred for 30 minutes at ambient temperature. To the mixture was added 3-bromo-4-carboxymethyl-8-(2,6-dichlorobenzoylamino)quinoline (90 mg) at 0° C., and the mixture was stirred for 1 hour at the same temperature. To the mixture was added 2-aminomethylpyridine (107 mg) at 0° C., and the mixture was stirred for 30 minutes at ambient temperature. The mixture was partitioned between dichloromethane and saturated ammonium chloride solution. The organic layer was washed with saturated sodium bicarbonate solution and brine, dried over magnesium sulfate and evaporated in vacuo. The residue was purified by preparative thin layer chromatography and recrystallized from ethanol to give 3-bromo-8-(2,6-dichlorobenzoylamino)-4-[(pyridin-2-ylmethyl)carbamoylmethyl]quinoline (58.0 mg).

mp: 197–199° C. NMR (DMSO-d$_6$, δ): 4.34 (2H, s), 4.39 (2H, d, J=7 Hz), 7.27 (1H, dd, J=5, 8 Hz), 7.32 (1H, d, J=8 Hz), 7.45–7.60 (3H, mn), 7.72 (1H, t, J=8 Hz), 7.77 (1H, t, J=8 Hz), 7.98 (1H, d, J=8 Hz), 8.51 (1H, d, J=5 Hz), 8.73 (1H, d, J=8 Hz), 8.85 (1H, t, J=7 Hz), 8.96 (1H, s)

its hydrochloride mp: 241–248° C. NMR (DMSO-d$_6$, δ): 4.39 (2H, S), 4.56 (2H, d, J=7 Hz), 7.45–7.75 (6H, m), 7.98 (1H, d, J=8 Hz), 8.24 (1H, t, J=8 Hz), 8.70 (1H, d, J=5 Hz), 8.76 (1H, d, J=8 Hz), 8.95 (1H, s), 9.06 (1H, t, J=7 Hz)

Example 27

(1) 4-Carboxymethoxy-8-(2,6-dichlorobenzoylamino)quinoline was obtained from 8-(2,6-dichlorobenzoylamino)-4-(ethoxycarbonylmethoxy)quinoline according to a similar manner to that of Example 18.

mp: 190–204° C. NMR (DMSO-d$_6$, δ): 4.64 (2H, s), 6.87 (1H, d, J=5 Hz), 7.45–7.63 (4H, m), 7.95 (1H, d, J=7.5 Hz), 8.63 (1H, d, J=5 Hz), 8.68 (1H, d, J=7.5 Hz)

(2) 8-(2,6-Dichlorobenzoylamino)-4-(dimethylcarbamoylmethoxy)quinoline was obtained from 4-carboxymethoxy-8-(2,6-dichlorobenzoylamino)quinoline and dimethylamine hydrochloride according to a similar manner to that of Example 22-(2).

mp: 222–224.5° C. NMR (CDCl$_3$, δ): 2.99 (3H, s), 3.14 (3H, s), 4.97 (2H, s), 6.84 (1H, d, J=4 Hz), 7.26–7.43 (3H, m), 7.57 (1H, t, J=7.5 Hz), 7.98 (1H, d, J=7.5 Hz), 8.57 (1H, d, J=4 Hz), 8.96 (1H, d, J=7.5 Hz)

Example 28

8-(2,6-Dichlorobenzoylamino)-4-(imidazol-2-ylthio)-3-allylquinoline was obtained by reacting 3-allyl-4-chloro-8-(2,6-dichlorobenzoylamino)quinoline with 2-mercaptoimidazole according to a similar manner to that of Example 25.

mp: 206–208° C. NMR (DMSO-d$_6$, δ):3.91 (2H, d, J=6 Hz), 5.00 (1H, d, J=17 Hz), 5.07 (1H, d, J=11 Hz), 5.99 (1H, m), 7.02 (2H, br s), 7.40–7.60 (3H, m), 7.67 (1H, t, J=8 Hz), 8.20 (1H, d, J=8 Hz), 8.66 (1H, d, J=8 Hz), 8.72 (1H, s)

its dihydrochloride mp: 138–170° C. NMR (DMSO-d$_6$, δ): 3.90 (2H, d, J=6 Hz), 4.94 (1H, d, J=16 Hz), 5.05 (1H, d, J=11 Hz), 5.97 (1H, m), 7.45–7.60 (3H, m), 7.74 (1H, t, J=8 Hz), 8.00 (1H, d, J=8 Hz), 8.74 (1H, d, J=8 Hz), 8.94 (1H, s)

Example 29

To a suspension of 8-(2,6-dichlorobenzoylamino)-4-vinylquinoline (150 mg) in dioxane and water was added catalytic amount of osmium tetroxide in tert-butanol under ice-cooling, and the mixture was stirred for 5 minutes. To the mixture was added sodium periodate (206 mg) under ice-cooling, and the mixture was stirred for 30 minutes at the same temperature and for 6 hours at ambient temperature. To the mixture was added saturated sodium bicarbonate solution and extracted with dichloromethane. The organic layer was dried over magnesium sulfate and evaporated in vacuo. The residue was purified by flash chromatography (dichloromethane-n-hexane) to give 8-(2,6-dichlorobenzoylamino)-4-formylquinoline (85 mg).

mp: 239.3° C. NMR (CDCl$_3$, δ): 7.29–7.46 (3H, m), 7.81 (1H, t, J=7.5 Hz), 7.86 (1H, d, J=5 Hz), 8.70 (1H, d, J=7.5 Hz), 9.03 (1H, d, J=5 Hz), 9.06 (1H, d, J=7.5 Hz), 10.02 (1H, br s), 10.27 (1H, s)

Example 30

To a stirred suspension of 8-(2,6-dichlorobenzoylamino)-4-formylquinoline (100 mg), N-(2-methoxyethyl)methylamine (28 mg) and acetic acid (17 mg) was added sodium triacetoxyborohydride (91.6 mg) portionwise over a period of 5 minutes at ambient temperature, and the resulting mixture was stirred at the same temperature for four hours. The crude product was partitioned in dichloromethane and aqueous saturated sodium bicarbonate solution. The organic phase was dried over anhydrous magnesium sulfate, filtered, evaporated under reduced pressure. The residue was purified by a preparative thin layer chromatography (5%0 methanoldichloromethane) and recrystallized from ethanol to give 8-(2,6-dichlorobenzoylamino)-4-[N-(2-methoxyethyl)-N-methylaminomethyl]quinoline (77 mg) as a colorless powder.

mp: 127.7–133.7° C. NMR (CDCl$_3$, δ): 2.32 (3H, s), 2.72 (2H, t, J=7.5 Hz), 3.36 (3H, s), 3.58 (2H, t, J=7.5 Hz), 3.99 (2H, s), 7.26–7.44 (3H, m), 7.54 (1H, d, J=5 Hz), 7.61 (1H, t, J=7.5 Hz), 7.96 (1H, d, J=7.5 Hz), 8.70 (1H, d, J=5 Hz), 8.95 (1H, d, J=7.5 Hz)

Example 31

8-(2,6-Dichlorobenzoylamino)-4-((E)-2-ethoxycarbonylvinyl)quinoline was obtained by reacting 8-(2,6-dichlorobenzoylamino)-4-formylquinoline with ethyl (triphenylphosphoranilidene)acetate according to a similar manner to that of Preparation 19-(2).

mp: 157.4° C. NMR (CDCl$_3$, δ): 1.39 (3H, t, J=7.5 Hz), 4.34 (2H, q, J=7.5 Hz), 6.64 (1H, d, J=18 Hz), 7.29–7.44 (3H, m), 7.59 (1H, d, J=4 Hz), 7.70 (1H, t, J=7.5 Hz), 7.90 (1H, d, J=7.5 Hz), 8.38 (1H, d, J=18 Hz), 8.77 (1H, d, J=4 Hz), 9.01 (1H, d, J=7.5 Hz)

Example 32

To a solution of 8-(2,6-dichlorobenzoylamino)-3-methylthioquinoline (106 mg) in dichloromethane and water was added m-chloroperbenzoic acid (68 mg) under ice-cooling, and the mixture was stirred for 1 hour. The mixture was washed with saturated sodium bicarbonate solution and brine, dried over magnesium sulfate and evaporated in vacuo. The residue was purified by preparative thin layer chromatography (dichloromethane-methanol) to give 8-(2,6-dichlorobenzoylamino)-3-methylsulfinylquinoline (71 mg) and 8-(2,6-dichlorobenzoylamino)-3-methylsulfonylquinoline (68 mg). 8-(2,6-Dichlorobenzoylamino)-3-methylsulfinylquinoline mp: 229–231° C. NMR (CDCl$_3$, δ): 2.89 (3H, s), 7.32–7.45 (3H, m), 7.69–7.78 (2H, m), 8.60 (1H, d, J=2 Hz), 8.87 (1H, d, J=2 Hz), 9.09 (1H, d, J=8 Hz) 8-(2,6-Dichlorobenzoylamino)-3-methylsulfonylquinoline mp: 253–255° C. NMR (CDCl$_3$, δ): 3.19 (3H, s), 7.35–7.48 (3H, m), 7.74–7.86 (2H, m), 8.83 (1H, s), 9.16–9.22 (2H, m)

Example 33

(1) 8-(2,6-Dichlorobenzoylamino)-3-formylquinoline was obtained from 8-(2,6-dichlorobenzoylamino)-3-vinylquinoline according to a similar manner to that of Example 29.

mp: 232–233° C. NMR (CDCl$_3$, δ): 7.32–7.46 (3H, m), 7.70–7.80 (2H, m), 8.64 (1H, s), 9.14 (1H, d, J=7.5 Hz), 9.24 (1H, s), 10.00 (1H, br s), 10.28 (1H, s)

(2) A mixture of 8-(2,6-dichlorobenzoylamino)-3-formylquinoline (150 mg), nitromethane (1.5 ml) and ammonium acetate (30 mg) in dioxane (1 ml) was stirred for 2 hours at 90° C. The mixture was evaporated in vacuo. The residue was purified by column chromatography on silica gel (dichloromethane-methanol) to give 8-(2,6-7 dichlorobenzoylamino)-3-(1-hydroxy-2-nitroethyl) quinoline (126 mg).

mp: 190–191° C. NMR (CDCl$_3$-CD$_3$OD, δ): 4.62 (1H, dd, J=4, 14 Hz), 4.71 (1H, dd, J=8, 14 Hz), 5.68 (1H, dd, J=4, 8 Hz), 7.32–7.46 (3H, m), 7.60–7.70 (2H, m), 8.29 (1H, s), 8.82 (1H, s), 8.97 (1H, d, J=8 Hz)

Example 34

(1) To a mixture of 8-(2,6-dichlorobenzoylamino)-3-formylquinoline (700 mg) and methyl methylsulfinylmethyl sulfide (302 mg) in tetrahydrofuran was added potassium tert-butoxide (501 mg) at 4° C., and the mixture was stirred for 30 minutes at the same temperature and then refluxed for 1.5 hours. The mixture was poured into cold saturated ammonium chloride solution and extracted with ethyl acetate. The organic layer was washed with brine, dried over magnesium sulfate and evaporated in vacuo. A mixture of the obtained residue in dichloromethane (3 ml) and 34% solution of hydrogen chloride in ethanol (5 ml) was stirred for 2 hours at ambient temperature. The mixture was concentrated in vacuo, and the residue was partitioned between ethyl acetate and saturated sodium bicarbonate solution. The organic layer was washed with brine, dried over magnesium sulfate and evaporated in vacuo. The residue was purified by column chromatography on silica gel (ethyl acetate-n-hexane) to give 8-(2,6-dichlorobenzoylamino)-3-(ethoxycarbonylmethyl)quinoline (329 mg).

mp: 151° C. NMR (CDCl$_3$, δ): 1.27 (3H, t, J=7 Hz), 3.81 (2H, s), 4.18 (2H, q, J=7 Hz), 7.30–7.50 (3H, m), 7.56 (1H, d, J=8 Hz), 7.62 (1H, t, J=8 Hz), 8.10 (1H, s), 8.70 (1H, s), 8.94 (1H, d, J=8 Hz)

its hydrochloride mp: 174–184° C. NMR (DMSO-d$_6$, δ): 1.20 (3H, t, J=7 Hz), 3.97 (2H, s), 4.30 (2H, overlapping), 7.40–7.60 (3H, in), 7.66 (1H, t, J=8 Hz), 7.75 (1H, d, J=8 Hz), 8.31 (1H, s), 8.68 (1H, d, J=8 Hz), 8.82 (1H, s)

(2) 3-Carboxymethyl-8-(2,6-dichlorobenzoylamino) quinoline was obtained according to a similar manner to that of Example 18.

mp: >250° C. NMR (CDCl$_3$, δ): 3.81 (2H, s), 7.30–7.50 (3H, m), 7.57 (1H, d, J=8 Hz), 7.62 (1H, d, J=8 Hz), 8.11 (1H, s), 8.71 (1H, s), 8.92 (1H, d, J=8 Hz)

(3) 3-Carbamoylmethyl-8-(2,6-dichlorobenzoylamino) quinoline was obtained according to a similar manner to that of Example 22-(2).

mp: 251–253° C. NMR (DMSO-d$_6$, δ): 3.66 (2H, s), 7.04 (1H, br s), 7.40–7.70 (5H, m), 7.74 (1H, d, J=8 Hz), 8.24 (1H, s), 8.67 (1H, d, J=8 Hz), 8.78 (1H, s)

its hydrochloride mp: 248–251° C. NMR (DMSO-d$_6$, δ): 3.66 (2H, s), 7.05 (1H, br s), 7.40–7.70 (5H, m), 7.74 (1H, d, J=8 Hz), 8.25 (1H, s), 8.67 (1H, d, J=8 Hz), 8.79 (1H, s)

Example 35

(1) 8-(2,6-Dichlorobenzoylamino)-3-(1-hydroxyethyl) quinoline was obtained by reacting 8-(2,6-dichlorobenzoylamino)-3-formylquinoline with methylmagnesium bromide according to a similar manner to that of Example 17.

mp: 215–217° C. NMR (CDCl$_3$, δ): 1.62 (3H, d, J=7 Hz), 2.03 (1H, d, J=5 Hz), 5.16 (1H, m), 7.30–7.50 (3H, m), 7.59 (1H, d, J=8 Hz), 7.62 (1H, t, J=8 Hz), 8.17 (1H, s), 8.80 (1H, s), 8.93 (1H, d, J=8 Hz)

its hydrochloride mp: 200–204° C. NMR (DMSO-d$_6$, δ): 1.46 (3H, d, J=7 Hz), 5.01 (1H, m), 7.40–7.70 (4H, m), 7.78 (1H, d, J=8 Hz), 8.33 (1H, s), 8.67 (1H, d, J=8 Hz), 8.90 (1H, s)

(2) To a solution of 8-(2,6-dichlorobenzoylamino)-3-(1-hydroxyethyl)quinoline (562 mg) in dichloromethane (20 ml) was added manganese (IV) oxide (2.71 g), and the mixture was stirred at ambient temperature overnight. Insoluble material was filtered off, and the filtrate was concentrated in vacuo. The residue was crystallized from ethanol to give 3-acetyl-8-(2,6-dichlorobenzoylamino) quinoline (101 mg).

mp: 243–245° C. NMR (CDCl$_3$, δ): 2.75 (3H, s), 7.30–7.50 (3H, m), 7.60–7.80 (2H, m), 8.74 (1H, s), 9.10 (1H, d, J=8 Hz), 9.30 (1H, s), 9.98 (1H, s)

(3) A mixture of 3-acetyl-8-(2,6-dichlorobenzoylamino) quinoline (399 mg), hydroxylamine hydrochloride (232 mg) and sodium bicarbonate (467 mg) in ethanol was refluxed for 5 hours. The mixture was poured into water and extracted with dichloromethane. The organic layer was washed with brine, dried over magnesium sulfate and evaporated in vacuo. The residue was crystallized from ethanol to give 8-(2,6-dichlorobenzoylamino)-3-(1-hydroxyiminoethyl) quinoline (313 mg).

mp: 215–243° C. NMR (DMSO-d$_6$, δ): 2.30 (3H, m), 7.45–7.60 (3H, m), 7.69 (1H, t, J=8 Hz), 7.84 (1H, d, J=8 Hz), 8.59 (1H, s), 8.72 (1H, d, J=8 Hz), 9.26 (1H, s), 10.81 (1H, s), 11.66 (1H, s)

(4) To a solution of 8-(2,6-dichlorobenzoylamino)-3-(1-hydroxyiminoethyl)quinoline (168 mg) in pyridine was added phosphoryl chloride (516 mg) at 4° C., and the mixture was stirred for 50 minutes at the same temperature. The mixture was poured into ice and extracted with dichloromethane. The organic layer was washed with saturated sodium bicarbonate solution and brine, dried over magnesium sulfate and evaporated in vacuo. The residue was recrystallized from ethanol and water to give 3-acetylamino-8-(2,6-dichlorobenzoylamino)quinoline (19 mg).

mp: 244–245° C. NMR (DMSO-d$_6$, δ): 2.14 (3H, s), 7.40–7.65 (4H, m), 7.71 (1H, d, J=8 Hz), 8.59 (1H, d, J=8 Hz), 8.73 (1H, s), 8.89 (1H, s), 10.50 (1H, s), 10.71 (1H, s)

Example 36

8-(2,6-Dichlorobenzoylamino)-3-(a-hydroxybenzyl) quinoline was obtained by reacting 8-(2,6-dichlorobenzoylamino)-3-formylquinoline with phenylmagnesium bromide according to a similar manner to that of Example 17.

mp: 218–220° C. NMR (DMSO-d$_6$, δ): 6.02 (1H, d, J=4 Hz), 6.28 (1H, d, J=4 Hz), 7.23 (1H, t, J=7 Hz), 7.33 (2H, t, J=7 Hz), 7.45 (2H, d, J=7 Hz), 7.50–7.60 (3H, in), 7.64 (1H, t, J=8 Hz), 7.77 (1H, d, J=8 Hz), 8.37 (1H, s), 8.66 (1H, d, J=8 Hz), 8.86 (1H, s)

its hydrochloride mp: 130–134° C. NMR (DMSO-d$_6$, δ): 6.01 (1H, s), 7.23 (1H, t, J=7 Hz), 7.33 (2H, t, J=7 Hz), 7.45 (2H, d, J=7 Hz), 7.45–7.60 (3H, m), 7.64 (1H, t, J=8 Hz), 7.78 (1H, d, J=8 Hz), 8.37 (1H, s), 8.66 (1H, d, J=8 Hz), 8.86 (1H, s)

Example 37

A mixture of 8-(2,6-dichlorobenzoylamino)-4-ethoxycarbonylmethylquinazoline (90 mg) and 1N sodium hydroxide solution (1 ml) in ethanol (5 ml) was refluxed for 30 minutes. The mixture was diluted with water, and the resulting precipitate was collected by filtration and washed with water to give 8-(2,6-dichlorobenzoylamino)-4-methylquinazoline (70 mg).

mp: 223–225° C. NMR (CDCl$_3$, δ): 2.98 (3H, s), 7.30–7.45 (3H, m), 7.70 (1H, t, J=8 Hz), 7.84 (1H, d, J=8 Hz), 9.09 (1H, s), 9.11 (1H, d, J=8 Hz), 9.80 (1H, br s)

Example 38

8-(2,6-Dichlorobenzoylamino)-3-(pyridin-2-yl)quinoline hydrochloride was obtained from 3-bromo-8-(2,6-dichlorobenzoylamino)quinoline and tri-n-butyl(2-pyridyl)tin according to a similar manner to that of Preparation 14.

mp: 248–249° C. NMR (DMSO-d$_6$, δ): 7.50–7.62 (4H, m), 7.74 (1H, t, J=8 Hz), 7.93 (1H, d, J=8 Hz), 8.12 (1H, t, J=8 Hz), 8.31 (1H, d, J=8 Hz), 8.78 (1H, d, J=8 Hz), 8.82 (1H, d, J=8 Hz), 9.13 (1H, s), 9.59 (1H, s)

Example 39

3-(3-Aminophenyl)-8-(2,6-dichlorobenzoylamino) quinoline was obtained from 3-bromo-8-(2,6-dichlorobenzoylamino)quinoline and 3-aminophenylboric acid according to a similar manner to that of Preparation 16-(1).

mp: 193–194° C. NMR (CDCl$_3$, δ): 3.83 (2H, br s), 6.78 (1H, dd, J=2, 8 Hz), 7.00 (1H, d, J=2 Hz), 7.08 (1H, d, J=8 Hz), 7.28–7.38 (2H, m), 7.40–7.45 (2H, m), 7.62–7.66 (2H, m), 8.30 (1H, d, J=2 Hz), 8–95 (1H, t, J=8 Hz), 9.00 (1H, d, J=2 Hz)

Example 40

(1) 8-(2,6-Dichlorobenzoylamino)-3-((E)-2-carboxyvinyl)quinoline was obtained from 8-(2,6-dichlorobenzoylamino)-3-((E)-2-ethoxycarbonylvinyl)quinoline according to a similar manner to that of Example 18.

mp: >250° C. NMR (CDCl$_3$, δ): 6.89 (1H, d, J=16 Hz), 7.45–7.60 (3H, m), 7.70 (1H, t, J=8 Hz), 7.78–7.85 (2H, m), 8.72 (1H, d, J=8 Hz), 8.77 (1H, s), 9.20 (1H, s)

(2) 3-((E)-2-Carbamoylvinyl)-8-(2,6-dichlorobenzoylamino)quinoline hydrochloride was obtained according to a similar manner to that of Example 19.

mp: 210–225° C. NMR (DMSO-d$_6$, δ): 6.91 (1H, d, J=16 Hz), 7.26 (1H, br s), 7.50–7.80 (5H, m), 7.83 (1H, d, J=8 Hz), 8.62 (1H, s), 8.74 (1H, d, J=8 Hz), 9.11 (1H, s)

(3) 8-(2,6-Dichlorobenzoylamino)-3-[(E)-2-(dimethylcarbamoyl)vinyl]quinoline was obtained according to a similar manner to that of Example 19.

mp: 241–242° C. NMR (CDCl$_3$, δ): 3.11 (3H, s), 3.22 (3H, s), 7.11 (1H, d, J=15 Hz), 7.30–7.50 (3H, m), 7.50–7.70 (2H, m), 7.82 (1H, d, J=15 Hz), 8.27 (1H, s), 8.94 (1H, s), 8.97 (1H, d, J=8 Hz)

its hydrochloride mp: 241–243° C. NMR (CDCl$_3$, δ): 3.12 (3H, s), 3.23 (3H, s), 7.14 (1H, d, J=15 Hz), 7.30–7.50 (3H, m), 7.60–7.80 (2H, m), 7.83 (1H, d, J=15 Hz), 8.35 (1H, s), 8.98 (1H, s), 9.02 (1H, d, J=8 Hz)

Example 41

A mixture of 8-(2,6-dichlorobenzoylamino)-3-((E)-2-ethoxycarbonylvinyl)quinoline (40 mg) and platinum (IV) oxide (5 mg) in dioxane (1 ml) was stirred for 3 hours at ambient temperature under hydrogen atmosphere. Insoluble material was filtered off and the filtrate was concentrated in vacuo. The residue was purified by preparative thin layer chromatography (ethyl acetate-n-hexane) to give 8-(2,6-dichlorobenzoylamino)-3-(2-ethoxycarbonylethyl)quinoline (16 mg).

mp: 110–111° C. NMR (CDCl$_3$, δ): 1.22 (3H, t, J=7 Hz), 2.73 (2H, t, J=7 Hz), 3.15 (2H, t, J=7 Hz), 4.13 (2H, q, J=7 Hz), 7.30–7.50 (3H, m), 7.52 (1H, d, J=8 Hz), 7.59 (1H, t, J=8 Hz), 8.00 (1H, s), 8.66 (1H, s), 8.91 (1H, d, J=8 Hz)

Example 42

8-(2,6-Dichlorobenzoylamino)-3-ethoxycarbonyl-4-vinylquinoline was obtained from 4-chloro-8-(2,6-dichlorobenzoylamino)-3-ethoxycarbonylquinoline and tri-n-butyl(vinyl)tin according to a similar manner to that of Preparation 12-(2).

mp: 155–156° C. NMR (CDCl$_3$, δ): 1.42 (3H, t, J=7 Hz), 4.43 (2H, q, J=7 Hz), 5.00 (1H, d, J=15 Hz), 5.88 (1H, d, J=11 Hz), 7.30–7.50 (4H, m), 7.67 (1H, t, J=8 Hz), 8.04 (1H, d, J=8 Hz), 9.05 (1H, d, J=8 Hz), 9.17 (1H, s)

Example 43

The following compounds were obtained according to a similar manner to that of Example 18.

(1) 3-Carboxy-8-(2,6-dichlorobenzoylamino)-4-(imidazol-1-yl)quinoline mp: >250° C. NMR (DMSO-d$_6$, δ): 7.13 (1H, d, J=8 Hz), 7.22 (1H, s), 7.50–7.70 (4H, m), 7.79 (1H, t, J=8 Hz), 7.97 (1H, s), 8.8.6 (1H, d, J=8 Hz), 9.31 (1H, s)

(2) 3-Carboxy-8-(2,6-dichlorobenzoylamino)-4-morpholinoquinoline mp: 155–164° C. NMR (CDCl$_3$, δ): 3.61 (4H, m), 4.07 (4H, m), 7.30–7.50 (3H, m), 7.75 (1H, t, J=8 Hz), 8.05 (1H, d, J=8 Hz), 9.12 (1H, d, J=8 Hz), 9.53 (1H, s)

(3) 3-Carboxy-4-chloro-8-(2,6-dichlorobenzoylamino) quinoline mp: 243–244° C. NMR (DMSO-d$_6$, δ): 7.40–7.60 (3H, m), 7.90 (1H, t, J=8 Hz), 8.16 (1H, d, J=8 Hz), 8.87 (1H, d, J=8 Hz), 9.12 (1H, s)

Example 44

The following compounds were obtained according to a similar manner to that of Example 19 or 22-(2).

(1) 3-Carbamoyl-8-(2,6-dichlorobenzoylamino)-4-(imidazol-1-yl)quinoline mp: 232–233° C. NMR (CDCl$_3$, δ): 5.34 (1H, br s), 5.67 (1H, br s), 7.20–7.50 (6H, m), 7.73 (1H, t, J=8 Hz), 7.79 (1H, s), 9.13 (1H, d, J=8 Hz), 9.23 (1H, s)

(2) 3-Carbamoyl-8-(2,6-dichlorobenzoylamino)-4-morpholinoquinoline mp: >250° C. NMR (DMSO-d$_6$, δ): 3.45 (4H, m), 3.97 (4H, m), 5.95 (1H, br s), 6.44 (1H, br s), 7.30–7.50 (3H, m), 7.61 (1H, t, J=8 Hz), 7.89 (1H, d, J=8 Hz), 8.74 (1H, s), 8.95 (11H, d, J=8 Hz)

(3) 3-Carbamoyl-4-chloro-8-(2,6-dichlorobenzoylamino) quinoline mp: >251° C. NMR (DMSO-d$_6$, δ): 7.45–7.60 (3H, m), 7.87 (1H, t, J=8 Hz), 8.00 (1H, s), 8.07 (1H, d, J=8 Hz), 8.21 (1H, s), 8.82 (1H, d, J=8 Hz), 8.84 (1H, s)

Example 45

3-Carbamoyl-8-(2,6-dichlorobenzoylamino)-4-(4-methylpiperazin-1-yl)quinoline was obtained from 8-(2,6-dichlorobenzoylamino)-3-ethoxycarbonyl-4-(4-methylpiperazin-1-yl)quinoline and conc. ammonia solution according to a similar manner to those of Examples 18 and 22-(2).

mp: 195–198° C. NMR (CDCl$_3$, δ): 2.34 (3H, s), 2.69 (4H, m), 3.50 (4H, m), 5.93 (1H, br s), 6.74 (1H, br s), 7.30–7.50 (3H, m), 7.59 (1H, t, J=8 Hz), 7.91 (1H, d, J=8 Hz), 8.82 (1H, s), 8.96 (1H, d, J=8 Hz)

Example 46

The following compounds were obtained according to a similar manner to that of Example 22-(3).
(1) 3-Cyano-8-(2,6-dichlorobenzoylamino)-4-(imidazol-1-yl)quinoline mp: 211–212° C. NMR (CDCl$_3$, δ): 7.30–7.50 (5H, m), 7.52 (1H, d, J=8 Hz), 7.82 (1H, t, J=8 Hz), 7.89 (1H, s), 9.02 (1H, s), 9.23 (1H, d, J=8 Hz), 9.37 (1H, s)
its hydrochloride mp: 213–215° C. NMR (DMSO-d$_6$, δ): 7.48 (1H, d, J=8 Hz), 7.50–7.70 (3H, m), 7.79 (1H, s), 7.92 (1H, t, J=8 Hz), 8.06 (1H, s), 8.95 (1H, d, J=8 Hz), 9.04 (1H, s), 9.45 (1H, s)
(2) 3-Cyano-8-(2,6-dichlorobenzoylamino)-4-morpholinoquinoline mp: 236–237° C. NMR (CDCl$_3$, δ): 3.76 (4H, m), 4.00 (4H, m), 7.30–7.50 (3H, m), 7.62 (1H, t, J=8 Hz), 7.73 (1H, d, j=8 Hz), 8.62 (1H, s), 9.04 (1H, d, J=8 Hz)
its hydrochloride mp: 145–150° C. NMR (DMSO-d$_6$, δ): 3.70 (4H, m), 3.90 (4H, m), 7.40–7.60 (3H, m), 7.69 (1H, t, J=8 Hz), 7.88 (1H, d, J=8 Hz), 8.77 (1H, d, J=8 Hz), 8.78 (1H, s)
(3) 3-Cyano-8-(2,6-dichlorobenzoylamino)-4-(4-methylpiperazin-1-yl)quinoline mp: 196–200° C. NMR (DMSO-d$_6$, δ): 2.30 (3H, s), 2.62 (4H, m), 3.69 (4H, in), 7.40–7.60 (3H, m), 7.67 (1H, t, J=8 Hz), 7.84 (1H, d, J=8 Hz), 8.73 (1H, s), 8.76 (1H, d, J=8 Hz)
its dihydrochloride mp: 211–220° C. NMR (DMSO-d$_6$, δ): 2.90 (3H, s), 3.43 (2H, m), 3.60 (2H, m), 3.80–4.20 (4H, m), 7.40–7.60 (3H, m), 7.73 (1H, t, J=8 Hz), 7.85 (1H, d, J=8 Hz), 8.80 (1H, d, J=8 Hz), 8.84 (1H, s)
(4) 4-Chloro-3-cyano-8-(2,6-dichlorobenzoylamino)quinoline mp: 239–241° C. NMR (CDCl$_3$, δ): 7.30–7.50 (3H, m), 7.86 (1H, t, J=8 Hz), 8.06 (1H, d, J=8 Hz), 8.85 (1H, s), 9.20 (1H, d, J=8 Hz), 9.83 (1H, br s)

Example 47

(1) 8-(2,6-Dichlorobenzoylamino)-3-(N-methoxy-N-methylcarbamoyl)-4-morpholinoquinoline was obtained from 3-carboxy-8-(2,6-dichlorobenzoylamino)-4-morpholinoquinoline and N-methoxy-N-methylamine hydrochloride according to a similar manner to that of Example 22-(2).

mp: 236–237° C. NMR (CDCl$_3$, δ): 3.31 (4H, m), 3.43 (3H, s), 3.47 (3H, s), 3.94 (4H, m), 7.30–7.50 (3H, m), 7.59 (1H, t, J=8 Hz), 7.82 (1H, d, J=8 Hz), 8.48 (1H, s), 8.95 (1H, d, J=8 Hz)
(2) To a 0.9M solution of methylmagnesium bromide in tetrahydrofuran (1.3 ml) was added dropwise a solution of 8-(2,6-dichlorobenzoylamino)-3-(N-methoxy-N-methylcarbamoyl)-4-morpholinoquinoline (107 mg) in dry tetrahydrofuran (1 ml) with cooling in an ice bath. The mixture was stirred at the same temperature for 1 hour, at ambient temperature for 1 hour, at 50° C. for 2 hours. The mixture was partitioned between ethyl acetate and saturated ammonium chloride aqueous solution. The organic layer was washed with brine, dried over anhydrous magnesium sulfate, and evaporated in vacuo. The residue was purified by preparative thin layer chromatography on silica gel. The obtained oil was crystallized from ethanol to give 3-acetyl-8-(2,6-dichlorobenzoylamino)-4-morpholinoquinoline (19 mg) as a white crystal.

mp: 231–233° C. NMR (CDCl$_3$, δ): 2.67 (3H, s), 3.28 (4H, m), 3.96 (4H, m), 7.30–7.50 (3H, m), 7.61 (1H, t, J=8 Hz), 7.89 (1H, d, J=8 Hz), 8.68 (1H, s), 8.97 (1H, d, J=8 Hz)

Example 48

3-Cyano-8-(2,6-dichlorobenzoylamino)-4-[(pyridin-2-ylmethyl)amino]quinoline was obtained by reacting 4-chloro-8-(2,6-dichlorobenzoylamino)-3-cyanoquinoline with 2-aminomethylpyridine according to a similar manner to that of Example 8.

mp: 247–249° C. NMR (DMSO-d$_6$, δ): 5.17 (2H, d, J=6 Hz), 7.29 (1H, dd, J=6, 8 Hz), 7.35 (1H, d, J=8 Hz), 7.45–7.60 (3H, m), 7.67 (1H, t, J=8 Hz), 7.78 (1H, t, J=8 Hz), 8.20 (1H, d, J=8 Hz), 8.45 (1H, s), 8.53 (1H, d, J=6 Hz), 8.77 (1H, d, J=8 Hz), 8.92 (1H, m)
its dihydrochloride mp: 241–250° C. NMR (CDCl$_3$, δ): 5.34 (2H, d, J=6 Hz), 7.45–7.60 (3H, m), 7.65–7.80 (3H, m), 8.24 (1H, m), 8.32 (1H, d, J=8 Hz), 8.51 (1H, s), 8.70–8.80 (2H, m), 9.13 (1H, m)

Example 49

(1) 4-[Bis(ethoxycarbonyl)methyl]-3-cyano-8-(2,6-dichlorobenzoylamino)quinoline was obtained by reacting 4-chloro-8-(2,6-dichlorobenzoylamino)-3-cyanoquinoline with diethyl malonate according to a similar manner to that of Preparation 7-(1).

NMR (CDCl$_3$, δ): 1.20–1.40 (6H, m), 4.20–4.40 (4H, m), 5.61 (1H, s), 7.30–7.50 (3H, m), 7.78 (1H, t, J=8 Hz), 7.88 (1H, d, J=8 Hz), 8.94 (1H, s), 9.15 (1H, d, J=8 Hz)
(2) 3-Cyano-8-(2,6-dichlorobenzoylamino)-4-(ethoxycarbonylmethyl)quinoline was obtained according to a similar manner to that of Preparation 7-(2).

mp: 171–173° C. NMR (CDCl$_3$, δ): 1.26 (3H, t, J=7 Hz), 4.20 (2H, q, J=7 Hz), 4.37 (2H, s), 7.30–7.50 (3H, m), 7.79 (2H, m), 8.90 (1H, s), 9.13 (1H, m)
(3) A mixture of 8-(2,6-dichlorobenzoylamino)-3-cyano-4-(ethoxycarbonylmethyl)quinoline (225 mg) and 1N sodium hydroxide solution in dioxane was stirred for 20 minutes at ambient temperature. The mixture was neutralized with 1N hydrochloric acid and extracted with dichloromethane. The organic layer was washed with brine, dried over magnesium sulfate and evaporated in vacuo to give a residue containing 4-carboxymethyl-8-(2,6-dichlorobenzoylamino)-3-cyanoquinoline.

To a mixture of dimethylformamide (49.9 mg) and dichloromethane was added oxalyl chloride (86.7 mg), and the mixture was stirred for 30 minutes at ambient temperature. To the mixture was added the residue obtained above at 0° C., and the mixture was stirred for 20 minutes at the same temperature. To the mixture was added 2-aminomethylpyridine (568 mg) at 0° C., and the mixture was stirred for 40 minutes at the same temperature. The mixture was partitioned between ethyl acetate and saturated ammonium chloride solution. The organic layer-was washed with saturated sodium bicarbonate solution and brine, dried over magnesium sulfate and evaporated in vacuo. The residue was purified by column chromatography on silica gel to give 3-cyano-8-(2,6-dichlorobenzoylamino)-4-[(pyridin-2-ylmethyl)carbamoylmethyl]quinoline.

To a solution of the obtained compound in dichloromethane was added 10% solution of hydrogen chloride in methanol (1.2 ml), and the mixture was concentrated in vacuo to give 3-cyano-8-(2,6-dichlorobenzoylamino)-4-[(pyridin-2-ylmethyl)carbamoylmethyl]quinoline hydrochloride (133.2 mg).

mp: 240–245° C. (dec.) NMR (DMSO-$d_6$, δ): 4.45 (2H, s), 4.58 (2H, d, J=6 Hz), 7.40–7.60 (3H, m), 7.60–7.70 (2H, m), 7.84 (1H, t, J=8 Hz), 8.12 (1H, d, J=8 Hz), 8.22 (1H, t, J=8 Hz), 8.71 (1H, d, J=5 Hz), 9.15 (1H, s), 9.31 (1H, t, J=6 Hz)

Example 50

3-Cyano-8-(2,6-dichlorobenzoylamino)-4-[(2-hydroxyethyl)carbamoylmethyl]quinoline was obtained from 8-(2,6-dichlorobenzoylamino)-3-cyano-4-ethoxycarbonylquinoline and 2-hydroxyethylamine according to a similar manner to that of Example 49-(3).

mp: 234–236° C. NMR (DMSO-$d_6$, δ): 3.16 (2H, q, J=6 Hz), 3.44 (2H, q, J=6 Hz), 4.29 (2H, s), 4.75 (1H, t, J=6 Hz), 7.40–7.60 (3H, m), 7.83 (1H, t, J=8 Hz), 8.03 (1H, d, J=8 Hz), 8.49 (1H, t, J=6 Hz), 8.84 (1H, d, J=8 Hz), 9.13 (1H, s)

Example 51

3-Cyano-8-(2,6-dichlorobenzoylamino)-4-methylquinoline was obtained from 8-(2,6-dichlorobenzoylamino)-3-cyano-4-(ethoxycarbonylmethyl)quinoline according to a similar manner to that of Example 37.

mp: 236–237° C. NMR (CDCl$_3$, δ): 2.98 (3H, s), 7.30–7.50 (3H, m), 7.77 (1H, t, J=8 Hz), 7.85 (1H, d, J=8 Hz), 8.83 (1H, s), 9.13 (1H, d, J=8 Hz)

Example 52

A mixture of 8-(2,6-dichlorobenzoylamino)-3-cyano-4-methylquinoline (139 mg), N-bromosuccinimide (312 mg) and 2,2'-azobis(isobutyronitrile) (38.8 mg) in ethylene chloride (1 ml) and carbon tetrachloride (4 ml) was refluxed for 7 hours. After cooling, the mixture was partitioned between water and dichloromethane, and the organic layer was washed with saturated sodium thiosulfate solution and brine, dried over magnesium sulfate and evaporated in vacuo to give a residue containing 4-bromomethyl-8-(2,6-dichlorobenzoylamino)-3-cyanoquinoline.

The residue was dissolved in ethylene chloride, and imidazole (79.7 mg) was added thereto. After stirring for 30 minutes at 65° C., the mixture was partitioned between water and dichloromethane. The organic layer was washed with brine, dried over magnesium sulfate and evaporated in vacuo. The residue was purified by preparative thin layer chromatography (methanol-dichloromethane) to give 3-cyano-8-(2,6-dichlorobenzoylamino)-4-(imidazol-1-ylmethyl)quinoline.

To a solution of the obtained compound in dichloromethane was added 10% solution of hydrogen chloride in methanol (0.5 ml), and the mixture was concentrated in vacuo to give 3-cyano-8-(2,6-dichlorobenzoylamino)-4-(imidazol-1-ylmethyl)quinoline hydrochloride (59.8 mg).

mp: >250° C. NMR (CDCl$_3$, δ): 6.20 (2H, s), 7.40–7.60 (3H, m), 7.70 (1H, s), 7.75 (1H, s), 7.90 (1H, t, J=8 Hz), 8.13 (1H, d, J=8 Hz), 8.90 (1H, d, J=8 Hz), 9.19 (1H, s), 9.27 (1H, s)

Example 53

(1) A mixture of 4-bromomethyl-8-(2,6-dichlorobenzoylamino)-3-cyanoquinoline (238 mg) and sodium acetate (94 mg) in dimethylformamide (1 ml) was stirred at ambient temperature overnight. To the residue was added water and extracted with ethyl acetate. The organic layer was washed with brine, dried over magnesium sulfate and evaporated in vacuo. The residue was purified by preparative thin layer chromatography (n-hexane-dichloromethane) to give 4-acetoxymethyl-3-cyano-8-(2,6-dichlorobenzoylamino)quinoline (54 mg).

mp: 201–203° C. NMR (CDCl$_3$, δ): 2.15 (3H, s), 5.75 (2H, s), 7.33–7.47 (3H, m), 7.81 (1H, t, J=7.5 Hz), 7.89 (1H, d, J=7.5 Hz), 8.91 (1H, s), 9.16 (1H, d, J=7.5 Hz)

(2) 3-Cyano-8-(2,6-dichlorobenzoylamino)-4-hydroxymethylquinoline was obtained according to a similar manner to that of Example 12-(2).

mp: 249–250° C. NMR (DMSO-$d_6$, δ): 5.81 (2H, s), 7.48–7.60 (3H, m), 7.78–7.86 (2H, m), 8.88 (1H, dd, J=7 and 4 Hz), 9.24 (1H, br s), 11.00 (1H, s)

Example 54

To a solution of 4-chloro-8-(2,6-dichlorobenzoylamino)-3-ethoxycarbonylquinoline (251 mg) in N-methylpyrrolidone (2 ml) was added 2-mercaptoimidazole (89 mg), and the mixture was stirred for 1 hour at 65° C. The mixture was poured into water and extracted with ethyl acetate. The organic layer was washed with saturated ammonium chloride solution, saturated sodium bicarbonate solution and brine, dried over magnesium sulfate and evaporated in vacuo. The residue was crystallized from ethanol to give 4-(2,6-dichlorobenzoylamino)-7H-imidazo[2',1':2,3][1,3]thiazino-[5,6-c]quinolin-7-one (248.2 mg).

mp: >250° C. NMR (DMSO-$d_6$, δ): 7.45–7.65 (4H, m), 7.93 (1H, t, J=8 Hz), 8.15 (1H, d, J=8 Hz), 8.30 (1H, s), 8.95 (1H, d, J=8 Hz), 9.57 (1H, s), 11.14 (1H, s)

Example 55

(1) 4-[Bis(ethoxycarbonyl)methyl]-8-(2,6-dichlorobenzoylamino)-3-ethoxycarbonylquinoline was obtained by reacting 4-chloro-8-(2,6-dichlorobenzoylamino)-3-ethoxycarbonylquinoline with diethyl malonate according to a similar manner to that of Preparation 7-(1).

mp: 139.5° C. NMR (CDCl$_3$, δ): 1.20 (6H, t, J=7.5 Hz), 1.41 (3H, t, J=7.5 Hz), 4.11–4.30 (4H, m), 4.44 (2H, q, J=7.5 Hz), 6.31 (1H, s), 7.29–7.45 (3H, m), 7.67 (1H, t, J=7.5 Hz), 7.85 (1H, d, J=7.5 Hz), 9.03 (1H, d, J=7.5 Hz), 9.25 (1H, s)

(2) 8-(2,6-Dichlorobenzoylamino)-3-ethoxycarbonyl-4-(ethoxycarbonylmethyl)quinoline was obtained according to a similar manner to that of Preparation 7-(2).

mp: 158.7° C. NMR (CDCl$_3$, δ): 1.25 (3H, t, J=7.5 Hz), 1.42 (3H, t, J=7.5 Hz), 4.17 (2H, q, J=7.5 Hz), 4.45 (2H, q, J=7.5 Hz), 4.63 (2H, s), 7.30–7.45 (3H, m), 7.70 (1H, t, J=7.5 Hz), 7.84 (1H, d, J=7.5 Hz), 9.05 (1H, d, J=7.5 Hz), 9.26 (1H, s)

Example 56

(1) 4-[Bis(tert-butoxycarbonyl)methyl)-8-(2,6-dichlorobenzoylamino)-3-ethoxycarbonylquinoline was obtained by reacting 4-chloro-8-(2,6-dichlorobenzoylamino)-3-ethoxycarbonylquinoline with di-tert-butyl malonate according to a similar manner to that of Preparation 7-(1).

mp: 154° c NMR (CDCl$_3$, δ): 1.43 (18H, s), 1.44 (3H, t, J=7.5 Hz), 4.46 (2H, q, J=7.5 Hz), 6.10 (1H, s), 7.30–7.44

(3H, m), 7.65 (1H, t, J=7.5 Hz), 7.94 (1H, d, J=7.5 Hz), 9.00 (1H, d, J=7.5 Hz), 9.20 (1H, s)

(2) To a solution of 4-[bis(tert-butoxycarbonyl)methyl]-8-(2,6-dichlorobenzoylamino)-3-ethoxycarbonylquinoline (5.8 g) in dichloromethane (15 ml) was dropwise added trifluoroacetic acid (45 ml) under ice-cooling, and the mixture was stirred for 1 hour at ambient temperature. The mixture was concentrated in vacuo, and the residue was pulverized with diethyl ether to give 4-carboxymethyl-8-(2,6 -dichlorobenzoylamino)-3-ethoxycarbonylquinoline (4.08 g).

mp: 149–159° C. NMR (CDCl$_3$, δ): 1.44 (3H, t, J=7.5 Hz), 4.47 (2H, q, J=7.5 Hz), 5.60 (2H, s), 7.27–7.46 (3H, m), 7.75 (1H, t, J=7.5 Hz), 7.95 (1H, d, J=7.5 Hz), 9.07 (1H, d, J=7.5 Hz), 9.25 (1H, s)

Example 57

The following compounds were obtained according to a similar manner to that of Example 26-(2).

(1) 8-(2,6-Dichlorobenzoylamino)-3-ethoxycarbonyl-4-((pyridin-2-ylmethyl)carbamoylmethyl]quinoline hydrochloride mp: 217–220° C. NMR (DMSO-d$_6$, δ): 1.33 (3H, t, J=7 Hz), 4.37 (2H, q, J=7 Hz), 4.54 (2H, d, J=6 Hz), 4.62 (2H, s), 7.45–7.60 (3H, m), 7.60–7.70 (2H, m), 7.78 (1H, t, J=8 Hz), 8.12 (1H, d, J=8 Hz), 8.23 (1H, m), 8.70 (1H, m), 8.80 (1H, d, j=8 Hz), 8.93 (1H, m), 9.17 (1H, s)

(2) 8-(2,6-Dichlorobenzoylamino)-3-ethoxycarbonyl-4-[(2-hydroxyethyl)carbamoylmethyl]quinoline mp: 131–136° C. NMR (CDCl$_3$, δ): 1.46 (3H, t, J=7 Hz), 2.39 (1H, t, J=6 Hz), 3.35 (2H, m), 3.67 (2H, m), 4.38 (2H, s), 4.50 (2H, q, J=7 Hz), 7.30–7.50 (3H, m), 7.77 (1H, t, J=8 Hz), 8.32 (1H, d, J=8 Hz), 9.08 (1H, d, J=8 Hz), 9.18 (1H, s)

(3) 8-(2,6-Dichlorobenzoylamino)-3-ethoxycarbonyl-4-(dimethylcarbamoylmethyl)quinoline mp: 185–186° C. NMR (CDCl$_3$, δ): 1.42 (3H, t, J=7 Hz), 3.03 (3H, s), 3.30 (3H, s), 4.41 (2H, q, J=7 Hz), 4.67 (2H, s), 7.30–7.50 (3H, m), 7.68 (1H, t, j=8 Hz), 7.79 (1H, d, J=8 Hz), 9.03 (1H, d, J=8 Hz), 9.29 (1H, s)

(4) 4-Carbamoylmethyl-8-(2,6-dichlorobenzoylamino)-3-ethoxycarbonylquinoline mp: 226–228° C. NMR (CDCl$_3$, δ): 1.47 (3H, t, J=7 Hz), 4.38 (2H, s), 4.50 (2H, q, J=7 Hz), 5.31 (1H, br s), 6.95 (1H, br s), 7.30–7.50 (3H, m), 7.78 (1H, t, J=8 Hz), 8.30 (1H, d, J=8 Hz), 9.07 (1H, d, J=8 Hz), 9.19 (1H, s)

(5) 8-(2,6-Dichlorobenzoylamino)-3-ethoxycarbonyl-4-(morpholinocarbonylmethyl)quinoline mp: 168.5° C. NMR (CDCl$_3$, δ): 1.40 (3H, t, J=7.5 Hz), 3.57–3.90 (8H, m), 4.40 (2H, q, J=7.5 Hz), 4.65 (2H, s), 7.28–7.44 (3H, m), 7.68 (1H, t, J=7.5 Hz), 7.78 (1H, d, J=7.5 Hz), 9.02 (1H, d, J=7.5 Hz), 9.29 (1H, s)

its hydrochloride mp: 175° C. NMR (DMSO-d$_6$-d$_6$, δ): 1.33 (3H, t, J=7.5 Hz), 3.40–3.49 (2H, m), 3.55–3.64 (2H, m), 3.67–3.80 (4H, m), 4.35 (2H, q, J=7.5 Hz), 4.65 (2H, s), 7.48–7.62 (3H, m), 7.76 (1H, t, J=7.5 Hz), 8.04 (1H, d, J=7.5 Hz), 8.79 (1H, d, J=7.5 Hz), 9.19 (1H, s)

(6) 8-(2,6-Dichlorobenzoylamino)-3-ethoxycarbonyl-4-[N-(2-methoxyethyl)-N-methylcarbamoylmethyl]quinoline mp: 163° C. NMR (CDCl$_3$, δ): 1.32–1.45 (3H, m), 3.00 (1.5H, s), 3.34 (1.5H, s), 3.35 (1.5H, s), 3.47–3.53 (2H, m), 3.51 (1.5H, s), 4.33–4.47 (2H, m), 4.65 (1H, s), 4.84 (1H, s), 7.27–7.44 (3H, m), 7.60–7.70 (1H, r), 7.7 (0.5H, d, J=7.5 Hz), 7.89 (0.5H, d, J=7.5 Hz), 8.94–9.05 (1H, m), 9.26 (0.5H, r), 9.27 (0.5H, s)

(7) 8-(2,6-Dichlorobenzoylamino)-3-ethoxycarbonyl-4-m [(3-trifluoromethylphenyl) carbamoylmethyl] quinoline mp: 218–222° C. NMR (CDCl$_3$, δ): 1.50 (3H, t, J=7.5 Hz), 4.46 (2H, s), 4.59 (2H, q, J=7.5 Hz), 7.25–7.44 (5H, m), 7.70 (1H, br d, J=9 Hz), 7.74 (5H, br s), 7.82 (1H, t J=7.5 Hz), 8.48 (1H, d, J=7.5 Hz), 9.09 (1H, d, J=7.5 Hz), 9.20 (1H, s), 9.97 (1H, br 3)

(8) 8-(2,6-Dichlorobenzoylamino)-3-ethoxycarbonyl-4-[(4-methylpiperazin-1-yl) carbonylmethyl] quinoline mp: 232° C. NMR (CDCl$_3$, δ): 1.40 (3H, t, J=7.5 Hz), 2.36 (3H, s), 2.38–2.47 (2H, m), 2.50–2.62 (2H, rn), 3.60–3.69 (2H, rn), 3.70–3.80 (2H, m), 4.38 (2H, q, J=7.5 Hz), 4.65 (2H, s), 7.28–7.43 (3H, m), 7.67 (1H, t, J=7.5 Hz), 7.76 (1H, d, J=7.5 Hz), 9.01 (2H, d, J=7.5 Hz), 9.26 (1H, s)

Example 58

(1) A suspension of 4-carboxymethyl-8-(2,6-dichlorobenzoylamino)-3-ethoxycarbonylquinoline (2–5 g) in 1,2-dichloroethane (60 ml) was refluxed for 14 hours. The solvent was removed under reduced pressure and the residual solid was treated with hot ethanol (45 ml) to afford 8-(2,6-dichlorobenzoylamino)-3-ethoxycarbonyl-4-methylquinoline (2.08 g) as a colorless prism.

mp: 159–162° C. NMR (CDCl$_1$, δ): 1.42 (3H, t, J=7.5 Hz), 3.00 (3H, s), 4.45 (2H, q, J=7.5 Hz), 7.28–7.45 (3H, m), 7.69 (1H, t, J=7.5 Hz), 7.92 (1H, d, J=7.5 Hz), 9.02 (1H, d, J=7.5 Hz), 9.10 (1H, s)

its hydrochloride mp: 171° C. NMR (DMSO-d$_6$, δ): 1.36 (3H, t, J=7.5 Hz), 2.94 (3H, s), 4.40 (2H, q, J=7.5 Hz), 7.46–7.61 (3H, m), 7.78 (1H, t, J=7.5 Hz), 8.09 (1H, d, J=7.5 Hz), 8.80 (1H, d, J=7.5 Hz), 9.07 (1H, s)

(2) 4-Bromomethyl-8-(2,6-dichlorobenzoylamino)-3-ethoxycarbonylquinoline was obtained according to a similar manner to that of the first step of Example 52.

mp: 199° C. NMR (CDCl$_3$, δ): 1.47 (3H, t, J=7.5 Hz), 4.40 (2H, q, J=7.5 Hz), 5.37 (2H, s), 7.27–7.46 (3H, m), 7.79 (1H, t, J=7.5 Hz), 8.00 (1H, d, J=7.5 Hz), 9.06 (1H, d, J=7.5 Hz), 9.23 (1H, s)

Example 59

A mixture of 4-bromomethyl-8-(2,6-dichlorobenzoylamino)-3-ethoxycarbonylquinoline (150 mg) and imidazole (106 mg) in dimethoxyethane was stirred for 1 hour at 70° C. The mixture was evaporated in vacuo, and the residue was purified by preparative thin layer chromatography (methanoldichloromethane) to give 8-(2,6-dichlorobenzoylamino)-3-ethoxycarbonyl-4-(imidazol-1-ylmethyl)quinoline (110 mg).

NMR (CDCl$_3$, δ): 1.41 (3H, t, J=7.5 Hz), 4.47 (2H, q, J=7.5 Hz), 6.00 (2H, s), 6.90 (1H, s), 6.99 (1H, s), 7.30–7.47 (3H, m), 7.60 (1H, s), 7.76 (1H, t, J=7.5 Hz), 7.94 (1H, d, J=7.5 Hz), 9.08 (1H, d, J=7.5 Hz), 9.28 (1H, s)

its dihydrochloride mp: 240–245° C. NMR (DMSO-d$_6$, δ): 1.30 (3H, t, J=7.5 Hz), 4.40 (2H, q, J=7.5 Hz), 6.18 (2H, s), 7.46–7.61 (3H, m), 7.65 (1H, d, J=2 Hz), 7.72 (1H, d, J=2 Hz), 7.84 (1H, t, J=7.5 Hz), 8.14 (1H, d, J=7.5 Hz), 8.84 (1H, d, J=7.5 Hz), 9.07 (1H, br s), 9.30 (1H, s)

Example 60

The following compounds were obtained according to a similar manner to that of Example 59.

(1) 4-(1H-Benzimidazol-1-ylmethyl)-8-(2,6-dichlorobenzoylamino)-3-ethoxycarbonylquinoline mp: 202° C. NMR (CDCl$_3$, δ): 1.30 (3H, t, J=7.5 Hz), 4.38 (2H, q, J=7.5 Hz), 6.10 (2H, s), 7.21–7.51 (6H, m), 7.63 (1H, s), 7.70 (1H, t, J=7.5 Hz), 7.75–7.86 (2H, m), 9.07 (1H, d, J=7.5 Hz), 9.27 (1H, s)

(2) 8-(2,6-Dichlorobenzoylamino)-3-ethoxycarbonyl-4-[N-(2-methoxyethyl)-N-methylaminomethyl]quinoline NMR (CDCl$_3$, δ): 1.42 (3H, t, J=7.5 Hz), 2.24 (3H, s), 2.67 (2H, t, J=6 Hz), 3.31 (3H, s), 3.50 (2H, t, J=6 Hz), 4.26 (2H, s), 4.43 (2H, q, J=7.5 Hz), 7.28–7.43 (3H, m), 7.66 (1H, t, J=7.5 Hz), 8.16 (1H, d, J=7.5 Hz), 8.91 (1H, s), 9.00 (1H, d, J=7.5 Hz)

its hydrochloride mp: 187–191° C. NMR (DMSO-d$_6$, δ): 1.41 (3H, t, J=7.5 Hz), 2.70 (3H, s), 3.35 (3H, m), 3.52–3.68 (2H, m), 3.75–3.88 (2H, m), 4.46 (2H, q, J=7.5 Hz), 5.13–5.26 (1H, m), 5.30–5.41 (1H, m), 7.48–7.63 (3H, m), 7.91 (1H, t, J=7.5 Hz), 8.43 (1H, d, J=7.5 Hz), 8.88 (1H, d, J=7.5 Hz), 9.34 (1H, br s), 9.40 (1H, s)

(3) 8-(2,6-Dichlorobenzoylamino)-4-dimethylaminomethyl-3-ethoxycarbonylquinoline mp: 121° C. NMR (CDCl$_3$, δ): 1.43 (3H, t, J=7.5 Hz), 2.26 (6H, s), 4.14 (2H, s), 4.44 (2H, q, J=7.5 Hz), 7.28–7.46 (3H, m), 7.69 (1H, t, J=7.5 Hz), 8.10 (1H, d, J=7.5 Hz), 8.94 (1H, s), 9.01 (1H, d, J=7.5 Hz)

Example 61

A mixture of 4-bromomethyl-8-(2,6-dichlorobenzoylamino)-3-ethoxycarbonylquinoline (100 mg), 2-methoxyethylamine (18.7 mg) and N,N-diisopropyl-N-ethylamine (134 mg) in ethylene chloride (1 ml) was stirred for 2 hours at ambient temperature. The mixture was diluted with dichloromethane, washed with saturated sodium bicarbonate solution, dried over magnesium sulfate and evaporated in vacuo. The residue was purified by preparative thin layer chromatography (methanoldichloromethane) to give 6-(2,6-dichlorobenzoylamino)-2,3-dihydro-2-(2-methoxyethyl)-1H-pyrrolo-[3,4-c]quinolin-3-one (76 mg).

mp: 246° C. NMR (CDCl$_3$, δ): 3.39 (3H, s), 3.69 (2H, t, J=6 Hz), 3.88 (2H, t, J=6 Hz), 4.95 (2H, s), 7.30–7.46 (3H, m), 7.64 (1H, t, J=7.5 Hz), 7.74 (1H, d, J=7.5 Hz), 9.10 (1H, d, J=7.5 Hz), 9.15 (1H, s)

Example 62

To a solution of 2-mercaptoimidazole (27.4 mg) in dimethylformamide (1.5 ml) was added potassium carbonate (51.6 mg) under ice-cooling, and the mixture was stirred for 15 minutes at the same temperature. To the mixture was added 4-bromomethyl-8-(2,6-dichlorobenzoylamino)-3-ethoxycarbonylquinoline (120 mg) under ice-cooling, and the mixture was stirred for 1 hour at ambient temperature. To the mixture was added water under ice-cooling, and the resulting precipitate was collected by filtration and washed with water to give 8-(2,6-dichlorobenzoylamino)-3-ethoxycarbonyl-4-[(imidazol-2-yl)thiomethyl]quinoline (115 mg).

mp: 120–123° C. NMR (CDCl$_3$, δ): 1.44 (3H, t, J=7.5 Hz), 4.46 (2H, q, J=7.5 Hz), 5.01 (2H, s), 6.94 (1H, s), 7.18 (1H, s), 7.29–7.46 (3H, m), 7.55–7.63 (2H, m), 8.96–9.05 (1H, m), 9.10 (1H, s), 9.16 (1H, br s)

its hydrochloride mp: 219–224° C. NMR (DMSO-d$_6$, δ): 1.32 (3H, t, J=7.5 Hz), 4.26 (2H, q, J=7.5 Hz), 5.20 (2H, s), 7.47–7.61 (3H, m), 7.75 (2H, s), 7.76 (1H, t, J=7.5 Hz), 7.97 (1H, d, J=7.5 Hz), 8.80 (1H, d, J=7.5 Hz), 9.13 (1H, s)

Example 63

8-(2,6-Dichlorobenzoylamino)-3-ethoxycarbonyl-4-[(pyridin-4-yl)thiomethyl]quinoline was obtained according to a similar manner to that of Example 62.

mp: 179–181° C. NMR (CDCl$_3$, δ): 1.39 (3H, t, J=7.5 Hz), 4.40 (2H, q, j=7.5 Hz), 5.15 (2H, s), 7.24 (2H, d, J=6 Hz), 7.29–7.45 (3H, m), 7.72 (1H, t, J=7.5 Hz), 7.90 (1H, d, J=7.5 Hz), 8.86 (2H, d, J=6 Hz) 9.07 (1H, d, J=7.5 Hz), 9.23 (1H, s)

its hydrochloride mp: 206° C. NMR (DMSO-d$_6$, δ): 1.28 (3H, t, J=7.5 Hz), 4.37 (2H, q, J=7.5 Hz), 5.36 (2H, s), 7.46–7.61 (3H, m), 7.84 (1H, t, J=7.5 Hz), 7.95 (2H, d, J=7 Hz), 8.20 (1H, d, J=7.5 Hz), 8.70 (2H, d, J=7 Hz), 8.84 (1H, d, J=7.5 Hz), 9.21 (1H, s)

Example 64

4-Acetoxymethyl-8-(2,6-dichlorobenzoylamino)-3-ethoxycarbonylquinoline was obtained according to a similar manner to that of Example 53-(1).

mp: 138–142° C. NMR (CDCl$_3$, δ): 1.45 (3H, t, J=7.5 Hz), 2.05 (3H, s), 4.49 (2H, q, J=7.5 Hz), 5.91 (2H, s), 7.30–7.46 (3H, m), 7.74 (1H, t, J=7.5 Hz), 7.93 (1H, d, J=7.5 Hz), 9.05 (1H, d, J=7.5 Hz), 9.16 (1H, s)

Example 65

To a mixture of sodium sulfide nonahydrate (202 mg) in dimethylformamide (5 ml) was dropwise added 4-chloro-8-(2,6-dichlorobenzoylamino)-3-ethoxycarbonylquinoline (297 mg), and the mixture was stirred for 1 hour at ambient temperature. To the mixture was added ice-water, and the mixture was adjusted to pH 3 with 1N hydrochloric acid. The resulting precipitate was collected by filtration and washed with water to give 8-(2,6-dichlorobenzoylamino)-3-ethoxycarbonyl-4-mercaptoquinoline (260 mg).

mp: 197–199° C. NMR (CDCl$_3$, δ): 1.43 (3H, t, J=7 Hz), 4.47 (2H, q, J=7 Hz), 7.27–7.45 (3H, m), 7.68 (1H, t, J=8 Hz), 7.99 (1H, d, J=8 Hz), 8.49 (1H, s), 9.03 (1H, d, J=8 Hz), 9.21 (1H, s)

Example 66

(1) 4-(tert-Butoxycarbonylmethylthio)-8-(2,6-dichlorobenzoylamino)-3-ethoxycarbonylquinoline was obtained by reacting 8-(2,6-dichlorobenzoylamino)-3-ethoxycarbonyl-4-mercaptoquinoline with tert-butyl bromoacetate according to a similar manner to that of Preparation 8-(1).

NMR (CDCl$_3$, δ): 1.24 (9H, s), 1.45 (3H, t, J=7 Hz), 3.66 (2H, s), 7.29–7.45 (3H, m), 7.76 (1H, t, J=8 Hz), 8.88 (1H, d, J=8 Hz), 8.98 (1H, s), 9.05 (1H, d, J=8 Hz)

(2) A solution of 4-(tert-butoxycarbonylmethylthio)-8-(2,6-dichlorobenzoylamino)-3-ethoxycarbonylquinoline (140 mg) in 4N solution of hydrogen chloride in ethyl acetate was allowed to stand for 1 hour at ambient temperature. The mixture was concentrated in vacuo, and the residue was dissolved in ethyl acetate. The solution was washed with brine, dried over magnesium sulfate and evaporated in vacuo to give 4-carboxymethylthio-8-(2,6-dichlorobenzoylamino)-3-ethoxycarbonylquinoline (110 mg).

mp: 174–175° C. NMR (CDCl$_3$, δ): 1.45 (3H, t, J=7 Hz), 3.79 (2H, s), 4.51 (2H, q, J=7 Hz), 7.30–7.46 (3H, m), 7.79 (1H, t, J=8 Hz), 8.86 (1H, d, J=8 Hz), 8.99 (1H, s), 9.08 (1H, d, J=8 Hz)

(3) 8-(2,6-Dichlorobenzoylamino)-3-ethoxycarbonyl-4-[[N-(pyridin-2-ylmethyl)carbamoyl]methylthio]quinoline was obtained from 4-carboxymethylthio-8-(2,6-dichlorobenzoylamino)-3-ethoxycarbonylquinoline and 2-aminomethylpyridine according to a similar manner to that of Example 22-(2).

NMR (DMSO-d$_6$, δ): 1.34 (3H, t, J=7 Hz), 3.75 (2H, s), 4.22 (2H, d, J=7 Hz), 4.39 (2H, q, J=7 Hz), 6.96 (1H, d, J=8 Hz), 7.20 (1H, d, J=7 Hz), 7.45–7.70 (4H, m), 7.78 (1H, t, J=8 Hz), 8.32 (1H, d, J=8 Hz), 8.42 (1H, m), 8.55 (1H, m), 8.80 (1H, d, J=8 Hz), 8.99 (1H, s)
its hydrochloride
mp: 191–194° C. NMR (DMSO-d$_6$, δ): 1.35 (3H, t, J=7 Hz), 3.78 (2H, s), 4.35–4.50 (4H, m), 7.40 (1H, d, J=8 Hz), 7.45–7.60 (3H, m), 7.64 (1H, t, J=7 Hz), 7.80 (1H, t, J=8 Hz), 8.17 (1H, t, J=7 Hz), 8.32 (1H, t, J=8 Hz), 8.64 (1H, d, J=6 Hz), 8.75–8.85 (2H, m), 8.99 (1H, s)

Example 67

The following compounds were obtained according to a similar manner to that of Example 25.
(1) 8-(2,6-Dichlorobenzoylamino)-3-ethoxycarbonyl-4-(1-methylimidazol-2-ylthio)quinoline hydrochloride
mp: 234–236° C. NMR (DMSO-d$_6$, δ): 1.31 (3H, t, J=7 Hz), 3.53 (3H, s), 4.28 (2H, q, J=7 Hz), 6.98 (1H, s), 7.30 (1H, s), 7.45–7.60 (3H, m), 7.75 (1H, t, J=8 Hz), 8.18 (1H, d, J=8 Hz), 8.78 (1H, d, J=8 Hz), 8.98 (1H, s)
(2) 8-(2,6-Dichlorobenzoylamino)-3-ethoxycarbonyl-4-(pyridin-4-ylthio)quinoline
mp: 183–185° C. NMR (DMSO-d$_6$, δ): 1.19 (3H, t, J=7 Hz), 4.27 (2H, q, J=7 Hz), 7.04 (2H, d, J=6 Hz), 7.45–7.62 (3H, m), 7.79 (1H, t, J=8 Hz), 8.06 (1H, d, J=8 Hz), 8.33 (2H, d, J=6 Hz), 8.83 (1H, d, J=8 Hz), 9.17 (1H, s)
its hydrochloride
mp: 204–205° C. NMR (DMSO-d$_6$, δ): 1.19 (3H, t, J=7 Hz), 4.30 (2H, q, J=7 Hz), 7.45–7.65 (5H, m), 7.83 (1H, t, J=8 Hz), 8.08 (1H, d, J=8 Hz), 8.52 (2H, d, J=6 Hz), 8.87 (1H, a, J=8 Hz), 9.28 (1H, s)

Example 68

A mixture of 4-chloro-8-(2,6-dichlorobenzoylamino)-3-ethoxycarbonylquinoline (297 mg) and hydrazine monohydrate (175 mg) in ethanol (3 ml) was refluxed for 1 hour. To the mixture was added ice-water, and the resulting precipitate was collected by filtration and washed with water to give 6-(2,6-dichlorobenzoylamino)-2,3-dihydro-1H-pyrazolo[4,3-c]-quinolin-3-one (250 mg).

To a suspension of the obtained compound in ethanol (20 ml) was added a solution of hydrogen chloride in ethanol, and the mixture was stirred for 15 minutes at 60° C. The resulting precipitate was collected by filtration and washed with ethanol to give 6-(2,6-dichlorobenzoylamino)-2,3-dihydro-1H-pyrazolo[4,3-c]quinolin-3-one hydrochloride (220 mg).
mp: >250° C. NMR (DMSO-d$_6$, δ): 7.50–7.65 (3H, m), 7.79 (1H, t, J=8 Hz), 8.20 (1H, d, J=8 Hz), 8.63 (1H, d, J=8 Hz), 9.25 (1H, s)

Example 69

(1) 3-Bromo-8-(2,6-dichlorobenzoylamino)-4-methylquinoline was obtained from 3-bromo-4-carboxymethyl-8-(2,6-dichlorobenzoylamino)quinoline according to a similar manner to that of Example 58-(1).
mp: >250° C. NMR (CDCl$_3$, δ): 2.82 (3H, s), 7.30–7.50 (3H, m), 7.66 (1H, t, J=8 Hz), 7.79 (1H, d, J=8 Hz), 8.77 (1H, s), 8.97 (1H, d, J=8 Hz)
(2) 3-Bromo-4-bromomethyl-8-(2,6-dichlorobenzoylamino)quinoline was obtained according to a similar manner to that of the first step of Example 52.
mp: 210–213° C. NMR (CDCl$_3$, δ): 5.00 (2H, s), 7.30–7.50 (3H, m), 7.77 (1H, t, J=8 Hz), 7.85 (1H, d, J=8 Hz), 8.82 (1H, s), 9.03 (1H, d, J=8 Hz)
(3) 4-Acetoxymethyl-3-bromo-8-(2,6-dichlorobenzoylamino)quinoline was obtained according to a similar manner to that of Example 53-(1).
mp: 201–202° C. NMR (CDCl$_3$, δ): 2.10 (3H, s), 5.70 (2H, s), 7.30–7.50 (3H, m), 7.71 (1H, t, J=8 Hz), 7.80 (1H, d, J=8 Hz), 8.85 (1H, s), 9.00 (1H, d, J=8 Hz)
(4) 3-Bromo-8-(2,6-dichlorobenzoylamino)-4-hydroxymethylquinoline was obtained according to a similar manner to that of Example 12-(2).
mp: 246–247° C. NMR (DMSO-d$_6$, δ): 5.07 (2H, d, J=5 Hz), 5.67 (1H, t, J=5 Hz), 7.45–7.60 (3H, m), 7.76 (1H, t, J=8 Hz), 8.12 (1H, d, J=8 Hz), 8.72 (1H, d, J=8 Hz), 8.96 (1H, s)

Example 70

3-Bromo-8-(2,6-dichlorobenzoylamino)-4-(imidazol-1-ylmethyl)quinoline was obtained by reacting 3-bromo-4-bromomethyl-8-(2,6-dichlorobenzoylamino)quinoline with imidazole according to a similar manner to that of Example 59.
mp: 217–218° C. NMR (DMSO-d$_6$, δ): 5.84 (2H, s), 6.85 (1H, s), 7.08 (1H, s), 7.45–7.60 (3H, m), 7.77 (1H, t, J=8 Hz), 7.83 (1H, s), 8.14 (1H, d, J=8 Hz), 8.76 (1H, d, J=8 Hz), 9.05 (1H, s)
its hydrochloride
mp: >250° C. NMR (DMSO-d$_6$, δ): 3.07 (2H, s), 7.45–7.60 (3H, m), 7.67 (2H, s), 7.81 (1H, t, J=8 Hz), 8.10 (1H, d, J=8 Hz), 8.80 (1H, d, J=8 Hz), 9.10 (2H, s)

Example 71

(1) 4-Carboxymethyl-8-(2,6-dichlorobenzoylamino)-3-vinylquinoline was obtained from 8-(2,6-dichlorobenzoylamino)-4-ethoxycarbonylmethyl-3-vinylquinoline according to a similar manner to that of Example 18.
mp: 252–253° C. NMR (DMSO-d$_6$, δ): 4.25 (2H, s), 5.60 (1H, d, J=13 Hz), 6.02 (1H, d, J=15 Hz), 7.21 (1H, dd, J=13, 15 Hz), 7.45–7.60 (3H, m), 7.68 (1H, t, J=8 Hz), 7.92 (1H, d, J=8 Hz), 8.69 (1H, d, J=8 Hz), 9.06 (1H, s)
(2) To a solution of 4-carboxymethyl-8-(2,6-dichlorobenzoylamino)-3-vinylquinoline (190.1 mg) were added pivaloyl chloride (62.8 mg) and triethylamine (52.7 mg) at 0° C., and the mixture was stirred for 1 hour at the same temperature. To the mixture was added 2-aminomethylpyridine (154 mg) at 0° C., and the mixture was stirred for 30 minutes at the same temperature and for 1 hour at ambient temperature. The mixture was partitioned between dichloromethane and water. The organic layer was washed with brine, dried over magnesium sulfate and evaporated in vacuo. The residue was purified by preparative thin layer chromatography (methanol-dichloromethane) to give 8-(2,6-dichlorobenzoylamino)-4-[(pyridin-2-ylmethyl)carbamoylmethyl]-3-vinylquinoline (34.4 mg).
mp: 194–195° C. NMR (DMSO-d$_6$, δ): 4.24 (2H, s), 4.38 (2H, d, J=7 Hz), 5.58 (1H, d, J=12 Hz), 6.01 (1H, d, J=17 Hz), 7.20–7.25 (3H, m), 7.50–7.60 (3H, m), 7.67 (1H, t, J=8 Hz), 7.75 (1H, t, J=8 Hz), 8.01 (1H, d, J=8 Hz), 8.51 (1H, d, J=6 Hz), 8.68 (1H, d, J=8 Hz), 8.86 (1H, t, J=7 Hz), 9.05 (1H, s)

Example 72

To a mixture of dimethylformamide (80.5 mg) and dichloromethane (2 ml) was added oxalyl chloride (140 mg), and the mixture was stirred for 30 minutes at ambient temperature. To the mixture was added 4-carboxymethyl-8-(2,6-dichlorobenzoylamino)-3-vinylquinoline (340 mg) at 0° C., and the mixture was stirred for 30 minutes at the same temperature. To the mixture was added a solution of 2-aminomethylpyridine (458 mg) in dichloromethane (2 ml) at 0° C., and the mixture was stirred for 30 minutes at the same temperature. The mixture was partitioned between dichloromethane and saturated sodium bicarbonate solution. The organic layer was washed with saturated ammonium chloride solution and brine, dried over magnesium sulfate and evaporated in vacuo. The residue was purified by column chromatography on silica gel (dichloromethane-methanol) to give 4-(2,6-dichlorobenzoylamino)-9-hydroxyphenanthridine (75.7 mg).

mp: >250° C. NMR (DMSO-$d_6$, δ): 7.33 (1H, d, J=8 Hz), 7.45–7.60 (3H, m), 7.72 (1H, t, J=8 Hz), 8.00 (1H, s), 8.13 (1H, d, J=8 Hz), 8.35 (1H, d, J=8 Hz), 8.74 (1H, d, J=8 Hz), 9.17 (1H, s)

Example 73

(1) 4-Carboxymethyl-8-(2,6-dichlorobenzoylamino)-3-ethylquinoline was obtained from 4-carboxymethyl-8-(2,6-dichlorobenzoylamino)-3-vinylquinoline according to a similar manner to that of Example 41.

mp: 115–116° C. NMR (CDCl$_3$, δ): 1.27 (3H, t, J=7 Hz), 2.37 (1H, q, J=7 Hz), 4.13 (2H, s), 7.30–7.55 (3H, m), 7.61 (1H, t, J=8 Hz), 7.68 (1H, d, J=8 Hz), 8.63 (1H, s), 8.90 (1H, d, J=8 Hz)

(2) 8-(2,6-Dichlorobenzoylamino)-3-ethyl-4-[(pyridin-2-ylmethyl)carbamoylmethyl]quinoline was obtained according to a similar manner to that of Example 26-(2).

mp: 162–163° C. NMR (DMSO-$d_6$, δ): 1.21 (3H, t, J=7 Hz), 2.89 (2H, q, J=7 Hz), 4.17 (2H, s), 4.38 (2H, d, J=7 Hz), 7.20–7.30 (2H, m), 7.45–7.65 (4H, m), 7.75 (1H, t, J=8 Hz), 7.92 (1H, d, J=8 Hz), 8.51. (1H, d, J=8 Hz), 8.65 (1H, d, of J=8 Hz), 8.74 (1H, s), 8.87 (1H, t, J=7 Hz)

its dihydrochporide mp: 223–237° C. NMR (DMSO-$d_6$, δ): 1.19 (3H, t, J=7 Hz), 2.88 (2H, q, J=7 Hz), 4.23 (2H, s), 4.61 (1H, d, J=7 Hz), 7.50–7.70 (4H, m), 7.70–7.80 (2H, m), 7.90 (1H, d, J=8 Hz), 8.37 (1H, t, J=8 Hz), 8.64 (1H, d, J=8 Hz), 8.74 (1H, s), 8.70–8.80 (1H, overlapping), 9.17 (1H, t, J=7 Hz)

Example 74

A solution of 8-(2,6-dichlorobenzoylamino)quinoline (100 mg) and m-chloroperbenzoic acid (71 mg) in ethylene chloride was stirred for 1 hour at 40° C. To the mixture was added 5% sodium thiosulfate solution, and the mixture was partitioned between dichloromethane and saturated sodium bicarbonate solution. The organic layer was dried over magnesium sulfate and evaporated in vacuo. The residue was recrystallized from dichloromethane-methanol to give 8-(2,6-dichlorobenzoylamino)quinoline 1-oxide (48 mg).

mp: >250° C. NMR (DMSO-$d_6$, δ): 7.50–7.60 (2H, m), 7.60–7.67 (2H, m), 7.77 (1H, t, J=8 Hz), 7.87 (1H, d, J=8 Hz), 8.15 (1H, d, J=8 Hz), 8.55 (1H, d, J=8 Hz), 9.02 (1H, d, J=8 Hz)

Example 75

A mixture of 8-quinolinecarboxylic acid (100 mg), oxalyl chloride (0.08 ml) and dimethylformamide (1 drop) in dichloromethane (3 ml) was stirred for 4 hours at ambient temperature. The mixture was concentrated in vacuo, and the residue was dissolved in dichloromethane (3 ml). To the solution were added 2,6-dichloroaniline (93 mg) and triethylamine (117 mg), and the mixture was stirred for 2 hours at ambient temperature. The mixture was washed with water, dried over magnesium sulfate and evaporated in vacuo. The residue was purified by column chromatography on silica gel (n-hexane-ethyl acetate) to give 8-[N-(2,6-dichlorophenyl)carbamoyl]quinoline (78 mg).

mp: 168–169° C. NMR (CDCl$_3$, δ): 7.20 (1H, t, J=8 Hz), 7.43 (2H, d, J=8 Hz), 7.56 (1H, m), 7.75 (1H, t, J=8 Hz), 8.06 (1H, d, J=8 Hz), 8.36 (1H, d, J=8 Hz), 8.94–9.01 (2H, m)

Example 76

A solution of 8-nitrocinnoline (104 mg) in N,N-dimethylacetamide (1 ml), containing 10% palladium on activated carbon (15 mg), was hydrogenated under atmospheric pressure at ambient temperature for 6 hours. The catalyst was removed by filtration and washed with hot N,N-dimethylacetamide and hot chloroform. The combined filtrate was concentrated to small volume under reduced pressure. To this solution were added triethylamine (87 mg) and 2,6-dichlorobenzoyl chloride (144 mg), and the resulting mixture was stirred at 95° C. for 1 hour. The mixture was partitioned between ethyl acetate and saturated ammonium chloride aqueous solution. The organic layer was washed with saturated sodium bicarbonate aqueous solution and brine, dried over anhydrous magnesium sulfate, and evaporated in vacuo. The residue was purified by preparative thin layer chromatography on silica gel. The obtained oil was crystallized from ethanol to give 8-(2,6-dichlorobenzoylamino)cinnoline (9 mg) as gray crystal.

mp: 226–228° C. NMR (CDCl$_3$, δ): 7.30–7.50 (3H, m), 7.60 (1H, d, J=8 Hz), 7.85 (1H, t, J=8 Hz), 7.92 (1H, d, J=6 Hz), 9.09 (1H, d, J=8 Hz), 9.36 (1H, d, J=6 Hz)

Example 77

The following compounds were obtained according to a similar manner to that of Example 22-(2).

(1) 8-(2,6-Dichlorobenzoylamino)-4-[ (pyridin-2-ylmethyl)carbamoylmethyl]-3-vinylquinoline (from 4-carboxymethyl-8-(2,6-dichlorobenzoylamino)-3-vinyiquinoline and 2-aminomethylpyridine)

(2) 4-Carbamoylmethyl-8-(2,6-dichlorobenzoylamino)-3-vinylaquinoline (from 4-carboxymethyl-8-(2,6-dichlorobenzoylamino)-3-vinylquinoline and conc. ammonia solution)

mp: 232–234° C. NMR (DMSO-$d_6$, δ): 4.08 (2H, s), 5.58 (1H, d, J=11 Hz), 6.00 (1H, d, J=17 Hz), 7.15 (1H, brs), 7.22 (1H, dd, J=11, 17 Hz), 7.50–7.65 (3H, m), 7.67 (1H, t, J=8 Hz), 7.70 (1H, brs), 7.95 (1H, d, J=8 Hz), 8.67 (1H, d, J=8 Hz), 9.03 (1H, s)

its hydrochloride mp: 199–205° C. NMR (DMSO-$d_6$, δ): 4.09 (2H, s), 5.57 (1H, d, J=11 Hz), 6.00 (1H, d, J=17 Hz), 7.15 (1H, brs), 7.22 (1H, dd, J=11, 17 Hz), 7.50–7.65 (3H, m), 7.67 (1H, t, J=8 Hz), 7.72 (1H, brs), 7.95 (1H, d, J=8 Hz), 8.67 (1H, d, J=8 Hz), 9.03 (1H, s)

Example 78

(1) 4-Acetoxymethyl-8-(2,6-dichlorobenzoylamino)-3-vinylquinoline was obtained from 4-acetoxymethyl-3-bromo-8-(2,6-dichlorobenzoylamino)quinoline and tri-n-butyl(vinyl)tin according to a similar manner to that of Preparation 14.

mp: 166–167° C. NMR (CDCl$_3$, δ): 2.08 (3H, s), 5.61 (2H, s), 5.55–5.65 (1H, overlapping), 7.30–7.45 (3H, m), 7.68 (1H, t, J=8 Hz), 7.85 (1H, t, J=8 Hz), 8.91 (1H, s), 8.95 (1H, d, J=8 Hz)

(2) 8-(2,6-Dichlorobenzoylamino)-4-hydroxymethyl-3-vinylquinoline was obtained according to a similar manner to that of Example 12-(2).

mp: 243–244° C. NMR (DMSO-d$_6$, δ): 4.99 (2H, d, J=5 Hz), 5.48 (1H, t, J=5 Hz), 5.60 (1H, d, J=12 Hz), 6.01 (1H, d, J=16 Hz), 7.32 (1H, dd, J=12, 16 Hz), 7.50–7.60 (3H, m), 7.69 (1H, t, J=8 Hz), 8.09 (1H, d, J=8 Hz), 8.67 (1H, d, J=8 Hz), 9.05 (1H, s)
its hydrochloride
mp: 215–221° C. NMR (DMSO-d$_6$, δ): 4.98 (2H, s), 5.60 (1H, d, J=12 Hz), 6.02 (1H, d, 16 Hz), 7.32 (1H, dd, J=12, 16 Hz), 7.50–7.60 (3H, m), 7.68 (1H, t, J=8 Hz), 8.09 (1H, d, J=8 Hz), 8.66 (1H, d, J=8 Hz), 9.05 (1H, s)
(3) To N,N-dimethylformamide (1 ml) was added thionyl chloride (73.2 mg), and the mixture was stirred for 15 minutes at ambient temperature. To the mixture was added 8-(2,6-dichlorobenzoylamino)-4-hydroxymethyl-3-vinylquinoline (176.7 mg), and the mixture was stirred for 30 minutes at ambient temperature. To the mixture was added saturated sodium bicarbonate solution (10 ml) under ice-cooling, and the mixture was stirred for 15 minutes at the same temperature. The resulting precipitate was collected by filtration and washed with water to give 4-chloromethyl-8-(2,6-dichlorobenzoylamino)-3-vinylquinoline (182.8 mg).
mp: 184–186° C. NMR (CDCl$_3$, δ): 5,05 (2H, s), 5.70 (1H, d, J=10 Hz), 5.93 (1H, d, J=17 Hz), 7.17 (1H, d, J=10, 17 Hz), 7.30–7.45 (3H, m), 7.72 (1H, t, J=8 Hz), 7.88 (1H, d, J=8 Hz), 8.90 (1H, s), 8.97 (1H, d, J=8 Hz)
(4) 8-(2,6-Dichlorobenzoylamino)-4-(imidazol-1-ylmethyl)-3-vinylquinoline was obtained according to a similar manner to that of Example 59.
mp: 189–191° C. NMR (DMSO-d$_6$, δ): 5.67 (1H, d, J=10 Hz), 5.83 (2H, s), 6.10 (1H, d, J=16 Hz), 6.82 (1H, s), 6.98 (1H, s), 7.45 (1H, dd, J=10, 16 Hz), 7.45–7.60 (3H, m), 7.72 (1H, t, J=8 Hz), 7.23 (1H, s), 8.13 (1H, d, j=8 Hz), 8.70 (1H, d, J=8 Hz), 9.14 (1H, s)
its hydrochloride
mp: 244–247° C. NMR (DMSO-d$_6$, δ): 5.69 (1H, d, J=11 Hz), 6.07 (2H, s), 6.13 (1H, d, J=17 Hz), 7.38 (1H, dd, J=11, 17 Hz), 7.50–7.65 (5H, m), 7.74 (1H, t, J=8 Hz), 8.05 (1H, d, J=8 Hz), 8.73 (1H, d, J=8 Hz), 9.03 (1H, s), 9.19 (1H, s)

Example 79

(1) 8-(2,6-Dichlorobenzoylamino)-3-ethyl-4-hydroxymethylquinoline was obtained from 8-(2,6-dichlorobenzoylamino)-4-hydroxymethyl-3-vinylquinoline according to a similar manner to that of Example 41.
mp: 226–228° C. NMR (DMSO-d$_6$, δ): 1.24 (3H, t, J=7 Hz), 2.92 (2H, q, J=7 Hz), 4.95 (2H, d, J=5 Hz), 5.39 (1H, t, J=5 Hz), 7.50–7.60 (3H, m), 7.65 (1H, t, J=8 Hz), 8.05 (1H, d, J=8 Hz), 8.64 (1H, d, J=8 Hz), 8.75 (1H, s)
its hydrochloride
mp: 220–225° C. NMR (DMSO-d$_6$, δ): 1.25 (3H, t, J=7 Hz), 2.93 (2H, c, J=7 Hz), 4.95 (2H, s), 7.50–7.60 (3H, m), 7.66 (1H, t, J=8 Hz), 8.06 (1H, d, J=8 Hz), 8.64 (1H, d, J=8 Hz), 8.76 (1H, s)
(2) 4-Chloromethyl-8-(2,6-dichlorobenzoylamino)-3-ethylquinoline was obtained according to a similar manner to that of Example 78-(3).
mp: 193–194° C. NMR (CDCl$_3$, δ): 1.37 (3H, t, J=7 Hz), 2.96 (2H, q, J=7 Hz), 5.03 (2H, s), 7.30–7.55 (3H, m), 7.70 (1H, t, J=8 Hz), 7.86 (1H, d, J=8 Hz), 8.66 (1H, s), 8.94 (1H, d, J=8 Hz)
(3) 8-(2,6-Dichlorobenzoylamino)-3-ethyl-4-(imidazol-1-ylmethyl)quinoline was obtained according to a similar manner to that of Example 59.
NMR (CDCl$_3$, δ): 1.23 (3H, t, J=7 Hz), 2.92 (2H, q, J=7 Hz), 5.58 (2H, s), 6.78 (1H, s), 7.03 (1H, s), 7.30–7.55 (3H, m), 7.60–7.70 (2H, m), 8.72 (1H, s), 8.94 (1H, d, J=8 Hz)
its hydrochloride
mp: 258–260° C. (dec.) NMR (DMSO-d$_6$, δ): 1.18 (3H, t, J=7 Hz), 2.99 (2H, q, J=7 Hz), 5.99 (2H, s), 7.50–7.60 (4H, m), 7.65 (1H, s), 7.69 (1H, t, J=8 Hz), 7.91 (1H, d, J=8 Hz), 8.71 (1H, d, J=8 Hz), 8.92 (1H, s), 9.02 (1H, s)

Example 80

(1) 4-Bromomethyl-8-(2,6-dichlorobenzoylamino)quinoline was obtained from 8-(2,6-dichlorobenzoylamino)-4-methylquinoline according to a similar manner to that of the first step of Example 52.
NMR (CDCl$_3$, δ): 4.97 (2H, s), 7.30–7.45 (3H, m), 7.50 (1H, d, J=5 Hz), 7.73 (1H, t, J=8 Hz), 7.88 (1H, d, J=8 Hz), 8.74 (1H, d, J=5 Hz), 9.01 (1H, d, J=8 Hz)
(2) 8-(2,6-Dichlorobenzoylamino)-4-(imidazol-1-ylmethyl)quinoline was obtained according to a similar manner to that of Example 59.
mp: >250° C. NMR (DMSO-d$_6$, δ): 5.85 (2H, s), 6.97 (1H, d, J=4 Hz), 7.00 (1H, s), 7.45–7.60 (3H, m), 7.74 (1H, t, J=8 Hz), 7.85 (1H, s), 8.01 (1H, d, J=8 Hz), 8.77 (1H, d, J=8 Hz), 8.83 (1H, d, J=4 Hz)
its hydrochloride
mp: 167–172° C. NMR (DMSO-d$_6$, δ): 6.08 (2H, s), 7.28 (1H, d, J=4 Hz), 7.45–7.60 (3H, m), 7.76 (1H, s), 7.78 (1H, t, J=8 Hz), 7.83 (1H, s), 8.00 (1H, d, J=8 Hz), 8.79 (1H, d, J=8 Hz), 8.90 (1H, d, J=4 Hz), 9.26 (1H, s)

Example 81

(1) 4-(Bromomethyl)-8-(2,6-dichlorobenzoylamino)quinoline was obtained from 8-(2,6-dichlorobenzoylamino)-4-hydroxymethylquinoline according to a similar manner to that of Example 12-(3).
NMR (CDCl$_3$, δ): 4.85 (2H, s), 7.29 (3H, m), 7.49 (1H, d, J=4 Hz), 7.73 (1H, t, J=8 Hz), 7.87 (1H, d, J=8 Hz), 8.72 (1H, d, J=4 Hz), 9.00 (1H, d, J=8 Hz)
(2) To a stirred solution of benzimidazole (26.5 mg) in N,N-dimethylformamide (1 ml) was added sodium hydride (60% in oil, 8.6 mg) in an ice bath, and the mixture was stirred at the same temperature for half an hour. To this mixture was added 4-bromomethyl-8-(2,6-dichlorobenzoylamino)quinoline (80 mg) one portion, and the reaction mixture was stirred at the same temperature for half an hour and then at ambient temperature for one hour. Water was added thereto, and the resulting precipitate was collected by filtration. The solid was washed with hot 95% aqueous ethanol (1 ml) and allowed to cool to ambient temperature. The solid was collected by filtration and air-dried to give 4-(1H-benzimidazol-1-ylmethyl)-8-(2,6-dichlorobenzoylamino)quinoline (65 mg) as an off-white solid.
mp: 248–253° C. NMR (CDCl$_3$, δ): 5.89 (2H, s), 6.69 (1H, d, J=4 Hz), 7.17–7.25 (1H, m), 7.26–7.45 (1H, m), 7.70–7.81 (2H, m), 7.90 (1H, d, J=8 Hz), 8.01 (1H, s), 8.60 (1H, d, J=4 Hz), 9.06 (1H, br d, J=8 Hz)

Example 82

(1) 4-[Bis(ethoxycabonyl)methyl]-8-nitroquinoline was obtained by reacting 4-chloro-8-nitroquinoline with diethyl malonate according to a similar manner to that of Preparation 7-(1).
mp: 48–50° C. NMR (CDCl$_3$, δ): 1.20–1.30 (6H, m), 4.20–4.32 (4H, m), 7.63–7.72 (2H, m), 8.01 (1H, d, J=8 Hz), 8.20 (1H, dd, J=8, 2 Hz), 9.07 (1H, d, J=5 Hz)
(2) 8-Nitro-4-(ethoxycarbonylmethyl)quinoline was obtained according to a similar manner to that of Preparation 7-(2).
mp: 67–69° C. NMR (CDCl$_3$, δ): 1.23 (3H, t, J=6 Hz), 4.10 (2H, s), 4.18 (2H, q, J=6 Hz), 7.49 (1H, d, J=4 Hz), 7.67 (1H, t, J=8 Hz), 8.00 (1H, d, J=8 Hz), 8.23 (1H, d, J=8 Hz), 9.00 (1H, d, J=5 Hz)
(3) 8-Amino-4-(ethoxycarbonylmethyl)quinoline was obtained according to a similar manner to that of Preparation 2-(3).

mp: 71–77° C. NMR (CDCl₃, δ): 1.22 (3H, t, J=6 Hz), 4.00 (2H, s), 4.16 (2H, q, J=6 Hz), 5.03 (2H, s), 6.94 (1H, d, J=8 Hz), 7.28–7.40 (3H, m), 8.70 (1H, d, J=5 Hz)

(4) 8-(2,6-Dichlorobenzoylamino)-4-(ethoxycarbonylmethyl)quinoline was obtained according to a similar manner to that of Example 1.

mp: 150–152° C. NMR (CDCl₃, δ): 1.24 (3H, t, J=6 Hz), 4.08 (2H, s), 4.18 (2H, q, J=6 Hz), 7.30–7.44 (4H, m), 7.65 (1H, t, J=8 Hz), 7.75 (1H, d, J=8 Hz), 8.72 (1H, d, J=4 Hz), 8.99 (1H, d, J=8 Hz)

(5) To a suspension of 4-ethoxycarbonylmethyl-8-(2,6-dichlorobenzoylamino)quinoline (1.03 g) in ethanol (6 ml) was added 1N-aqueous sodium hydroxide solution (3.83 ml), and the mixture was stirred at 50° C. for two hours. The organic solvent was removed in vacuo and the aqueous residue was neutralized with 1N hydrochloric acid and extracted with ethyl acetate. The extract was dried and evaporated. The residue was crystallized spontaneously and it was triturated with ethyl acetate to give 4-carboxymethyl-8-(2,6-dichlorobenzoylamino)quinoline (703 mg).

mp: 228–230° C. NMR (DMSO-d₆, δ): 4.18 (2H, s), 7.50–7.64 (4H, m), 7.70 (1H, t, J=8 Hz), 7.85 (1H, d, J=8 Hz), 8.75 (1H, d, J=8 Hz), 8.83 (1H, d, J=4 Hz)

(6) 4-(Morpholinocarbonylmethyl)-8-(2,6-dichlorobenzoylamino)quinoline was obtained from 4-carboxymethyl-8-(2,6-dichlorobenzoylamino)quinoline with morpholine according to a similar manner to that of Example 22-(2).

mp: 245–251° C. NMR (CDCl₃, δ): 3.47 (2H, t, j=6 Hz), 3.62 (2H, t, J=6 Hz), 3.70 (4H, s), 4.15 (2H, s), 7.30–7.45 (4H, m),-7.60–7.70 (2H, m), 8.71 (1H, d, J=5 Hz), 8.95–9.01 (1H, m)

Example 83

(1) 4-[Cyano(ethoxycarbonyl)methyl]-8-(2,6-dichlorobenzoylamino)quinoline was obtained by reacting 4-chloro-8-(2,6-dichlorobenzoylamino)quinoline with ethyl cyanoacetate according to a similar manner to that of Preparation 7-(1).

NMR (CDCl₃, δ): 1.28 (3H, t, J=6 Hz), 4.28 (2H, q, J=6 Hz), 5.40 (1H, s), 7.30–7.45 (3H, m), 7.20–7.77 (3H, m), 8.85 (1H, d, J=4 Hz), 9.02–9.08 (1H, m)

(2) 4-Cyanomethyl-8-(2,6-dichlorobenzoylamino)quinoline was obtained according to a similar manner to that of Preparation 7-(2).

mp: 234–236° C. NMR (CDCl₃, δ): 4.20 (2H, s), 7.30–7.45 (3H, m), 7.60 (1H, d, J=8 Hz), 7.66 (1H, d, J=4 Hz), 7.75 (1H, t, J=8 Hz), 8.80 (1H, d, J=4 Hz), 9.05 (1H, d, J=8 Hz)

Example 84

(1) 4-[Bis(ethoxycarbonyl)methyl]-8-(2,6-dichlorobenzoylamino)quinoline was obtained by reacting 4-chloro-8-(2,6-dichlorobenzoylamino)quinoline with diethyl malonate according to a similar manner to that of Preparation 7-(1).

mp: 127–128° C. NMR (CDCl₃, δ): 1.38 (6H, t, J=6 Hz), 4.28 (4H, q, J=6 Hz), 5.43 (1H, s), 7.30–7.45 (3H, m), 7.61 (1H, d, J=5 Hz), 7.64–7.76 (2H, m), 8.80 (1H, d, J=5 Hz), 9.01 (1H, d, J=8 Hz)

(2) A mixture or 4-[bis(ethoxycarbonyl)methyl]-8-(2,6-dichlorobenzoylamino)quinoline (200 mg) and hydrazine monohydrate (211 mg) in ethanol (2 ml) was refluxed overnight. After cooling, the resulting precipitates were collected by the filtration, and the residue was washed with ethanol to give 8-(2,6-dichlorobenzoylamino)-4-(3,5-dihydroxypyrazol-4-yl)quinoline as a solid. The obtained solid was treated with ethanol solution of hydrogen chloride, and the precipitates were collected and recrystallized from isopropyl alcohol to give 8-(2,6-dichlorobenzoylamino)-4-(3,5-dihydroxypyrazol-4-yl)quinoline hydrochloride (95 mg).

mp: 210–230° C. NMR (DMSO-d₆, δ): 7.50–7.67 (5H, m), 7.84 (1H, d, J=8 Hz), 8.65 (1H, d, J=8 Hz), 8–78 (1H, d, J=5 Hz)

Example 85

The following compounds were obtained according to a similar manner to that of Example 8.

(1) 8-(2,6-Dichlorobenzoylamino)-4-(2-methylimidazol-1-yl)quinoline mp: 210–212° C. NMR (CDCl₃, δ): 2.25 (3H, s), 7.10 (1H, s), 7.17–7.30 (2H, m), 7.33–7.48 (4H, m), 7.68 (1H, t, J=8 Hz), 8.91 (1H, d, J=4 Hz), 9.08 (1H, d, J=8 Hz)

its hydrochloride mp: >250° C. NMR (DMSO-d₆, δ): 2.46 (3H, s), 7.36 (1H, d, J=8 Hz), 7.50–7.62 (3H, m), 7.80 (1H, t, J=8 Hz), 7.91–8.02 (3H, m), 8.87 (1H, d, J=8 Hz), 9.17 (1H, d, J=4 Hz)

(2) 8-(2,6-Dichlorobenzoylamino)-4-(pyrazol-1-yl)quinoline mp: 194–197° C. NMR (CDCl₃, δ): 6.59–6.65 (1H, m), 7.30–7.46 (3H, m), 7.55 (1H, d, J=5 Hz), 7.69 (1H, t, J=8 Hz), 7.91 (1H, d, J=2 Hz), 7.96 (1H, d, J=3 Hz), 7.99 (1H, d, J=8 Hz), 8.82 (1H, d, J=5 Hz), 9.03 (1H, d, J=8 Hz)

its hydrochloride mp: 204–207° C. NMR (DMSO-d₆, δ): 6.71 (1H, d, J=2 Hz), 7.48–7.62 (3H, m), 7.70–7.81 (2H, m), 8.00 (1H, d, J=2 Hz), 8.11 (1H, d, J=8 Hz), 8.46 (1H, t, J=2 Hz), 8.80 (1H, d, J=8 Hz), 8.99 (1H, d, J=6 Hz)

(3) 8-(2,6-Dichlorobenzoylamino)-4-(1,2,4-triazol-1-yl)quinoline mp: 210–214° C. NMR (CDCl₃, δ): 7.31–7.46 (3H, m), 7.56 (1H, d, J=5 Hz), 7.73 (1H, t, J=8 Hz), 7.80 (1H, d, J=8 Hz), 8.30 (1H, s), 8.60 (1H, s), 8.90 (1H, d, J=5 Hz), 9.09 (1H, d, J=8 Hz)

its hydrochloride mp: 220–232° C. NMR (DMSO-d₆, δ): 7.47–7.62 (3H, m), 7.75 (1H, t, J=8 Hz), 7.88 (1H, d, J=8 Hz), 8.00 (1H, d, J=5 Hz), 8.48 (1H, s), 8.81 (1H, d, J=8 Hz), 9.06 (1H, d, J=5 Hz), 9.26 (1H, s)

(4) 8-(2,6-Dichlorobenzoylamino)-4-(N-methylamino)quinoline mp: 226–228° C. NMR (DMSO-d₆, δ): 2.90 (3H, d, j=6 Hz), 6.46 (1H, d, J=6 Hz), 7.37–7.68 (5H, m), 7.90 (1H, d, J=8 Hz), 8.36 (1H, d, J=6 Hz), 8.60 (1H, d, J=8 Hz)

(5) 8-(2,6-Dichlorobenzoylamino)-4-[N-(2-methoxyethyl)-N-methylamino]quinoline mp: 156–158° C. NMR (CDCl₃, δ): 3.05 (3H, s), 3.38 (3H, s), 3.53 (2H, t, J=5 Hz), 3.70 (2H, t, J=5 Hz), 6.88 (1H, d, J=5 Hz), 7.27–7.42 (4H, m), 7.51 (1H, t, J=8 Hz), 7.90 (1H, d, J=8 Hz), 8.51 (1H, d, J=5 Hz), 8.90 (1H, d, J=8 Hz)

(6) 4-[(3-Aminopropyl)amino]-8-(2,6-dichlorobenzoylamino)quinoline mp: 146–150° C. NMR (CDCl₃, δ): 1.30–1.70 (3H, br), 1.90 (2H, quint, J=61 Hz), 3.05 (2H, t, j=6 Hz), 3.43 (2H, q, J=6 Hz), 6.39 (1H, d, J=5 Hz), 7.25–7.48 (4H, m), 7.55 (1H, d, J=8 Hz), 8.38 (1H, d, J=5 Hz), 8.88 (1H, d, J=8 Hz)

(7) 8-(2,6-Dichlorobenzoylamino)-4-[N-(2-methylaminoethyl)N-methylamino]quinoline mp: 173–178° C. NMR (CDCl₃, δ): 2.45 (3H, s), 2.91 (2H, t, J=8 Hz), 3.01 (3H, s), 3.44 (2H, t, J=8 Hz), 6.87 (1H, d, J=6 Hz), 7.27–7.42 (3H, m), 7.52 (1H, t, J=8 Hz), 7.88 (1H, d, J=8 Hz), 8.50 (1H, d, J=6 Hz), 8.90 (1H, d, J=8 Hz)

(8) 8-(2,6-Dichlorobenzoylamino)-4-(pyrazol-3-ylamino)quinoline hydrochloride mp: >250° C. NMR (DMSO-d$_6$, δ): 6.45 (1H, d, J=4 Hz), 7.52–7.65 (3H, m), 7.86 (1H, t, J=8 Hz), 7.90 (1H, s), 7.97 (1H, ds, J=8 Hz), 8.55–8.70 (3H, m)

(9) 8-(2,6-Dichlorobenzoylamino)-4-(1,2,4-triazol-$^4$-ylamino)quinoline mp: 236–238° C. NMR (DMSO-d$_6$, δ): 6.61 (1H, d, J=5 Hz), 7.00 (2H, s), 7.42 (1H, t, J=8 Hz), 7.50–7.63 (3H, m), 7.93 (1H, d, J=8 Hz), 8.26 (1H, d, J=5 Hz), 8.61 (1H, d, J=8 Hz)

(10) 3-Bromo-8-(2,6-dichlorobenzoylamino)-4-(2-methylimidazol-1-yl)quinoline mp: 200° C. NMR (CDCl$_3$, δ): 2.16 (3H, s), 6.97 (1H, s), 7.04 (1H, d, J=8 Hz), 7.24 (1H, s), 7.32–7.48 (3H, m), 7.68 (1H, t, J=8 Hz), 8.97 (1H, S), 9.06 (1H, d, J=8 Hz)

its hydrochloride mp: 269° C. NMR (DMSO-d$_6$, δ): 2.41 (3H, s), 7.28 (1H, d, J=8 Hz), 7.49–7.64 (3H, m), 7.84 (1H, t, J=8 Hz), 7.92 (1H, s), 7.96 (1H, s), 8.86 (1H, d, J=8 Hz), 9.30 (1H, s)

(11) 8-(2,6-Dichlorobenzoylamino)-3-ethoxycarbonyl-4-[N-(2-hydroxyethyl)-N-methylamino]quinoline mp: 139–141° C. NMR (CDCl$_3$, δ): 1.43 (3H, t, J=6 Hz), 3.05 (3H, s), 3.72–3.87 (4H, m), 4.48 (2H, q, J=6 Hz), 7.28–7.43 (3H, m), 7.57 (1H, t, J=7 Hz), 7.82 (1H, d, J=7 Hz), 8.83 (1H, s), 8.97 (1H, d, J=7 Hz)

(12) 8-(2,6-Dichlorobenzoylamino)-3-methyl-4-(pyrazol-1-yl)quinoline mp: 236° C. NMR (CDCl$_3$, δ): 2.30 (3H, s), 6.60–6.65 (1H, m), 7.11 (1H, d, J=8 Hz), 7.30–7.45 (3H, m), 7.57 (1H, d, J=8 Hz), 7.65 (1H, s), 7.90 (1H, s), 8.75 (1H, s), 8.93 (1H, d, J=8 Hz)

(13) 8-(2,6-Dichlorobenzoylamino)-3-methyl-4-(1,2,4-triazol-1-yl)cquinoline mp: 248–250° C. NMR (DMSO-d$_6$, δ): 2.26 (3H, s), 7.02 (1H, d, J=8 Hz), 7.48–7.61 (3H, m), 7.69 (1H, t, J=8 Hz), 8.48 (1H, s), 8.73 (1H, d, J=8 Hz), 9.03 (1H, s), 9.08 (1H, s)

(14) 8-(2,6-Dichlorobenzoylamino)-3-methoxymethyl-4-(piperidino)quiH, ine NMR (CDCl$_3$, δ): 1.67–1.88 (6H, m), 3.23–3.35 (4H, m), 3.38 (3H, s), 4.63 (2H, s), 7.28–7.44 (3H, m), 7.54 (1H, dd, J=8, 8 Hz), 7.91 (1H, d, J=8 Hz), 8.57 (1H, S), 8.88 (1H, d, J=8 Hz), 10.12 (1H, s)

(15) 8-(2,6-Dichlorobenzoylamino)-4-(pyridin-3-ylmethylamino)quinoline NMR (CDCl$_3$, δ): 4.61 (2H, d, J=6 Hz), 5.50 (1H, t, J=6 Hz), 6.46 (1H, d, J=5 Hz), 7.25–7.42 (4H, m), 7.49–7.56 (2H, m), 7.72 (1H, d, j=8 Hz), 8.40 (1H, d, J=5 Hz), 8.60 (1H, d, J=5 Hz), 8.69 (1H, s), 8.90–8.96 (1H, m)

its dihydrochloride mp: >250° C. NMR (DMSO-d$_6$, δ): 5.03 (2H, d, J=5 Hz), 6.95 (1H, d, J=8 Hz), 7.50–7.65 (3H, m), 7.80–7.90 (2H, m), 8.42 (1H, d, J=8 Hz), 8.55 (1H, d, J=8 Hz), 8.55 (2H, m), 8.63 (1H, d, J=8 Hz), 8.78 (1H, d, J=5 Hz), 9.00 (1H, s)

Example 86

A suspension of 8-(2,6-dichlorobenzoylamino)-4-methylaminoquinoline (130 mg) in acetic anhydride (2 ml) was heated at 120° C. for 3 hours. The solvent was removed in vacuo and the residue was dissolved in methanol (3 ml). To a solution was added 1N sodium hydroxide solution (0.5 ml) and the mixture was stirred for 30 minutes. The solvent was removed in vacuo and the residue was washed with hot 50% ethanol (2 ml) and filtered. The residue was washed with hot 95% ethanol (1 ml) and the filtrate was allowed to stand to ambient temperature. The resulting precipitates were collected by filtration and dried to give 8-(2,6-dichlorobenzoylamino)-4-(N-methylacetamido)quinoline (90 mg).

mp: 227–230° C. NMR (CDCl$_3$, δ): 1.80 (3H, s), 3.36 (3H, s), 7.29– 7.48 (4H, m), 7.57 (1H, d, J=8 Hz), 7.71 (1H, t, J=8 Hz), 8.83 (1H, d, J=5 Hz), 9.04 (1H, d, J=8 Hz)

Example 87

A mixture of 8-(2,6-dichlorobenzoylamino)-4-[N-(2-methylaminoethyl)-N-methylamino]quinoline (130 mg), phenyl 3-pyridylcarbamate (76 mg) and triethylamine (97.9 mg) in dimethylformamide (1.5 ml) was stirred for 1 hour at ambient temperature. The mixture was diluted with ethyl acetate, washed with 1N sodium hydroxide solution, water and brine, dried over magnesium sulfate and evaporated in vacuo. The residue was purified by preparative thin layer chromatography (methanol-dichloromethane) to give 8-(2,6-dichlorobenzoylamino)-4-[N-[2-[1-methyl-3-(3-pyridyl)ureido)ethyl]-N-methylamino]quinoline (168 mg).

NMR (CDCl$_3$, δ): 2.73 (3H, s), 3.10 (3H, s), 3.60–3.75 (4H, m), 6.20 (1H, br s), 6.88 (1H, d, J=6 Hz), 7.22 (1H, dd, J=8, 7 Hz), 7.28–7.41 (3H, m), 7.49 (1H, t, J=8 Hz), 7.77 (1H, d, J=8 Hz), 7.85 (1H, dd, J=7, 2 Hz), 8.27 (1H, d, J=7 Hz), 8.36 (1H, d, J=2 Hz), 8.44 (1H, d, J=6 Hz), 8.88 (1H, d, J=8 Hz)

its dihydrochloride mp: 261–266° C. NMR (DMSO-d$_6$, δ): 2.97 (3H, s), 3.48 (3H, s), 3.71–3.83 (2H, m), 3.94–4.08 (2H, m), 7.16 (1H, d, J=8 Hz), 7.49–7.67 (4H, m), 7.83 (1H, dd, J=8, 7 Hz), 8.11 (1H, d, J=8 Hz), 8.39–8.51 (4H, m), 9.00 (1H, s), 9.40 (1H, br s)

Example 88

8-(2,6-Dichlorobenzoylamino)-4-[N-[2-[1-methyl-3-(4-pyridyl)ureido]ethyl]-N-methylamino]quinoline was obtained by reacting 8-(2,6-dichlorobenzoylamino)-4-[N-(2-methylaminoethyl)-N-methylamino]quinoline with phenyl 4 -pyridylcarbamate according to a similar manner to that of Example 87.

mp: 283–290° C. NMR (CDCl$_3$, δ): 2.74 (3H, s), 3.11 (3H, s), 3.60–3.76 (4H, m), 6.32 (1H, br s), 6.89 (1H, d, J=6 Hz), 7.18–7.44 (1H, m), 7.49 (1H, t, J=8 Hz), 7.77 (1H, d, J=8 Hz), 8.35–8.46 (3H, m), 8.89 (1H, d, J=8 Hz)

Example 89

A mixture of 8-(2,6-dichlorobenzoylamino)-4-[N-(2-methylaminoethyl)-N-methylamino]quinoline (130 mg), 3-pyridinecarbonyl chloride (60.3 mg) and triethylamine (97.9 mg) in dichloromethane (2 ml) was stirred at ambient temperature overnight. The mixture was diluted with dichloromethane, washed with water, dried over magnesium sulfate and evaporated in vacuo. The residue was crystallized from ethanol and collected by filtration. The residue was washed with ethanol to give 8-(2,6-dichlorobenzoylamino)-4-[N-[2-(N-methyl-3-pyridinecarboxamido)ethyl]-N-methylamino]quinoline (150 mg).

mp: 195–203° C. NMR (CDCl$_3$, δ): 2.80 (3H, br s), 3.17 (3H, br s), 3.36–3.93 (4H, m), 6.95 (1H, br d), 7.27–7.47 (5H, m), 7.53 (1H, t, J=8 Hz), 7.80 (1H, br d), 8.40–8.66 (3H, m), 8.90 (1H, d, J=8 Hz)

Example 90

(1) 4-(2-Aminophenylamino)-8-(2,6-dichlorobenzoylamino)quinoline was obtained from 4-chloro-8-(2,6-dichlorobenzoylamino)quinoline and 1,2-phenylenediamine according to a similar manner to that of Example 8.

mp: 224–228° C. NMR (CDCl₃, δ): 3.80 (2H, br s), 6.36–6.46 (2H, m), 6.80–6.91 (2H, m), 7.13–7.22 (2H, m), 7.29–7.44 (3H, m), 7.60 (1H, t, J=8 Hz), 7.70 (1H, d, J=8 Hz), 8.37 (1H, d, J=5 Hz), 8.98 (1H, d, J=8 Hz)

(2) 8-(2,6-Dichlorobenzoylamino)-4-(2-(3-pyridinecarboxamido)phenylamino]quinoline was obtained according to a similar manner to that of Example 89.

mp: 151–154° C. NMR (CDCl₃, δ): 6.63 (1H, d, j=6 Hz), 7.37–7.70 (7H, m), 7.84 (1H, t, J=8 Hz), 7.87 (1H, d, J=8 Hz), 8.40 (1H, br d, J=9 Hz), 8.47 (1H, d, J=6 Hz), 8.52 (1H, d, J=8 Hz), 8.73–8.81 (2H, m), 9.10 (1H, br s)

its hydrochloride mp: 277–283° C. NMR (DMSO-d₆, δ): 6.63 (1H, d, J=6 Hz), 7.37–7.70 (7H, m), 7.84 (1H, t, J=8 Hz), 7.87 (1H, d, j=8 Hz), 8.40 (1H, br d, J=9 Hz), 8.47 (1H, d, J=6 Hz), 8.52 (1H, d, J=8 Hz), 8.73–8.81 (2H, m), 9.10 (1H, br s)

(3) A solution of 8-(2,6-dichlorobenzoylamino)-4-[2-(3-pyridinecarboxamido)phenylamino]quinoline (150 mg) in acetic acid was refluxed for 60 hours. After cooling, the mixture was concentrated in vacuo and diluted with ethyl acetate. The solution was washed with saturated sodium bicarbonate solution, dried over magnesium sulfate and evaporated in vacuo. The residue was crystallized from acetonitrile and collected by filtration to give 8-(2,6-dichlorobenzoylamino)-4-[2-(3-pyridyl)-1H-benzimidazol-1-yl]quinoline (136 mg).

mp: 203–204° C. NMR (CDCl₃, δ): 6.93 (1H, d, J=8 Hz), 7.20–7.48 (8H, m), 7.60 (1H, t, J=8 Hz), 7.89 (1H, dd, J=8, 3 Hz), 7.98 (1H, t, J=8 Hz), 8.54 (1H, m), 8.66 (1H, d, J=3 Hz), 8.87 (1H, m), 9.08 (1H, d, J=8 Hz)

its dihydrochloride mp: 249–254° C. NMR (DMSO-d₆, δ): 7.10 (1H, d, J=8 Hz), 7.16 (1H, d, J=8 Hz), 7.31. (1H, t, J=8 Hz), 7.40–7.69 (6H, m), 7.92–8.04 (3H, m), 8.62 (1H, d, J=6 Hz), 8.80 (1H, d, J=8 Hz), 8.83 (1H, br s), 9.10 (1H, d, J=8 Hz)

Example 91

8-(2,6-Dichlorobenzoylamino)-4-(imidazol-2-ylthio) quinoline was obtained by reacting 4-chloro-8-(2,6-dichlorobenzoylamino)quinoline with 2-mercaptoimidazole according to a similar manner to that of Example 25.

mp: 211–215° C. NMR (CDCl₃, δ): 6.80 (1H, d, J=4 Hz), 7.28–7.45 (6H, m), 7.61 (1H, d, J=8 Hz), 8.42 (1H, d, J=4 Hz), 8.86 (1H, d, J=8 Hz)

Example 92

(1) 4-(2-Aminoethylamino)-8-(2,6-dichlorobenzoylamino) quinoline was obtained by reacting 4-chloro-8-(2,6-dichlorobenzoylamino)quinoline with ethylenediamine according to a similar manner to that of Example 8.

mp: 184–192° C. NMR (CDCl₃, δ): 3.07–3.16 (2H, m), 3.30–3.40 (2H, m), 5.78 (1H, m), 6.44 (1H, d, J=6 Hz), 7.22–7.40 (3H, m), 7.42–7.59 (2H, m), 8.39 (1H, d, J=6 Hz), 8.90 (1H, d, J=8 Hz), (2) To a suspension of 8-(2,6-dichlorobenzoylamino)-4-(2-aminoethylamino)quinoline (250 mg) in dioxane (3 ml) was added 1,1'-carbonyldiimidazole (119 mg) at ambient temperature, and the mixture was stirred for 1 hour at the same temperature. To the mixture was added a solution of 1,8-diazabicyclo[5.4.0]undec-7-ene (112 mg) in dioxane (1 ml), and the mixture was stirred at 70° C. for 2 hours. The mixture was concentrated in vacuo, and the residue was crystallized from ethanol to give 8-(2,6-dichlorobenzoylamino)-4-(2-oxoimidazolidin-71-yl) quinoline (200 mg).

mp: 265–269° C. NMR (DMSO-d₆, δ): 3.55 (2H, t, J=8 Hz), 4.02 (2H, t, J=8 Hz), 7.31 (1H, br s), 7.47–7.65 (5H, m), 7.80 (1H, d, J=8 Hz), 8.70 (1H, d, J=8 Hz), 8.81 (1H, d, J=5 Hz)

Example 93

(1) 8-(2,6-Dichlorobenzoylamino)-4-[2-(N-methylamino) ethylamino]quinoline was obtained by reacting 4-chloro-8-(2,6-dichlorobenzoylamino)quinoline with N-methylethylenediamine according to a similar manner to that of Example 8.

mp: 172–175° C. NMR (CDCl₃, δ): 2.49 (3H, s), 2.99 (2H, t, J=8 Hz), 3.30–3.40 (2H, m), 5.32–5.41 (1H, m), 6.43 (1H, d, J=6 Hz), 7.26–7.56 (5H, m), 8.38 (1H, d, J=6 Hz), 8.88 (1H; d, J=8 Hz)

(2) 8-(2,6-Dichlorobenzoylamino)-4-(3-methyl-2-oxoimidazolidin-1-yl)quinoline was obtained according to a similar manner to that of Example 92-(2).

mp: 238–242° C. NMR (CDCl₃, δ): 2.98 (3H, s), 3.65 (2H, t, J=8 Hz), 3.96 (2H, t, J=8 Hz), 7.29–7.45 (4H, m), 7.60 (1H, t, J=8 Hz), 7.75 (1H, d, J=8 Hz), 8.25 (1H, d, J=6 Hz), 8.97 (1H, d, J=8 Hz)

(3) 8-(2,6-Dichlorobenzoylamino)-4-(3-methyl-2-thioxoimidazolidin-1-yl)quinoline was obtained by reacting 8-(2,6-dichlorobenzoylamino)-4-[2-(N-methylamino) ethylamino]-quinoline with 1,1'-thiocarbonyldiimidazole according to a similar manner to that of Example 92-(2).

mp: 295° C. NMR (CDCl₃, δ): 3.30 (3H, s), 3.87–4.09 (4H, m), 7.27–7.42 (3H, m), 7.50 (1H, d, J=5 Hz), 7.59–7.69 (2H, m), 8.81 (1H, d, J=5 Hz), 8.96 (1H, dd, J=8, 5 Hz)

(4) To a solution of 8-(2,6-dichlorobenzoylamino)-4-(2-methylaminoethylamino)quinoline (120 mg) in tetrahydrofuran (2.5 ml) was added 1,11-carbonyldiimidazole (90 mg) under ice-cooling, and the mixture was stirred for 2 hours at ambient temperature. The mixture was concentrated in vacuo, and the residue was crystallized from ethanol to give 8-(2,6-dichlorobenzoylamino)-4-[2-[N-(1-imidazolylcarbonyl)-N-methylamino]ethylamino]quinoline (148 mg).

mp: 202° C. NMR (DMSO-d₆, δ): 3.08 (3H, s), 3.56–3.74 (4H, m), 6.66 (1H, m), 6.97 (1H, s), 7.36–7.62 (6H, m), 7.92 (1H, d, J=8 Hz), 7.98 (1H, br s), 8.35 (1H, d, J=6 Hz), 8.63 (1H, d, J=8 Hz)

Example 94

(1) 4-(2-Methylaminoethylamino)-8-nitroquinazoline was obtained by reacting 4-chloro-8-nitroquinazoline with N-methylethylenediamine according to a similar manner to that of Example 8.

mp: 166–169° C. NMR (DMSO-d₆, δ): 2.31 (3H, s), 2.73 (2H, t, J=6 Hz), 3.63 (2H, t, J=6 Hz), 7.62 (1H, t, J=7 Hz), 8.22 (1H, d, J=7 Hz), 8.50 (1H, d, J=7 Hz), 8.51 (1H, s)

(2) 4-(3-Methyl-2-oxoimidazolidin-1-yl)-8-nitroquinazoline was obtained according to a similar manner to that of Example 92-(2).

mp: 207–210° C. NMR (CDCl₃, δ): 3.01 (3H, s), 3.67 (2H, t, J=6 Hz), 4.23 (2H, t, J=6 Hz), 7.59 (1H, t, J=7 Hz), 8.20 (1H, d, J=7 Hz), 8.48 (1H, d, J=7 Hz), 9.10 (1H, s)

(3) 8-Amino-4-(3-methyl-2-oxoimidazolidin-1-yl) quinazoline was obtained according to a similar manner to that of Preparation 2-(3).

mp: 187–189° C. NMR (DMSO-d₆, δ): 2.84 (3H, s), 3.56 (2H, t, J=6 Hz), 4.07 (2H, t, J=6 Hz), 5.92 (2H, br s), 6.99 (1H, d, J=7 Hz), 7.22 (1H, d, J=7 Hz), 7.28 (1H, t, J=7 Hz), 8.87 (1H, s)

(4) 8-(2,6-Dichlorobenzoylamino)-4-(3-methyl-2-oxoimidazolidin-1-yl)quinazoline was obtained according to a similar manner to that of Example 1.

mp: >250° C. NMR (DMSO-d₆, δ): 2.88 (3H, s), 3.60 (2H, t, J=6 Hz), 4.12 (2H, t, J=6 Hz), 7.45–7.58 (3H, m), 7.62 (1H, t, J=7 Hz), 7.98 (1H, d, J=7 Hz), 8.79 (1H, d, J=7 Hz), 9.00 (1H, s)

Example 95

8-(2,6-Dichlorobenzoylamino)-4-(3,4,5,6-tetrahydro-2 (1H)-pyrimidinon-1-yl)quinoline was obtained by reacting 4-(3-aminopropylamino)-8-(2,6-dichlorobenzoylamino)quinoline with 1,1'-carbonyldiimidazole according to a similar manner to that of Example 92-(2).

mp: >250° C. NMR (CDCl₃, δ): 2.08–2.40 (2H, br), 3.50–3.60 (2H, m), 3.64–3.82 (2H, m), 5.18 (1H, s), 7.29–7.43 (4H, m), 7.59–7.62 (2H, m), 8.79 (1H, d, J=5 Hz), 8.91–9.00 (1H, m)

Example 96

4-(Benzimidazolidon-1-yl)-8-(2,6-dichlorobenzoylamino)quinoline was obtained by reacting 4-(2-aminophenylamino)-8 -(2,6-dichlorobenzoylamino)quinoline with 1,1'-carbonyldiimidazole according to a similar manner to that of Example 92-(2).

mp: 246–248° C. NMR (CDCl₃, δ): 6.70 (1H, d, J=8 Hz), 7.01–7.25 (3H, m), 7.32–7.50 (4H, m), 7.58–7.68 (2H, m), 8.98 (1H, d, J=5 Hz), 9.06 (1H, d, J=8 Hz), 9.31 (1H, s)

Example 97

4-(1H-Imidazo[4,5-b]pyridin-2-ylthio)-8-(2,6-dichlorobenzoylamino)quinoline hydrochloride was obtained by reacting 4-chloro-8-(2,6-dichlorobenzoylamino)quinoline with 2-mercapto-1H-imidazo[4,5-b]pyridine according to a similar manner to that of Example 25.

mp: 182–190° C. NMR (DMSO-d₆, δ): 7.44–7.63 (4H, m), 7.77 (1H, t, J=8 Hz), 7.88 (1H, d, J=4 Hz), 8.01 (1H, d, j=8 Hz), 8.25 (1H, d, J=8 Hz), 8.46 (1H, d, J=4 Hz), 8.80 (1H, d, J=8 Hz), 8.91 (1H, d, J=4 Hz)

Example 98

(1) 3-Chloro-1,4-dihydro-8-nitro-4-oxoquinoline was obtained by reacting 1,4-dihydro-8-nitro-4-oxoquinoline with N-chlorosuccinimide according to a similar manner to that of Preparation 6-(1).

mp: 290–297° C. NMR (DMSO-d₆, δ): 7.59 (1H, t, J=8 Hz), 8.26 (1H, s), 8.61 (1H, dd, J=8, 2 Hz), 8.78 (1H, dd, J=8, 2 Hz)

(2) 3,4-Dichloro-8-nitroquinoline was obtained according to a similar manner to that of Preparation 2-(1).

mp: 123° C. NMR (CDCl₃, δ): 7.76 (1H, t, J=8 Hz), 8.06 (1H, d, J=8 Hz), 8.45 (1H, d, J=8 Hz), 8.98 (1H, s)

(3) 4-[Bis(ethoxycarbonyl)methyl]-3-chloro-8-nitroquinoline was obtained according to a similar manner to that of Preparation 7-(1).

mp: 101.5° C. 5 NMR (CDCl₃, δ): 1.23 (6H, t, J=8 Hz), 4.14–4.33 (4H, m), 5.75 (1H, s), 7.67 (1H, t, J=8 Hz), 7.99 (1H, d, J=8 Hz), 8.27 (1H, d, J=8 Hz), 9.02 (1H, s)

(4) 3-Chloro-4-(ethoxycarbonylmethyl)-8-nitroquinoline was 10 obtained according to a similar manner to that of Preparation 7-(2). imp 156° C. NMR (CDCl₃, δ): 1.23 (3H, t, J=8 Hz), 4.18 (2H, q, J=8 Hz), 4.30 (2H, s), 7.70 (1H, t, J=8 Hz), 8.00 (1H, d, J=8 Hz), 8.16 (1H, d, J=8 Hz), 8.98 (1H, s)

(5) 8-Amino-3-chloro-4-(ethoxycarbonylmethyl)quinoline was obtained according to a similar manner to that of Preparation 2-(3). 20 mp: 144° C. NMR (CDCl₃, δ): 1.21 (3H, t, J=8 Hz), 4.14 (2H, q, J=8 Hz), 4.20 (2H, s), 5.01 (2H, br s), 6.90 (1H, d, J=8 Hz), 7.20 (1H, d, J=8 Hz), 7.38 (1H, t, J=8 Hz), 8.67 (1H, s) 25

(6) 3-Chloro-8-(2,6-dichlorobenzoylamino)-4-(ethoxycarbonylmethyl)quinoline was obtained according to a similar manner to that of Example 1.

mp: 161° C. 30 NMR (CDCl₃, δ): 1.23 (3H, t, J=8 Hz), 4.18 (2H, q, J=8 Hz), 4.26 (2H, s), 7.30–7.45 (3H, m), 7.66–7.71 (2H, m), 8.70 (1H, s), 8.91–9.01 (1H, s)

(7) 4-Carboxymethyl-3-chloro-8-(2,6-dichlorobenzoylamino)quinoline was obtained according to a similar manner to that of Example 18.

mp: 257–259° C. NMR (DMSO-d₆, δ): 4.31 (2H, s), 7.47–7.61 (3H, m), 7.75 (1H, t, J=8 Hz), 7.96 (1H, d, J=8 Hz), 8.72 (1H, d, J=8 Hz), 8.99 (1H, s)

(8) 4-Carbamoylmethyl-3-chloro-8-(2,6-dichlorobenzoylamino)quinoline was obtained according to a similar manner to that of Example 22-(2).

mp: >300° C. NMR (DMSO-d₆, δ): 4.17 (2H, s), 7.20 (1H, br s), 7.46–7.61 (3H, m), 7.70 (1H, br s), 7.72 (1H, t, J=8 Hz), 7.90 (1H, d, j=8 Hz), 8.70 (1H, d, J=8 Hz), 8.86 (1H, s)

(9) 3-Chloro-8-(2,6-dichlorobenzoylamino)-4-methylquinoline was obtained from 3-chloro-8-(2,6-dichlorobenzoylamino)-4-(ethoxycarbonylmethyl)quinoline according to a similar manner to that of Example 37.

mp: 259° C. NMR (DMSO-d₆, δ): 2.76 (3H, s), 7.46–7.60 (3H, m), 7.75 (1H, t, J=8 Hz), 7.96 (1H, d, J=8 Hz), 8.70 (1H, d, J=8 Hz), 8.80 (1H, d, J=8 Hz)

Example 99

Cerium(III) chloride heptahydrate (580 mg) was dried at 150° C. under reduced pressure, cooled to ambient temperature under nitrogen atmosphere and suspended in tetrahydrofuran (2 ml). To the suspension were added 3-bromo-8-(2,6-dichlorobenzoylamino)-4-(ethoxycarbonylmethyl)quinoline (300 mg) and 0.9M solution of methylmagnesium bromide in tetrahydrofuran (3.5 ml) under ice-cooling, and the mixture was stirred for 1 hour. The mixture was poured into saturated ammonium chloride solution and extracted with ethyl acetate. The organic layer was washed with brine, dried over magnesium sulfate and evaporated in vacuo. The residue was crystallized from isopropyl alcohol to give 3-bromo-8-(2,6-dichlorobenzoylamino)-4-(2-hydroxy-2-methylpropyl)quinoline (216 mg).

mp: 260–262° C. NMR (CDCl₃, δ): 1.38 (6H, s), 3.56 (2H, s), 7.30–7.55 (3H, m), 7.67 (1H, t, J=8 Hz), 8.02 (1H, d, J=8 Hz), 8.82 (1H, s), 8.97 (1H, d, J=8 Hz)

Example 100

To a mixture of 3-carboxy-8-(2,6-dichlorobenzoylamino)-4-(imidazol-1-yl)quinoline (147.6 mg) and triethylamine (12.2 mg) in dioxane was added diphenylphosphoryl azide (99.8 mg) at 90° C., and the mixture was stirred for 2 hours at the same temperature. After cooling to 70° C., methanol (12.2 mg) was added thereto and the mixture was stirred for 1 hour at 85° C. The mixture was partitioned between ethyl acetate and water. The organic layer was washed with brine, dried over magnesium sulfate and evaporated in vacuo. The residue was purified by preparative thin layer chromatography (methanoldichloromethane) and crystallized from isopropyl alcohol to give 8-(2,6-dichlorobenzoylamino)-4-(imidazol-1-yl)-3-(methoxycarbonylamino)quinoline (21.3 mg).

mp: 236–238° C. NMR (CDCl₃, δ): 3.78 (3H, s), 6.59 (1H, br s), 6.96 (1H, d, J=8 Hz), 7.12 (1H, br s), 7.30–7.50 (4H, m), 7.60 (1H, t, J=8 Hz), 7.65 (1H, br s), 8.93 (1H, d, J=8 Hz), 9.67 (1H, s)

Example 101

(1) 3-tert-Butoxycarbonylamino-8-(2,6-dichlorobenzoylamino)-4-(imidazol-1-yl)quinoline was obtained from 3-carboxy-8-(2,6-dichlorobenzoylamino)-4-(imidazol-1-yl)quinoline and tert-butanol according to a similar manner to that of Example 100.

mp: 205–206° C. NMR (CDCl$_3$, δ): 1.50 (9H, s), 6.30 (1H, s), 6.94 (1H, d, J=8 Hz), 7.13 (1H, s), 7.30–7.50 (4H, m), 7.59 (1H, t, J=8 Hz), 7.67 (1H, s), 8.91 (1H, d, J=8 Hz), 9.69 (1H, s)

(2) To a solution of 3-tert-butoxycarbonylamino-8-(2,6-dichlorobenzoylamino)-4-(imidazol-1-yl)quinoline (869 mg) in dichloromethane (2 ml) was added trifluoroacetic acid (5 ml) under ice-cooling, and the mixture was stirred for 2 hours at ambient temperature. The mixture was partitioned between dichloromethane and saturated sodium bicarbonate solution. The organic layer was washed with brine, dried over magnesium sulfate and evaporated in vacuo. The residue was crystallized from isopropyl alcohol to give 3-amino-8-(2,6-dichlorobenzoylamino)-4-(imidazol-1-yl) quinoline (581.4 mg).

mp: >250° C. NMR (CDCl$_3$, δ): 4.01 (2H, s), 6.93 (1H, d, J=8 Hz), 7.12 (1H, s), 7.30–7.50 (4H, m), 7.53 (1H, t, J=8 Hz), 7.68 (1H, s), 8.51 (1H, s), 8.77 (1H, d, J=8 Hz), 9.88 (1H, s)

its dihydrochloride mp: 248–250° C. NMR (DMSO-d$_6$, δ): 6.23 (2H, br), 6.68 (1H, d, J=8 Hz), 7.45–7.60 (4H, m), 7.95 (1H, s), 8.09 (1H, s), 8.42 (1H, d, J=8 Hz), 8.71 (1H, s), 9.52 (1H, s)

Example 102

8-(2,6-Dichlorobenzoylamino)-4-(imidazol-1-yl)-3-(4-pyridylthio)quinoline was obtained by reacting 3-bromo-8-(2,6-dichlorobenzoylamino)-4-(imidazol-1-yl)quinoline with 4-mercaptopyridine according to a similar manner to that of Example 25.

mp: 218–220° C. NMR (DMSO-d$_6$, δ): 7.10–7.20 (4H, m), 7.45–7.60 (4H, m), 7.82 (1H, t, J=7 Hz), 7.90 (1H, s), 8.34 (2H, d, J=5 Hz), 8.86 (1H, d, J=7 Hz), 9.03 (1H, s)

its dimethanesulfonate mp: >250° C. NMR (DMSO-d$_6$, δ): 2.32 (6H, s), 7.34 (1H, d, J=7 Hz), 7.48–7.62 (5H, m), 7.88 (1H, s), 7.91 (1H, t, J=7 Hz), 7.97 (1H, s), 8.55 (2H, d, J=6 Hz), 8.94 (1H, d, J=7 Hz), 9.21 (1H, s), 9.23 (1H, s)

Example 103

8-(2,6-Dichlorobenzoylamino)-4-(imidazol-1-yl)-3-(methylthio)quinoline hydrochloride was obtained by reacting 3-bromo-8-(2,6-dichlorobenzoylamino)-4-(imidazol-1-yl)quinoline with sodium thiomethoxide according to a similar manner to that of Preparation 13.

mp: 212–216° C. NMR (DMSO-d$_6$, δ): 2.19 (3H, s), 7.12 (1H, d, J=7 Hz), 7.47–7.63 (3H, m), 7.77 (1H, t, J=7 Hz), 8.02 (2H, br s), 8.73 (1H, d, J=7 Hz), 9.14 (1H, s), 9.38 (1H, br s)

Example 104

(1) A suspension of 3-chloromethyl-1,4-dihydro-8-nitro-4-oxoquinoline (2.0 g) in water (30 ml) was refluxed for 15 minutes and allowed to stand to ambient temperature. The resulting precipitates were collected by filtration and washed with water to give 1,4-dihydro-3-hydroxymethyl-8-nitro-4-oxoquinoline (1.82 g). mpD 182–184° C. NMR (DMSO-d$_6$, δ): 4.41 (2H, s), 5.14 (1H, br), 7.49 (1H, t, J=7 Hz), 8.00 (1H, s), 8.59 (1H, d, J=7 Hz), 8.66 (1H, d, J=7 Hz)

(2) To a solution of 1,4-dihydro-3-hydroxymethyl-8-nitro-4-oxoquinoline (3.1 g) in trifluoroacetic acid (10 ml) and dichloromethane (10 ml) was added triethylsilane (6.55 g), and the mixture was stirred at ambient temperature overnight. The mixture was partitioned between dichloromethane and saturated sodium bicarbonate solution. The organic layer was washed with brine, dried over sodium sulfate and evaporated in vacuo. The residue was purified by column chromatography on silica gel to give 1,4-dihydro-3-methyl-8-nitro-4-oxoquinoline (2.3 g).

mp: 235–243° C. NMR (CDCl$_3$, δ): 2.16 (3H, s), 7.41 (1H, t, J=7 Hz), 7.69 (1H, d, J=7 Hz), 8.65 (1H, d, J=7 Hz), 8.82 (1H, d, J=7 Hz)

(3) 4-Chloro-3-methyl-8-nitroquinoline was obtained according to a similar manner to that of Preparation 2-(1).

mp: 126° C. NMR (CDCl$_3$, δ): 2.61 (3H, s), 7.68 (1H, t, J=8 Hz), 8.00 (1H, d, J=8 Hz), 8.46 (1H, d, J=8 Hz), 8.88 (1H, s)

(4) 8-Amino-4-chloro-3-methylquinoline was obtained according to a similar manner to that of Preparation 2-(3).

mp: 112–114° C. NMR (CDCl$_3$, δ): 2.54 (3H, s), 4.99 (2H, br s), 6.90 (1H, d, J=8 Hz), 7.38 (1H, t, J=8 Hz), 7.50 (1H, d, J=8 Hz), 8.55 (1H, s)

(5) 4-Chloro-8-(2,6-dichlorobenzoylamino)-3-methylquinoline was obtained according to a similar manner to that of Example 1.

mp: 216–227° C. NMR (CDCl$_3$, δ): 2.57 (3H, s), 7.28–7.46 (3H, m), 7.67 (1H, t, J=8 Hz), 7.96 (1H, a, J=8 Hz), 8.59 (1H, s), 8.94 (1H, d, J=8 Hz)

(6) 8-(2,6-Dichlorobenzoylamino)-4-(imidazol-1-yl)-3-methylquinoline was obtained according to a similar manner to that of Example 8.

mp: 224–228° C. NMR (CDCl$_3$, δ): 2.30 (3H, s), 7.09 (1H, d, J=8 Hz), 7.10 (1H, s), 7.30–7.45 (4H, m), 7.60 (1H, t, J=8 Hz), 7.63 (1H, s), 8.77 (1H, s), 8.96 (1H, d, J=8 Hz)

its hydrochloride mp: 231–235° C. NMR (DMSO-d$_6$, δ): 2.30 (3H, s), 7.11 (1H, d, J=8 Hz), 7.47–7.66 (4H, m), 7.75 (1H, t, J=8 Hz), 8.00–8.14 (2H, m), 8.75 (1H, d, J=8 Hz), 9.08 (1H, s), 9.37 (1H, s)

Example 105

(1) 8-(2,6-Dichlorobenzoylamino)-3-methyl-4-[2-(N-methylamino)ethylamino]quinoline was obtained by reacting with 4-chloro-8-(2,6-dichlorobenzoylamino)-3-methylquinoline with N-methylethylenediamine according to a similar manner to that of Example 8.

mp: 274–278° C. NMR (DMSO-d$_6$, δ): 2.40 (3H, s), 2.56 (3H, s), 3.07–3.20 (2H, m), 3.69–3.75 (2H, m), 6.19 (1H, br t, J=7 Hz), 7.41–7.66 (4H, m), 8.03 (1H, d, J=8 Hz), 8.37 (1H, s), 8.59 (1H, d, j=8 Hz), 8.74 (1H, br s)

(2) 8-(2,6-Dichlorobenzoylamino)-3-methyl-4-(3-methyl-2-oxoimidazolidin-1-yl)quinoline was obtained according to a similar manner to that of Example 92-(2).

mp: 288° C. NMR (DMSO-d$_6$, δ): 2.36 (3H, s), 2.81 (3H, s), 3.56–3.86 (4H, m), 7.46–7.61 (3H, m), 7.65–7.70 (2H, m), 8.65 (1H, t, J=8 Hz), 8.85 (1H, s)

Example 106

(1) 8-(2,6-Dichlorobenzoylamino)-4-(imidazol-1-yl)-3-vinylquinoline was obtained from 3-bromo-8-(2,6-dichlorobenzoylamino)-4-(imidazol-1-yl)quinoline and tri-n-butyl(vinyl)tin according to a similar manner to that of Preparation 14.

mp: 194–195° C. NMR (CDCl$_3$, δ): 5.53 (1H, d, J=11 Hz), 5.96 (1H, d, J=15 Hz), 6.45 (1H, dd, J=11, 15 Hz), 7.10–7.20 (2H, overlapping), 7.30–7.50 (3H, m), 7.63 (1H, t, J=8 Hz), 7.66 (1H, s), 9.00 (1H, d, J=8 Hz), 9.10 (1H, s)

(2) 8-(2,6-Dichlorobenzoylamino)-3-ethyl-4-(imidazol-1-yl)quinoline was obtained according to a similar manner to that of Example 41.

mp: 187–188° C. NMR (CDCl$_3$, δ): 1.21 (3H, t, J=7 Hz), 2.63 (2H, q, J=7 Hz), 7.05 (1H, d, J=8 Hz), 7.13 (1H, s), 7.30–7.50 (4H, m), 7.60 (1H, t, J=8 Hz), 7.64 (1H, s), 8.82 (1H, s), 8.98 (1H, d, J=8 Hz)

its hydrochloride mp: 238–242° C. NMR (DMSO-d$_6$, δ): 1.16 (3H, t, J=7 Hz), 2.59 (2H, q, J=7 Hz), 7.07 (1H, d, J=8 Hz), 7.50–7.60 (3H, m), 7.75 (1H, t, J=8 Hz), 8.04 (1H, s), 8.10 (1H, s), 8.77 (1H, d, J=8 Hz), 9.12 (1H, s), 9.41 (1H, s)

Example 107

8-(2,6-Dichlorobenzoylamino)-3-ethyl-4-(2-methylimidazol-1-yl)quinoline was obtained from 3-bromo-8-(2,6-dichlorobenzoylamino)-4-(2-methylimidazol-1-yl) quinoline according to a similar manner to that of Example 106-(1) and (2).

NMR (CDCl$_3$, δ): 1.20 (3H, t, J=8 Hz), 2.10 (3H, s), 2.46–2.70 (2H, m), 6.90 (1H, d, J=8 Hz), 6.95 (1H, s), 7.20–7.71 (5H, m), 8.81 (1H, s), 8.97 (1H, d, J=8 Hz)
its hydrochloride mp: 169–176° C. NMR (DMSO-d$_6$, δ): 1.17 (3H, t, J=8 Hz), 2.36 (3H, s), 2.40–2.56 (1H, m), 2.58–2.76 (1H, m), 7.05 (1H, d, J=8 Hz), 7.48–7.63 (3H, m), 7.74 (1H, t, J=8 Hz), 7.98–8.07 (2H, m), 8.76 (1H, d, J=8 Hz), 9.13 (1H, s)

Example 108

(1) To a solution of 4-carboxymethyl-8-(2,6-dichlorobenzoylamino)-3-ethylquinoline (405 mg) in dimethylformamide were added potassium carbonate (305 mg) and methyl iodide (314 mg) and the mixture was stirred for 2 hours at ambient temperature. The mixture was partitioned between ethyl acetate and water. The organic layer was washed with brine, dried over magnesium sulfate and evaporated in vacuo. The residue was purified by column chromatography on silica gel (ethyl acetate: n-hexane, 1:3, v/v) and crystallized from ethanol-water to give 8-(2,6-dichlorobenzoylamino)-3-ethyl-4-(methoxycarbonylmethyl)quinoline (282 mg).

mp: 167–168° C. NMR (CDCl$_3$, δ): 1.28 (3H, t, J=7 Hz), 2.90 (2H, q, J=7 Hz), 3.69 (3H, s), 4.64 (2H, s), 7.30–7.45 (3H, m), 7.62 (1H, t, J=8 Hz), 7.72 (1H, d, J=8 Hz), 8.63 (1H, s), 8.90 (1H, d, J=8 Hz)

(2) 8-(2,6-Dichlorobenzoylamino)-3-ethyl-4-(2-hydroxy-2-methylpropyl)quinoline was obtained according to a similar manner to that of Example 99.

mp: 203–204° C. NMR (CDCl$_3$, δ): 1.24 (3H, t, J=7 Hz), 1.33 (6H, s), 2.97 (2H, q, J=7 Hz), 3.38 (2H, s), 7.30–7.45 (3H, m), 7.59 (1H, t, J=8 Hz), 7.91 (1H, d, J=8 Hz), 8.63 (1H, s), 8.88 (1H, d, J=8 Hz)

Example-109

4-Carbamoylmethyl-8-(2,6-dichlorobenzoylamino)-3-ethylquinoline was obtained from 4-carboxymethyl-8-(2,6-dichlorobenzoylamino)-3-ethylquinoline and conc. ammonia solution according to a similar manner to that of Example 22-(2).

mp: 180–182° C. NMR (DMSO-d$_6$, δ): 1.21 (3H, t, J=7 Hz), 2.86 (2H, q, J=7 Hz), 4.02 (2H, s), 7.12 (2H, br s), 7.50–7.65 (4H, m), 7.71 (1H, br s), 7.87 (1H, d, j=8 Hz), 8.64 (1H, d, J=8 Hz), 8.73 (1H, s)
its hydrochloride mp: 223–227° C. NMR (DMSO-d$_6$, δ): 1.20 (3H, t, J=7 Hz), 2.87 (2H, q, J=7 Hz), 4.03 (2H, s), 7.13 (1H, br s), 7.50–7.65 (4H, m), 7.73 (1H, br s), 7.88 (1H, d, J=8 Hz), 8.64 (1H, d, J=8 Hz), 8.74 (1H, s)

Example 110

(1) To a solution of 3-bromo-4-carboxymethyl-8-(2,6-dichlorobenzoylamino)quinoline (130 mg) in dry tetrahydrofuran was added 10M solution of borane-methyl sulfide complex in tetrahydrofuran (0.286 ml) at ambient temperature, and the mixture was stirred for 4 hours at the same temperature. The mixture was quenched by 1N hydrochloric acid and stirred for 1 hour at the same temperature. The mixture was extracted with ethyl acetate, and the extract was washed with saturated sodium bicarbonate solution and brine, dried over magnesium sulfate and evaporated in vacuo. The residue was purified by column chromatography on silica gel (ethyl acetate: n-hexane, 1:2, v/v) and crystallized from ethyl acetate-n-hexane to give 3-bromo-8-(2,6-dichlorobenzoylamino)-4-(2-hydroxyethyl)quinoline (68.4 mg).

mp: 199–200° C. NMR (CDCl$_3$, δ): 1.53 (1H, t, J=6 Hz), 3.58 (2H, t, J=6 Hz), 4.01 (2H, q, J=6 Hz), 7.30–7.45 (3H, m), 7.68 (1H, t, J=8 Hz), 7.87 (1H, d, J=8 Hz), 8.79 (1H, s), 8.98 (1H, d, J=8 Hz)

(2) 8-(2,6-Dichlorobenzoylamino)-4-(2-hydroxyethyl]-3-vinylquinoline was obtained according to a similar manner to that of Preparation 14.

mp: 133–135° C. NMR (CDCl$_3$, δ): 1.50 (1H, t, J=6 Hz), 3.48 (2H, t, J=6 Hz), 3.97 (2H, q, J=6 Hz), 5.58 (1H, d, J=11 Hz), 5.84 (1H, d, J=17 Hz), 7.22 (1H, dd, J=11, 17 Hz), 7.30–7.50 (3H, m), 7.65 (1H, t, J=8 Hz), 7.86 (1H, d, J=8 Hz), 8.89 (1H, s), 8.94 (1H, d, J=8 Hz)
its hydrochloride mp: 187–203° C. NMR (DMSO-d$_6$, δ): 3.36 (2H, t, J=6 Hz), 3.65 (2H, t, J=6 Hz), 5.57 (1H, d, J=11 Hz), 5.98 (1H, d, J=17 Hz), 7.27 (1H, dd, J=11, 17 Hz), 7.50–7.60 (3H, m), 7.67 (1H, t, J=8 Hz), 8.00 (1H, d, J=8 Hz), 8.67 (1H, d, J=8 Hz), 9.00 (1H, s)

(3) 8-(2,6-Dichlorobenzoylamino)-3-ethyl-4-(2-hydroxyethyl)quinoline was obtained according to a similar manner to that of Example 41.

mp: 180–182° C. NMR (CDCl$_3$, δ): 1.31 (3H, t, J=7 Hz), 1.51 (1H, t, J=6 Hz), 2.92 (2H, q, J=7 Hz), 3.42 (2H, t, J=6 Hz), 3.97 (1H, q, J=6 Hz), 7.30–7.45 (3H, m), 7.61 (1H, t, J=8 Hz), 7.80 (1H, d, J=8 Hz), 8.60 (1H, s), 8.89 (1H, d, J=8 Hz)

(4) To a solution of 8-(2,6-dichlorobenzoylamino)-3-ethyl-4-(2-hydroxyethyl)quinoline (405 mg) in dichloromethane were added N-bromosuccinimide (241 mg) and triphenylphosphine (355 mg) under water cooling, and the mixture was stirred for 30 minutes at the same temperature. The mixture was concentrated in vacuo, and the residue was purified by column chromatography on silica gel (dichloromethane) and crystallized from n-hexane to give 4-(2-bromoethyl)-8-(2,6-dichlorobenzoylamino)-3-ethylquinoline (424 mg).

mp: 187–188° C. NMR (CDCl$_3$, δ): 1.32 (3H, t, J=7 Hz), 2.90 (2H, q, J=7 Hz), 3.62 (4H, m), 7.30–7.45 (3H, m), 7.65 (1H, t, J=8 Hz), 7.73 (1H, d, J=8 Hz), 8.62 (1H, s), 8.92 (1H, d, J=8 Hz), 10.14 (1H, br s)

Example 111

8-(2,6-Dichlorobenzoylamino)-3-ethyl-4-[2-(imidazol-2-ylthio)ethyl]quinoline was obtained by reacting 4-(2-bromoethyl)-8-(2,6-dichlorobenzoylamino)-3-ethylquinoline with 2-mercaptoimidazole according to a similar manner to that of Example 62.

mp: 214–215° C. NMR (DMSO-d$_6$, δ): 1.18 (3H, t, J=7 Hz), 2.81 (2H, q, J=7 Hz), 3.20 (2H, m), 3.44 (2H, m), 7.16 (2H, br s), 7.50–7.70 (4H, m), 7.93 (1H, d, J=8 Hz), 8.65 (1H, d, J=8 Hz), 8.71 (1H, s)
its dihydrochloride mp: 233–235° C. NMR (DMSO-d$_6$, δ): 1.18 (3H, t, J=7 Hz), 2.79 (2H, q, J=7 Hz), 3.42 (2H, m), 3.55 (2H, m), 7.50–7.60 (3H, m), 7.65 (1H, t, J=8 Hz), 7.72 (2H, s), 7.79 (1H, d, J=8 Hz), 8.66 (1H, d, J=8 Hz), 8.73 (1H, s)

Example 112

The following compounds were obtained from 4-(2-bromoethyl)-8-(2,6-dichlorobenzoylamino)-3-ethylquinoline and amine or imine compound according to a similar manner to that of Example 8.

(1) 8-(2,6-Dichlorobenzoylamino)-4-[2-(N,N-dimethylamino)ethyl]-3-ethylquinoline mp: 73–75° C. NMR (CDCl$_3$, δ): 1.81 (3H, t, j=7 Hz), 2.41 (6H, s), 2.55 (1H, m), 2.87 (2H, q, J=7 Hz), 3.28 (2H, m), 7.30–7.45 (3H, m), 7.61 (1H, t, J=8 Hz), 7.78 (1H, d, J=8 Hz), 8.58 (1H, s), 8.89 (1H, d, J=8 Hz)

(2) 8-(2,6-Dichlorobenzoylamino)-3-ethyl-4-[2-[N-(2-hydroxyethyl)-N-methylamino]ethyl]quinoline mp: 123–125° C. NMR (DMSO-d$_6$, δ): 1.27 (3H, t, J=7 Hz), 2.38 (3H, s), 2.56 (2H, t, J=6 Hz), 2.62 (2H, m), 2.87 (2H, q, J=7 Hz), 3.25 (2H, m), 3.50 (2H, q, J=6 Hz), 4.42 (1H, t, J=6 Hz), 7.45–7.60 (3H, m), 7.66 (1H, t, J=8 Hz), 7.79 (1H, d, J=8 Hz), 9.65 (1H, d, J=7 Hz), 9.71 (1H, s)

(3) 8-(2,6-Dichlorobenzoylamino)-3-ethyl-4-[2-(imidazol-1-yl)ethyl]quinoline mp: 190–191° C. NMR (DMSO-d$_6$, δ): 1.17 (3H, t, J=7 Hz), 2.67 (2H, q, J=7 Hz), 3.55 (2H, t, J=7 Hz), 4.27 (2H, t, J=7 Hz), 6.86 (1H, s), 7.20 (1H, s), 7.45–7.65 (4H, m), 7.66 (1H, t, J=8 Hz), 7.96 (1H, d, J=8 Hz), 8.67 (1H, d, J=8 Hz), 8.71 (1H, s)

its dihydrochloride mp: 219–222° C. NMR (DMSO-d$_6$, δ): 1.20 (3H, t, J=7 Hz), 2.77 (2H, q, J=7 Hz), 3.69 (2H, t, J=7 Hz), 4.48 (2H, t, J=7 Hz), 7.50–7.65 (3H, m), 7.67 (1H, t, J=8 Hz), 7.68 (1H, s), 7.89 (1H, s), 7.97 (1H, d, J=8 Hz), 8.68 (1H, d, J=8 Hz), 8.76 (1H, s), 9.13 (1H, s)

(4) 4-[2-(1H-Benzimidazol-1-yl)ethyl]-8-(2,6-dichlorobenzoylamino)-3-ethylquinoline mp: 196–1907° C. NMR (DMSO-d$_6$, δ): 1.08 (3H, t, J=7 Hz), 2.56 (2H, q, J=7 Hz), 3.65 (2H, t, J=7 Hz), 4.58 (2H, t, J=7 Hz), 7.15–7.25 (2H, m), 7.43 (1H, dd, J=3, 7 Hz), 7.45–7.70 (5H, m), 7.95 (1H, d, J=8 Hz), 8.09 (1H, s), 8.67 (1H, s), 8.68 (1H, d, J=8 Hz)

its dihydrochoride mp: 236–238° C. NMR (DMSO-d$_6$, δ): 1.17 (3H, t, j=7 Hz), 2.75 (2H, q, J=7 Hz), 3.83 (2H, t, J=7 Hz), 4.78 (2H, t, J=7 Hz), 7.50–7.70 (6H, m), 7.80–7.95 (3H, m), 8.68 (!H, d, J=8 Hz), 8.75 (1H, s), 9.65 (1H, s)

Example 113

(1) To a solution of 8-(2,6-dichlorobenzoylamino)-3-ethyl-4-hydroxymethylquinoline (300 mg) and triethylamine (404 mg) in dimethyl sulfoxide (3 ml) and dichloromethane (1 ml) was added sulfur trioxide pyridine complex (191 mg) under ice-cooling, and the mixture was stirred for 1 hour at the same temperature. The mixture was partitioned between dichloroethane and water, and the organic layer was washed with water, dried over magnesium sulfate and evaporated in vacuo to give 8-(2,6-dichlorobenzoylamino).-3-ethyl-4-formylquinoline (235 mg).

mp: 208° C. NMR (CDCl$_3$, δ): 1.37 (3H, t, J=8 Hz), 3.14 (2H, q, J=8 Hz), 7.30–7.47 (3H, m), 7.72 (1H, t, J=8 Hz), 8.38 (1H, d, J=8 Hz), 8.76 (1H, s), 8.96 (1H, d, J=8 Hz), 10.95 (1H, s)

(2) 8-(2,6-Dichlorobenzoylamino)-4-((E)-2-ethoxycarbonylvinyl)-3-ethylquinoline was obtained according to a similar manner to that of Preparation 19-(2).

mp: 115–118° C. NMR (CDCl$_3$, δ): 1.27 (3H, t, J=7 Hz), 1.40 (3H, t, J=7 Hz), 2.86 (2H, q, J=7 Hz), 4.35 (2H, q, J=7 Hz), 6.30 (1H, d, J=15 Hz), 7.30–7.45 (3H, m), 7.61 (1H, t, J=8 Hz), 7.73 (1H, d, J=8 Hz), 8.07 (1H, d, J=15 Hz), 8.67 (1H, s), 8.93 (1H, d, J=8 Hz)

(3) 4-((E)-2-Carboxyvinyl)-8-(2,6-dichlorobenzoylamino)-3-ethylquinoline was obtained according to a similar manner to that of Example 18.

mp: 235–236° C. NMR (DMSO-d$_6$, δ): 1.22 (3H, t, J=7 Hz), 2.83 (2H, q, J=7 Hz), 6.28 (1H, d, J=15 Hz), 7.50–7.60 (3H, m), 7.67 (1H, t, J=8 Hz), 7.74 (1H, d, J=8 Hz), 7.99 (1H, d, J=15 Hz), 8.68 (1H, d, J=8 Hz), 8.83 (1H, s)

(4) 4-((E)-2-Carbamoylvinyl)-8-(2,6-dichlorobenzoylamino)-3-ethylquinoline was obtained according to a similar manner to that of Example 22-(2).

mp: >250° C. NMR (DMSO-d$_6$, δ): 1.22 (3H, t, J=7 Hz), 2.33 (2H, q, J=7 Hz), 6.43 (1H, d, J=15 Hz), 7.40 (1H, br s), 7.50–7.60 (3H, m), 7.67 (1H, t, J=8 Hz), 7.77 (1H, d, J=8 Hz), 7.80 (1H, br s), 7.82 (1H, d, J=15 Hz), 8.69 (1H, d, J=8 Hz), 8.82 (1H, s)

Example 114

(1) 8-(2,6-Dichlorobenzoylamino)-4-(2-ethoxycarbonylethyl)-3-ethylquinoline was obtained from 8-(2,6-dichlorobenzoyl-amino)-4-((E)-2-ethoxycarbonylvinyl)-3-ethylquinoline according to a similar manner to that of Example 41.

mp: 88–90° C. NMR (CDCl$_3$, δ): 1.29 (3H, t, J=7 Hz), 1.31 (3H, t, J=7 Hz), 2.63 (2H, t, J=7 Hz), 2.87 (2H, q, J=7 Hz), 3.43 (2H, t, J=7 Hz), 4.18 (2H, a, J=7 Hz), 7.30–7.45 (3H, m), 7.62 (1H, t, J=8 Hz), 7.75 (1H, d, J=8 Hz), 8.58 (1H, s), 8.89 (1H, d, J=8 Hz)

(2) 4-(2-Carboxyethyl)-8-(2,6-dichlorobenzoylamino)-3-ethylquinoline was obtained according to a similar manner to that of Example 18.

mp: 236–237° C. NMR (DMSO-d$_6$, δ): 1.24 (3H, t, J=7 Hz), 2.45–2.55 (2H, m), 2.88 (1H, q, J=7 Hz), 3.30–3.40 (2H, m), 7.45–7.60 (3H, m), 7.67 (1H, t, J=8 Hz), 7.90 (1H, d, J=8 Hz), 8.66 (1H, d, J=8 Hz), 8.72 (1H, s)

(3) 4-(2-Carbamoylethyl)-8-(2,6-dichlorobenzoylamino)-3-ethylquinoline was obtained according to a similar manner to that of Example 22-(2).

mp: 235–236° C. NMR (DMSO-d$_6$, δ): 1.24 (3H, t, J=7 Hz), 2.37 (2H, m), 2.88 (2H, q, J=7 Hz), 3.30–3.40 (2H, m), 6.91 (1H, br s), 7.41 (1H, br s), 7.50–7.60 (3H, m), 7.66 (1H, t, J=8 Hz), 7.92 (1H, d, J=8 Hz), 8.65 (1H, d, J=8 Hz), 8.71 (1H, s)

its hydrochloride mp: 230–232° C. NMR (DMSO-d$_6$, δ): 1.25 (3H, t, J=7 Hz), 2.38 (2H, t, J=8 Hz), 2.88 (2H, q, J=7 Hz), 3.32 (2H, t, J=8 Hz), 6.92 (1H, br s), 7.43 (1H, br s), 7.50–7.60 (3H, m), 7.67 (1H, t, J=8 Hz), 7.93 (1H, d, J=8 Hz), 8.66 (1H, d, J=8 Hz), 8.72 (1H, s)

Example 115

8-(2,6-Dichlorobenzoylamino)-3-ethyl-4-(3-hydroxy-3-methylbutyl)quinoline was obtained by reacting 8-(2,6-dichlorobenzoylamino)-4-(2-ethoxycarbonylethyl)-3-ethylquinoline with methylmagnesium bromide according to a similar manner to that of Example 99.

mp: 158–160° C. NMR (CDCl$_3$, δ): 1.33 (3H, t, j=7 Hz), 1.40 (6H, s), 1.78 (2H, m), 2.86 (2H, q, J=7 Hz), 3.21 (2H, m), 7.30–7.45 (3H, m), 7.61 (1H, t, J=8 Hz), 7.81 (1H, d, J=8 Hz), 8.58 (1H, s), 7.89 (1H, d, J=8 Hz)

its hydrochloride mp: 211–214° C. NMR (CDCl$_3$, δ): 1.41 (3H, t, J=7 Hz), 1.78 (2H, m), 2.99 (2H, q, J=7 Hz), 3.44 (2H, m), 7.30–7.45 (3H, m), 7.91 (1H, t, J=8 Hz), 8.09 (1H, d, J=8 Hz), 8.74 (1H, s), 9.14 (1H, d, J=8 Hz)

Example 116

(1) To a solution of sodium dihydrogenphosphate (395 mg) and 2-methyl-2-butene (578 mg) in tert-butanol (6 ml) and water (1.5 ml) was added 8-(2,6-dichlorobenzoylamino)-3-ethyl-4-formylquinoline (615 mg) at ambient temperature, and to the mixture was portionwise added sodium chlorite (298 mg) at the same temperature. The mixture was stirred for 3 hours at the same temperature. The mixture was quenched by diluted hydrochloric acid and extracted with dichloromethane. The extract was dried over magnesium sulfate and evaporated in vacuo. The residue was recrystallized from ethyl acetate-n-hexane to give 4-carboxy-8-(2,6-dichlorobenzoylamino)-3-ethylquinoline (404 mg).

mp: 231–233° C. NMR (CDCl$_3$, δ): 1.35 (3H, t, J=7 Hz), 2.94 (2H, q, J=7 Hz), 7.30–7.45 (3H, m), 7.67 (1H, t, J=8 Hz), 7.73 (1H, d, J=8 Hz), 8.73 (1H, s), 8.94 (1H, d, J=8 Hz)

(2) 4-Carbamoyl-8-(2,6-dichlorobenzoylamino)-3-ethylquinoline was obtained according to a similar manner to that of Example 22-(2)

mp: 247–248° C. NMR (DMSO-d$_6$, δ): 1.27 (3H, t, J=7 Hz), 2.80 (2H, q, J=7 Hz), 7.50–7.60 (4H, m), 7.68 (1H, t, J=8 Hz), 8.05 (1H, br s), 8.20 (1H, br s), 8.66 (1H, d, J=8 Hz), 8.85 (1H, s)

Example 117

(1) 8-(2,6-Dichlorobenzoylamino)-3-ethyl-4-(methoxycarbonyl)quinoline was obtained from 4-carboxy-8-(2,6-dichlorobenzoylamino)-3-ethylquinoline and methyl iodide according to a similar manner to that of Example 108-(1).

mp: 160–161° C. NMR (CDCl$_3$, δ): 1.31 (3H, t, J=7 Hz), 2.82 (2H, q, J=7 Hz), 4.07 (3H, s), 7.30–7.50 (3H, m), 7.51 (1H, d, J=8 Hz), 7.64 (1H, t, J=8 Hz), 8.70 (1H, s), 8.93 (1H, d, J=8 Hz)

(2) 4-Acetyl-8-(2,6-dichlorobenzoylamino)-3-ethylquinoline was obtained according to a similar manner to that of Example 99.

mp: 194–195° C. NMR (CDCl$_3$, δ): 1.33 (3H, t, J=7 Hz), 2.67 (3H, s), 2.75 (2H, q, J=7 Hz), 7.30–7.45 (4H, m), 7.64 (1H, t, J=8 Hz), 8.69 (1H, s), 8.95 (1H, d, J=8 Hz)

Example 118

8-(2,6-Dichlorobenzoylamino)-3-ethyl-4-(methoxymethyl)quinoline was obtained by reacting 4-chloromethyl-8-(2,6-dichlorobenzoylamino)-3-ethylquinoline with sodium methoxide according to a similar manner to that of Preparation 2-(2).

mp: 142–143° C. NMR (CDCl$_3$, δ): 1.29 (3H, t, J=7 Hz), 2.95 (2H, q, J=7 Hz), 3.48 (3H, s), 4.89 (2H, s), 7.30–7.45 (3H, m), 7.63 (1H, t, J=8 Hz), 7.90 (1H, d, J=8 Hz), 8.63 (1H, s), 8.88 (1H, d, J=8 Hz)
its hydrochloride
mp: 155–163° C. NMR (CDCl$_3$, δ): 1.38 (3H, t, J=7 Hz), 3.06 (2H, q, J=7 Hz), 3.55 (3H, s), 5.00 (2H, s), 7.30–7.45 (3H, m), 7.92 (1H, t, J=8 Hz), 8.14 (1H, d, J=8 Hz), 8.82 (1H, s), 9.17 (1H, d, J=8 Hz)

Example 119

The following compounds were obtained according to a similar manner to that of Example 59.
(1) 8-(2,6-Dichlorobenzoylamino)-4-dimethylaminomethyl-3-ethylquinoline NMR (CDCl$_3$, δ): 1.27 (3H, t, J=7 Hz), 2.29 (6H, s), 2.95 (2H, a, J=7 Hz), 3.84 (2H, s), 7.30–7.45 (3H, m), 7.60 (1H, t, J=8 Hz), 8.05 (1H, d, J=8 Hz), 8.60 (1H, s), 8.87 (1H, d, J=8 Hz)
its hydrochloride
mp: >250° C. NMR (DMSO-d$_6$, δ): 1.24 (3H, t, J=7 Hz), 2.80 (3H, s), 2.87 (3H, s), 3.05 (2H, q, J=7 Hz), 4.88 (2H, br s), 7.50–7.60 (3H, m), 7.77 (1H, t, J=8 Hz), 8.15 (1H, d, J=8 Hz), 8.73 (1H, d, j=8 Hz), 8.92 (1H, s)

(2) 8-(2,6-Dichlorobenzoylamino)-3-ethyl-4-(2-methyl-2-imidazolin-1-ylmethyl)quinoline
mp: 203–205° C. NMR (DMSO-d$_6$, δ): 1.23 (3H, t, J=7 Hz), 2.17 (3H, s), 2.89 (2H, t, J=8 Hz), 2.96 (2H, q, J=7 Hz), 3.35 (2H, t, J=8 Hz), 4.82 (2H, s), 7.50–7.60 (3H, m), 7.68 (1H, t, J=8 Hz), 8.03 (1H, d, J=8 Hz), 8.67 (1H, d, J=8 Hz), 8.80 (1H, s)
(3) 8-(2,6-Dichlorobenzoylamino)-3-ethyl-4-[N-(2-hydroxyethyl)-N-methylaminomethyl]quinoline NMR (CDCl$_3$, δ): 1.30 (3H, t, J=7 Hz), 2.30 (3H, s), 2.65 (2H, t, J=5 Hz), 2.95 (2H, q, J=7 Hz), 3.60 (2H, t, J=5 Hz), 4.03 (2H, s), 7.30–7.50 (3H, m), 7.62 (1H, t, J=8 Hz), 7.99 (1H, d, J=8 Hz), 8.62 (2H, s), 8.89 (1H, d, J=8 Hz)
its hydrochloride
mp: 215–217° C. NMR (DMSO-d$_6$, δ): 1.24 (3H, t, J=7 Hz), 2.73 (3H, br s), 3.06 (2H, q, J=7 Hz), 3.44 (2H, m), 3.91 (2H, m), 4.84 (1H, m), 5.07 (1H, m), 5.58 (1H, br s), 7.50–7.65 (3H, m), 7.78 (1H, t, J=8 Hz), 8.16 (1H, d, J=8 Hz), 8.74 (1H, d, J=8 Hz), 8.92 (1H, s), 9.05 (1H, br s)
(4) 8-(2,6-Dichlorobenzoylamino)-3-ethyl-4-(2-methylimidazol-1-ylmethyl)quinoline NMR (DMSO-d$_6$, δ): 1.24 (3H, t, J=7 Hz), 2.63 (3H, s), 2.88 (2H, q, J=8 Hz), 5.41 (2H, s), 6.25 (1H, s), 6.80 (1H, s), 7.30–7.50 (3H, m), 7.53 (1H, d, J=8 Hz), 7.63 (1H, t, J=8 Hz), 8.7.3 (1H, s), 8.95 (1H, d, J=8 Hz)
its hydrochloride
mp: >250° C. NMR (DMSO-d$_6$, δ): 1.18 (3H, t, J=7 Hz), 2.81 (3H, s), 2.92 (2H, q, J=7 Hz), 5.80 (2H, s), 6.84 (1H, s), 7.43 (1H, s), 7.50–7.65 (3H, m), 7.67 (1H, t, J=8 Hz), 7.73 (1H, d, J=8 Hz), 8.71 (1H, d, J=8 Hz), 8.93 (1H, s)
(5) 8-(2,6-Dichlorobenzoylamino)-3-ethyl-4-(2-phenylimidazol-1-ylmethyl) quinoline NMR (CDCl$_3$, δ): 1.10 (3H, t, J=7 Hz), 2.72 (2H, q, J=7 Hz), 5.62 (2H, s), 6.47 (1H, s), 6.99 (1H, s), 7.30–7.45 (3H, m), 7.45–7.65 (5H, m), 7.79 (2H, d, J=8 Hz), 8.66 (1H, s), 8.92 (1H, d, J=8 Hz)
its hydrochloride
mp: 237–239° C. NMR (DMSO-d$_6$, δ): 1.11 (3H, t, J=7 Hz), 2.80 (2H, q, J=7 Hz), 5.91 (2H, s), 7.19 (1H, s), 7.45–7.80 (9H, m), 7.99 (2H, d, J=8 Hz), 8.69 (1H, d, J=8 Hz), 8.87 (1H, s)
(6) 4-(1H-Benzimidazol-1-ylmethyl)-8-(2,6-dichlorobenzoylamino)-3-ethylquinoline NMR (CDCl$_3$, δ): 1.23 (3H, t, J=7 Hz), 2.92 (2H, q, J=7 Hz), 5.71 (2H, s), 7.30–7.50 (6H, m), 7.50–7.60 (3H, m), 7.83 (1H, d, J=8 Hz), 8.77 (1H, s), 8.94 (1H, d, J=8 Hz)
its hydrochloride
mp: 246–248° C. NMR (CDCl$_3$, δ): 1.27 (3H, t, J=7 Hz), 3.00 (2H, q, J=7 Hz), 6.05 (2H, br s), 7.30–7.50 (3H, m), 7.52 (1H, m), 7.60–7.70 (4H, m), 8.02 (1H, m), 8.82 (1H, s), 8.90–9.00 (2H, m)
(7) 8-(2,6-Dichlorobenzoylamino)-3-ethyl-4-(2-methylthioimidazol-1-ylmethyl)quinoline NMR (CDCl$_3$, δ): 1.21 (3H, t, J=7 Hz), 2.76 (3H, s), 2.90 (2H, q, J=7 Hz), 5.45 (2H, s), 6.37 (1H, s), 6.93 (1H, s), 7.30–7.45 (3H, m), 7.55–7.65 (2H, m), 8.70 (1H, s), 8.93 (1H, d, J=8 Hz)
its hydrochloride
mp: 195–203° C. NMR (DMSO-d$_6$, δ): 1.17 (3H, t, J=7 Hz), 2.94 (2H, q, J=7 Hz), 5.82 (2H, s), 7.20 (1H, s), 7.50–7.65 (3H, m), 7.65–7.75 (3H, m), 8.71 (1H, t, J=4 Hz), 8.93 (1H, s)

Example 120

A mixture of 4-chloromethyl-8-(2,6-dichlorobenzoylamino)-3-ethylquinoline (150 mg) and N-methylethylenediamine (141 mg) in 1,2-dimethoxyethane was stirred for 2 hours at 70° C. The mixture was partitioned between dichloroethane and water, and the organic layer was washed with brine, dried over magnesium sulfate and evaporated in vacuo to give a residue containing 8-(2,6-dichlorobenzoylamino)-3-ethyl-4-[(2-methylaminoethyl-amino)methyl]quinoline. To the solution of the obtained residue in 1,3-dimethyl-2-imidazolidinone was added 1,1'-carbonyldiimidazole (309 mg), and the mixture was stirred for 30 minutes at 70° C., for 1 hour at 100° C. and for 1 hour at 150° C. Water was added to the mixture, and the resulting precipitates were collected by filtration. The residue was purified by preparative thin layer chromatography (methanol-dichloromethane) and crystallized from isopropyl alcohol to give 8-(2,6-dichlorobenzoylamino)-3-ethyl-4-(3-methyl-2-oxoimidazolidin-1-ylmethyl)quinoline (28.6 mg).

mp: 202–203° C. NMR (CDCl$_3$, δ): 1.29 (3H, t, J=7 Hz), 2.95 (2H, q, J=7 Hz), 3.05 (2H, m), 3.18 (2H, m), 4.87 (2H, s), 7.30–7.45 (3H, m), 7.63 (1H, t, J=8 Hz), 7.99 (1H, d, J=8 Hz), 8.62 (1H, s), 8.90 (1H, d, J=8 Hz)

Example 121

8-(2,6-Dichlorobenzoylamino)-3-ethyl-4-[(imidazol-2-yl)thiomethyl]quinoline was obtained by reacting 4-chloromethyl-8-(2,6-dichlorobenzoylamino)-3-ethylquinoline with 2-mercaptoimidazole according to a similar manner to that of Example 62.

mp: 203–204° C. NMR (DMSO-d$_6$, δ): 1.18 (3H, t, J=7 Hz), 2.70 (2H, q, J=7 Hz), 4.70 (2H, s), 7.10 (2H, br s), 7.45–7.60 (3H, m), 7.63 (1H, t, J=8 Hz), 7.84 (1H, d, J=8 Hz), 8.64 (1H, d, J=8 Hz), 8.72 (1H, s)
its hydrochloride mp: 237–239° C. NMR (DMSO-d$_6$, δ): 1.22 (3H, t, J=7 Hz) 2.76 (2H, a, J=7 Hz), 4.99 (2H, s), 7.50–7.65 (3H, m), 7.67 (1H, t, J=8 Hz), 7.75 (2H, s), 7.95 (1H, t, J=8 Hz), 8.68 (1H, t, J=8 Hz), 8.78 (1H, s)

Example 122

(1) 8-(2,6-Dichlorobenzoylamino)-4-(imidazol-1-yl)-3-((E)-1-propenyl)quinoline was obtained by reacting 3-allyl-4-chloro-8-(2,6-dichlorobenzoylamino)quinoline with imidazole according to a similar manner to that of Example 8.

mp: 205–206° C. NMR (DMSO-d$_6$, δ): 1.84 (3H, d, J=7 Hz), 6.00 (1H, d, J=15 Hz), 6.69 (1H, dq, J=7, 15 Hz), 6.96 (1H, d, J=8 Hz), 7.30 (1H, s), 7.50–7.60 (4H, m), 7.67 (1H, t, J=8 Hz), 7.94 (1H, s), 8.69 (1H, d, J=8 Hz), 9.30 (1H, s)
(2) 8-(2,6-Dichlorobenzoylamino)-4-(imidazol-1-yl)-3-propylquinoline was obtained according to a similar manner to that of Example 41.

mp: 160–161° C. NMR (CDCl$_3$, δ): 0.91 (3H, t, J=7 Hz), 1.59 (2H, m), 2.58 (2H, m), 7.04 (1H, d, J=8 Hz), 7.12 (1H, s), 7.30–7.50 (4H, m), 7.61 (1H, t, J=8 Hz), 7.64 (1H, s), 8.81 (1H, s), 8.99 (1H, d, J=8 Hz)
its hydrochloride mp: 220–222° C. NMR (CDCl$_3$, δ): 0.94 (3H, t, J=7 Hz), 1.63 (2H, m), 2.59 (2H, m), 6.87 (1H, d, J=8 Hz), 7.32 (1H, s), 7.35–7.50 (3H, m), 7.71 (1H, t, J=8 Hz), 7.79 (1H, s), 8.74 (1H, s), 8.88 (1H, s), 9.06 (1H, d, J=8 Hz)

Example 123

(1) 8-(2,6-Dichlorobenzoylamino)-4-(imidazol-1-yl)-3-(trimethylsilylethynyl)quinoline was obtained from 3-bromo-8-(2,6-dichlorobenzoylamino)-4-(imidazol-1-yl) quinoline and trimethylsilylacetylene according to a similar manner to that of Preparation 21.

mp: 213° C. NMR (CDCl$_3$, δ): 0.20 (9H, s), 7.30–7.48 (6H, m), 7.67 (1H, t, J=8 Hz), 7.80 (1H, br s), 8.85 (1H, s), 9.04 (1H, d, J=8 Hz)
(2) 8-(2,6-Dichlorobenzoylamino)-3-ethynyl-4-(imidazol-1-yl)quinoline was obtained according to a similar manner to that of Example 5.

mp: 235° C. (dec.) NMR (CDCl$_3$, δ): 3.35 (1H, s), 7.23–7.50 (6H, m), 7.69 (1H, t, J=8 Hz), 7.82 (1H, s), 8.90 (1H, s), 9.05 (1H, d, J=8 Hz)
its hydrochloride mp: 293° C. NMR (DMSO-d$_6$, δ): 4.86 (1H, s), 7.34 (1H, d, J=8 Hz), 7.47–7.62 (3H, m), 7.83 (1H, t, J=8 Hz), 7.99 (1H, s), 8.10 (1H, s), 8.83 (1H, d, J=8 Hz), 9.18 (1H, s), 9.44 (1H, s)

Example 124

(1) A mixture of 1,4-dihydro-8-nitro-4-oxoquinoline (10 g) and 1,3,5-trioxane (23.7 g) in dioxane (100 ml) and conc. hydrochloric acid (200 ml) was stirred for 3.5 hours at 90° C. and allowed to stand to ambient temperature. To the mixture was added ice water (700 g), and the mixture was stirred for 1 hour. The resulting precipitates were collected by filtration and washed with cold water to give 3-chloromethyl-1,4-dihydro-8-nitro-4-oxoquinoline (6.5 g).

mp: 228–235° C. NMR (DMSO-d$_6$, δ): 4.70 (2H, s), 7.53 (1H, t, J=7 Hz), 8.25 (1H, d, J=7 Hz), 8.59 (1H, d, J=7 Hz), 8.66 (1H, d, J=7 Hz)
(2) A suspension of 3-chloromethyl-1,4-dihydro-8-nitro-4-oxoquinoline (2 g) in dichloromethane (70 ml) and methanol (30 ml) was refluxed for 15 minutes and concentrated in vacuo. The crystalline residue was suspended in hot methanol (30 ml), and the mixture was allowed to stand to ambient temperature. The resulting precipitates were collected by filtration to give 1,4-dihydro-3-methoxymethyl-8-nitro-4-oxoquinoline (1.5 g).

mp: >250° C. NMR (DMSO-d$_6$, δ): 3.33 (3H, s), 4–32 (2H, s), 7.51 (1H, t, J=7 Hz), 7.98 (1H, d, J=7. Hz), 8.59 (1H, d, J=7 Hz), 8.67 (1H, d, J=7 Hz)
(3) 4-Chloro-3-methoxymethyl-8-nitroquinoline was obtained according to a similar manner to that of Preparation 2-(1).

mp: 91–94° C. NMR (CDCl$_3$, δ): 3.51 (3H, s), 4.81 (2H, s), 7.73 (1H, t, J=8 Hz), 8.05 (1H, d, J=8 Hz), 8.48 (1H, d, J=8 Hz), 9.10 (1H, s)
(4) 8-Amino-4-chloro-3-(methoxymethyl)quinoline was obtained according to a similar manner to that of Preparation 2-(3).

mp: 107° C. NMR (CDCl$_3$, δ): 3.50 (3H, s), 4.79 (2H, s), 5.03 (2H, br s), 6.95 (1H, d, J=8 Hz), 7.41 (1H, t, J=8 Hz), 7.54 (1H, d, J=8 Hz), 8.77 (1H, s)
(5) 4-Chloro-8-(2,6-dichlorobenzoylamino)-3-(methoxymethyl)quinoline was obtained according to a similar manner to that of Example 1.

mp: 177° C. NMR (CDCl$_3$, δ): 3.50 (3H, s), 4.79 (2H, s), 7.30–7.44 (3H, m), 7.70 (1H, t, J=8 Hz), 8.00 (1H, d, J=8 Hz), 8.80 (1H, s), 9.00 (1H, d, J=8 Hz)
(6) 8-(2,6-Dichlorobenzoylamino)-4-(imidazol-1-yl)-3-(methoxymethyl)quinoline was obtained according to a similar manner to that of Example 8.

mp: 145–150° C. NMR (CDCl$_3$, δ): 3.36 (3H, s), 4.31 (2H, s), 7.14–7.22 (2H, m), 7.31–7.46 (4H, m), 7.63 (1H, t, J=8 Hz), 7.70 (1H, s), 8.95 (1H, s), 9.01 (1H, d, J=8 Hz)
its methanesulfonate mp: 188–196° C. NMR (DMSO-d$_6$, δ): 2.30 (3H, s), 3.22 (3H, s), 4.48 (2H, s), 7.20 (1H, d, J=8 Hz), 7.49–7.63 (3H, m), 7.80 (1H, t, J=8 Hz), 8.02 (1H, d, J=1 Hz), 8.08 (1H, d, J=1 Hz), 8.82 (1H, d, J=8 Hz), 9.15 (1H, d, J=1 Hz), 9.36 (1H, br s)
(7) 8-(2,6-Dichlorobenzoylamino)-3-methoxymethyl-4-(pyrazol-1-yl)quinoline was obtained from 4-chloro-8-(2,6-dichlorobenzoylamino)-3-methoxymethylquinoline and pyrazole according to a similar manner to that of Example 8.

mp: 156–157° C. NMR (DMSO-d$_6$, δ): 3.23 (3H, s), 4.38 (2H, s), 6.71 (1H, d, J=2 Hz), 7.15 (1H, d, J=8 Hz), 7.48–7.62 (3H, m), 7.70 (1H, dd, J=8, 8 Hz), 7.95 (1H, s), 8.20 (1H, d, J=2 Hz), 8.77 (1H, d, J=8 Hz), 9.09 (1H, s), 11.00 (1H, s)

Example 125

(1) 3-Carboxy-8-(2,6-dichlorobenzoylamino)-4-hydroxymethyl)quinoline was obtained from 4-acetoxymethyl-8-(2,6-dichlorobenzoylamino)-3-ethoxycarbonylquinoline according to a similar manner to that of Example 18.

mp: 244–247° C. (dec.) NMR (DMSO-$d_6$, δ): 5.05 (2H, s), 7.50–7.60 (3H, m), 7.76 (1H, t, J=8 Hz), 8.21 (1H, d, J=8 Hz), 8.78 (1H, d, J=8 Hz), 9.08 (1H, s)

(2) To a solution of 3-carboxy-8-(2,6-dichlorobenzoylamino)-4-hydroxymethylquinoline (1.11 g) in dimethylformamide were added imidazole (637 mg) and tert-butyldiphenylsilyl chloride (2.57 g) under ice-cooling, and the mixture was stirred for 5 hours at ambient temperature. The mixture was partitioned between ethyl acetate and water, and the organic layer was washed with brine, dried over magnesium sulfate and evaporated in vacuo. To the solution of the obtained residue in dioxane (10 ml) was added 1N sodium hydroxide solution (2.9 ml), and the mixture was stirred for 30 minutes at ambient temperature. The mixture was diluted with water and washed with diethyl ether. The aqueous layer was acidified with 1N hydrochloric acid and extracted with ethyl acetate. The extract was washed with water and brine, dried over magnesium sulfate and evaporated in vacuo. The residue was dissolved in isopropyl alcohol-diisopropyl ether, and insoluble material was filtered off. The filtrate was concentrated in vacuo to give 4-(tert-butyldiphenylsilyloxymethyl)-3-carboxy-8-(2,6-dichlorobenzoylamino)quinoline (1.22 g).

NMR (CDCl$_3$, δ): 1.00 (9H, s), 5.49 (2H, s), 7.30–7.50 (9H, m), 7.59 (1H, t, j=8 Hz), 7.64 (4H, d, J=8 Hz), 7.79 (1H, d, J=8 Hz), 9.04 (1H, d, J=8 Hz), 9.14 (1H, s)

(3) 4-(tert-Butyldiphenylsilyloxymethyl)-8-(2,6-dichlorobenzoylamino)-3-(N-methoxy-N-methylcarbamoyl)quinoline was obtained according to a similar manner to that of Example 22-(2).

NMR (CDCl$_3$, δ): 1.03 (9H, s), 3.24 (3H, s), 3.29 (3H, s), 5.16 (2H, s), 7.30–7.50 (9H, m), 7.62 (1H, t, J=8 Hz), 7.70 (4H, d, J=8 Hz), 7.89 (1H, d, J=8 Hz), 8.68 (1H, s), 8.99 (1H, d, J=8 Hz)

(4) To a solution of 4-(tert-butyldiphenylsilyloxymethyl)-8-(2,6-dichlorobenzoylamino)-3-(N-methoxy-N-methylcarbamoyl)quinoline (1.03 g) in tetrahydrofuran (10 ml) was dropwise added 1M solution of diisobutylaluminum hydride in tetrahydrofuran (15 ml) at −55° C., and the mixture was stirred for 50 minutes at −60 to −45° C. The mixture was quenched by saturated ammonium chloride solution and 101, aqueous solution of potassium sodium tartrate. Diethyl ether (50 ml) was added to the mixture, and the mixture was stirred for 1.5 hours at ambient temperature. The separated aqueous layer was extracted with ethyl acetate. The combined organic layer was washed with brine, dried over magnesium sulfate and evaporated in vacuo. The residue was purified by column chromatography on silica gel (ethyl acetate-n-hexane) to give 4-(tert-butyldiphenylsilyloxymethyl)-8-(2,6-dichlorobenzoylamino)-3-formylquinoline (809 mg).

NMR (CDCl$_3$, δ): 1.01 (9H, s), 5.48 (2H, s), 7.30–7.50 (10H, m), 7.63 (4H, d, J=8 Hz), 7.77 (1H, d, J=8 Hz), 9.06 (1H, d, J=8 Hz), 9.02 (1H, s), 10.07 (1H, s), 10.46 (1H, s)

(5) 4-(tert-Butyldiphenylsilyloxymethyl)-8-(2,6-dichlorobenzoylamino)-3-(hydroxymethyl)quinoline was obtained according to a similar manner to that of Example 16.

NMR (CDCl$_3$, δ): 1.03 (9H, s), 2.53 (1H, t, J=6 Hz), 4.78 (2H, d, J=8 Hz), 5.22 (2H, s), 7.30–7.80 (15H, m), 8.77 (1H, s), 8.92 (1H, d, J=8 Hz)

(6) 3-Bromomethyl-4-(tert-butyldiphenylsilyloxymethyl)-8-(2,6-dichlorobenzoylamino)quinoline was obtained according to a similar manner to that of Example 110-(4). NMR (CDCl$_3$, δ): 1.04 (9H, s), 4.42 (2H, s), 5.22 (2H, s), 7.30–7.50 (9H, m), 7.59 (1H, t, J=8 Hz), 7.65–7.75 (4H, m), 7.82 (1H, d, J=8 Hz), 8.65 (1H, s), 8.95 (1H, d, J=8 Hz)

(7) 4-(tert-Butyldiphenylsilyloxymethyl)-8-(2,6-dichlorobenzoylamino)-3-(methoxymethyl)quinoline was obtained according to a similar manner to that of Preparation 2-(2). NMR (CDCl$_3$, δ): 1.03 (9H, s), 3.22 (3H, s), 4.32 (2H, s), 5.16 (2H, s), 7.30–7.50 (9H, m), 7.60 (1H, t, J=8 Hz), 7.67 (4H, d, J=8 Hz), 7.96 (1H, d, J=8 Hz), 8.68 (1H, s), 8.94 (1H, d, J=8 Hz)

(8) To a solution of 4-(tert-butyldiphenylsilyloxymethyl)-8-(2,6-dichlorobenzoylamino)-3-(methoxymethyl)quinoline (359 mg) in tetrahydrofuran was added 1M solution of tetrabutylammonium fluoride in tetrahydrofuran (0.684 ml) at ambient temperature, and the mixture was stirred for 1 hour at the same temperature. The mixture was partitioned between water and ethyl acetate, and the organic layer was washed with brine, dried over magnesium sulfate and evaporated in vacuo. The residue was crystallized from isopropyl alcohol to give 8-(2,6-dichlorobenzoylamino)-4-hydroxymethyl-3-(methoxymethyl)quinoline (186 mg).

mp: 199–200° C. NMR (CDCl$_3$, δ): 2.88 (1H, t, J=7 Hz), 3.50 (3H, s), 4.77 (2H, s), 5.14 (2H, d, J=7 Hz), 7.30–7.50 (3H, m), 7.70 (1H, t, J=8 Hz), 8.02 (1H, d, J=8 Hz), 8.71 (1H, s), 8.98 (1H, d, J=8 Hz)

(9) 4-Chloromethyl-8-(2,6-dichlorobenzoylamino)-3-(methoxymethyl)quinoline was obtained according to a similar manner to that of Example 78-(3).

mp: 164° C. NMR (CDCl$_3$, δ): 3.47 (3H, s), 4.76 (2H, s), 5.10 (2H, s), 7.30–7.50 (3H, m), 7.73 (1H, t, J=8 Hz), 7.90 (1H, d, J=8 Hz), 8.77 (1H, s), 9.00 (1H, d, J=8 Hz)

(10) 8-(2,6-Dichlorobenzoylamino)-4-(imidazol-1-ylmethyl)-3-(methoxymethyl)quinoline was obtained according to a similar manner to that of Example 59.

mp: 190–191° C. NMR (CDCl$_3$, δ): 3.45 (3H, s), 4.67 (2H, s), 5.67 (2H, s), 6.84 (1H, s), 7.03 (1H, s), 7.30–7.50 (3H, m), 7.53 (1H, s), 7.66 (1H, t, J=8 Hz), 7.73 (1H, d, J=8 Hz), 8.79 (1H, s), 8.99 (1H, d, J=8 Hz)
its hydrochloride mp: 238–240° C. NMR (DMSO-$d_6$, δ): 4.82 (2H, d), 6.02 (2H, s), 7.50–7.70 (5H, m), 7.73 (1H, t, J=8 Hz), 7.95 (1H, d, J=8 Hz), 8.76 (1H, d, J=8 Hz), 9.00 (1H, s), 9.03 (1H, s)

Example 126

(1) 8-(2,6-Dichlorobenzoyl amino)-3-formyl-4-(imidazol—yl)quinoline was obtained from 8-(2,6-dichlorobenzoylamino)-4-(imidazol-1-yl)-3-vinylquinoline according to a similar manner to that of Example 29.

NMR (CDCl$_3$, δ): 7.35–7.50 (7H, m), 7.77 (2H, t, J=8 Hz), 7.84 (1H, d), 9.21 (1H, d, J=8 Hz), 9.32 (1H, s), 9.89 (1H, s) is (2) 8-(2,6-Dichlorobenzoylamino)-3-hydroxymethyl-4-(imidazol-1-yl)quinoline was obtained according to a similar manner to that of Example 16.

mp: 196–198° C. NMR (CDCl$_3$, δ): 4.37 (2H, d, J=6 Hz), 7.18 (1H, d, J=8 Hz), 7.21 (1H, s), 7.30–7.50 (4H, m), 7.65 (1H, t, J=8 Hz), 7.73 (1H, s), 9.03 (1H, d, J=8 Hz), 9.06 (1H, s)

(3) 8-(2,6-Dichlorobenzoylamino)-3-hydroxymethyl-4-(imidazol-1-yl)quinoline was obtained according to a similar manner to that of Example 8.

NMR (DMSO-$d_6$, δ): 4.44 (2H, d, J=6 Hz), 5.59 (1H, d, J=6 Hz), 7.07 (1H, d, J=8 Hz), 7.28 (1H, m), 7.50–7.65 (4H, m), 7.70 (1H, t, J=8 Hz), 7.97 (1H, s), 8.76 (1H, d, J=5 Hz), 9.15 (1H, s)

(4) Thionyl chloride (52.8 mg) was dropwise added to dimethylformamide at ambient temperature, and the mixture was stirred for 10 minutes at the same temperature. To the mixture was added 8-(2,6-dichlorobenzoylamino)-3-hydroxymethyl-4-(imidazol-1-yl)quinoline (141 mg), and the mixture was stirred for 20 minutes at ambient temperature. The mixture was partitioned between saturated sodium bicarbonate solution and ethyl acetate, and the organic layer was washed with brine, dried over magnesium sulfate and evaporated in vacuo. The obtained residue was dissolved in dichloromethane-methanol, and the solution was added to a solution of sodium methoxide, which was prepared by adding sodium (17.3 mg) to dry methanol (1.5 ml) and then stirring for 15 minutes at ambient temperature. The mixture was stirred for 3 hours at 40° C. The mixture was partitioned between saturated ammonium chloride solution and ethyl acetate, and the organic layer was washed with brine, dried over magnesium sulfate and evaporated in vacuo. The residue was purified by preparative thin layer chromatography to give 8-(2,6-dichlorobenzoylamino)-4-(imidazol-1-yl)-3-(methoxymethyl)quinoline (55 mg).

mp: 145–150° C. NMR (CDCl$_3$, δ): 3.36 (3H, s), 4.31 (2H, s), 7.14–7.22 (2H, m), 7.31–7.46 (4H, m), 7.63 (1H, t, J=8 Hz), 7.70 (1H, s), 8.95 (1H, s), 9.01 (!H, d, J=8 Hz)

Example 127

(1) 3-Bromomethyl-4-chloro-8-(2,6-dichlorobenzoylamino)quinoline was obtained from 4-chloro-8-(2,6-dichlorobenzoylamino)-3-hydroxymethylquinoline according to a similar manner to that of Example 110-(4).

NMR (CDCl$_3$, δ): 4.79 (2H, s), 7.30–7.50 (3H, m), 7.74 (1H, t, J=8 Hz), 8.02 (1H, d, J=8 Hz), 8.75 (1H, s), 9.03 (1H, d, J=8 Hz)

(2) 4-Chloro-8-(2,6-dichlorobenzoylamino)-3-(methoxymethyl)quinoline was obtained according to a similar manner to that of Preparation 2-(2).

(3) 8-(2,6-Dichlorobenzoylamino)-3-methoxymethyl-4-[2-(methylamino)ethylamino]quinoline was obtained according to a similar manner to that of Example 8.

NMR (CDCl$_3$, δ): 2.48 (3H, s), 2.88 (2H, t, J=6 Hz), 3.37 (3H, s), 3.75 (2H, dt, J=6, 6 Hz), 4.58 (2H, s), 6.08 (1H, br t, J=6 Hz), 7.27–7.49 (4H, m), 7.81 (1H, d, J=8 Hz), 8.28 (1H, s), 8.86 (1H, d, j=8 Hz), 10.15 (1H, br)

(4) 8-(2,6-Dichlorobenzoylamino)-3-methoxymethyl-4-(3-methyl-2-oxoimidazolidin-1-yl)quinoline was obtained according to a similar manner to that of Example 92-(2).

mp: 199–201° C. NMR (DMSO-d$_6$, δ): 2.83 (3H, s), 3.33 (3H, s), 3.59–3.73 (3H, m), 3.85 (1H, m), 4.57 (1H, d, J=12 Hz), 4.61 (1H, d, J=12 Hz), 7.48–7.62 (3H, m), 7.70 (2×1H, d, J=7 Hz), 8.73 (1H, dd, J=4, 4 Hz) 7.98 (1H, d, J=8 Hz), 8.95 (1H, s), 10.86 (1H, s).

(5) 8-(2,6-Dichlorobenzoylamino)-3-methoxymethyl-4-(3-methyl-2-thioxoimidazolidin-1-yl)quinoline was obtained from 8-(2,6-dichlorobenzoylamino)-3-methoxymethyl-4-[2-(methylamino)ethylamino]quinoline and 1,11-thiocarbonyldiimidazole according to a similar manner to that of Example 92-(2).

mp: 184–185° C. NMR (DMSO-d$_6$, δ): 3.16 (3H, s), 3.37 (3H, s), 3.85–4.08 (4H, m), 4.56 (1H, d, J=12 Hz), 4.64 (1H, d, J=12 Hz), 6.98–7.15 (4H, m), 7.21 (1H, dd, J=7.5, 7.5 Hz), 8.73 (1H, d, J=7.5 Hz), 9.00 (1H, s), 10.91 (1H, s)

Example 128

A mixture of 4-chloromethyl-8-(2,6-dichlorobenzoylamino)-3-methoxymethylquinoline (70 mg) and potassium carbonate (26 mg) in 1,2-dimethoxyethane and methanol was refluxed for 2 hours. After cooling, the mixture was partitioned between saturated ammonium chloride solution and dichloromethane, and the organic layer was washed with brine, dried over magnesium sulfate and evaporated in vacuo. The residue was purified by preparative thin layer chromatography and crystallized from isopropyl alcohol to give 3,4-bis(methoxymethyl)-8-(2,6-dichlorobenzoylamino)quinoline (19.2 mg).

mp: 160–161° C. NMR (CDCl$_3$, δ): 3.45 (3H, s), 3.46 (3H, s), 4.73 (2H, s), 4.96 (2H, s), 7.30–7.45 (3H, m), 7.66 (1H, t, J=8 Hz), 7.97 (1H, d, J=8 Hz), 8.77 (1H, s), 8.95 (1H, d, J=8 Hz)

Example 129

(1) 1,4-Dihydro-3-methylthiomethyl-8-nitro-4-oxoquinoline was obtained by reacting 3-chloromethyl-1,4-dihydro-8-nitro-4-oxoquinoline with sodium thiomethoxide according to a similar manner to that of Preparation 13.

mp: 200–203° C. NMR (CDCl$_3$, δ): 2.13 (3H, s), 3.70 (2H, s), 7.44 (1H, t, J=7 Hz), 7.90 (1H, d, J=7 Hz), 8.67 (1H, d, J=7 Hz), 8.82 (1H, d, J=7 Hz)

(2) 4-Chloro-3-methylthiomethyl-8-nitroquinoline was obtained according to a similar manner to that of Preparation 2-(1).

mp: 96–98° C. NMR (CDCl$_3$, δ): 2.10 (3H, s), 4.03 (2H, s), 7.74 (1H, t, J=7 Hz), 8.06 (1H, d, J=7 Hz), 8.49 (1H, d, J=7 Hz), 8.98 (1H, s)

(3) 8-Amino-4-chloro-3-(methylthiomethyl)quinoline was obtained according to a similar manner to that of Preparation 2-(3) MP 107–108° C. NMR (CDCl$_3$, δ): 2.08 (3H, s), 3.99 (2H, s), 5.00 (2H, br s), 6.93 (1H, d, J=7 Hz), 7.41 (1H, t, J=7 Hz), 7.52 (1H, d, J=7 Hz), 8.67 (1H, s)

(4) 4-Chloro-8-(2,6-dichlorobenzoylamino)-3-(methylthiomethyl)quinoline was obtained according to a similar manner to that of Example 1.

mp: 173–175° C. NMR (CDCl$_3$, δ): 2.09 (3H, s), 4.02 (2H, s), 7.28–7.45 (3H, m), 7.72 (1H, t, J=7 Hz), 7.99 (1H, d, J=7 Hz), 8.72 (1H, d), 9.00 (1H, d, J=17 Hz)

(5)-8-(2,6-Dichlorobenzoylamino)-4-(imidazol-1-yl)-3-(methylthiomethyl)quinoline was obtained according to a similar manner to that of Example B.

mp: 198–200° C. NMR (DMSO-d$_6$, δ): 1.92 (3H, s), 3.68 (2H, s), 6.98 (1H, d, J=7 Hz), 7.29 (1H, s), 7.48–7.63 (3H, m), 7.70 (1H, t, J=7 Hz), 7.99 (1H, s), 8.75 (1H, d, J=7 Hz), 9.08 (1H, d)

its methanesulfonate mp: 209–211° C. NMR (DMSO-d$_6$, δ): 1.96 (3H, s), 2.31 (3H, s), 3.77 (1H, d, J=74 Hz), 3.82 (1H, d, J=74 Hz), 7.12 (3H, d, J=7 Hz), 7.47–7.61 (3H, m), 7.76 (1H, t, J=7 Hz), 8.02 (1H, s), 8.08 (1H, s), 8.80 (1H, s), 9.15 (1H, s), 9.38 (1H, s)

Example 130

8-(2,6-Dichlorobenzoylamino)-4-(imidazol-1-yl)-3-phenylquinoline was obtained from 3-bromo-8-(2,6-dichlorobenzoylamino)-4-(imidazol-1-yl) quinoline and phenylboric acid according to a similar manner to that of Preparation 16-(1).

mp: 261° C. NMR (CDCl$_3$, δ): 7.02 (1H, s), 7.07–7.16 (2H, m), 7.20 (1H, s), 7.30–7.49 (8H, m), 7.68 (1H, t, J=8 Hz), 8.93 (1H, s), 9.05 (1H, d, J=8 Hz)

its hydrochloride mp: 249–254° C. NMR (DMSO-d$_6$, δ): 7.25–7.65 (9H, m), 7.78–7.90 (2H, m), 7.99 (1H, s), 8.86 (1H, d, J=8 Hz), 9.14 (1H, s), 9.24 (1H, br s)

Example 131

8-(2,6-Dichlorobenzoylamino)-4-(imidazol-1-yl)-3-(2-pyridyl)quinoline was obtained from 3-bromo-8-(2,6- dichlorobenzoylamino)-4-(imidazol-1-yl)quinoline and tri-n-butyl(2-pyridyl)tin according to a similar manner to that of Preparation 12-(2).

mp: 253–265° C. NMR (CDCl$_3$, δ): 6.82 (1H, d, J=8 Hz), 7.10 (1H, s), 7.23–7.30 (1H, m), 7.32–7.46 (4H, m), 7.51 (1H, s), 7.59 (1H, t, J=8 Hz), 7.67–7.75 (2H, m), 8.71 (1H, br d, J=6 Hz), 9.07 (1H, d, J=7 Hz), 9.24 (1H, s)

Example 132

To a solution of 9-fluorenecarboxylic acid (158 mg) and dimethylformamide (1 drop) in dichloromethane (2 ml) was dropwise added oxalyl chloride (191 mg), and the mixture was stirred for 1 hour at ambient temperature. The mixture was concentrated in vacuo, and the residue was added to a solution of 8-amino-3-bromoquinoline (112 mg) and triethylamine (152 mg) in 1,3-dimethyl-2-imidazolidinone (1 ml). The mixture was stirred for 3 hours at ambient temperature. The mixture was partitioned between ethyl acetate and water, and the organic layer was washed with brine, dried over magnesium sulfate and evaporated in vacuo. The residue was purified by column chromatography on silica gel and crystallized from diethyl ether-diisopropyl ether to give 3-bromo-8-[(fluoren-9-yl)carbonylamino]quinoline (22 mg).

mp: 196–198° C. NMR (CDCl$_3$, δ): 5.03 (1H, s), 7.32–7.43 (3H, m), 7.45–7.55 (3H, m), 7.80–7.90 (4H, m), 8.20 (1H, s), 8.50 (1H, s), 8.75 (1H, d, J=7 Hz), 9.65 (1H, br s)

Example 133

To a mixture of 3-bromo-8-(2,6-dichlorobenzoylamino)-4-(imidazol-1-yl)quinoline (50 mg) and N-methylpyrrolidone were added imidazole (11 mg), potassium carbonate (22.4 mg) and copper(I) oxide (7.74 mg), and the mixture was stirred for 1.5 hours at 60° C. and for 1 hour at 80° C. The mixture was partitioned between dichloromethane and water, and the organic layer was washed with brine, dried over magnesium sulfate and evaporated in vacuo. The residue was purified by preparative thin layer chromatography and crystallized from diisopropyl ether to give 3-bromo-8-[2,6-bis(imidazol-1-yl)benzoylamino]-4-(imidazol-1-yl)quinoline (17 mg).

mp: 175–185° C. NMR (CDCl$_3$, δ): 7.00–7.15 (4H, m), 7.20–7.30 (1H, overlapping), 7.37 (1H, s), 7.50–7.60 (3H, m), 7.67 (1H, s), 7.70–7.85 (3H, m), 8.65 (1H, d, J=8 Hz), 8.83 (1H, s), 9.55 (1H, s)

Example 134

(1) 8-Amino-1,4-dihydro-4-oxoquinazoline was obtained from 1,4-dihydro-8-nitro-4-oxoquinazoline according to a similar manner to that of Preparation 1.

mp: >250° C. NMR (DMSO-d$_6$, δ): 5.65 (2H, br s), 6.98 (1H, d, J=7 Hz), 7.18 (1H, t, J=7 Hz), 7.22 (1H, d, J=7 Hz), 7.98 (1H, s)

(2) 8-(2,6-Dichlorobenzoylamino)-4-(2,6-dichlorobenzoyloxy)quinazoline was obtained by reacting 8-amino-1,4-dihydro-4-oxoquinoline with 2,6-dichlorobenzoyl chloride according to a similar manner to that of Example 3-(1).

mp: >250° C. NMR (DMSO-d$_6$, δ): 7.45–7.70 (7H, m), 7.90 (1H, d, J=7 Hz), 8.75 (1H, d, J=7 Hz), 8.91 (1H, s)

(3) A mixture of 8-(2,6-dichlorobenzoylamino)-4-(2,6-dichlorobenzoyloxy)quinazoline (40 mg) and imidazole (53.7 mg) in 1,3-dimethyl-2-imidazolidinone (0.6 ml) was stirred for 1 hour at ambient temperature. Cold water was added to the mixture, and the resulting precipitates were collected by filtration to give 8-(2,6-dichlorobenzoylamino)-1,4-dihydro-4-oxoquinazoline (23 mg).

mp: >250° C. NMR (DMSO-d$_6$, δ): 7.45–7.60 (4H, m), 7.90 (1H, d, J=7 Hz), 8.13 (1H, s), 8.70 (1H, d, J=7 Hz)

Example 135

A mixture of 4-chloro-8-(2,6-dichlorobenzoylamino)-3-ethoxycarbonylquinoline (200 mg), formamidine acetate (246 mg) and N-methylpyrrolidone was stirred for 4 hours at 100° C., for 45 minutes at 120° C. and for 6 hours at 130° C. The mixture was partitioned between water and ethyl acetate. The organic layer was washed with water and evaporated in vacuo. The residue was crystallized from isopropyl alcohol and collected by filtration to give 7-(2,6-dichlorobenzoylamino)-3,4-dihydropyrimido[5,4-c]quinolin-4-one (116 mg).

mp: >250° C. NMR (DMSO-d$_6$, δ): 7.50–7.60 (3H, m), 7.84 (1H, t, J=8 Hz), 8.57 (1H, d, J=8 Hz), 8.60 (1H, s), 8.91 (1H, d, J=8 Hz), 9.39 (1H, s)

Example 136

(1) 3-(Imidazol-1-ylthiomethyl)-1,4-dihydro-8-nitro-4-oxoquinoline was obtained from 3-chloromethyl-1,4-dihydro-8-nitro-4-oxoquinoline and 2-mercaptoimidazole according to a similar manner to that of Example 62.

mp: 185–189° C. NMR (DMSO-d$_6$, δ): 4.09 (2H, s), 6.90–7.20 (2H, m), 7.50 (1H, t, J=7 Hz), 7.90 (1H, s), 8.58 (1H, d, J=7 Hz), 8.62 (1H, d, J=7 Hz)

(2) A suspension of 3-(imidazol-1-ylthiomethyl)-1,4-dihydro-8-nitro-4-oxoquinoline (185 mg) in phosphoryl chloride (1 ml) was stirred for 1 hour at 100° C. After cooling, diethyl ether was added thereto, and the resulting precipitates were collected by filtration and washed with diethyl ether. To the residue were added dichloromethane-methanol and saturated sodium bicarbonate solution. The separated organic layer was washed with brine, dried over magnesium sulfate and evaporated in vacuo. The residue was purified by column chromatography on silica gel to give 4-nitro-7H-imidazo[2',1':2,3][1,3]thiazino[5,4-c]quinoline (135 mg).

mp: 236–242° C. NMR (DMSO-d$_6$, δ): 4.39 (2H, s), 7.33 (1H, s), 7.88 (1H, t, J=7 Hz), 8.24 (1H, s), 8.36 (1H, d, J=7 Hz), 8.60 (1H, d, J=7 Hz), 9.13 (1H, s)

(3) 4-Amino-7H-imidazo[2',1':2,3][1,3]thiazino[5,4-c]-quinoline was obtained according to a similar manner to that of Preparation 2-(3).

mp: >250° C. NMR (DMSO-d$_6$, δ): 4.29 (2H, s), 6.18 (2H, br s), 6.93 (1H, t, J=7 Hz), 7.24 (1H, s), 7.37–7.47 (2H, m), 8.12 (1H, s), 8.81 (1H, s)

(4) 4-(2,6-Dichlorobenzoylamino)-7H-imidazo[2',1':2,3][1,3]-thiazino[5,4-c]quinoline was obtained according to a similar manner to that of Example 1.

mp: >250° C. NMR (DMSO-d$_6$, δ): 4.37 (2H, s), 7.32 (1H, s), 7.47–7.62 (3H, m), 7.80 (1H, t, J=7 Hz), 8.14 (1H, d, J=7 Hz), 8.23 (1H, s), 8.80 (1H, d, J=7 Hz), 9.01 (1H, s)

Example 137

3-Bromo-8-[2-(2-ethylimidazol-1-yl)benzoylamino]-quinoline was obtained from 2-(2-ethylimidazol-1-yl)benzo-c acid and 8-amino-3-bromoquinoline according to a similar manner to that of Example 132.

mp: 168–169° C. NMR (CDCl$_3$, δ): 1.26 (3H, t, J=7 Hz), 2.67 (2H, q, J=7 Hz), 7.00 (1H, s), 7.10 (1H, s), 7.34 (1H, m), 7.42 (1H, d, J=8 Hz), 7.57 (1H, t, J=8 Hz), 7.60–7.70 (2H, m), 8.09 (1H, m), 8.30 (1H, d, J=2 Hz), 8.70 (1H, d, J=2 Hz), 9.74 (1H, br s)

Example 138

(1) A mixture of 4-chloro-8-(2,6-dichlorobenzoylamino)quinoline (200 mg) and hydrazine monohydrate (285 mg) in ethanol (4 ml) and N-methylpyrrolidone (1 ml) was heated at 100° C. overnight. After cooling, the resulting precipitates were collected by filtration, and the residue was recrystallized from ethanol to give 8-(2,6-dichlorobenzoylamino)-4-hydrazinoquinoline (173 mg).

mp: 204–206° C. NMR (CDCl$_3$-CD$_3$OD, δ): 6.92 (1H, d, J=6 Hz), 7.28–7.59 (5H, m), 8.44 (1H, d, J=6 Hz), 8.85 (1H, d, J=8 Hz)

(2) 4-(2-Acetylhydrazino)-8-(2,6-dichlorobenzoylamino)quinoline was obtained according to a similar manner to that of Example 86.

mp: 252° C. NMR (DMSO-d$_6$, δ): 2.00 (3H, s), 6.64 (1H, d, J=6 Hz), 7.45–7.64 (4H, m), 7.99 (1H, d, J=8 Hz), 8.41 (1H, d, J=6 Hz), 8.65 (1H, d, J=8 Hz), 9.27 (1H, br s), 10.02 (1H, br s), 10.51 (1H, s)

Example 139

(1) 8-(2,6-Dichlorobenzoylamino)-4-hydrazino-3-methylquinoline was obtained from 4-chloro-8-(2,6-dichlorobenzoylamino)-3-methylquinoline and hydrazine monohydrate according to a similar manner to that of Example 8.

mp: 190–197° C. NMR (CDCl$_3$, δ): 2.30 (3H, s), 4.04 (2H, br s), 5.93 (1H, br s), 7.20–7.51 (4H, m), 8.12 (1H, d, J=8 Hz), 8.31 (1H, s), 8.83 (1H, d, J=8 Hz)

(2) 4-(2-Acetylhydrazino)-8-(2,6-dichlorobenzoylamino)-3-methylquinoline was obtained according to a similar manner to that of Example 86.

mp: 249–254° C. NMR (DMSO-d$_6$, δ): 1.87 (3H, s), 2.35 (3H, s), 7.42–7.63-(4H, m), 8.10 (1H, d, J=8 Hz), 8.25 (1H, s), 8.33 (1H, s), 8.57 (1H, d, J=8 Hz)

Example 140

To a suspension of 8-(2,6-dichlorobenzoylamino)-4-hydrazino-3-hydroxymethylquinoline (100 mg) in dichloroethane (3 ml) was added acetic anhydride (30 mg). After stirring for 7 hours at ambient temperature, the reaction mixture was evaporated, and the residue was triturated with the minimum volume of hot ethanol to give 3-acetoxymethyl-4-(2-acetylhydrazino)-8-(2,6-dichlorobenzoylamino)quinoline as a pale yellow crystal (53 mg). The mother liquid was evaporated and purified by silica gel column chromatography (methanol:ethyl acetate=1:10, V/V) to give 4-(2-acetylhydrazino)-8-(2,6-dichlorobenzoylamino)-3-hydroxymethylquinoline as a pale yellow powder (35 mg). 4-(2-Acetylhydrazino)-8-(2,6-dichlorobenzoylamino)-3-hydroxymethylquinoline mp: 142–145° C. NMR (DMSO-d$_6$, δ): 1.87 (3H, s), 4.73 (2H, d, J=6 Hz), 5.30 (1H, t, J=6 Hz), 7.45–7.63 (4H, m), 8.13 (1H, d, J=8 Hz), 8.33 (1H, s), 8.58 (1H, s), 8.62 (1H, d, J=8 Hz), 10.15 (1H, s), 10.58 (1H, s) 3-Acetoxymethyl-4-(2-acetylhydrazino)-8-(2,6-dichlorobenzoylamino)quinoline mp: 181–183° C. NMR (DMSO-d$_6$, δ): 1.87 (3H, s), 2.02 (3H, s), 5.23 (2H, s), 7.46–7.63 (4H, m), 8.14 (1H, d, J=8 Hz), 8.45 (1H, s), 8.66 (1H, d, J=8 Hz), 8.79 (1H, s), 10.22 (1H, s), 10.55 (1H, s)

Example 141

The following compounds were obtained according to a similar manner to that of Example 139-(1).

(1) 8-(2,6-Dichlorobenzoylamino)-4-hydrazino-3-methoxymethylquinoline mp: 176–178° C. NMR (DMSO-d$_6$, δ): 3.28 (3H, s), 4.81 (2H, s), 4.82 (2H, s), 7.38 (1H, dd, j=8, 8 Hz), 7.49–7.63 (3H, ic), 8.20 (1H, br s), 8.29 (1H, s), 8.35 (1H, d, J=8 Hz), 8.53 (1H, d, J=8 Hz), 10.46 (1H, s)

(2) 8-(2,6-Dichlorobenzoylamino)-4-hydrazino-3-isopropoxymethylquinoline NMR (DMSO-d$_6$, δ): 1.25 (2×3×2/3H, d, J=7 Hz), 1.27 (3×1/3H, d, J=7 Hz), 3.67 (1H, qq, J=7, 7 Hz), 4.75–4.92 (4H, m), 7.34–7.63 (4H, m), 8.13 (1×2/3H, s), 8.32 (1×2/3H, s), 8.45 (1×2/3H, d, J=8 Hz), 8.48 (1×1/3H, s), 8.57 (1×2/3H, d, J=8 Hz), 8.63 (1×1/3H, d, J=8 Hz), 8.82 (1×1/3H, d, J=8 Hz), 10.46 (1×2/3H, s), 10.55 (1×1/3H, s)

(3) 8-(2,6-Dichlorobenzoylamino)-4-(2-methylhydrazino)quinoline mp: 223–225° C. NMR (CDCl$_3$, δ): 3.26 (3H, s), 3.90 (2H, s), 7.07 (1H, d, J=6 Hz), 7.27–7.44 (3H, m), 7.52 (1H, t, J=8 Hz), 8.03 (1H, d, J=8 Hz), 8.54 (1H, d, J=6 Hz), 8.90 (1H, d, J=8 Hz)

(4) 8-(2,6-Dichlorobenzoylamino)-4-(2,2-dimethylhydrazino)quinoline mp: 202–204° C. NMR (DMSO-d$_6$, δ): 3.03 (2×3H, s), 6.95 (1H, d, J=6 Hz), 7.48–7.63 (4H, m), 7.84 (1H, d, J=8 Hz), 8.55 (1H, d, J=6 Hz), 8.65 (1H, d, J=8 Hz), 10.58 (1H, s)

(5) 8-(2,6-Dichlorobenzoylamino)-4-(4-methylpiperazin-1-ylamino)quinoline mp: 196–200° C. NMR (CDCl$_3$, δ): 2.44 (3H, s), 2.72 (4H, t, J=5 Hz), 3.29 (4H, t, J=5 Hz), 6.90 (1H, d, J=5 Hz), 7.30–7.44 (3H, m), 7.53 (1H, t, J=8 Hz), 7.75 (1H, d, J=8 Hz), 8.58 (1H, d, J=5 Hz), 8.90 (1H, d, J=8 Hz)

its dihydrochloride mp: >250° C. NMR (DMSO-d$_6$, δ): 2.88 (3H, d, J=4 Hz), 3.45–3.90 (8H, m), 7.25 (1H, d, J=6 Hz), 7.50–7.62 (3H, m), 7.70 (1H, t, J=8 Hz), 7.87 (1H, d, J=8 Hz), 8.68 (1H, d, J=8 Hz), 8.74 (1H, d, J=6 Hz)

(6) 8-(2,6-Dichlorobenzoylamino)-4-(morpholinoamino)quinoline mp: 258–260° C. NMR (CDCl$_3$, δ): 3.20–3.30 (4H, m), 3.95–4.63 (4H, m), 6.90 (1H, d, J=4 Hz), 7.30–7.45 (3H, m), 7.55 (1H, t, J=8 Hz), 7.75 (1H, d, J=8 Hz), 8.60 (1H, d, J=4 Hz), 8.92 (1H, d, J=7 Hz)

its hydrochloride mp: >260° C. NMR (CDCl$_3$, δ): 3.74–3.86 (4H, m), 3.99–4.09 (4H, m), 7.05 (1H, d, J=7 Hz), 7.30–7.45 (3H, m), 7.70–7.85 (2H, m), 8.62 (1H, d, J=7 Hz), 8.88–8.97 (1H, m)

Example 142

The following compounds were obtained according to a similar manner to that of Example 86.

(1) 4-(2-Acetylhydrazino)-8-(2,6-dichlorobenzoylamino)-3-methoxymethylquinoline mp: 186–187° C. NMR (DMSO-d$_6$, δ): 1.87 (3H, s), 3.32 (3H, s), 4.60 (2H, s), 7.47–7.63 (4H, m), 8.15 (1H, d, J=8 Hz), 8.46 (1H, s), 8.46 (1H, s), 8.65 (1H, d, J=8 Hz), 10.17 (1H, s), 10.57 (1H, s)

(2) 4-(2-Acetylhydrazino)-8-(2,6-dichlorobenzoylamino)-3-isopropoxymethylquinoline mp: 106–110° C. NMR (DMSO-d$_6$, δ): 1.15 (2×3H, d, J=7 Hz), 1.87 (3H, s), 3.65 (1H, qq, J=7, 7 Hz), 4.70 (2H, s), 7.47–7.63 (4H, m), 8.14 (1H, d, J=8 Hz), 8.32 (1H, s), 8.53 (1H, s), 8.63 (1H, d, J=8 Hz), 10.17 (1H, s), 10.55 (1H, s)

Example 143

To a stirred suspension of 8-(2,6-dichlorobenzoylamino)-4-(2-methylhydrazino)quinoline (500 mg) and triethylamine (700 mg) in dichloromethane (5 ml) was added acetic anhydride (155 mg) at ambient temperature, and the mixture was allowed to stand for 10 days at the same temperature. The mixture was diluted with dichloromethane, washed with water and evaporated in vacuo. The obtained residue was dissolved in methanol (10 ml), and a 28%0 solution of sodium methoxide in methanol (0.53 ml) was added thereto under ice-cooling. The mixture was stirred for 1 hour at the same temperature, and neutralized with 1N hydrochloric acid. The mixture was concentrated in vacuo and extracted with dichloromethane. The organic layer was washed with water, dried over magnesium sulfate and evaporated in vacuo. The residue was purified by column chromatography on silica gel (ethyl acetate) and crystallized from ethanol to give 4-(2-acetyl-2-methylhydrazino)-8-(2,6-dichlorobenzoylamino)quinoline (544 mg).

mp: 215° C. NMR (DMSO-$d_6$, $\delta$): 1.80 (3H, s), 3.22 (3H, s), 7.04 (1H, d, J=6 Hz), 7.45–7.62 (4H, m), 7.98 (1H, d, J=8 Hz), 8.59 (1H, d, J=6 Hz), 8.64 (1H, d, J=8 Hz)

Example 144

To a solution of 4-(2-acetyl-2-methylhydrazino)-8-(2,6-dichlorobenzoylamino)quinoline (140 mg) in N-methylpyrrolidone (1.5 ml) was added potassium tert-butoxide (40.9 mg) under ice-cooling, and the mixture was stirred for 30 minutes at the same temperature. Methyl iodide (59.1 mg) was added thereto under ice-cooling, and the mixture was stirred for 12 hours at ambient temperature. The mixture was diluted with ethyl acetate, washed with water and brine, dried over magnesium sulfate and evaporated in vacuo. The residue was purified by preparative thin layer chromatography (methanol-dichloromethane) and recrystallized from ethanol to give 4-(2-acetyl-1,2-dimethylhydrazino)-8-(2,6-dichlorobenzoylamino) quinoline (62 mg).

mp: 243–244° C. NMR (DMSO-$d_6$, $\delta$): 2.17 (3H, s), 2.96 (3H, s), 3.34 (3H, s), 6.99 (1H, d, J=6 Hz), 7.47–7.62 (4H, m), 7.74 (1H, d, J=8 Hz), 8.63 (1H, d, j=6 Hz), 8.70 (1H, d, J=8 Hz)

Example 145

To a suspension of 8-(2,6-dichlorobenzoylamino)-4-hydrazinoquinoline (200 mg) in ethylene chloride (2 ml) was dropwise added propionic anhydride (82.5 mg) at ambient temperature, and the mixture was stirred at the same temperature overnight. The mixture was evaporated in vacuo, and the residue was crystallized from ethanol to give 8-(2,6-dichlorobenzoylamino)-4-(2-propionylhydrazino) quinoline (40 mg).

mp: 246–248° C. NMR (DMSO-$d_6$, $\delta$): 1.15 (3H, t, J=7.5 Hz), 2.30 (2H, q, J=7.5 Hz), 6.63 (1H, d, J=7.0 Hz), 7.50–7.62 (4H, m), 8.00 (1H, d, J=8.0 Hz), 8.42 (1H, d, J=7.0 Hz), 8.66 (1H, d, J=8.0 Hz), 9.27 (1H, br s)

Example 146

A mixture of 8-(2,6-dichlorobenzoylamino)-4-hydrazinoquinoline (200 mg), crotonic acid (54.5 mg), 1-ethyl-3-(3-dimethylaminopropyl)carbodiimide hydrochloride (133 mg) and 1-hydroxybenzotriazole (93.4 mg) in dimethylformamide (4 ml) was stirred at ambient temperature overnight. The mixture was diluted with ethyl acetate, washed with water, saturated sodium bicarbonate solution and brine, dried over magnesium sulfate and evaporated in vacuo.

The residue was purified by column chromatography on silica gel (methanol-dichloromethane) to give 4-(2-crotonoylhydrazino)-8-(2,6-dichlorobenzoylamino) quinoline (90 mg) and 8-(2,6-dichlorobenzoylamino)-4-(3-methyl-5-oxopyrazolidin-1-yl)quinoline (25 mg). 4-(2-Crotonoylhydrazino)-8-(2,6-dichlorobenzoylamino) quinoline mp: 257–259° C. NMR (DMSO-$d_6$, $\delta$): 1.86 (3H, d, J=7.5 Hz), 6.10 (1H, d, J=15.0 Hz), 6.58 (1H, d, J=6.0 Hz), 6.83 (1H, dq, J=15.0, 7.5 Hz), 7.50–7.60 (4H, m), 8.01 (1H, d, J=8.0 Hz), 8.43 (1H, d, J=6.0 Hz), 8.68 (1H, d, J=8.0 Hz), 9.37 (1H, s), 10.06 (1H, s), 10.26 (1H, s) 8-(2,6-Dichlorobenzoylamino)-4-(3-methyl-5-oxopyrazolidin-1-yl)quinoline mp: 228–230° C. NMR (DMSO-$d_6$, $\delta$): 1.32 (3H, d, J=7.0 Hz), 2.40 (1H, dd, J=16.0, 7.5 Hz), 2.85 (1H, dd, J=16.0, 7.5 Hz), 3.88 (1H, dddq, J=9.0, 7.5, 7.5, 7.0 Hz), 6.58 (1H, d, J=9.0 Hz), 7.48–7.64 (1H, m), 7.89 (1H, d, J=8.0 Hz), 8.70 (1H, d, J=8.0 Hz), 8.88 (1H, d, J=5.0 Hz), 10.73 (1H, s)

Example 147

A mixture of 8-(2,6-dichlorobenzoylamino)-4-hydrazinoquinoline (200 mg), methacrylic acid (54.5 mg), 1-ethyl-3-(3-dimethylaminopropyl)-arbodiimide hydrochloride (133 mg) and 1-hydroxybenzotriazole (93.4 mg) in dimethylformamide (4 ml) was stirred for 4.5 hours at ambient temperature. The mixture was diluted with ethyl acetate and washed with water, saturated sodium bicarbonate solution and brine. The insoluble materials were collected by filtration and recrystallized from ethanol to give 8-(2,6-dichlorobenzoylamino)-4-(2-methacryloylhydrazino)quinoline (190 mg).

mp: 277–280° C. NMR (DMSO-$d_6$, $\delta$): 1.97 (3H, s), 5.53 (1H, s), 5.87 (1H, s), 6.64 (1H, d, J=7.0 Hz), 7.48–7.60 (4H, m), 8.03 (1H, d, J=8.0 Hz), 8.44 (1H, d, J=7.0 Hz), 8.66 (1H, d, J=8.0 Hz), 9.33 (1H, s)

Example 148

The following compounds were obtained according to a similar manner to that of Example 147.
(1) 4-(2-Cyclopropanecarbonylhydrazino)-8-(2,6-dichlorobenzoylamino)quinoline mp: 267–269° C. NMR (DMSO-$d_6$, $\delta$): 0.78–0.84 (4H, m), 1.71–1.80 (1H, m), 6.61 (1H, d, J=7.0 Hz), 7.50–7.60 (4H, m), 7.99 (1H, d, J=8.0 Hz), 8.45 (1H, d, J=7.0 Hz), 8.66 (1H, d, J=8.0 Hz), 9.31 (1H, s)
(2) 4-(2-Cyclopentanecarbonylhydrazino)-8-(2,6-dichlorobenzoylamino)quinoline mp: 249–251° C. NMR (DMSO-$d_6$, $\delta$): 1.54–1.77 (6H, m), 1.86–1.93 (2H, m), 2.76 (1H, qn, J=7.5 Hz), 6.57 (1H, d, J=6.0 Hz), 7.47–7.60 (4H, m), 8.00 (1H, d, J=8.0 Hz), 8.43 (1H, d, J=6.0 Hz), 8.66 (1H, d, J=8.0 Hz), 9.30 (1H, br s)
(3) 8-(2,6-Dichlorobenzoylamino)-4-(2-methoxyacetylhydrazino)quinoline mp: 223–225° C. NMR (DMSO-$d_6$, $\delta$): 3.41 (3H, s), 4.08 (2H, s), 6.63 (1H, d, J=6 Hz), 7.48–7.63 (4H, m), 8.00 (1H, d, J=8 Hz), 8.43 (1H, d, J=6 Hz), 8.67 (1H, d, J=8 Hz), 9.30 (1H, s), 10.18 (1H, s), 10.52 (1H, s)
(4) 4-(2-Acetamidoacetylhydrazino)-8-(2,6-dichlorobenzoylamino)quinoline mp: 263–269° C. NMR (DMSO-$d_6$, $\delta$): 1.90 (3H, s), 3.85 (2H, d, J=6 Hz), 6.71 (1H, d, J=6 Hz), 7.46–7.63 (4H, m), 8.00 (1H, d, J=8 Hz), 8.32 (1H, t, J=6 Hz), 8.42 (1H, d, J=6 Hz), 8.66 (1H, t, J=8 Hz), 9.32 (1H, s), 10.13 (1H, s), 10.52 (1H, s)
(5) 8-(2,6-Dichlorobenzoylamino)-4-[2-(2-furylcarbonyl) hydrazino]quinoline hydrochloride mp: >250° C. NMR (DMSO-d$_6$, δ): 6.78 (1H, d, J=3 Hz), 6.96 (1H, d, J=5 Hz), 7.45 (1H, d, J=4 Hz), 7.50–7.68 (3H, m), 7.86 (1H, t, J=8 Hz), 8.04 (1H, s), 8.43 (1H, d, J=8 Hz), 8.55–8.65 (2H, m)

(6) 8-(2,6-Dichlorobenzoylamino)-4-[2-(1-methylimidazol-2-yl)carbonyl]hydrazino]quinoline mp: 217–220° C. NMR (DMSO-d$_6$, δ): 3.95 (3H, s), 6.65 (1H, d, J=6 Hz), 7.10 (1H, s), 7.47 (1H, s), 7.49–7.63 (4H, m), 8.05 (1H, d, J=8 Hz), 8.42 (1H, d, J=6 Hz), 8.68 (1H, d, J=8 Hz), 9.45 (1H, s)

(7) 8-(2,6-Dichlorobenzoylamino)-4-[2-(pyridin-2-ylcarbonyl)hydrazino]quinoline dihydrochloride mp: 200–220° C. NMR (DMSO-d$_6$, δ): 6.95 (1H, d, J=6 Hz), 7.52–7.68 (3H, m), 7.77 (1H, t, J=6 Hz), 7.90 (1H, r, J=8 Hz), 8.08–8.18 (2H, m), 8.50 (1H, d, J=8 Hz), 8.55–8.67 (2H, m), 8.80 (1H, d, J=4 Hz)

Example 149

(1) 4-(2-Acetoxyacetylhydrazino)-8-(2,6-dichlorobenzoylamino)quinoline was obtained from 8-(2,6-dichlorobenzoylamino)-4-hydrazinoquinoline and acetoxyacetic acid according to a similar manner to that of Example 147.

mp: 234–236° C. NMR (DMSO-d$_6$, δ): 2.14 (3H, s), 4.70 (2H, s), 6.68 (1H, d, J=6.0 Hz), 7.50–7.60 (4H, m), 8.00 (1H, d, J=8.0 Hz), 8.43 (1H, d, j=6.0 Hz), 8.66 (1H, d, J=8.0 Hz), 9.36 (1H, s)

(2) 8-(2,6-Dichlorobenzoylamino)-4-(2-hydroxyacetylhydrazino)quinoline was obtained according to a similar manner to that of Example 12-(2).

mp: 248–250° C. NMR (DMSO-d$_6$, δ): 4.07 (2H, d, J=7.0 Hz), 5.63 (1H, t, J=7.0 Hz), 6.65 (1H, d, J=6.0 Hz), 7.48–7.61 (4H, m), 8.03 (1H, d, J=8.0 Hz), 8.43 (1H, d, J=6.0 Hz), 8.65 (1H, d, J=8.0 Hz), 9.25 (1H, s)

Example 150

To a stirred suspension of 8-(2,6-dichlorobenzoylamino)-4-hydrazinoquinoline (200 mg) in pyridine (2 ml) was added a solution of ethyl chloroformate (68.8 mg) in dichloromethane (0.5 ml) under ice-cooling, and the mixture was stirred for 1 hour at ambient temperature. The mixture was concentrated in vacuo, and the residue was diluted with dichloromethane. The mixture was washed with water and brine, dried over magnesium sulfate and evaporated in vacuo. The residue was recrystallized from ethanol to give 8-(2,6-dichlorobenzoylamino)-4-(2-ethoxycarbonylhydrazino)quinoline (115 mg).

mp: 151–155° C. NMR (DMSO-d$_6$, δ): 1.24 (3H, br t, j=8 Hz), 4.11 (2H, br a, J=8 Hz), 6.64 (1H, d, J=6 Hz), 7.46–7.63 (4H, m), 7.94 (1H, d, J=8 Hz), 8.44 (1H, d, J=5 Hz), 8.66 (1H, d, J=8 Hz), 9.31 (1H, br s), 9.49 (1H, br s)

Example 151

A suspension of 8-(2,6-dichlorobenzoylamino)-4-hydrazinoquinoline (200 mg) and methyl isothiocyanate (54.8 mg) in ethylene chloride (4 ml) was stirred for 2 hours at ambient temperature and then gently refluxed for 24 hours. The mixture was concentrated in vacuo, and the residue was recrystallized from ethanol to give 8-(2,6-dichlorobenzoylamino)-4-[4-(methyl)thiosemicarbazido]quinoline (213 mg).

mp: >258° C. NMR (DMSO-d$_6$, δ): 2.87 (3H, d, J=5 Hz), 6.60 (1H, d, J=5 Hz), 7.47–7.64 (4H, m), 7.98 (1H, d, J=8 Hz), 8.26 (1H, br q, J=5 Hz), 8.47 (1H, d, J=5 Hz), 8.67 (1H, d, J=8 Hz), 9.43 (1H, br s), 9.63 (1H, br s)

Example 152

The following compounds were obtained according to a similar manner to that of Example 151.

(1) 8-(2,6-Dichlorobenzoylamino)-4-(4-phenylsemicarbazido)quinoline mp: >234° C. NMR (DMSO-d$_6$, δ): 6.77 (1H, d, J=6 Hz), 6.94 (1H, t, J=8 Hz), 7.19–7.29 (2H, m), 7.45–7.64 (6H, m), 8.03 (1H, d, J=8 Hz), 8.47 (1H, d, J=6 Hz), 8.53 (1H, br s), 8.67 (1H, d, J=8 Hz), 8.93 (1H, br s), 9.30 (1H, br s)

(2) 8-(2,6-Dichlorobenzoylamino)-4-[4-(phenyl)thiosemicarbazido]quinoline mp: 227–232° C. NMR (DMSO-d$_6$, δ): 6.71 (1H, d, J=6 Hz), 7.16 (1H, t, J=8 Hz), 7.25–7.36 (2H, m), 7.38–7.47 (2H, m), 7.49–7.70 (4H, m), 8.03 (1H, d, J=8 Hz), 8.55 (1H, d, J=6 Hz), 8.67 (1H, d, J=8 Hz), 9.63 (1H, br s), 9.91–10.13 (2H, m), 10.56 (1H, s)

Example 153

(1) 8-(2,6-Dichlorobenzoylamino)-4-[2-(2-hydroxyethyl)hydrazino]quinoline was obtained from 4-chloro-8-(2,6-dichlorobenzoylamino)quinoline and 2-hydroxyethylhydrazine according to a similar manner to that of Example 8.

mp: 125–137° C. NMR (CDCl$_3$, δ): 1.92 (1H, br), 3.10–3.20 (2H, m), 3.83–3.41 (2H, m), 4.05 (1H, t, J=6 Hz), 6.57 (1H, s), 7.12 (1H, d, J=5 Hz), 7.28–7.50 (4H, n), 8.47 (1H, d, J=5 Hz), 8.91 (1H, d, J=6 Hz)

its dihydrochloride mp: 153–167° C. NMR (DMSO-d$_6$, δ): 3.02 (2H, t, J=6 Hz), 3.54 (2H, t, J=6 Hz), 7.33 (1H, d, J=8 Hz), 7.50–7.67 (3H, m), 7.75 (1H, t, J=6 Hz), 8.39 (1H, d, J=8 Hz), 8.40–8.50 (2H, m)

(2) 8-(2,6-Dichlorobenzoylamino)-4-(2-oxazolidinon-3-ylamino)quinoline was obtained according to a similar manner to that of Example 92-(2)

mp: >250° C. NMR (CDCl$_3$, δ): 3.92 (2H, t, J=8 Hz), 4.58 (2H, t, J=8 Hz), 6.81 (1H, d, J=4 Hz), 7.33–7.44 (3H, m), 7.50–7.67 (2H, m), 8.53 (1H, d, J=4 Hz), 8.93 (1H, d, J=6 Hz)

Example 154

To a stirred suspension of 8-(2,6-dichlorobenzoylamino)-4-hydrazinoquinoline (216 mg) in pyridine (2 ml) was added a solution of methanesulfonyl chloride (78.4 mg) in dimethylformamide under ice-cooling, and the mixture was stirred for 50 minutes at the same temperature. The mixture was concentrated in vacuo, and ethyl acetate, methanol and water were added to the residue. The separated organic layer was washed with water and brine, dried over magnesium sulfate and evaporated in vacuo. The residue was purified by preparative thin layer chromatography and recrystallized from ethanol to give 8-(2,6-dichlorobenzoylamino)-4-(2-methanesulfonylhydrazino)quinoline (16 mg).

mp: 156–164° C. NMR (DMSO-d$_6$, δ): 3.10 (3H, s), 7.10 (1H, d, J=6 Hz), 7.48–7.63 (4H, m), 8.05 (1H, d, J=8 Hz), 8.50 (1H, d, J=6 Hz), 8.68 (1H, d, J=8 Hz), 9.45 (1H, s), 9.56 (1H, s), 10.55 (1H, s)

Example 155

4-(2-Benzenesulfonylhydrazino)-8-(2,6-dichlorobenzoylamino)quinoline was obtained by reacting 8-(2,6-dichlorobenzoylamino)-4-hydrazinoquinoline with benzenesulfonyl chloride according to a similar manner to that of Example 154.

mp: 197–201° C. NMR (DMSO-d$_6$, δ): 6.89 (1H, d, J=6 Hz), 7.43–7.73 (7H, m), 7.80–7.92 (3H, m), 8.38 (1H, d, J=6 Hz), 8.64 (1H, d, J=8 Hz), 9.34 (1H, s), 10.12 (1H, s), 10.52 (!H, s)

Example 156

(1) 8-(2,6-Dichlorobenzoylamino)-4-[(2-ethylaminoethyl)amino]quinoline was obtained from 4-chloro-8-(2,6- dichlorobenzoylamino)quinoline and N-ethylethylenediamine according to a similar manner to that of Example 8.

mp: 140–144° C. NMR (CDCl₃, δ): 1.17 (3H, t, J=8 Hz), 2.73 (2H, q, J=8 Hz), 3.06 (2H, t, J=7 Hz), 3.37 (2H, q, J=7 Hz), 5.93 (1H, t, J=7 Hz), 6.46 (1H, d, j=6 Hz), 7.30–7.43 (3H, m), 7.45–7.57 (2H, m), 8.40 (1H, d, J=6 Hz), 8.92 (1H, d, J=8 Hz)

(2) 8-(2,6-Dichlorobenzoylamino)-4-(3-ethyl-2-oxoimidazolidin-1-yl)quinoline was obtained according to a similar manner to that of Example 92-(2).

mp: 249–253° C. NMR (CDCl₃, δ): 1.25 (3H, t, J=8 Hz), 3.45 (2H, q, j=8 Hz), 3.65 (2H, t, J=6 Hz), 3.97 (2H, t, J=8 Hz), 7.30–7.45 (4H, m), 7.62 (1H, t, J=8 Hz), 7.77 (1H, d, J=8 Hz), 8.73 (1H, d, J=5 Hz), 8.98 (1H, d, J=8 Hz)

Example 157

A mixture of 4-chloro-8-(2,6-dichlorobenzoylamino) quinoline (400 mg) and N-benzylethylenediamine (854 mg) was stirred for 6 hours at 130° C. The mixture was partitioned between ethyl acetate and water, and the organic layer was washed with water and brine, dried over magnesium sulfate and evaporated in vacuo. The residue was purified by flash chromatography on silica gel (methanol-dichloromethane) to give a residue containing 4-(2-benzylaminoethylamino)-8-(2,6-dichlorobenzoylamino) quinoline. A mixture of the obtained residue, 1,1'-carbonyldiimidazole (221 mg) and 1,8-diazabicyclo[5.4.0] undec-7-ene (191 mg) in dimethylformamide was stirred for 4 hours at ambient temperature and for 2 hours at 130° C. The mixture was partitioned between ethyl acetate and water, and the organic layer was washed with water and brine, dried over magnesium sulfate and evaporated in vacuo. The residue was purified by flash chromatography on silica gel (methanol-dichloromethane) to give 4-(3-benzyl-2-oxoimidazolidin-1-yl)-8-(2,6-dichlorobenzoylamino) quinoline (150 mg).

mp: 178–191° C. NMR (CDCl₃, δ): 3.52 (2H, t, J=8 Hz), 3.93 (2H, t, J=8 Hz), 4.55 (2H, s), 7.30–7.45 (9H, m), 7.62 (1H, t, J=8 Hz), 7.75 (1H, d, J=8 Hz), 8.74 (1H, d, J=5 Hz), 8.98 (1H, d, J=8 Hz)

Example 158

8-(2,6-Dichlorobenzoylamino)-4-(3-methyl-3,4,5,6-tetrahydro-2(1H)-pyrimidinon-1-yl)quinoline was obtained from 4-chloro-8-(2,6-dichlorobenzoylamino)quinoline and 3-methylaminopropylamine according to a similar manner to that of Example 157.

mp: 252–254° C. NMR (CDCl₃, δ): 2.60–2.45 (4H, m), 3.07 (3H, s), 3.47–3.85 (6H, m), 7.30–7.45 (4H, m), 7.58–7.65 (2H, m), 8.76 (1H, d, J=5 Hz), 8.90–8.98 (1H, m)

Example 159

8-(2,6-Dichlorobenzoylamino)-3-methyl-4-(3-methyl-2-thioxoimidazolidin-1-yl)quinoline was obtained from 8-(2,6-dichlorobenzoylamino)-3-methyl-4-[(2-methylaminoethyl)amino]-quinoline and 1,1'-thiocarbonyldiimidazole according to a similar manner to that of Example 92-(2).

mp: 248–250° C. NMR (DMSO-d₆, δ): 2.37 (3H, s), 3.16 (3H, s), 3.82–4.08 (4H, m), 7.48–7.70 (5H, m), 8.65 (1H, d, J=8 Hz), 8.89 (1H, s)

Example 160

(1) 3-tert-Butyldimethylsilyloxymethyl-4-chloro-8-(2,6-dichlorobenzoylamino)quinoline was obtained from 4-chloro-8-(2,6-dichlorobenzoylamino)-3-hydroxymethylquinoline and tert-butyldimethylsilyl chloride according to a similar manner to that of Example 125-(2).

mp: 205–207° C. NMR (CDCl₃, δ): 0.16 (2×3H, s), 0.96 (3×3H, s), 5.02 (2H, s), 7.30–7.44 (3H, m), 7.70 (1H, dd, J=8, 8 Hz), 7.97 (1H, d, J=8 Hz), 8.93 (1H, s), 9.00 (1H, d, J=8 Hz), 10.09 (1H, br s)

(2) 3-tert-Butyldimethylsilyloxymethyl-8-(2,6-dichlorobenzoylamino)-4-[(2-methylaminoethyl)amino] quinoline was obtained according to a similar manner to that of Example 8.

NMR (DMSO-d₆, δ): 0.06 (2×3H, s), 0.86 (3×3H, s), 2.31 (3H, s), 2.73 (2H, t, J=6 Hz), 3.69 (2H, dt, J=6, 6 Hz), 4.84 (2H, s), 6.45 (1H, t, J=6 Hz), 7.43–7.62 (4H, m), 7.98 (1H, d, J=8 Hz), 8.37 (1H, s), 8.61 (1H, d, J=8 Hz), 10.51 (1H, s)

(3) 3-tert-Butyldimethylsilyloxymethyl-8-(2,6-dichlorobenzoylamino)-4-(3-methyl-2-oxoimidazolidin-1-yl)quinoline was obtained according to a similar manner to that of Example 92-(2).

NMR (DMSO-d₆, δ): 0.10 (3H, s), 0.12 (3H, s), 0.90 (3×3H, s), 2.81 (3H, s), 3.60 (1H, m), 3.63–3.75 (2H, m), 3.83 (1H, m), 4.86 (2H, s), 7.47–7.61 (3H, m), 7.66–7.74 (2H, m), 8.73 (1H, m), 9.00 (1H, s), 10.86 (1H, s)

(4) 8-(2,6-Dichlorobenzoylamino)-3-hydroxymethyl-4-(3-methyl-2-oxoimidazolidin-1-yl)quinoline was obtained according to a similar manner to that of Example 125-(8).

mp: 251–253° C. NMR (DMSO-d₆, δ): 2.82 (3H, s), 3.55–3.77 (3H, m), 3.83 (1H, m), 4.65 (2H, d, J=6 Hz), 5.45 (1H, t, J=6 Hz), 7.48–7.62 (3H, m), 7.69 (1H, d, J=5 Hz), 8.70 (1H, dd, J=5, 5 Hz), 9.03 (1H, s), 11.06 (1H, s)

Example 161

(1) 3-Ethoxymethyl-1,4-dihydro-8-nitro-4-oxoquinoline was obtained from 3-chloromethyl-1,4-dihydro-8-nitro-4-oxoquinoline and ethanol according to a similar manner to that of Example 124-(2).

mp: 175–180° C. NMR (DMSO-d₆, δ): 1.17 (3H, t, J=8 Hz), 3.55 (2H, q, J=8 Hz), 4.37 (2H, s), 7.50–7.60 (1H, m), 7.99 (1H, d, J=6 Hz), 8.57–8.69 (2H, m)

(2) 4-Chloro-3-ethoxymethyl-8-nitroquinoline was obtained according to a similar manner to that of Preparation 2-(1).

mp: 110–126° C. NMR (CDCl₃, δ): 1.30 (3H, t, J=8 Hz), 3.68 (2H, q, J=8 Hz), 4.85 (2H, s), 7.73 (1H, t, J=8 Hz), 8.05 (1H, d, J=8 Hz), 8.48 (1H, d, J=8 Hz), 9.13 (1H, s)

(3) 8-Amino-4-chloro-3-ethoxymethylquinoline was obtained according to a similar manner to that of Preparation 2-(3).

mp: 90–93° C. NMR (CDCl₃, δ): 1.30 (3H, t, J=8 Hz), 3.64 (2H, q, J=8 Hz), 4.82 (2H, s), 5.05 (2H, s), 6.95 (1H, d, J=8 Hz), 7.41 (1H, t, j=8 Hz), 7.53 (1H, d, J=8 Hz), 8.78 (1H, s)

(4) 4-Chloro-8-(2,6-dichlorobenzoylamino)-3-ethoxymethylquinoline was obtained according to a similar manner to that of Example 1.

mp: 121–123° C. NMR (CDCl₃, δ): 1.30 (3H, t, J=8 Hz), 3.66 (2H, d, J=8 Hz), 4.85 (2H, s), 7.30–7.45 (3H, m), 7.71 (1H, t, J=8 Hz), 8.01 (1H, d, J=8 Hz), 8.85 (1H, s), 9.01 (1H, d, J=8 Hz)

(5) 8-(2,6-Dichlorobenzoylamino)-3-ethoxymethyl-4-(3-methyl-2-oxoimidazolidin-1-yl)quinoline was obtained according to a similar manner to that of Example 157.

mp: 173–177° C. NMR (CDCl₃, δ): 1.25 (3H, t, J=8 Hz), 2.98 (3H, s), 3.53–3.99 (6H, m), 4.57–4.80 (2H, m), 7.28–7.44 (3H, m), 7.63 (2H, d, J=4 Hz), 8.88 (1H, s), 8.96 (1H, t, J=4 Hz)

Example 162

(1) 3-tert-Butyldiphenylsilyloxymethyl-1,4-dihydro-8-nitro-4-oxoquinoline was obtained from 1,4-dihydro-3- hydroxymethyl-8-nitro-4-oxoquinoline and tert-butyldiphenylsilyl chloride according to a similar manner to that of Example 125-(2).

mp: 168–171° C. NMR (CDCl$_3$, δ): 1.14 (9H, s), 4.83 (2H, s), 7.32–7.47 (7H, m), 7.53–7.63 (4H, m), 8.06 (1H, d, J=7 Hz), 8.65 (1H, d, J=8 Hz), 8.76 (1H, d, J=7.5 Hz)

(2) 3-tert-Butyldiphenylsilyloxymethyl-4-chloro-8-nitroquinoline was obtained according to a similar manner to that of Preparation 2-(1)

mp: 100–105° C. NMR (CDCl$_3$, δ): 1.11 (3×3H, s), 5.04 (2H, s), 7.33–7.50 (6H, m), 7.65–7.75 (5H, m), 8.05 (1H, d, J=7.5 Hz), 8.42 (1H, d, J=7.5 Hz), 9.40 (1H, s)

(3) 8-Amino-3-tert-butyldiphenylsilyloxymethyl-4-chloroquinoline was obtained according to a similar manner to that of Preparation 2-(3).

mp: 107–108° C. NMR (DMSO-d$_6$, δ): 1.06 (3×3H, s), 5.04 (2H, s), 6.15 (2H, s), 6.93 (1H, d, J=8 Hz), 7.23 (1H, d, J=8 Hz), 7.39–7.53 (7H, m), 7.68 (4×1H, d, J=7.5 Hz), 8.86 (1H, s)

(4) 3-tert-Butyldiphenylsilyloxymethyl-4-chloro-8-(2,6-dichlorobenzoylamino)quinoline was obtained according to a similar manner to that of Example 1.

mp: 123–124° C. NMR (DMSO-d$_6$, δ): 1.06 (3×3H, s), 5.10 (2H, s), 7.40–7.62 (9H, m), 7.67 (4×1H, d, J=7.5 Hz), 7.82 (1H, dd, J=8, 8 Hz), 7.97 (1H, d, J=8 Hz), 8.82 (1H, d, J=8 Hz), 9.06 (1H, s), 10.98 (1H, s)

(5) 3-tert-Butyldiphenylsilyloxymethyl-4-(imidazol-1-yl)-8-(2,6-dichlorobenzoylamino)quinoline was obtained according to a similar manner to that of Example 8.

NMR (CDCl$_3$, δ): 1.04 (9H, s), 4.61 (2H, s), 6.99 (1H, s), 7.09 (1H, d, J=7.5 Hz), 7.27 (1H, d, J=7.5 Hz), 7.31–7.47 (9H, m), 7.50–7.65 (6H, m), 8.98–9.05 (2H, m)

(6) 8-(2,6-Dichlorobenzoylamino)-3-hydroxymethyl-4-(imidazol-1-yl)quinoline was obtained according to a similar manner to that of Example 125-(8).

mp: 205–207° C. NMR (DMSO-d$_6$, δ): 4.44 (2H, d, J=6 Hz), 5.59 (1H, t, J=6 Hz), 7.07 (1H, d, J=8 Hz), 7.28 (1H, s), 7.49–7.63 (4H, m), 7.70 (1H, dd, J=8, 8 Hz), 7.97 (1H, s), 8.76 (1H, d, J=8 Hz), 9.14 (1H, s), 11.00 (1H, s)

Example 163

To a suspension of 8-(2,6-dichlorobenzoylamino)-3-hydroxymethyl-4-(imidazol-1-yl)quinoline (250 mg) in dichloromethane (3 ml) were dropwise added pyridine (57.4 mg) and acetic anhydride (0.12 ml) at ambient temperature, and the mixture was stirred for 22 hours at ambient temperature. The mixture was concentrated in vacuo, and the residue was dissolved in ethyl acetate. The mixture was washed with water, dried over magnesium sulfate and evaporated in vacuo. The residue was purified by flash chromatography on silica gel (methanol-dichloromethane) to give 3-acetoxymethyl-8-(2,6-dichlorobenzoylamino)-4-(imidazol-1-yl)quinoline (270 mg).

NMR (CDCl$_3$, δ): 2.07 (3H, S), 5.00 (1H, d, J=13.5 Hz), 5.13 (1H, d, J=13.5 Hz), 7.16–7.23 (2H, m), 7.34–7.45 (2H, m), 7.67 (1H, t, J=8.0 Hz), 7.74 (1H, s), 8.95 (1H, s), 9.06 (1H, d, J=8.0 Hz)

Example 164

(1) To a suspension of 8-(2,6-dichlorobenzoylamino)-3-hydroxymethyl-4-(imidazol-1-yl)quinoline (800 mg) in dichloromethane (10 ml) were dropwise added pyridine (230 mg) and phenyl chloroformate (333 mg) at ambient temperature, and the mixture was stirred for 1 hour at ambient temperature. The mixture was washed with saturated ammonium chloride solution, saturated sodium bicarbonate solution and brine, dried over magnesium sulfate and evaporated in vacuo. The residue was purified by column chromatography on silica gel (ethyl acetate-n-hexane) to give 8-(2,6-dichlorobenzoylamino)-4-(imidazol-1-yl)-3-(phenoxycarbonyloxymethyl)quinoline (100 mg).

NMR (CDCl$_3$, δ): 5.23 (2H, d, J=7.0 Hz), 7.12–7.45 (11H, m), 7.67 (1H, t, J=7.5 Hz), 7.75 (1H, s), 9.03–9.10 (2H, m)

(2) To a solution of 8-(2,6-dichlorobenzoylamino)-3-(phenoxycarbonyloxymethyl)-4-(imidazol-1-yl)quinoline (100 mg) in methanol (4 ml) was dropwise added a solution of 2M solution of methylamine in methanol (4 ml) under ice-cooling, and the mixture was stirred for 1 hour at ambient temperature. The mixture was concentrated in vacuo, and the residue was crystallized from ethanol to give 8-(2,6-dichlorobenzoylamino)-4-(imidazol-1-yl)-3-(methylcarbamoyloxymethyl)quinoline (50 mg).

mp: 240–242° C. NMR (CDCl$_3$, δ): 2.80 (3H, d, J=6.0 Hz), 4.70 (1H, br), 4.99 (1H, d, J=8.0 Hz), 5.15 (1H, d, J=8.0 Hz), 7.16 (1H, d, J=8.0 Hz), 7.23 (1H, s), 7.34–7.45 (4H, m), 7.65 (1H, t, J=8.0 Hz), 7.73 (1H, s), 9.00 (1H, s), 9.05 (1H, d, J=8.0 Hz)

Example 165

(1) To a suspension of 8-(2,6-dichlorobenzoylamino)-3-hydroxymethyl-4-(imidazol-1-yl)quinoline (300 mg) in dichloromethane (5 ml) were dropwise added triethylamine (294 mg) and phenyl chloroformate (375 mg) under ice-cooling, and the mixture was stirred for 2.5 hours at ambient temperature. To the mixture was further added phenyl chloroformate (250 mg), and the mixture was stirred for 1.5 hours at ambient temperature. Insoluble material was filtered off, and the filtrate was concentrated in vacuo. The residue was dissolved in dichloromethane, and phenyl chloroformate (375 mg) and diisopropylethylamine (0.506 ml) were added thereto. The mixture was evaporated in vacuo, and the residue was purified by flash chromatography on silica gel (ethyl acetate-n-hexane) to give 8-[N-(2,6-dichlorobenzoyl)-N-phenoxycarbonylamino]-4-[2-(phenoxycarbonyl)imidazol-1-yl]-3-(phenoxycarbonyloxymethyl)quinoline (250 mg).

NMR (CDCl$_3$, δ): 5.22 (2H, d, J=8.5 Hz), 6.86 (2H, d, J=7.5 Hz), 6.93 (2H, t, J=7.0 Hz), 7.02–7.45 (14H, m), 7.65–7.75 (3H, m), 8.03–8.06 (1H, m), 9.02 (1H, s), 9.27 (1H, s)

(2) To a solution of 8-[N-(2,6-dichlorobenzoyl)-N-phenoxycarbonylamino]-4-[2-(phenoxycarbonyl)imidazol-1-yl]-3-(phenoxycarbonyloxymethyl)quinoline (250 mg) in methanol (4 ml) was added 50% aqueous solution of dimethylamine (8 ml), and the mixture was stirred for 66 hours at ambient temperature. The mixture was concentrated in vacuo, and the residue was purified by preparative thin layer chromatography (ethyl acetate) to give 8-(2,6-dichlorobenzoylamino)-4-[2-(dimethylcarbamoyl)imidazol-1-yl]-3-(dimethylcarbamoyloxymethyl)quinoline (25 mg).

NMR (CDCl$_3$, δ): 2.87 (9H, s), 3.54 (3H, s), 5.07 (1H, d, J=14.0 Hz), 5.16 (1H, d, J=14.0 Hz), 6.82 (1H, d, J=8.0 Hz), 7.16 (1H, s), 7.32–7.43 (4H, m), 7.57 (1H, t, J=8.0 Hz), 8.96 (1H, s), 8.99 (1H, d, J=8.0 Hz), 10.02 (1H, s)

Example 166

(1) 3-Isopropoxymethyl-1,4-dihydro-8-nitro-4-oxoquinoline was obtained from 3-chloromethyl-1,4-dihydro-8-nitro-4-oxoquinoline and isopropyl alcohol according to a similar manner to that of Example 124-(2).

mp: 167–170.5° C. NMR (CDCl$_3$, δ): 1.26 (2×3H, d, J=7 Hz), 3.79 (1H, qq, J=7, 7 Hz), 4.55 (2H, s), 7.43 (1H, dd, J=8, 8 Hz), 7.95 (1H, d, J=6 Hz), 8.67 (1H, d, J=8 Hz), 8.82 (1H, d, J=8 Hz)

(2) 4-Chloro-3-isopropoxymethyl-8-nitroquinoline was obtained according to a similar manner to that of Preparation 2-(1).

mp: 83–86° C. NMR (CDCl$_3$, δ): 1.27 (2×3H, d, J=7 Hz), 3.79 (1H, qq, j=7, 7 Hz), 4.83 (2H, s), 7.71 (1H, dd, J=8, 8 Hz), 8.04 (1H, d, J=8 Hz), 8.47 (1H, d, J=8 Hz), 9.15 (1H, s)

(3) 8-Amino-4-chloro-3-isopropoxymethylquinoline was obtained according to a similar manner to that of Preparation 2-(3).

mp: 94–95° C. NMR (CDCl$_3$, δ): 1.27 (2×3H, d, J=7 Hz), 3.77 (1H, qq, J=7, 7 Hz), 4.80 (2H, s), 5.02 (2H, br), 6.93 (1H, d, J=8 Hz), 7.40 (1H, dd, J=8, 8 Hz), 7.52 (1H, d, J=8 Hz), 8.80 (1H, s)

(4) 4-Chloro-8-(2,6-dichlorobenzoylamino)-3-isopropoxymethylquinoline was obtained according to a similar manner to that of Example 1.

mp: 117–118° C. NMR (CDCl$_3$, δ): 1.27 (2×3H, d, J=7 Hz), 3.78 (1H, qq, J=7, 7 Hz), 4.82 (2H, s), 7.30–7.43 (3H, m), 7.70 (1H, dd, J=8, 8 Hz), 7.98 (1H, d, J=8 Hz), 8.86 (1H, s), 8.98 (1H, d, J=8 Hz), 10.03 (1H, br s)

(5) 8-(2,6-Dichlorobenzoylamino)-4-(imidazol-1-yl)-3-isopropoxymethylquinoline was obtained according to a similar manner to that of Example 8.

NMR (DMSO-d$_6$, δ): 1.05 (2×3H, d, J=7 Hz), 3.54 (1H, qq, J=7, 7 Hz), 4.40 (2H, s), 7.07 (1H, d, J=8 Hz), 7.28 (1H, s), 7.48–7.63 (4H, m), 7.72 (1H, dd, J=8, 8 Hz), 7.97 (1H, s), 8.77 (1H, d, J=8 Hz), 9.10 (1H, s), 10.98 (1H, s)

(6) 8-(2,6-Dichlorobenzoylamino)-3-isopropoxymethyl-4-(pyrazol-1-yl)quinoline was obtained from 4-chloro-8-(2,6-dichlorobenzoylamino)-3-isopropoxymethylquinoline and pyrazole according to a similar manner to that of Example 8.

mp: 153–154° C. NMR (DMSO-d$_6$, δ): 1.03 (2×3H, d, J=7 Hz), 3.54 (1H, qq, J=7, 7 Hz), 4.43 (2H, s), 6.70 (1H, dd, J=1.5, 1 Hz), 7.15 (1H, d, J=8 Hz), 7.49–7.62 (3H, m), 7.70 (1H, dd, J=8, 8 Hz), 7.95 (1H, d, J=1 Hz), 8.20 (1H, d, J=1.5 Hz), 8.75 (1H, d, J=8 Hz), 9.09 (1H, s), 10.46 (1H, s)

Example 167

To a stirred solution of 2-methoxyethanol (130 mg) in N-methylpyrrolidone (2 ml) was added potassium tert-butoxide (172 mg) under ice-cooling, and the mixture was stirred for 30 minutes at ambient temperature. To the mixture was added 4-chloro-8-(2,6-dichlorobenzoylamino) quinoline (200 mg), and the mixture was stirred for 5 hours at 80° C. The mixture was diluted with ethyl acetate, washed with water and brine, dried over magnesium sulfate and evaporated in vacuo. The residue was recrystallized from ethanol to give 8-(2,6-dichlorobenzoylamino)-4-(2-methoxyethoxy)quinoline (175 mg).

mp: 150–152° C. NMR (CDCl$_3$, δ): 3.50 (3H, s), 3.87–3.96 (2H, m), 4.30–4.40 (2H, m), 6.78 (1H, d, J=6 Hz), 7.28–7.43 (3H, m), 7.56 (1H, t, J=8 Hz), 7.98 (1H, d, J=8 Hz), 8.59 (1H, d, J=6 Hz), 8.94 (1H, d, J=8 Hz)

Example 168

The following compounds were obtained according to a similar manner to that of Example 167.

(1) 8-(2,6-Dichlorobenzoylamino)-4-(2-methoxyethoxy)-3-methylquinoline (from 4-chloro-8-(2,6-dichlorobenzoylamino)-3-methylquinoline and 2-methoxyethanol)

mp: 118–119° C. NMR (CDCl$_3$, δ): 2.48 (3H, s), 3.51 (3H, s), 3.80–3.83 (2H, m), 4.23–4.27 (2H, m), 7.30–7.43 (3H, m), 7.60 (1H, t, J=8.0 Hz), 7.91 (1H, d, J=8.0 Hz), 8.58 (1H, s), 8.89 (1H, d, J=8.0 Hz)

(2) 8-(2,6-Dichlorobenzoylamino)-3-isopropoxymethyl-4-(2-methoxyethoxy)quinoline (from 4-chloro-8-(2,6-dichlorobenzoylamino)-3-isopropoxymethylquinoline and 2-methoxyethanol)

mp: 86–87° C. NMR (DMSO-d$_6$, δ): 1.17 (2×3H, d, j=7 Hz), 3.36 (3H, s), 3.66–3.80 (3H, m), 4.31–4.38 (2H, m), 4.71 (2H, s), 7.48–7.62 (3H, m), 7.67 (1H, dd, J=8, 8 Hz), 7.97 (1H, d, J=8 Hz), 8.70 (!H, d, J=8 Hz), 8.83 (1H, s), 10.74 (1H, s)

(3) 8-(2,6-Dichlorobenzoylamino)-4-(2-furylmethoxy) quinoline (from 4-chloro-8-(2,6-dichlorobenzoylamino) quinoline and 2-furylmethanol)

mp: 145–149° C. NMR (CDCl$_3$, δ): 5.25 (2H, s), 6.40–6.45 (1H, m), 6.55 (1H, d, J=4 Hz), 6.94 (1H, d, J=5 Hz), 7.30–7.43 (3H, m), 7.50 (1H, d, J=4 Hz), 7.55 (1H, t, J=8 Hz), 7.95 (1H, d, J=8 Hz), 8.61 (1H, d, J=5 Hz), 8.95 (1H, d, j=8 Hz)

Example 169

To a solution of 4-chloro-8-(2,6-dichlorobenzoylamino)-3-hydroxymethylquinoline (297 mg) in N-methylpyrrolidone (4 ml) was added hydrazine monohydrate (390 mg), and the mixture was stirred for 3 hours at 90° C. The mixture was diluted with ethyl acetate, washed with water and brine, dried over magnesium sulfate and evaporated in vacuo. The residue was purified by flash chromatography on silica gel and by preparative thin layer chromatography to give 8-(2,6-dichlorobenzoylamino)-4-hydrazino-3-hydroxymethylquinoline (127 mg) and 6-(2,6-dichlorobenzoylamino)-1H-pyrazolo[4,3-c]-quinoline (90 mg). 8-(2,6-Dichlorobenzoylamino)-4-hydrazino-3-hydroxymethylquinoline NMR (DMSO-d$_6$, δ): 4.70 (2H, d, J=6 Hz), 5.19 (2H, s), 5.35 (1H, t, J=6 Hz), 7.39 (1H, dd, J=8, 8 Hz), 7.49–7.63 (3H, m), 8.15 (1H, d, J=8 Hz), 8.28 (1H, s), 8.40 (1H, s), 8.56 (1H, d, J=8 Hz), 10.46 (1H, s) 6-(2,6-Dichlorobenzoylamino)-1H-pyrazolo[4,3-c] quinoline NMR (DMSO-d$_6$, δ): 7.49–7.63 (3H, m), 7.77 (1H, dd, J=8, 8 Hz), 8.20 (1H, d, J=8 Hz), 8.46 (1H, br s), 8.78 (1H, d, J=8 Hz), 9.25 (1H, s), 10.76 (1H, s)

Example 170

To a solution of 4-chloro-8-(2,6-dichlorobenzoylamino)-3-cyanoquinoline (300 mg) in N-methylpyrrolidone (6 ml) was dropwise added hydrazine monohydrate (399 mg), and the mixture was stirred for 2 hours at 90° C. Water (15 ml) was added thereto, the resulting precipitates were collected by filtration to give 3-amino-6-(2,6-dichlorobenzoylamino)-1H-pyrazolo[4,3-c]quinoline (260 mg).

mp: >300° C. NMR (DMSO-d$_6$, δ): 5.93 (2H, br s), 7.50–7.61 (3H, m), 7.64 (1H, t, J=8.0 Hz), 8.02 (1H, d, J=8.0 Hz), 8.70 (1H, d, J=8.0 Hz), 9.09 (1H, s)

Example 171

To a suspension of 3-amino-6-(2,6-dichlorobenzoylamino)-1H-pyrazolo[4,3-c]quinoline (200 mg) in 1,2-dichloroethane (2 ml) was added acetic anhydride (302 mg), and the reaction mixture was refluxed for 12 hours. The solution was allowed to cool to ambient temperature and the solvent was evaporated in vacuo. The residue was triturated with water-ethanol, and the precipitate was collected. The crude product was purified by column chromatography on silica gel (ethyl acetate-n-hexane) to give 2-acetyl-6-(2,6-dichlorobenzoylamino)-2,3-dihydro-3-imino-1H-pyrazolo[4,3-c]-quinoline as a yellow crystal (60 mg) and 3-acetamido-6-(2,6-dichlorobenzoylamino)-1H-pyrazolo[4,3-c]quinoline as a white crystal (30 mg). 2-Acetyl-6-(2,6-dichlorobenzoylamino)-2,3-dihydro-3-imino-1H-pyrazolo[4,3-cilquinoline mp: >300° C. NMR (DMSO-d$_6$, δ): 2.76 (3H, s), 7.47–7.60 (4H, m), 7.96 (1H, d, J=8.0 Hz), 8.46 (1H, br), 8.68 (1H, d, J=8.0 Hz), 9.05 (1H, s) 3-Acetamido-6-(2,6-dichlorobenzoylamino)-1H-pyrazolo[4,3-c]quinoline mp: >300° C. NMR (DMSO-d$_6$, δ): 2.16 (3H, s), 7.48–7.61 (3H, m), 7.74 (1H, t, J=8.0 Hz), 8.14 (1H, d, J=8.0 Hz), 8.75 (1H, d, J=8.0 Hz), 9.42 (1H, s), 10.77 (1H, s), 10.98 (1H, br)

Example 172

(1) To a stirred suspension of 5-methyl-2-nitroaniline (10.0 g) in ethanol (20 ml) were added 2,2-dimethyl-1,3-dioxane-4,6-dione (9.95 g) and triethyl orthoformate (10.7 g) at 50° C. The resulting mixture was heated at 120° C. for one hour during which time ethanol (20 ml) was added to the mixture and ethanol liberated was distilled off. After cooling, ethyl acetate (40 ml) was added thereto and the resulting precipitate was collected by filtration. The solid was washed with hot ethanol (40 ml) and allowed to cool to ambient temperature. The precipitate was collected by filtration and air-dried to afford isopropylidene (5-methyl-2-nitroanilino) methylenemalonate (15.2 g) as yellow needles.

mp: 218–220° C. NMR (CDCl$_3$, δ): 1.77 (6H, s), 2.50 (3H, s), 7.16 (1H, d, J=8 Hz), 7.40 (1H, br s), 8.20 (1H, d, j=8 Hz), 8.73 (1H, d, J=15 Hz)

(2) To a stirred mixture of diphenyl ether (37 g) and biphenyl (13 g) was added isopropylidene (5-methyl-2-nitroanilino) methylenemalonate (14.6 g) at 220° C., and the mixture was heated at the same temperature for half an hour. The reaction mixture was allowed to cool to 100° C. and then n-hexane (100 ml) was added dropwise to the mixture. After cooling to ambient temperature, the precipitate was collected by filtration. The solid was washed with hot ethanol (70 ml) and allowed to cool to ambient temperature. The solid was collected by filtration and air-dried to give 1,4-dihydro-5-methyl-8-nitro-4-oxoquinoline (8.8 g) as a dark brown solid.

mp: 219–225° C. NMR (DMSO-d$_6$, δ): 2.87 (3H, s), 6.15 (1H, d, J=8 Hz), 7.20 (1H, d, J=8 Hz), 7.86 (1H, d, J=8 Hz), 8.45 (1H, d, J=8 Hz)

(3) To a stirred mixture of 1,4-dihydro-5-methyl-8-nitro-4-oxoquinoline (1.5 g) and 1,3,5-trioxane (3.31 g) in dioxane (15 ml) was added conc. hydrochloric acid (30 ml), and the mixture was stirred at 100° C. overnight. The mixture was evaporated in vacuo, and the residue was treated with acetonitrile to give 1,4-dihydro-3-hydroxymethyl-5-methyl-8-nitro-4-oxoquinoline (1.3 g).

mp: 251–255° C. NMR (DMSO-d$_6$, δ): 4.37 (2H, s), 7.20 (1H, d, J=8 Hz), 7.93 (1H, d, J=6 Hz), 8.47 (1H, d, J=8 Hz)

(4) To a suspension of 1,4-dihydro-3-hydroxymethyl-5-methyl-8-nitro-4-oxoquinoline (1.12 g) in dichloromethane (10 ml) was dropwise added a solution of thionyl chloride (569 mg) in dichloromethane (5 ml) under ice-cooling, and the mixture was stirred for 1 hour at the same temperature and for 2 hours at ambient temperature. The mixture was concentrated in vacuo, suspended in dichloromethane-methanol and refluxed for 2 hours. The mixture was evaporated in vacuo, and the residue was recrystalized from methanol to give 1,4-dihydro-3-methoxymethyl-5-methyl-8-nitro-4-oxoquinoline (889 mg).

mp: 210–213° C. NMR (CDCl$_3$, δ): 3.05 (3H, s), 3.50 (3H, s), 4.45 (2H, s), 7.14 (!H, d, J=8 Hz), 7.77 (1H, d, J=6 Hz), 8.48 (!H, d, J=8 Hz)

(5) 4-Chloro-3-methoxymethyl-5-methyl-8-nitroquinoline was obtained according to a similar manner to that of Preparation 2-(1).

mp: 120–124° C. NMR (CDCl$_3$, δ): 3.10 (3H, s), 3.53 (3H, s), 4.76 (2H, s), 7.43 (1H, d, J=8 Hz), 7.80 (1H, d, j=8 Hz) 9.01 (1H, s)

(6) 8-Amino-4-chloro-3-methoxymethyl-5-methylquinoline was obtained according to a similar manner to that of Preparation 2-(3).

NMR (CDCl$_3$, δ): 2.90 (3H, s), 3.50 (3H, s), 4.75 (2H, s), 4.92 (2H, br s), 6.82 (1H, d, J=8 Hz), 7.16 (1H, d, J=8 Hz), 8.71 (1H, s)

(7) 4-Chloro-8-(2,6-dichlorobenzoylamino)-3-methoxymethyl-5-methylquinoline was obtained according to a similar manner to that of Example 1.

mp: 180° C. NMR (CDCl$_3$, δ): 3.01 (3H, s), 3.52 (3H, s), 4.75 (2H, s), 7.28–7.48 (4H, m), 8.75 (1H, s), 8.82 (1H, d, J=8 Hz)

(8) 8-(2,6-Dichlorobenzoylamino)-4-(imidazol-1-yl)-3-methoxymethyl-5-methylquinoline was obtained according to a similar manner to that of Example 8.

mp: 179–180° C. NMR (CDCl$_3$, δ): 1.99 (3H, s), 3.31 (3H, s), 4.15 (2H, s), 7.10 (1H, br s), 7.31–7.48 (5H, m), 7.61 (1H, br s), 8.88 (1H, d, J=8 Hz), 8.90 (1H, s)

its hydrochloride mp: 207–214° C. NMR (DMSO-d$_6$, δ): 1.94 (3H, s), 3.20 (3H, s), 4.30 (2H, s), 7.48–7.63 (4H, m), 7.94 (1H, br s), 8.06 (1H, br s), 8.70 (1H, d, J=8 Hz), 9.10 (1H, s), 9.31 (1H, br s)

Example 173

(1) 4-Chloro-5-methyl-8-nitroquinoline was obtained from 1,4-dihydro-5-methyl-8-nitro-4-oxoquinoline according to a similar manner to that of Preparation 2-(1).

mp: 125–130° C. NMR (CDCl$_3$, δ): 3.10 (3H, s), 7.44 (1H, d, J=8 Hz), 7.60 (1H, d, J=6 Hz), 7.84 (1H, d, J=8 Hz), 8.80 (1H, d, J=6 Hz)

(2) 8-Amino-4-chloro-5-methylquinoline was obtained according to a similar manner to that of Preparation 2-(3).

mp: 104–107° C. NMR (CDCl$_3$, δ): 2.90 (3H, s) 6.87 (1H, d, J=8 Hz), 7.18 (1H, d, J=8 Hz), 7.46 (1H, d, J=5 Hz), 8.54 (1H, d, J=5 Hz)

(3) 4-Chloro-8-(2,6-dichlorobenzoylamino)-5-methylquinoline was obtained according to a similar manner to that of Example 1.

mp: 258–260° C. NMR (DMSO-d$_6$, δ): 2.98 (3H, s), 7.47–7.63 (4H, m), 7.80 (1H, d, J=5 Hz), 8.66 (1H, d, J=8 Hz), 8.74 (1H, d, J=5 Hz)

(4) 8-(2,6-Dichlorobenzoylamino)-4-(imidazol-1-yl)-5-methylquinoline was obtained according to a similar manner to that of Example 8.

mp: 236° C. NMR (DMSO-d$_6$, δ): 1.96 (3H, s), 7.19 (1H, s), 7.47–7.65 (6H, m), 7.98 (1H, s), 8.68 (1H, d, J=8 Hz), 8.97 (1H, d, J=6 Hz)

its hydrochloride mp: 220–223° C. NMR (DMSO-d$_6$, δ): 1.98 (3H, s), 7.48–7.65 (4H, m), 7.87 (1H, d, J=4 Hz), 7.95 (1H, br s), 8.13 (1H, br s), 8.73 (1H, d, J=8 Hz), 9.09 (1H, d, J=4 Hz), 9.46 (1H, br s)

(5) 8-(2,6-Dichlorobenzoylamino)-4-hydrazino-5-methylquinoline was obtained from 4-chloro-8-(2,6-dichlorobenzoylamino)-5-methylquinoline and hydrazine monohydrate according to a similar manner to that of Example 8.

mp: 225–237° C. NMR (DMSO-d$_6$, δ): 2.84 (3H, s), 4.40 (2H, br s), 7.10–7.21 (2H, m), 7.46–7.65 (4H, m), 8.34 (1H, d, J=6 Hz), 8.45 (1H, d, J=8 Hz)

(6) 4-(2-Acetylhydrazino)-8-(2,6-dichlorobenzoylamino)-5-methylquinoline was obtained according to a similar manner to that of Example 86.

mp: 230–234° C. NMR (DMSO-d$_6$, δ): 2.00 (3H, s), 2.90 (3H, s), 6.80 (1H, d, J=6 Hz), 7.27 (1H, d, J=8 Hz), 7.48–7.62 (3H, m), 8.11 (1H, br s), 8.40 (1H, d, J=6 Hz), 8.51 (1H, d, J=8 Hz)

Example 174

(1) Isopropylidene (4-methyl-2-nitroanilino) methylenemalonate was obtained from 4-methyl-2-nitroaniline and isopropylidene malonate according to a similar manner to that of Example 172-(1).

mp: 193–195° C. NMR (DMSO-$d_6$, δ): 1.68 (2×3H, s), 2.40 (3H, s), 7.67 (1H, dd, J=8, 1 Hz), 7.97 (1H, d, J=8 Hz), 8.08 (1H, d, J=1 Hz), 8.73 (1H, d, J=14 Hz)

(2) 1,4-Dihydro-6-methyl-8-nitro-4-oxoquinoline was obtained according to a similar manner to that of Example 172-(2).

mp: 209–212° C. NMR (CDCl$_3$, δ): 2.54 (3H, s), 6.40 (1H, d, J=7.5 Hz), 7.73 (1H, dd, J=7.5, 7 Hz), 8.50 (1H, s), 8.60 (1H, s), 11.09 (1H, br)

(3) 1,4-Dihydro-3-hydroxymethyl-6-methyl-8-nitro-4-oxoquinoline was obtained according to a similar manner to that of Example 172-(3).

mp: >240° C. NMR (CDCl$_3$, δ): 2.57 (3H, s), 3.21 (1H, t, J=7 Hz), 4.67 (2H, d, J=7 Hz), 7.78 (1H, d, J=7 Hz), 8.52 (1H, d, J=1 Hz), 8.61 (1H, d, J=1 Hz)

(4) 1,4-Dihydro-3-methoxymethyl-6-methyl-8-nitro-4-oxoquinoline was obtained according to a similar manner to that of Example 172-(4).

mp: >240° C. NMR (CDCl$_3$, δ): 2.54 (3H, s), 3.50 (3H, s), 4.49 (2H, s), 7.85 (1H, d, J=7 Hz), 8.50 (1H, d, J=1 Hz), 8.62 (1H, d, J=1 Hz)

(5) 4-Chloro-3-methoxymethyl-6-methyl-8-nitroquinoline was obtained according to a similar manner to that of Preparation 2-(1).

mp: 107–111° C. NMR (CDCl$_3$, δ): 2.65 (3H, s), 3.51 (3H, s), 4.78 (2H, s), 7.90 (1H, d, J=1 Hz), 8.24 (1H, d, J=1 Hz), 9.02 (1H, s)

(6) 8-Amino-4-chloro-3-methoxymethyl-6-methylquinoline was obtained according to a similar manner to that of Preparation 2-(3).

mp: 135–138° C. NMR (CDCl$_3$, δ): 2.40 (3H, s), 3.39 (3H, s), 4.70 (2H, s), 6.06 (2H, s), 6.78 (1H, s), 7.08 (1H, S), 8.63 (1H, s)

(7) 4-Chloro-8-(2,6-dichlorobenzoylamino)-3-methoxymethyl-6-methylquinoline was obtained according to a similar manner to that of Example 1.

mp: 156–158° C. NMR (CDCl$_3$, δ): 2.61 (3H, s), 3.40 (3H, s), 4.75 (2H, s), 7.48–7.60 (3H, m), 7.80 (1H, s), 8.68 (1H, s), 8.83 (1H, s), 10.86 (1H, s)

(8) 8-(2,6-Dichlorobenzoylamino)-4-(imidazol-1-yl)-3-methoxymethyl-6-methylquinoline was obtained according to a similar manner to that of Example 8.

mp: 99–101° C. NMR (DMSO-$d_6$, δ): 2.50 (3H, s), 3.24 (3H, s), 4.33 (2H, s), 6.85 (1H, s), 7.28 (1H, s), 7.48–7.63 (4H, m), 7.95 (1H, s), 8.67 (1H, s), 9.00 (1H, s), 10.93 (1H, s)

(9) 8-(2,6-Dichlorobenzoylamino)-3-methoxymethyl-6-methyl-4-[(2-methylaminoethyl)amino]quinoline was obtained from 4-chloro-8-(2,6-dichlorobenzoylamino)-3-methoxymethyl-6-methylquinoline and N-methylethylenediamine according to a similar manner to that of Example 8.

NMR (CDCl$_3$, δ): 2.50 (3H, s), 2.57 (3H, s), 2.88 (2H, t, J=5 Hz), 3.37 (3H, s), 3.73 (2H, dt, J=5, 5 Hz), 4.59 (2H, s), 5.92 (1H, t, J=5 Hz), 7.27–7.42 (3H, m), 7.57 (1H, s), 8.24 (1H, s), 8.75 (1H, s)

(10) 8-(2,6-Dichlorobenzoylamiro)-3-methoxymethyl-6-methyl-4-(3-methyl-2-oxoimidazolidin-1-yl)quinoline was obtained according to a similar manner to that of Example 92-(2).

mp: 221–223° C. NMR (DMSO-$d_6$, δ): 2.57 (3H, s), 2.83 (3H, s), 3.32 (3H, s), 3.56–3.73 (3H, m), 3.88 (1H, m), 4.54 (1H, d, J=13 Hz), 4.57 (1H, d, J=13 Hz), 7.47–7.61 (4H, m), 8.61 (1H, s), 8.86 (1H, s), 10.79 (1H, s)

(11) 8-(2,6-Dichlorobenzoylamino)-3-methoxymethyl-6-methyl-4-(3-methyl-2-thioxoimidazolidin-1-yl)quinoline was obtained from 8-(2,6-dichlorobenzoylamino)-3-methoxymethyl-6-methyl-4-[(2-methylaminoethyl)amino]quinoline and 1,11-thiocarbonyldiimidazole according to a similar manner to that of Example 92-(2).

mp: 194–196° C. NMR (DMSO-$d_6$, δ): 2.57 (3H, s), 3.17 (3H, s), 3.35 (3H, s), 3.80–4.10 (4H, m), 4.54 (1H, d, J=12 Hz), 4.61 (1H, d, J=12 Hz), 7.40 (1H, s), 7.48–7.62 (3H, m), 8.62 (1H, s), 8.91 (1H, s), 10.83 (1H, s)

Example 175

The following compounds were obtained according to a similar manner to that of Example 1.

(1) 3-Bromo-8-(2-chlorobenzoylamino)quinoline mp: 193–195° C. NMR (CDCl$_3$, δ): 7.36–7.54 (4H, m), 7.63 (1H, d, J=8 Hz), 7.81 (1H, dd, J=8, 2 Hz), 8.34 (1H, d, J=2 Hz), 8.80 (1H, s), 8.97 (1H, d, J=8 Hz)

(2) 3-Bromo-8-(3-chlorobenzoylamino)quinoline mp: 189° C. NMR (CDCl$_3$, δ): 7.43–7.68 (4H, m), 7.86–7.95 (1H, m), 8.03 (1H, br s), 8.35 (1H, d, J=2 Hz), 8.85 (1H, d, J=2 Hz), 8.91 (1H, d, J=8 Hz)

(3) 3-Bromo-8-(4-chlorobenzoylamino)quinoline mp: 204° C. NMR (CDCl$_3$, δ): 7.44–7.57 (3H, m), 7.63 (1H, t, J=8 Hz), 7.96–8.03 (2H, d, J=9 Hz), 8.34 (1H, d, J=1 Hz), 8.84 (1H, d, J=2 Hz), 8.92 (1H, d, J=8 Hz)

(4) 3-Bromo-8-(2-methylbenzoylamino)quinoline mp: 163–165° C. NMR (CDCl$_3$, δ): 2.58 (3H, s), 7.26–7.49 (4H, m), 7.55–7.70 (2H, m), 8.30 (1H, d, J=2 Hz), 8.74 (1H, d, J=2 Hz), 8.94 (1H, d, J=8 Hz)

(5) 3-Bromo-8-(3-miethylbenzoylamino)quinoline mp: 160–163° C. NMR (CDCl$_3$, δ): 2.48 (3H, s), 7.35–7.50 (3H, m), 7.60 (1H, t, J=8 Hz), 7.80–7.90 (2H, m), 8.34 (1H, d, J=2 Hz), 8.83 (1H, d, J=1 Hz), 8.94 (1H, d, J=8 Hz)

(6) 3-Bromo-8-(4-methylbenzoylamino)quinoline mp: 142° C. NMR (CDCl$_3$, δ): 2.44 (3H, s), 7.35 (2H, d, J=9 Hz), 7.45 (1H, d, J=8 Hz), 7.61 (1H, d, J=8 Hz), 7.95 (2H, d, J=9 Hz), 8.33 (1H, d, J=1 Hz), 8.83 (1H, d, J=1 Hz), 8.94 (1H, d, J=8 Hz)

(7) 3-Bromo-8-(2-methoxybenzoylamino)quinoline mp: 192–194° C. NMR (CDCl$_3$, δ): 4.20 (3H, s), 7.09 (1H, d, J=8 Hz), 7.15 (1H, t, J=8 Hz), 7.44 (1H, d, J=8 Hz), 7.54 (1H, t, J=8 Hz), 7.62 (1H, t, J=8 Hz), 8.30–8.39 (2H, m), 8.87 (1H, d, J=2 Hz), 9.05 (1H, d, J=8 Hz)

(8) 3-Bromo-8-(3-methoxybenzoylamino)quinoline mp: 171° C. NR (CDCl$_3$, δ): 3.91 (3H, s), 7.11 (1H, dd, J=8, 2 Hz), 7.40–7.50 (2H, m), 7.57–7.67 (3H, mn), 8.35 (1H, d, J=2 Hz), 8.83 (1H, s), 8.95 (1H, d, J=8 Hz)

(9) 3-Bromo-8-(4-methoxybenzoylamino)quinoline mp: 158° C. NMR (CDCl$_3$, δ): 3.89 (3H, s), 7.03 (2H, d, J=9 Hz), 7.44 (1H, d, J=8 Hz), 7.60 (1H, t, j=8 Hz), 8.03 (2H, d, J=9 Hz), 8.33 (1H, d, J=2 Hz), 8.83 (1H, d, J=2 Hz), 8.94 (1H, d, J=8 Hz)

Example 176

To a solution of 8-(2,6-dichlorobenzoylamino)-4-hydrazinoquinoline (200 mg) in formic acid (4 ml) was added formamide (26 mg), and the mixture was stirred at ambient temperature for 3 hours. The solvent was azeotropically removed with toluene. The residue was diluted with ethyl acetate, washed with water and saturated aqueous sodium bicarbonate solution, dried over magnesium sulfate and concentrated in vacuo. The residual solid was treated with hot ethanol (2 ml), allowed to cool to ambient temperature, filtered and washed with ethanol to give 8-(2,6-dichlorobenzoylamino)-4-(2-formylhydrazino)quinoline (180 mg) as pale yellow crystal.

mp: 261–263° C. NMR (DMSO-d$_6$, δ): 6.70 (1H, d, J=5.5 Hz), 7.50–7.62 (4H, m), 8.00 (1H, d, J=8.0 Hz), 8.26 (1H, s), 8.45 (1H, d, J=5.5 Hz), 8.68 (1H, d, J=8.0 Hz), 9.34 (1H, br), 10.18 (1H, br), 10.52 (1H, s)

Example 177

8-(2,6-Dichlorobenzoylamino)-4-(2-formyl-2-methylhydrazino)quinoline was obtained from 8-(2,6-dichlorobenzoylamino)-4-(2-methylhydrazino)quinoline according to a similar manner to that of Example 176.

mp: 250–262° C. NMR (DNSO-d$_6$, δ): 3.17 (3H×1/5, d, J=6 Hz), 3.26 (3H×4/5, d, J=6 Hz), 7.12 (1H×4/5, d, J=6 Hz), 7.26 (1H×1/5, d, J=6 Hz), 7.47–7.67 (4H, m), 7.88–8.01 (9/5H, m), 8.37 (1H×1/5, d, J=8 Hz), 8.61–8.76 (2H, m), 10.25 (1H×1/5, d, J=8 Hz), 10.57–10.72 (9/5H, m)

Example 178

The following compounds were obtained according to a similar manner to that of Example 145.
(1) 8-(2,6-Dichlorobenzoylamino)-4-(2-trifluoroacetylhydrazino)quinoline mp: 299–302° C. NMR (DMSO-d$_6$, δ): 6.68 (1H, br s), 7.50–7.63 (4H, m), 7.97 (1H, br), 8.51 (1H, br s), 8.70 (1H, br), 9.68 (1H, br s), 10.56 (1H, s), 11.86 (1H, br s)
(2) 8-(2,6-Dichlorobenzoylamino)-4-(2-crotonoyl-2-methylhydrazino)quinoline mp: 244–249° C. (dec.) NMR (DMSO-d$_6$, δ): 1.80 (3H, d, J=7 Hz), 3.24 (3H, s), 5.87 (1H, d, J=15 Hz), 6.66 (1H, dq, J=15, 7 Hz), 7.06 (1H, d, J=6 Hz), 7.43–7.63 (4H, m), 7.96 (1H, d, J=8 Hz), 8.60 (1H, d, J=6 Hz), 8.62 (1H, d, J=8 Hz), 10.60 (1H, s)

Example 179

The following compounds were obtained according to a similar manner to that of Example 150.
(1) 8-(2,6-Dichlorobenzoylamrino)-4-(2-acryloylhydrazino)quinoline mp: 232–235° C. NMR (DMSO-d$_6$, δ): 5.81 (1H, dd, J=9.0, 1.5 Hz), 6.27 (1H, dd, J=15.5, 1.5 Hz), 6.42 (1H, dd, J=15.5, 9.0 Hz), 6.61 (1H, d, J=7.0 Hz), 7.50–7.60 (4H, m), 8.01 (1H, d, J=8.0 Hz), 8.45 (1H, d, J=7.0 Hz), 8.68 (1H, d, J=8.0 Hz), 9.43 (1H, br s), 10.48 (1H, s)
(2) 8-(2,6-Dichlorobenzoylamino)-4-[2-(2-thienylacetyl)hydrazino]quinoline mp: 140–142° C. NMR (DMSO-d$_6$, δ): 3.86 (2H, s), 6.62 (1H, d, J=5.5 Hz), 6.99–7.03 (2H, m), 7.41 (1H, d, J=5.0 Hz), 7.50–7.61 (4H, m), 7.99 (1H, d, J=8.0 Hz), 8.41 (1H, d, J=5.0 Hz), 8.66 (1H, d, J=8.0 Hz), 9.40 (1H, s), 10.33 (1H, s), 10.52 (1H, s)
(3) 8-(2,6-Dichlorobenzoylamino)-4-(4,4-dimethylsemicarbazido)quinoline mp: 265–268° C. NMR (DMSO-d$_6$, δ): 2.92 (6H, s), 6.70 (1H, d, J=6.0 Hz), 7.45–7.60 (4H, m), 8.03 (1H, d, J=8.0 Hz), 8.40 (1H, d, J=6.0 Hz), 8.65 (1H, d, J=8.0 Hz), 8.73 (1H, s), 9.05 (1H, s)

Example 180

The following compounds were obtained according to a similar manner to that of Example 147.
(1) 8-(2,6-Dichlorobenzoylamino)-4-(2-cinnamoylhydrazino)quinoline mp: 281–283° C. NMR (DMSO-d$_6$, δ): 6.66 (1H, d, J=7.0 Hz), 6.82 (1H, d, J=15.0 Hz), 7.43–7.68 (10H, m), 8.03 (1H, d, J=8.0 Hz), 8.43 (1H, d, J=7.0 Hz), 8.69 (1H, d, J=8.0 Hz), 9.47 (1H, s)
(2) 8-(2,6-Dichlorobenzoylamino)-4-[2-(4-imidazolylacetyl)hydrazino]quinoline mp: 248–250° C. NMR (DMSO-d$_6$, δ): 3.53 (2H, br), 6.71 (1H, br), 7.00 (1H, br), 7.47–7.64 (5H, m), 8.00 (1H, d, J=8 Hz), 8.40 (1H, d, J=6 Hz), 8.65 (1H, d, J=8 Hz), 9.33 (1H, br), 10.52 (1H, s)
(3) 8-(2,6-Dichlorobenzoylamino)-4-[2-(2-pyridylacetyl)hydrazino]quinoline dihydrochloride mp: 208–232° C. NMR (DMSO-d$_6$, δ): 4.27 (2H, s), 7.27 (1H, d, J=7.5 Hz), 7.52–7.62 (3H, m), 7.77–7.95 (3H, m), 8.34 (1H, br t, J=7.5 Hz), 8.46 (1H, d, J=8.0 Hz), 8.61–8.67 (2H, m), 8.85 (1H, d, J=5.0 Hz), 11.24 (1H, s), 11.39 (1H, br), 11.48 (1H, s)
(4) 8-(2,6-Dichlorobenzoylamino)-4-[2-(3-pyridylacetyl)hydrazino]quinoline mp: 238–242° C. NMR (DMSO-d$_6$, δ): 3.69 (2H, s), 6.63 (1H, d, J=6 Hz), 7.38 (1H, dd, J=8, 6 Hz), 7.48–7.64 (4H, m), 7.78 (1H, br d, J=8 Hz), 7.96 (1H, d, J=8 Hz), 8.40 (1H, d, J=6 Hz), 8.48 (1H, d, J=6 Hz), 8.57 (1H, d, J=2 Hz), 8.67 (1H, d, J=8 Hz), 9.38 (1H, br s)
its dihydrochloride mp: 216–240° C. NMR (DMSO-d$_6$, δ): 4.05 (2H, s), 7.03 (1H, d, J=8 Hz), 7.40–7.66 (3H, mn), 7.82 (1H, t, J=8 Hz), 7.96 (1H, dd, J=8, 6 Hz), 8.36–8.49 (2H, m), 8.56–8.65 (2H, m), 8.81 (1H, d, J=6 Hz), 8.90 (1H, br s)
(5) 4-(2-Benzoylhydrazino)-8-(2,6-dichlorobenzoylamino)quinoline hydrochloride mp: >250° C. NMR (DMSO-d$_6$, δ): 7.00 (1H, d, J=4 Hz), 7.50–7.75 (6H, m), 7.88 (1H, t, J=8 Hz), 8.05 (2H, d, J=8 Hz), 8.45 (1H, d, J=8 Hz), 8.60 (2H, t, J=8 Hz)
(6) 8-(2,6-Dichlorobenzoylamino)-4-[2-(2-methoxybenzoyl)hydrazino]quinoline mp: 263–266° C. NMR (DMSO-d$_6$, δ): 3.94 (3H, s), 6.80 (1H, d, J=5 Hz), 7.08 (1H, t, J=8 Hz), 7.20 (1H, d, J=8 Hz), 7.48–7.61 (4H, m), 7.66 (1H, d, J=8 Hz), 8.08 (1H, d, J=8 Hz), 8.47 (1H, d, J=5 Hz), 8.68 (1H, d, J=6 Hz), 9.54 (1H, s)
(7) 8-(2,6-Dichlorobenzoylamino)-4-[2-(3-methoxybenzoyl)hydrazino]quinoline mp: 247–252° C. NMR (DMSO-d$_6$, δ): 3.84 (3H, s), 6.70 (1H, d, J=5 Hz), 7.19 (1H, dd, J=8, 2 Hz), 7.41–7.64 (6H, m), 8.07 (1H, d, J=8 Hz), 8.43 (1H, d, J=5 Hz), 8.68 (1H, d, J=8 Hz), 9.53 (1H, s)
(8) 8-(2,6-Dichlorobenzoylamino)-4-[2-(4-methoxybenzoyl)hydrazino]quinoline hydrochloride mp: >250-C NMR (DMSO-d$_6$, δ): 6.97 (1H, d, J=4 Hz), 7.12 (2H, d, J=8 Hz), 7.53–7.68 (3H, m), 7.85 (1H, t, J=8 Hz), 8.01 (2H, d, J=8 Hz), 8.45 (1H, d, J=8 Hz), 8.58 (2H, t, J=8 Hz)
(9) 8-(2,6-Dichlorobenzoylamino)-4-[2-(4-trifluoromethylbenzoyl)hydrazino]quinoline hydrochloride mp: >250° C. NMR (DMSO-d$_6$, δ): 7.05 (1H, d, J=4 Hz), 7.52–7.67 (4H, m), 7.85 (1H, t, J=8 Hz), 8.00 (2H, d, J=8 Hz), 8.24 (2H, d, J=8 Hz), 8.40 (1H, d, J=4 Hz), 8.60 (2H, t, J=4 Hz)
(10) 8-(2,6-Dichlorobenzoylamino)-4-[2-(3-furylcarbonyl)hydrazino]quinoline mp: >250° C. NMR (DMSO-d$_6$, δ): 6.68 (1H, d, J=4 Hz), 7.00 (1H, s), 7.50–7.63 (4H, m), 7.35 (1H, s), 8.06 (1H, d, J=9 Hz), 8.40 (1H, s), 8.45 (1H, d, J=4 Hz), 8.70 (1H, d, J=6 Hz), 9.49 (1H, s)
its hydrochloride mp: >250° C. NMR (DMSO-d$_6$, δ): 6.95 (1H, d, J=6 Hz), 7.05 (1H, s), 7.52–7.66 (3H, m), 7.80–7.95 (2H, m), 8.42 (1H, d, J=6 Hz), 8.50 (1H, s), 8.55–8.65 (2H, m)

(11) 8-(2,6-Dichlorobenzoylamino)-4-[2-(2-thienylcarbonyl)hydrazino]quinoline mp: 263–265° C. NMR (DMSO-d$_6$, δ): 6.71 (1H, d, J=7.0 Hz), 7.27 (1H, dd, J=5.5, 4.0 Hz), 7.50–7.62 (4H, m), 7.91 (1H, d, J=7.0 Hz), 7.99 (1H, d, J=4.0 Hz), 8.06 (1H, d, J=8.0 Hz), 8.45 (1H, d, J=5.5 Hz), 8.70 (1H, d, J=8.0 Hz), 9.55 (1H, s)

(12) 8-(2,6-Dichlorobenzoylamino)-4-[2-(3-thienylcarbonyl)hydrazino]quinoline mp: 277–279° C. NMR (DMSO-d$_6$, δ): 6.70 (1H, d, J=6.0 Hz), 7.49–7.65 (5H, m), 7.69–7.71 (1H, m), 8.07 (1H, d, J=8.0 Hz), 8.36 (1H, d, J=3.0 Hz), 8.45 (1H, d, J=6.0 Hz), 8.70 (1H, d, J=8.0 Hz), 9.53 (1H, s)

(13) 8-(2,6-Dichlorobenzoylamino)-4-[2-(3-pyridylcarbonyl)hydrazino]quinoline dihydrochloride mpD >250° C. NMR (DMSO-d$_6$, δ): 7.15 (1H, d, J=6 Hz), 7.52–7.68 (3H, m), 7.24 (1H, dd, J=6, 4 Hz), 7.90 (1H, t, J=8 Hz), 8.48–8.55 (2H, m), 8.58–8.65 (2H, m), 8.90 (1H, d, J=4 Hz), 9.29 (1H, s)

(14) 8-(2,6-Dichlorobenzoylamino)-4-[2-(4-pyridylcarbonyl)hydrazino]quinoline mp: 249–251° C. NMR (DMSO-d$_6$, δ): 6.76 (1H, d, J=5 Hz), 7.50–7.63 (4H, m), 7.90 (1H, d, J=6 Hz), 8.07 (1H, d, J=9 Hz), 8.46 (1H, d, J=4 Hz), 8.70 (1H, d, J=6 Hz), 8.83 (2H, m), 9.61 (1H, s)

its dihydrochloride mp: >250° C. NMR (DMSO-d$_6$, δ): 7.12 (1H, d, J=6 Hz), 7.52–7.66 (3H, m), 7.90 (1H, t, J=8 Hz), 8.07 (2H, m), 8.50 (1H, d, J=8 Hz), 8.62 (2H, m), 8.93 (2H, m)

(15) 8-(2,6-Dichlorobenzoylamino)-4-[2-(3-hydroxy-3-methylbutyryl)hydrazino]quinoline mp: 243–245° C. NMR (DMSO-d$_6$, δ): 1.27 (2×3H, s), 2.39 (2H, s), 4.73 (1H, s), 6.75 (1H, d, J=6 Hz), 7.48–7.63 (4H, m), 8.01 (1H, d, J=8 Hz), 8.42 (1H, d, J=6 Hz), 8.67 (1H, d, J=8 Hz), 9.30 (1H, s), 9.95 (1H, s), 10.52 (1H, s)

(16) 8-(2,6-Dichlorobenzoylamino)-4-(2-isobutyrylhydrazino)quinoline mp: 269–272° C. (dec.) NMR (DMSO-d$_6$, δ): 1.15 (3H, d, J=7 Hz), 2.60 (1H, qq, J=7, 7 Hz), 6.59 (1H, d, J=6 Hz), 7.47–7.64 (4H, m), 8.00 (1H, d, J=8 Hz), 8.44 (1H, d, J=6 Hz), 8.67 (1H, d, J=8 Hz), 9.30 (1H, s), 10.03 (1H, s), 10.52 (1H, s)

(17) 8-(2,6-Dichlorobenzoylamino)-4-[2-(N,N-dimethylaminoacetyl)hydrazino]quinoline mp: 234–238° C. NMR (DMSO-d$_6$, δ): 2.31 (2×3H, s), 3.11 (2H, s), 6.63 (1H, d, J=6 Hz), 7.47–7.63 (4H, m), 8.00 (1H, d, J=8 Hz), 8.43 (1H, d, J=6 Hz), 8.67 (1H, d, J=8 Hz), 9.29 (1H, s), 10.06 (1H, s), 10.52 (1H, s)

(18) 8-(2,6-Dichlorobenzoylamino)-4-(2-oxamoylhydrazino)quinoline mp: 249–252° C. (dec.) NMR (DMSO-d$_6$, δ): 6.58 (1H, d, J=6 Hz), 7.48–7.63 (4H, m), 7.97 (1H, br s), 8.00 (1H, d, J=8 Hz), 8.28 (1H, br s), 8.44 (1H, d, J=6 Hz), 8.68 (1H, d, J=8 Hz), 9.42 (1H, s), 10.55 (1H, s), 10.97 (1H, s)

Example 181

8-(2,6-Dichlorobenzoylamino)-4-(4-methylsemicarbazido)quinoline was obtained by reacting 8-(2,6-dichlorobenzoylamino)-4-hydrazinoquinoline with phenyl methylcarbamate according to a similar manner to that of Example 87.

mp: 274–277° C. NMR (DMSO-d$_6$, δ): 2.58 (3H, d, J=5 Hz), 6.60 (1H, br q, J=5 Hz), 6.70 (1H, d, J=6 Hz), 7.45–7.63 (4H, m), 7.99 (1H, d, J=8 Hz), 8.20 (1H, s), 8.45 (1H, d, J=6 Hz), 8.66 (1H, d, J=8 Hz), 9.19 (1H, s)

Example 182

(1) To a solution of 8-(2,6-dichlorobenzoylamino)-4-hydrazinoquinoline (298 mg) in dimethylformamide (4 ml) was added succinic anhydride (94 mg), and the mixture was stirred at ambient temperature for 12 hours. To the mixture was added water (10 ml) and the precipitate was collected. The solid was treated with hot ethanol (5 ml), allowed to cool to ambient temperature, filtered and washed with water to give 8-(2,6-dichlorobenzoylamino)-4-[2-(3-carboxypropanoyl)hydrazino]quinoline as a yellow crystal (105 mg).

mp: 166–170° C. NMR (DMSO-d$_6$, δ): 2.36–2.62 (4H, m), 6.73 (1H, d, J=6 Hz), 7.47–7.64 (4H, m), 8.00 (1H, d, J=8 Hz), 8.40 (1H, d, J=6 Hz), 8.66 (1H, d, J=8 Hz), 9.31 (1H, s), 10.09 (1H, s), 10.51 (1H, s)

(2) To a solution of 8-(2,6-dichlorobenzoylamino)-4-[2-(3-carboxypropanoyl)hydrazino]quinoline (138 mg) in dimethylformamide (3 ml) were added 1-hydroxybenzotriazole (45.9 mg) and 1-ethyl-3-(3-dimethylaminopropyl) carbodiimide hydrochloride (65.1 mg) at ambient temperature, and the mixture was stirred at the same temperature overnight. To the mixture was added water, and the resulting precipitates were collected by filtration to give 8-(2,6-dichlorobenzoylamino)-4-(2,5-dioxopyrrolidin-1-ylamino)quinoline (72 mg).

mp: 170–173° C. NMR (DMSO-d$_6$, δ): 2.83–2.98 (4H, m), 6.72 (1H, d, J=6 Hz), 7.48–7.68 (4H, m), 8.03 (1H, d, J=8 Hz), 8.45 (1H, d, J=6 Hz), 9.72 (1H, d, J=8 Hz), 9.82 (1H, s), 10.58 (1H, s)

Example 183

The following compounds were obtained according to a similar manner to that of Example 154.

(1) 8-(2,6-Dichlorobenzoylamino)-4-(2-ethanesulfonylhydrazino)quinoline mp: 178–180° C. NMR (DMSO-d$_6$, δ): 1.32 (3H, t, J=7.5 Hz), 3.23 (2H, q, J=7.5 Hz), 7.10 (1H, d, J=6.0 Hz), 7.48–7.60 (4H, m), 8.01 (1H, d, J=8.0 Hz), 8.52 (1H, d, J=6.0 Hz), 8.67 (1H, d, J=8.0 Hz), 9.35 (1H, s), 9.58 (1H, s), 10.55 (1H, s)

(2) 4-(2-Benzylsulfonylhydrazino)-8-(2,6-dichlorobenzoylamino)quinoline mp: 191–193° C. NMR (DMSO-d$_6$, δ): 4.53 (2H, s), 7.08 (1H, d, J=6.0 Hz), 7.36–7.60 (9H, m), 8.05 (1H, d, J=8.0 Hz), 8.50 (1H, d, J=6.0 Hz), 8.69 (1H, d, J=8.0 Hz), 9.45 (1H, s), 9.71 (1H, s), 10.58 (1H, s)

(3) 8-(2,6-Dichlorobenzoylamino)-4-[2-(p-toluenesulfonyl)hydrazino]quinoline mp: 219–221° C. NMR (DMSO-d$_6$, δ): 2.40 (3H, s), 6.92 (1H, d, J=6.0 Hz), 7.41 (2H, d, J=7.5 Hz), 7.45–7.60 (4H, m), 7.74 (2H, d, J=7.5 Hz), 7.88 (1H, d, J=8.0 Hz), 8.40 (1H, d, J=6.0 Hz), 8.65 (1H, d, J=8.0 Hz), 9.27 (1H, s), 10.06 (1H, s), 10.56 (1H, s)

(4) 8-(2,6-Dichlorobenzoylamino)-4-(2-styrylsulfonylhydrazino)quinoline mp: 188–190° C. NMR (DMSO-d$_6$, δ): 7.14 (1H, d, J=6.0 Hz), 7.33–7.61 (7H, m), 7.70–7.75 (2H, m), 7.96 (1H, d, J=8.0 Hz), 8.49 (1H, d, J=6.0 Hz), 8.65 (1H, d, J=8.0 Hz), 9.46 (1H, s), 9.84 (1H, s)

(5) 8-(2,6-Dichlorobenzoylamino)-4-[2-(2-thienylsulfonyl)hydrazino]quinoline mp: 208–210° C. NMR (DMSO-d$_6$, δ): 6.88 (1H, d, J=5.5 Hz), 7.21 (1H, t, J=4.0 Hz), 7.46–7.60 (4H, m), 7.66 (1H, d, J=3.0 Hz), 7.93 (1H, d, J=8.0 Hz), 8.00 (1H, d, J=5.0 Hz), 8.40 (1H, d, J=5.5 Hz), 8.65 (1H, d, J=8.0 Hz), 9.43 (1H, s)

(6) 4-[2-(2-Acetamido-4-methylthiazol-5-ylsulfonyl)hydrazino]-8-(2,6-dichlorobenzoylamino)quinoline mp: 181–183° C. NMR (DMSO-d$_6$, δ): 2.17 (3H, s), 2.40 (3H, s), 6.98 (1H, d, J=5.5 Hz), 7.47–7.62 (4H, m), 7.92 (1H, d, J=8.0 Hz), 8.45 (1H, d, J=5.5 Hz), 8.67 (1H, d, J=8.0 Hz), 9.39 (1H, s)

Example 184

(1) 8-(2,6-Dichlorobenzoylamino)-4-hydrazino-3-propylquinoline was obtained from 4-chloro-8-(2,6-dichlorobenzoylamino)-3-propylquinoline and hydrazine monohydrate according to a similar manner to that of Example 139-(1).

NMR (DMSO-$d_6$, δ): 0.93 (3H, t, J=7.5 Hz), 1.50 (2H, qt, J=7.5, 7.5 Hz), 2.84 (2H, t, J=7.5 Hz), 4.65 (2H, s), 7.35 (1H, t, J=8.0 Hz), 7.50–7.60 (3H, m), 7.73 (1H, s), 8.16 (1H, s), 8.53 (2H, d, J=8.0 Hz)

(2) 4-(2-Acetylhydrazino)-8-(2,6-dichlorobenzoylamino)-3-propylquinoline was obtained according to a similar manner to that of Example 86.

mp: 223–226° C. NMR (DMSO-$d_6$, δ): 0.95 (3H, br t, J=7.5 Hz), 1.56 (2H, br), 1.86 (3H, s), 2.76 (2H, br t, J=7.5 Hz), 7.43–7.60 (4H, m), 8.10 (1H, br d, J=8.0 Hz), 8.16 (1H, s), 8.35 (1H, s), 8.57 (1H, br d, J=8.0 Hz), 10.20 (1H, s), 10.52 (1H, s)

Example 185

(1) 4-(2-Aminoethylamino)-8-(2,6-dichlorobenzoylamino)-3-methylquinoline was obtained from 4-chloro-8-(2,6-dichlorobenzoylamino)-3-methylquinoline and ethylenediamine according to a similar manner to that of Example 8.

mp: 128–142° C. NMR (CDCl$_3$, δ): 2.40 (3H, s), 3.00 (2H, t, J=6 Hz), 3.56 (2H, q, J=6 Hz), 5.65 (1H, br s), 7.29–7.42 (3H, m), 7.47 (1H, t, J=8 Hz), 7.78 (1H, d, J=8 Hz), 8.32 (1H, s), 8.83 (1H, d, J=6 Hz)

(2) 8-(2,6-Dichlorobenzoylamino)-3-methyl-4-(2-oxoimidazolidin-1-yl)quinoline was obtained according to a similar manner to that of Example 92-(2).

mp: >250° C. NMR (CDCl$_3$, δ): 2.48 (3H, s), 3.73–4.04 (4H, m), 4.94 (1H, s), 7.30–7.45 (3H, m), 7.60–7.67 (2H, m), 8.70 (1H, s), 8.92 (1H, t, J=4 Hz)

(3) 8-(2,6-Dichlorobenzoylamino)-3-methyl-4-(2-thioxoimidazolidin-1-yl)quinoline was obtained from 4-(2-aminoethylamino)-8-(2,6-dichlorobenzoylamino)-3-methylqainoline and 1,1'-thiocarbonyldiimidazole according to a similar manner to that of Example 92-(2).

mp: 165–170° C. NMR (CDCl$_3$, δ): 2.50 (3H, s), 3.92–4.27 (4H, m), 6.19 (1H, s), 7.32–7.45 (3H, m), 7.55 (1H, d, J=6 Hz), 7.67 (1H, t, J=6 Hz), 8.75 (1H, s), 8.95 (1H, d, J=6 Hz)

Example 186

(1) 3-tert-Butyldimethylsilyloxymethyl-8-(2,6-dichlorobenzoylamino)-4-(3-methyl-2-thioxoimidazolidin-1-yl)quinoline was obtained from 3-tert-butyldimethylsilyloxymethyl-8-(2,6-dichlorobenzoylamino)-4-[(2-methylaminoethyl)amino]quinoline and 1,1'-thiocarbonyldiimidazole according to a similar manner to that of Example 92-(2).

mp: 234–236° C. NMR (DMSO-$d_6$, δ): 0.11 (3H, s), 0.13 (3H, s), 0.92 (3×3H, s), 3.17 (3H, s), 3.87–4.09 (4H, m), 4.92 (2H, s), 7.49–7.63 (4H, m), 7.71 (1H, d, J=8 Hz), 8.74 (1H, d, J=8 Hz), 9.05 (1H, s), 10.91 (1H, s)

(2) 8-(2,6-Dichlorobenzoylamino)-3-hydroxymethyl-4-(3-methyl-2-thioxoimidazolidin-1-yl)quinoline was obtained according to a similar manner to that of Example 125-(8).

mp: 253–254° C. NMR (DMSO-$d_6$, δ): 3.15 (3H, s), 3.89–4.06 (4H, m), 4.67 (2H, d, J=6 Hz), 5.49 (1H, t, J=6 Hz), 7.49–7.63 (4H, m), 7.70 (1H, dd, J=8, 8 Hz), 8.70 (1H, d, J=8 Hz), 9.07 (1H, s), 10.93 (1H, s)

Example 187

(1) 4-(2-Aminoethylamino)-8-(2,6-dichlorobenzoylamino)-3-methoxymethylquinoline was obtained from 4-chloro-8-(2,6-dichlorobenzoylamino)-3-methoxymethylquinoline and ethylenediamine according to a similar manner to that of Example 8.

mp: 130–131° C. NMR (DMSO-$d_6$, δ): 2.80 (2H, t, J=7.0 Hz), 3.29 (3H, s), 3.57 (2H, td, J=7.0, 7.0 Hz), 4.53 (2H, s), 6.60 (1H, br t, J=7.0 Hz), 7.43–7.60 (4H, m), 8.00 (1H, d, J=8.0 Hz), 8.32 (1H, s), 8.61 (1H, d, J=8.0 Hz), 10.50 (1H, br s)

(2) 8-(2,6-Dichlorobenzoylamino)-3-methoxymethyl-4-(2-oxoimidazolidin-1-yl)quinoline was obtained according to a similar manner to that of Example 92-(2).

mp: 210–212° C. NMR (DMSO-$d_6$, δ): 3.34 (3H, s), 3.56–3.80 (3H, m), 3.88–3.95 (1H, m), 4.58 (1H, d, J=13.5 Hz), 4.63 (1H, d, J=13.5 Hz), 7.01 (1H, s), 7.47–7.59 (3H, m), 7.68–7.75 (2H, m), 8.70–8.73 (1H, m), 8.94 (1H, s)

Example 188

(1) Isopropylidene (5-chloro-2-nitroanilino)methyienemalonate was obtained from 5-chloro-2-nitroaniline and isopropylidene malonate according to a similar manner to that of Example 172-(1).

mp: 217–220° C. NMR (CDCl$_3$, δ): 1.78 (6H, s), 7.34 (1H, d, J=7 Hz), 7.62 (1H, br s), 8.28 (1H, d, J=7 Hz), 8.67 (1H, d, J=9 Hz), 13.60 (1H, br d, J=9 Hz)

(2) 5-Chloro-1,4-dihydro-8-nitro-4-oxoquinoline was obtained according to a similar manner to that of Example 172-(2).

mp: 220–225° C. (dec.) NMR (DMSO-$d_6$, δ): 6.21 (1H, d, J=8 Hz), 7.45 (1H, d, J=8 Hz), 7.87 (1H, t, J=8 Hz), 8.50 (1H, d, J=8 Hz), 11.88 (1H, br s)

(3) 4,5-Dichloro-8-nitroquinoline was obtained according to a similar manner to that of Preparation 2-(1).

mp: 116–118° C. NMR (CDCl$_3$, δ): 7.68 (1H, d, J=6 Hz), 7.74 (1H, d, J=8 Hz), 7.86 (1H, d, J=8 Hz), 8.85 (1H, d, J=6 Hz)

(4) 8-Amino-4,5-dichloroquinoline was obtained according to a similar manner to that of Preparation 2-(3).

mp: 135° C. NMR (CDCl$_3$, δ): 5.10 (2H, br s), 6.85 (1H, d, J=8 Hz), 7.43 (1H, d, J=8 Hz), 7.50 (1H, d, J=6 Hz), 8.55 (1H, d, J=6 Hz)

(5) 4,5-Dichloro-8-(2,6-dichlorobenzoylamino)quinoline was obtained according to a similar manner to that of Example 1.

mp: 243–247° C. NMR (DMSO-$d_6$, δ): 7.46–7.61 (3H, m), 7.88–7.95 (2H, m), 8.75 (1H, d, J=8 Hz), 8.81 (1H, d, J=4 Hz)

(6) 5-Chloro-8-(2,6-dichlorobenzoylamino)-4-(imidazol-1-yl)quinoline was obtained according to a similar manner to that of Example 8.

mp: 259–263° C. NMR (DMSO-$d_6$, δ): 7.13 (1H, s), 7.47–7.62 (4H, m), 7.74 (1H, d, J=5 Hz), 7.84 (1H, d, J=8 Hz), 7.94 (1H, s), 8.78 (1H, d, J=8 Hz), 9.05 (1H, d, J=5 Hz)

its hydrochloride mp: 263–272° C. NMR (DMSO-$d_6$, δ): 7.49–7.62 (3H, m), 7.89–7.97 (2H, m), 8.04 (1H, d, J=2 Hz), 8.10 (1H, s), 8.83 (1H, d, J=8 Hz), 9.20 (1H, d, J=4 Hz), 9.44 (1H, br s)

Example 189

(1) 5-Chloro-8-(2,6-dichlorobenzoylamino)-4-hydrazinoquinoline was obtained from 4,5-dichloro-8-(2,6-dichlorobenzoylamino)quinoline and hydrazine monohydrate according to a similar manner to that of Example 139-(1).

mp: 253–263° C. NMR (DMSO-$d_6$, δ): 4.61 (2H, br s), 7.23 (1H, d, j=6 Hz), 7.45–7.64 (4H, m), 8.38 (1H, d, J=6 Hz), 8.52 (1H, br s), 8.54 (1H, d, J=8 Hz)

(2) 4-(2-Acetylhydrazino)-5-chloro-8-(2,6-dichlorobenzoylamino)quinoline was obtained according to a similar manner to that of Example 86.

mp: 158–161° C. NMR (DMSO-$d_6$, δ): 2.00 (3H, s), 6.88 (1H, d, J=6 Hz), 7.47–7.63 (4H, m), 8.45 (1H, d, J=6 Hz), 8.60 (1H, d, J=8 Hz), 8.94 (1H, br s)

Example 190

(1) 5-Chloro-8-(2,6-dichlorobenzoylamino)-4-[(2-methylaminoethyl)amino]quinoline was obtained from 4,5-dichloro-8-(2,6-dichlorobenzoylamino)quinoline and N-methylethylenediamine according to a similar manner to that of Example 8.

mp: 233–238° C. NMR (DMSO-$d_6$, δ): 2.33 (3H, S), 2.80–2.87 (2H, m), 3.24–3.39 (2H, m), 6.63 (1H, d, J=6 Hz), 7.48–7.62 (4H, m), 7.92 (1H, br t, J=7 Hz), 8.36 (1H, d, J=6 Hz), 8.57 (1H, d, J=8 Hz)

(2) 5-Chloro-8-(2,6-dichlorobenzoylamino)-4-(3-methyl-2-oxoimidazolidin-1-yl)quinoline was obtained according to a similar manner to that of Example 92-(2).

mp: 259–263° C. NMR (CDCl$_3$, δ): 2.96 (3H, s), 3.50–3.86 (3H, m), 3.94–4.10 (1H, m), 7.30–7.44 (4H, m), 7.65 (1H, d, J=8 Hz), 8.75 (1H, d, J=6 Hz), 8.87 (1H, d, J=8 Hz)

Example 191

(1) 8-(2,6-Dichlorobenzoylamino)-5-methyl-4-[(2-methylaminoethyl)amino]quinoline was obtained from 4-chloro-8-(2,6-dichlorobenzoylamino)-5-methylquinoline and N-methylethylenediamine according to a similar manner to that of Example 8.

mp: 247–250° C. NMR (CDCl$_3$, δ): 2.47 (3H, s), 2.92 (3H, s), 2.97–3.04 (2H, m), 3.20–3.30 (2H, m), 6.37 (1H, d, J=6 Hz), 6.60 (1H, m), 7.16 (1H, d, J=8 Hz), 7.24–7.41 (3H, m), 8.30 (1H, d, J=6 Hz), 8.70 (1H, d, J=8 Hz)

(2) 8-(2,6-Dichlorobenzoylamino)-5-methyl-4-(3-methyl-2-oxoimidazolidin-1-yl)quinoline was obtained according to a similar manner to that of Example 92-(2).

mp: 262–264° C. NMR (DMSO-$d_6$, δ): 2.66 (3H, s), 2.80 (3H, s), 3.50–3.64 (2H, m), 3.83 (1H, m), 3.97 (1H, m), 7.40 (1H, d, J=8 Hz), 7.48–7.61 (4H, m), 8.59 (1H, d, J=8 Hz), 8.85 (1H, d, J=6 Hz)

Example 192

(1) 8-(2,6-Dichlorobenzoylamino)-4-[(2-ethylaminoethyl)amino]-5-methylquinoline was obtained from 4-chloro-8-(2,6-dichlorobenzoylamino)-5-methylquinoline and N-ethylethylenediamine according to a similar manner to that of Example 8.

mp: 201–205° C. NMR (DMSO-$d_6$, δ): 1.04 (3H, t, J=8 Hz), 2.57 (2H, q, J=8 Hz), 2.80–2.94 (2H, m), 2.89 (3H, s), 3.18–3.29 (2H, m), 6.52 (1H, d, J=6 Hz), 6.78 (1H, br s), 7.19 (1H, d, J=8 Hz), 7.48–7.63 (3H, m), 8.30 (1H, d, J=6 Hz), 8.47 (1H, d, J=8 Hz)

(2) 8-(2,6-Dichlorobenzoylamino)-4-(3-ethyl-2-oxoimidazolidin-1-yl)-5-methylquinoline was obtained according to a similar manner to that of Example 92-(2).

mp: 235–236° C. NMR (DMSO-$d_6$, δ): 1.12 (3H, t, J=8 Hz), 2.67 (3H, s), 3.26 (2H, q, J=8 Hz), 3.54–3.64 (2H, m), 3.78–3.89 (1H, m), 3.91–4.07 (1H, m), 7.41 (1H, d, J=8 Hz), 7.49–7.64 (4H, m), 8.59 (1H, d, J=8 Hz), 8.84 (1H, d, J=6 Hz)

Example 193

(1) 8-(2,6-Dichlorobenzoylamino)-3-methoxymethyl-5-methyl-4-[(2-methylaminoethyl)amino]quinoline was obtained from 4-chloro-8-(2,6-dichlorobenzoylamino)-3-methoxymethyl-5-methylquinoline and N-methylethylenediamine according to a similar manner to that of Example 8.

NMR (CDCl$_3$, δ): 2.46 (3H, s), 2.69–2.79 (2H, m), 2.90 (3H, s), 3.32–3.47 (2H, m), 3.40 (3H, s), 4.59 (2H, s), 5.59 (1H, br t, J=6 Hz), 7.20–7.43 (4H, m), 8.29 (1H, s), 8.73 (1H, d, J=8 Hz)

(2) 8-(2,6-Dichlorobenzoylamino)-3-methoxymethyl-5-methyl-4-(3-methyl-2-oxoimidazolidin-1-yl)quinoline was obtained according to a similar manner to that of Example 92-(2).

mp: 105–112° C. NMR (CDCl$_3$, δ): 2.74 (3H, s), 2.96 (3H, s), 3.44 (3H, s), 3.58–3.85 (4H, m), 4.40 (1H, d, J=9 Hz), 4.66 (1H, d, J=9 Hz), 7.27–7.46 (4H, m), 8.81 (1H, d, J=8 Hz), 8.85 (1H, s)

Example 194

(1) 1,4-Dihydro-3-hydroxymethyl-5-methyl-8-nitro-4-oxoquinoline was obtained from 1,4-dihydro-5-methyl-8-nitro-4-oxoquinoline according to a similar manner to that of Example 172-(3).

mp: 251–255° C. NMR (DMSO-$d_6$, δ): 4.37 (2H, s), 7.20 (1H, d, J=8 Hz), 7.93 (1H, d, J=6 Hz), 8.47 (1H, d, J=8 Hz)

(2) 1,4-Dihydro-3,5-dimethyl-8-nitro-4-oxoquinoline was obtained according to a similar manner to that of Example 104-(2).

mp: 250–262° C. NMR (DMSO-$d_6$, δ): 1.96 (3H, s), 2.90 (3H, s), 7.17 (1H, d, J=8 Hz), 7.83 (1H, d, J=6 Hz), 8.44 (1H, d, J=8 Hz)

(3) 4-Chloro-3,5-dimethyl-8-nitroquinoline was obtained according to a similar manner to that of Preparation 2-(1).

NMR (CDCl$_3$, δ): 2.58 (3H, s), 3.10 (3H, s), 7.41 (1H, d, J=8 Hz), 7.78 (1H, d, J=8 Hz), 8.79 (1H, s)

(4) 8-Amino-4-chloro-3,5-dimethylquinoline was obtained according to a similar manner to that of Preparation 2-(3).

mp: 120–122° C. NMR (DMSO-$d_6$, δ): 2.46 (3H, s), 2.81 (3H, s), 5.83 (2H, br s), 6.76 (1H, d, J=8 Hz), 7.15 (1H, d, J=8 Hz), 8.60 (1H, s)

(5) 4-Chloro-8-(2,6-dichlorobenzoylamino)-3,5-dimethylquinoline was obtained according to a similar manner to that of Example 1.

mp: 236–240° C. NMR (DMSO-$d_6$, δ): 2.52 (3H, s), 2.98 (3H, s), 7.47–7.61 (4H, m), 8.57 (1H, d, J=8 Hz), 8.78 (1H, s), 10.69 (1H, s)

(6) 8-(2,6-Dichlorobenzoylamino)-4-(imidazol-1-yl)-3,5-dimethylquinoline was obtained according to a similar manner to that of Example 8.

mp: 214–216° C. NMR (DMSO-$d_6$, δ): 1.92 (3H, s), 2.08 (3H, s), 7.24 (1H, s), 7.43–7.62 (5H, m), 7.90 (1H, s), 8.59 (1H, d, J=8 Hz), 8.93 (1H, s), 10.79 (1H, s)

Example 195

(1) Isopropylidene (5-methoxy-2-nitroanilino)methylenemalonate was obtained from 5-methoxy-2-nitroaniline and isopropylidene malonate according to a similar manner to that of Example 172-(1).

mp: 210–220° C. NMR (CDCl$_3$, δ): 1.77 (6H, s), 3.98 (3H, s), 6.84 (1H, dd, J=8, 2 Hz), 6.98 (1H, d, J=2 Hz), 8.32 (1H, d, J=8 Hz), 8.70 (1H, d, J=10 Hz)

(2) 1,4-Dihydro-5-methoxy-8-nitro-4-oxoquinoline was obtained according to a similar manner to that of Example 172-(2).

mp: 195–200° C. NMR (DMSO-$d_6$, δ): 4.00 (3H, s), 6.10 (1H, d, J=8 Hz), 7.00 (1H, d, J=8 Hz), 7.80 (1H, d, J=8 Hz), 8.60 (1H, d, J=8 Hz)

(3) 4-Chloro-5-methoxy-8-nitroquinoline was obtained according to a similar manner to that of Preparation 2-(1).

mp: 125–138° C. NMR (CDCl$_3$, δ): 4.07 (3H, s), 6.92 (1H, d, J=8 Hz), 7.55 (1H, d, J=4 Hz), 8.09 (1H, d, J=8 Hz), 8.83 (1H, d, J=4 Hz)

(4) 8-Amino-4-chloro-5-methoxyquinoline was obtained according to a similar manner to that of Preparation 2-(3).

mp: 111–115° C. NMR (CDCl$_3$, δ): 3.90 (3H, s), 4.74 (2H, br s), 6.87–6.95 (2H, m), 7.40 (1H, d, J=4 Hz), 8.57 (1H, d, J=4 Hz)

(5) 4-Chloro-8-(2,6-dichlorobenzoylamino)-5-methoxyquinoline was obtained according to a similar manner to that of Example 1.

mp: 238–242° C. NMR (CDCl$_3$, δ): 4.00 (3H, s), 7.01 (1H, d, J=8 Hz), 7.30–7.45 (3H, m), 7.48 (1H, d, J=4 Hz), 8.56 (1H, d, J=4 Hz), 8.95 (1H, d, J=8 Hz), 9.90 (1H, s)

(6) 8-(2,6-Dichlorobenzoylamino)-4-hydrazino-5-methoxyquinoline was obtained according to a similar manner to that of Example 139-(1).

mp: >250° C. NMR (DMSO-d$_6$, δ): 3.97 (3H, s), 4.54 (2H, s), 6.88 (1H, d, J=6 Hz), 7.01 (1H, d, J=4 Hz), 7.49–7.62 (3H, m), 8.28 (1H, d, J=4 Hz), 8.50 (1H, d, J=6 Hz), 8.77 (1H, s)

(7) 4-(2-Acetylhydrazino)-8-(2,6-dichlorobenzoylamino)-5-methoxyquinoline was obtained according to a similar manner to that of Example 86.

mp: >250° C. NMR (DMSO-d$_6$, δ): 2.00 (3H, s), 3.98 (3H, s), 6.68 (1H, d, J=4 Hz), 6.97 (1H, d, J=8 Hz), 7.48–7.61 (3H, m), 8.36 (1H, d, J=4 Hz), 8.57 (1H, d, J=8 Hz), 9.25 (1H, s)

Example 196

8-(2,6-Dichlorobenzoylamino)-4-(imidazol-1-yl)-5-methoxyquinoline was obtained from 4-chloro-8-(2,6-dichlorobenzoylamino)-5-methoxyquinoline and imidazole according to a similar manner to that of Example 8.

mp: 155–189° C. NMR (CDCl$_3$, δ): 3.70 (3H, s), 6.99 (1H, d, J=8 Hz), 7.16 (1H, d, J=2 Hz), 7.22 (1H, d, J=2 Hz), 7.32–7.45 (4H, m), 7.66 (1H, s), 8.83 (1H, d, J=3 Hz), 9.01 (1H, d, J=8 Hz)

Example 197

(1) 8-(2,6-Dichlorobenzoylamino)-5-methoxy-4-[(2-methylaminoethyl)amino]quinoline was obtained from 4-chloro-8-(2,6-dichlorobenzoylamino)-5-methoxyquinoline and N-methylethylenediamine according to a similar manner to that of Example 8.

mp: 210–217° C. NMR (CDCl$_3$, δ): 2.50 (3H, s), 2.95 (2H, t, J=6 Hz), 3.35 (2H, q, J=6 Hz), 3.99 (3H, s), 6.33 (1H, d, J=4 Hz), 6.76 (1H, d, J=8 Hz), 7.25–7.43 (4H, m), 8.08 (1H, br), 8.27 (1H, d, J=6 Hz), 8.79 (1H, d, J=8 Hz)

(2) 8-(2,6-Dichlorobenzoylamino)-5-methoxy-4-(3-methyl-2-oxoimidazolidin-1-yl)quinoline was obtained according to a similar manner to that of Example 92-(2).

mp: 227–237° C. NMR (CDCl$_3$, δ): 2.95 (3H, s), 3.57 (2H, t, J=6 Hz), 3.82 (2H, t, J=6 Hz), 3.44 (3H, s), 6.97 (1H, d, J=8 Hz), 7.30–7.45 (4H, m), 8.70–8.75 (1H, m), 8.90 (1H, d, J=8 Hz)

Example 198

(1) 4-Chloro-6-methyl-8-nitroquinoline was obtained from 1,4-dihydro-6-methyl-8-nitro-4-oxoquinoline according to a similar manner to that of Preparation 2-(1).

mp: 139–141° C. NMR (DMSO-d$_6$, δ): 2.66 (3H, s), 7.60 (1H, d, J=6 Hz), 7.92 (1H, s), 8.23 (1H, s), 8.86 (1H, d, J=6 Hz)

(2) 8-Amino-4-chloro-6-methylquinoline was obtained according to a similar manner to that of Preparation 2-(3).

mp: 115–116° C. NMR (DMSO-d$_6$, δ): 2.40 (3H, s), 6.04 (2H, s), 6.79 (1H, s), 7.05 (1H, s), 7.62 (1H, d, J=5 Hz), 8.05 (1H, d, J=5 Hz)

(3) 8-(2,6-Dichlorobenzoylamino)-4-chloro-6-methylquinoline was obtained according to a similar manner to that of Example 1.

mp: 203–205° C. NMR (DMSO-d$_6$, δ): 2.61 (3H, s), 7.48–7.61 (3H, m), 7.78 (1H, d, J=1 Hz), 7.83 (1H, d, J=6 Hz), 8.70 (1H, d, J=1 Hz), 8.75 (1H, d, J=6 Hz), 10.82 (1H, s)

(4) 8-(2,6-Dichlorobenzoylamino)-4-(imidazol-1-yl)-6-methylquinoline was obtained according to a similar manner to that of Example 8.

mp: 260–261° C. NMR (DMSO-d$_6$, δ): 2.54 (3H, s), 7.28 (1H, d, J=1 Hz), 7.34 (1H, d, J=1 Hz), 7.48–7.63 (3H, m), 7.70 (1H, d, J=5 Hz), 7.73 (1H, d, J=0.5 Hz), 8.16 (1H, d, J=0.5 Hz), 8.71 (1H, s), 8.93 (1H, d, J=5 Hz), 10.86 (1H, s)

Example 199

(1) 8-(2,6-Dichlorobenzoylamino)-6-methyl-4-[(2-methylaminoethyl)amino]quinoline was obtained from 4-chloro-8-(2 , 6-dichlorobenzoylamino)-6-methyl quinoline and N-methylethylenediamine according to a similar manner to that of Example 8.

NMR (DMSO-d$_6$, δ): 0.06 (2×3H, s), 0.86 (3×3H, a), 2.31 (3H, s), 2.73 (2H, t, J=6 Hz), 3.69 (2H, dt, J=6, 6 Hz), 4.84 (2H, s), 6.45 (1H, t, J=6 Hz), 7.43–7.62 (4H, m), 7.98 (4H, d, J=8 Hz), 8.37 (1H, s), 8.61 (1H, d, J=8 Hz), 10.51 (1H, s)

(2) 8-(2,6-Dichlorobenzoylamino)-6-methyl-4-(3-methyl-2-oxoimidazolidin-n-yl)quinoline was obtained according to a similar manner to that of Example 92-(2).

mp: 277–279° C. NMR (DMSO-d$_6$, δ): 2.54 (3H, s), 2.84 (3H, s), 3.60 (2H, t, J=7.5 Hz), 3.93 (2H, t, J=7.5 Hz), 7.48 (1H, d, J=6 Hz), 7.50–7.62 (4H, m), 8.60 (1H, d), 8.75 (1H, d, J=6 Hz), 10.66 (1H, s)

Example 200

8-(2,6-Dichlorobenzoylamino)-6-methyl-4-(3-methyl-2-thioxoimidazolidin-1-yl)quinoline was obtained from 8-(2,6-dichlorobenzoylamino)-6-methyl-4-[(2-methylaminoethyl)amino]-quinoline and 1,11-thiocarbonyldiimidazole according to a similar manner to that of Example 92-(2).

mp: 264–266° C. NMR (DMSO-d$_6$, δ): 2.55 (3H, s), 3.17 (3H, s), 3.96–4.10 (4H, m), 7.47–7.65 (5H, m), 8.62 (1H, s), 8.87 (1H, d, J=6 Hz), 10.75 (1H, s)

Example 201

(1) 8-(2,6-Dichlorobenzoylamino)-4-hydrazino-6-methylquinoline was obtained from 4-chloro-8-(2,6-dichlorobenzoylamino)-6-methylquinoline and hydrazine monohydrate according to a similar manner to that of Example 139-(1).

mp: 221–224° C. NMR (DMSO-d$_6$, δ): 2.48 (3H, s), 4.34 (2H, s), 6.92 (1H, d, J=6 Hz), 7.50–7.63 (3H, m), 7.73 (1H, s), 8.30 (1H, d, J=6 Hz), 8.47–8.55 (2H, m), 10.39 (1H, s)

(2) 4-(2-Acetylhydrazino)-8-(2,6-dichlorobenzoylamino)-6-methylquinoline was obtained according to a similar manner to that of Example 86.

mp: 263–266° C. NMR (DMSO-d$_6$, δ): 2.00 (3H, s), 2.53 (3H, s), 6.61 (1H, d, J=6 Hz), 7.50–7.63 (3H, m), 7.81 (1H, s), 8.36 (1H, d, J=6 Hz), 8.56 (1H, s), 9.14 (1H, s), 10.00 (1H, s), 10.46 (1H, s)

Example 202

8-(2,6-Dichlorobenzoylamino)-4-(2-methanesulfonylhydrazino)-6-methylquinoline was obtained from 8-(2,6-dichlorobenzoylamino)-4-hydrazino-6-methylquinoline and mesyl chloride according to a similar manner to that of Example 154.

mp: 156–161° C. NMR (DMSO-d$_6$, δ): 2.54 (3H, s), 3.10 (3H, s), 7.06 (1H, d, J=6 Hz), 7.48–7.63 (3H, m), 7.83 (1H, s), 8.44 (1H, d, J=6 Hz), 8.57 (1H, s), 9.34 (1H, br s), 9.53 (1H, s), 10.49 (1H, s)

Example 203

(1) To a solution of 4-chloro-8-(2,6-dichlorobenzoylamino)-6-methylquinoline (562 mg) in N-methylpyrrolidone (6 ml) was added hydrazine hydrate, and the mixture was heated at 90° C. for 6 hours. The mixture was diluted with ethyl acetate, washed with water and brine, dried over magnesium sulfate and concentrated. The residue was dissolved in methylene chloride and acetone and then concentrated. The residual solid was treated with hot ethanol (5 ml), allowed to cool to ambient temperature, filtered and washed with ethanol to give 8-(2,6-dichlorobenzoylamino)-6-methyl-4-(2-isopropylidenehydrazino)quinoline (560 mg) as an off-white crystal.

mp: 242–245° C. NMR (DMSO-$d_6$, δ): 2.07 (3H, s), 2.12 (3H, s), 2.55 (3H, s), 7.23 (1H, d, J=6 Hz), 7.49–7.63 (3H, m), 7.85 (1H, s), 8.40 (1H, d, j=6 Hz), 8.56 (1H, s), 9.27 (1H, s), 10.46 (1H, s)

(2) To a suspension of 8-(2,6-dichlorobenzoylamino)-6-methyl-4-(2-isopropylidenehydrazino)quinoline (159 mg) in methanol (5 ml) was added sodium cyanoborohydride (25 mg) and acetic acid (50 mg), and the mixture was stirred at ambient temperature for 24 hours. The mixture was concentrated to dryness and the residue was triturated with water (5 ml) and filtered. The solid was treated with hot water (5 ml), allowed to cool to ambient temperature, filtered and washed with water to give 8-(2,6-dichlorobenzoylamino)-6-methyl-4-(2-isopropylhydrazino)quinoline (117 mg) as pale yellow powder.

mp: 154–156° C. NMR (DMSO-$d_6$, δ): 1.03 (2×3H, d, J=7 Hz), 2.54 (3H, s), 3.28 (1H, m), 7.20 (1H, m), 7.51–7.68 (3H, m), 8.27–8.44 (3H, m), 10.51 (1H, s)

Example 204

(1) Isopropylidene (4-chloro-2-nitroanilino) methylenemalonate was obtained from 4-chloro-2-nitroaniline and isopropylidene malonate according to a similar manner to that of Example 172-(1).

mp: 204–206° C. NMR (CDCl$_3$, δ): 7.58 (1H, d, J=8 Hz), 7.74 (if, dd, J=8, 2 Hz), 8.33 (1H, s), 8.69 (1H, d, J=10 Hz)

(2) 6-Chloro-1,4-dihydro-8-nitro-4-oxoquinoline was obtained according to a similar manner to that of Example 172-(2).

mp: 238–241° C. NMR (DMSO-$d_6$, δ): 6.27 (1H, d, J=6 Hz), 8.00 (1H, d, J=6 Hz), 8.45 (1H, d, J=2 Hz), 8.64 (1H, d, J=2 Hz)

(3) 4,6-Dichloro-8-nitroquinoline was obtained according to a similar manner to that of Preparation 2-(1).

mp: 149–164° C. NMR (CDCl$_3$, δ): 7.68 (1H, d, J=4 Hz), 8.04 (1H, d, J=2 Hz), 8.45 (1H, s), 8.91 (1H, d, J=4 Hz)

(4) 8-Amino-4,6-dichloroquinoline was obtained according to a similar manner to that of Preparation 2-(3).

mp: 132–134° C. NMR (CDCl$_3$, δ): 5.15 (2H, br s), 6.90 (1H, s), 7.45–7.49 (2H, m), 8.57 (1H, d, J=4 Hz)

(5) 4,6-Dichloro-8-(2,6-dichlorobenzoylamino)quinoline was obtained according to a similar manner to that of Example 1.

mp: 201–205° C. NMR (CDCl$_3$, δ): 7.32–7.45 (3H, m), 7.58 (1H, d, J=4 Hz), 7.98 (1H, s), 8.62 (1H, d, J=4 Hz), 9.06 (1H, d, J=2 Hz)

(6) 6-Chloro-8-(2,6-dichlorobenzoylamino)-4-hydrazinoquinoline was obtained according to a similar manner to that of Example 139-(1).

mp: 142–150° C.

(7) 4-(2-Acetylhydrazino)-6-chloro-8-(2,6-dichlorobenzoylamino)quinoline was obtained according to a similar manner to that of Example 86.

mp: 117–180° C. NMR (CDCl$_3$, δ): 2.20 (3H, s), 6.72 (1H, d, J=4 Hz), 7.28–7.40 (4H, m), 8.40 (1H, d, J=4 Hz), 8.86 (1H, d, J=2 Hz)

Example 205

6-Chloro-8-(2,6-dichlorobenzoylamino)-4-(imidazol-1-yl)quinoline was obtained from 4,6-dichloro-8-(2,6-dichlorobenzoylamino)quinoline and imidazole according to a similar manner to that of Example 8.

mp: 179–181° C. NMR (CDCl$_3$, δ): 7.30–7.48 (6H, m), 7.57 (1H, s), 7.85 (1H, s), 8.85 (1H, d, J=4 Hz), 9.10 (1H, s)

Example 206

(1) 6-Chloro-8-(2,6-dichlorobenzoylamino)-4-[(2-methylaminoethyl)amino]quinoline was obtained from 4,6-dichloro-8-(2,6-dichlorobenzoylamino)quinoline and N-methylethylenediamine according to a similar manner to that of Example 8.

mp: 185–198° C. NMR (CDCl$_3$, δ): 2.50 (3H, s), 3.00 (2H, t, J=6 Hz), 3.34 (2H, q, J=6 Hz), 5.80 (1H, br), 6.45 (1H, d, J=4 Hz), 7.30–7.43 (3H, m), 7.51 (1H, d, J=2 Hz), 8.36 (1H, d, J=4 Hz), 8.93 (1H, s)

(2) 6-Chloro-8-(2,6-dichlorobenzoylamino)-4-(3-methyl-2-oxoimidazolidin-1-yl)quinoline was obtained according to a similar manner to that of Example 92-(2).

mp: >250° C. NMR (DMSO-$d_6$, δ): 2.85 (3H, s), 3.60 (1H, t, J=6 Hz), 3.97 (1H, t, J=6 Hz), 7.50–7.62 (4H, m), 7.80 (1H, s), 7.73 (1H, s), 8.86 (1H, d, J=4 Hz)

Example 207

(1) Isopropylidere (4-fluoro-2-nitroanilino) methylenemalonate was obtained from 4-fluoro-2-nitroaniline and isopropylidene malonate according to a similar manner to that of Example 172-(1).

mp: 195–196° C. NMR (CDCl$_3$, δ): 1.78 (2×3H, s), 7.53 (1H, ddd, J=8, 5, 3 Hz), 7.63 (1H, dd, J=8, 5 Hz), 8.05 (1H, dd, J=8, 3 Hz), 8.67 (1H, d, J=15 Hz)

(2) 6-Fluoro-1,4-dihydro-8-nitro-4-oxoquioline was obtained according to a similar manner to that of Example 172-(2).

mp: 178–182° C. NMR (CDCl$_3$, δ): 6.40 (1H, d, J=7.5 Hz), 7.76 (1H, dd, J=7.5, 7 Hz), 8.42 (1H, dd, J=7, 1 Hz), 8.50 (1H, dd, J=8, 1 Hz)

(3) 4-Chloro-6-fluoro-8-nitroquinoline was obtained according to a similar manner to that of Preparation 2-(1).

mp: 120–130° C. NMR (CDCl$_3$, δ): 7.68 (1H, d, J=6 Hz), 7.90 (1H, dd, J=7, 3 Hz), 8.12 (1H, dd, J=8, 3 Hz), 8.90 (1H, d, J=6 Hz)

(4) 8-Amino-4-chloro-6-fluoroquinoline was obtained according to a similar manner to that of Preparation 2-(3).

mp: 98–103° C. NMR (DMSO-$d_6$, δ): 6.54 (2H, s), 6.72 (1H, dd, J=11, 2 Hz), 6.87 (1H, dd, J=11, 2 Hz), 7.73 (1H, d, J=5 Hz), 8.60 (1H, d, J=5 Hz)

(5) 4-Chloro-8-(2,6-dichlorobenzoylamino)-6-fluoroquinoline was obtained according to a similar manner to that of Example 1.

mp: 200–213° C. NMR (DMSO-$d_6$, δ): 7.48–7.63 (3H, m), 7.70 (1H, dd, J=12, 3 Hz), 7.94 (1H, d, J=6 Hz), 8.71 (1H, dd, J=12, 3 Hz), 8.82 (1H, d, J=6 Hz), 11.27 (1H, s)

(6) B-(2,6-Dichlorobenzoylamino)-6-fluoro-4-(imidazol-1-yl)quinoline was obtained according to a similar manner to that of Example 8.

mp: 154–159° c NMR (DMSO-$d_6$, δ): 7.21 (1H, dd, J=10, 2 Hz), 7.28 (1H, s), 7.49–7.66 (3H, m), 7.76 (1H, s), 7.80 (1H, d, J=4 Hz), 8.18 (1H, s), 8.71 (1H, dd, J=10, 2 Hz), 9.00 (1H, d, J=4 Hz), 11.31 (1H, s)

Example 208

(1) 8-(2,6-Dichlorobenzoylamino)-6-fluoro-4-[(2-methylaminoethyl)amino]quinoline was obtained from 4-chloro-8-(2,6-dichlorobenzoylamino)-6-fluoroquinoline and N-methylethylenediamine according to a similar manner to that of Example 8.

mp: 198–200° C. NMR (DMSO-$d_6$, δ): 2.32 (3H, s), 2.77 (2H, t, J=6 Hz), 3.36 (1H, dt, J=6, 5 Hz), 6.60 (1H, d, J=6

Hz), 7.15 (1H, t, J=5 Hz), 7.50–7.63 (3H, m), 7.87 (1H, dd, J=11, 2 Hz), 8.34 (1H, d, J=6 Hz), 8.50 (1H, dd, J=11, 2 Hz), 10.72 (1H, br s)

(2) 8-(2,6-Dichlorobenzoylamino)-6-fluoro-4-(3-methyl-2-oxoimidazolidin-1-yl)quinoline was obtained according to a similar manner to that of Example 92-(2).

mp: 268–272° C. NMR (DMSO-$d_6$, δ): 2.84 (3H, s), 3.59 (2H, t, J=7 Hz), 3.94 (2H, t, J=7 Hz), 7.48–7.61 (5H, m), 8.60 (1H, dd, J=11, 2 Hz), 8.81 (1H, d, J=6 Hz), 11.06 (1H, s)

Example 209

(1) 8-(2,6-Dichlorobenzoylamino)-6-fluoro-4-hydrazinoquinoline was obtained from 4-chloro-8-(2,6-dichlorobenzoylamino)-6-fluoroquinoline and hydrazine monohydrate according to a similar manner to that of Example 139-(1).

mp: 208–212° C. NMR (DMSO-$d_6$, δ): 4.51 (2H, s), 6.99 (1H, d, J=6 Hz), 7.49–7.63 (3H, m), 7.75 (1H, dd, J=12, 3 Hz), 8.37 (1H, d, J=6 Hz), 8.47 (1H, dd, J=12, 3 Hz), 8.56 (1H, s), 10.72 (1H, s)

(2) 4-(2-Acetylhydrazino)-8-(2,6-dichlorobenzoylamino)-6-fluoroquinoline was obtained according to a similar manner to that of Example 86.

mp: 250–254° C. NMR (DMSO-$d_6$, δ): 2.01 (3H, s), 6.68 (1H, d, J=6 Hz), 7.48–7.62 (3H, m), 7.81 (1H, dd, J=10, 2 Hz), 8.42 (1H, d, J=6 Hz), 8.54 (1H, dd, J=10, 2 Hz), 9.18 (1H, s), 10.06 (1H, s), 10.82 (1H, s)

Example 210

(1) Isopropylidene (2-nitro-4-trifluoromethylanilino)methylenemalonate was obtained from 2-nitro-4-trifluoromethylaniline and isopropylidene malonate according to a similar manner to that of Example 172-(1).

mp: 218–220° C. NMR (CDCl$_3$, δ): 1.79 (6H, s), 7.77 (1H, d, J=8 Hz), 8.00 (1H, dd, J=8, 2 Hz), 8.61 (1H, d, J=2 Hz) 8.76 (1H, d, j=10 Hz)

(2) 1,4-Dihydro-8-nitro-4-oxo-6-trifluoromethylquinoline was obtained according to a similar manner to that of Example 172-(2).

mp: 153–156° C. NMR (DMSO-$d_6$, δ): 6.33 (1H, d, J=7.5 Hz), 8.03 (1H, dd, J=7.5, 7 Hz), 8.73 (1H, d, J=1 Hz), 8.83 (1H, d, J=1 Hz)

(3) 4-Chloro-8-nitro-6-trifluoromethylquinoline was obtained according to a similar manner to that of Preparation 2-(1).

mp: 100–107° C. NMR (CDCl$_3$, δ): 7.77 (1H, d, J=5 Hz) 8.25 (1H, d), 8.78 (1H, s), 9.05 (1H, d, J=5 Hz)

(4) 8-Amino-4-chloro-6-trifluoromethylquinoline was obtained according to a similar manner to that of Preparation 2-(3).

mp: 57–58° C. NMR (CDCl$_3$, δ): 5.1$ (2H, br s), 7.07 (1H, d, J=2 Hz), 7.55 (0H, d, J=6 Hz), 7.80 (1H, br), 8.70 (1H, d, J=6 Hz)

(7) 4-Chloro-8-(2,6-dichiorobenzoylamino)-6-trifluoromethylquinoline was obtained according to a similar manner to that of Example 1.

mp: 150–157° C. NMR (DMSO-$d_6$, δ): 7.47–7.61 (3H, m), 8.05 (1H, d, J=6 Hz), 8.29 (1H, s), 9.00 (1H, d, J=2 Hz), 9.10 (1H, s), 11.15 (1H, s)

(6) 8-(2,6-Dichiorobenzoylamino)-4-hydrazino-6-trifluoromethylquinoline was obtained according to a similar manner to that of Example 139-(p).

mp: 228–232° C. NMR (DMSO-$d_6$, δ): 4.61 (2H, d), 7.09 (8H, d, J=6 Hz), 7.50–7.63 (3H, m), 8.35 (1H, s), 8.37 (1H, d, J=6 Hz), 8.85 (1H, s), 9.10 (1H, s), 10.74 (1H, s)

(7) 4-(2-Acetylhydrazino)-8-(2,6-dichlorobenzoylamino)-6-trifluoromethylquinoline was obtained according to a similar manner to that of Example 86.

mp: 174–178° C. NMR (DMSO-$d_6$, δ): 2.03 (3H, s), 6.78 (1H, d, J=6 Hz), 7.49–7.63 (3H, m), 8.54 (1H, s), 8.56 (1H, d, J=6 Hz), 8.92 (1H, S), 9.69 (1H, s), 10.15 (1H, s), 10.86 (1H, s)

Example 211

8-(2,6-Dichlorobenzoylamino)-4-(imidazol-1-yl)-6-trifluoromethylquinoline was obtained from 4-chloro-8-(2,6-dichlorobenzoylamino)-6-trifluoromethylquinoline and imidazole according to a similar manner to that of Example 8.

mp: 201–203° C. NMR (DMSO-$d_6$, δ): 7.32 (1H, s), 7.49–7.64 (3H, m), 7.83 (2×1H, s), 7.93 (1H, d, J=6 Hz), 8.25 (1H, s), 9.09 (1H, s), 9.19 (1H, d, J=6 Hz), 11.40 (1H, s)

Example 212

(1) 8-(2,6-Dichlorobenzoylamino)-4-[(2-methylaminoethyl)amino]-6-trifluoromethylquinoline was obtained from 4-chloro-8-(2,6-dichlorobenzoylamino)-6-trifluoromethylquinoline and N-methylethylenediamine according to a similar manner to that of Example 8.

mp: 202–206° C. NMR (DMSO-$d_6$, δ): 2.36 (3H, s), 2.82 (2H, t, J=7 Hz), 3.43 (2H, dt, J=7, 5 Hz), 6.72 (1H, d, J=7 Hz), 7.50–7.63 (3H, m), 7.74 (1H, br t, J=5 Hz), 8.46 (1H, d, J=7 Hz), 8.53 (1H, s), 8.87 (1H, s), 10.75 (1H, br s)

(2) 8-(2,6-Dichlorobenzoylamino)-4-(3-methyl-2-oxoimidazolidin-1-yl)-6-trifluoromethylquinoline was obtained according to a similar manner to that of Example 92-(2).

mp: >285° C. NMR (DMSO-$d_6$, δ): 2.87 (3H, s), 3.63 (2H, t, J=7.5 Hz), 4.02 (2H, t, J=7.5 Hz), 7.48–7.61 (3H, m), 7.64 (1H, d, J=6 Hz), 8.13 (1H, d, J=0.5 Hz), 8.94 (1H, d, J=0.5 Hz), 8.98 (1H, d, J=6 Hz), 11.12 (1H, s)

Example 213

(1) Isopropylidene (3-methyl-2-nitroanilino)methylenemalonate was obtained from 3-methyl-2-nitroaniline and isopropylidene malonate according to a similar manner to that of Example 172-(1).

mp: 187–190° C. NMR (CDCl$_3$, δ): 1.75 (6H, s), 2.50 (3H, s), 7.25 (1H, d, J=8 Hz), 7.35 (1H, d, J=8 Hz), 7.52 (1H, t, J=8 Hz), 8.55 (1H, d, J=10 Hz)

(2) 1,4-Dihydro-7-methyl-8-nitro-4-oxoquinoline was obtained according to a similar manner to that of Example 172-(2).

mp: >250° C. NMR (DMSO-$d_6$, δ): 2.46 (3H, s), 6.20–6.50 (1H, br), 7.42 (1H, d, J=8 Hz), 7.90–8.20 (1H, br), 8.22 (1H, d, J=8 Hz)

(3) 4-Chloro-7-methyl-8-nitroquinoline was obtained according to a similar manner to that of Preparation 2-(1).

mp: 140–147° C. NMR (CDCl$_3$, δ): 2.56 (3H, s), 3.52–3.60 (2H, m), 8.26 (1H, d, J=8 Hz), 8.83 (1H, d, J=4 Hz)

(4) 8-Amino-4-chloro-7-methylquinoline was obtained according to a similar manner to that of Preparation 2-(3).

mp: 75–77° C. NMR (CDCl$_3$, δ): 2.37 (3H, s), 4.98 (2H, br s), 7.36 (1H, d, J=8 Hz), 7.41 (1H, d, J=4 Hz), 7.49 (1H, d, J=8 Hz), 8.59 (1H, d, J=4 Hz)

(5) 4-Chloro-8-(2,6-dichlorobenzoylamino)-7-methylquinoline was obtained according to a similar manner to that of Example 1.

mp: 202–205° C. NMR (CDCl$_3$, δ): 2.70 (3H, s), 7.30–7.45 (3H, m), 7.48 (1H, d, J=4 Hz), 7.60 (1H, d, J=8 Hz), 8.05 (1H, d, J=8 Hz), 8.68 (1H, d, J=4 Hz), 9.07 (1H, s)

(6) 8-(2,6-Dichlorobenzoylamino)-4-hydrazino-7-methylquinoline was obtained according to a similar manner to that of Example 139-(1).

mp: 202–204° C. NMR (DMSO-d$_6$, δ): 2.60 (3H, s), 7.46–7.62 (3H, m), 7.70–7.78 (2H, m), 8.10 (1H, d, J=8 Hz), 8.85 (1H, d, J=4 Hz)

(7) 4-(2-Acetylhydrazino)-8-(2,6-dichlorobenzoylamino)-7-methylquinoline was obtained according to a similar manner to that of Example 86.

mp: >250° C. NMR (DMSO-d$_6$, δ): 2.00 (3H, s), 2.50 (3H, s), 6.55 (1H, d, J=4 Hz), 7.37–7.70 (4H, m), 8.06 (2H, d, J=8 Hz), 8.45 (1H, d, J=4 Hz), 9.12 (1H, s)

Example 214

8-(2,6-Dichlorobenzoylamino)-4-(imidazol-1-yl)-7-methylquinoline was obtained from 4-chloro-8-(2,6-dichlorobenzoylamino)-7-methylquinoline and imidazole according to a similar manner to that of Example 8.

mp: 220–222° C. NMR (DMSO-d$_6$, δ): 2.59 (3H, s), 7.28 (1H, s), 7.46–7.68 (6H, m), 7.73 (1H, s), 8.16 (1H, s), 9.02 (1H, d, J=4 Hz)

its hydrochloride mp: 170–174° C. NMR (DMSO-d$_6$, δ): 2.62 (3H, s), 7.47–7.67 (4H, m), 7.74 (1H, d, J=8 Hz), 7.89 (1H, d, J=4 Hz), 8.08 (1H, d, J=2 Hz), 8.28 (1H, d, J=2 Hz), 9.17 (1H, d, J=4 Hz), 9.72 (1H, s)

Example 215

(1) 8-(2,6-Dichlorobenzoylamino)-7-methyl-4-[(2-methylaminoethyl)amino]quinoline was obtained from 4-chloro-8-(2,6-dichlorobenzoylamino)-7-methylquinoline and N-methylethylenediamine according to a similar manner to that of Example 8.

mp: 217–230° C. NMR (CDCl$_3$, δ): 2.50 (3H, s), 2.63 (3H, s), 3.00 (2H, t, J=6 Hz), 3.35 (2H, q, J=6 Hz), 5.75 (1H, br), 6.40 (1H, d, J=4 Hz), 7.28–7.44 (4H, m), 7.58 (1H, d, J=8 Hz), 8.42 (1H, d, J=4 Hz)

(2) 8-(2,6-Dichlorobenzoylamino)-7-methyl-4-(3-methyl-2-oxoimidazolidin-1-yl)quinoline was obtained according to a similar manner to that of Example 92-(2).

mp: >250° C. NMR (CDCl$_3$, δ): 2.68 (3H, s), 2.98 (3H, s), 3.63 (2H, t, J=7 Hz), 3.92 (2H, t, J=7 Hz), 7.25–7.44 (4H, m), 7.47 (1H, d, J=8 Hz), 7.79 (1H, d, J=8 Hz), 8.75 (1H, d, J=4 Hz), 9.12 (1H, s)

Example 216

(1) Isopropylidene (4,5-dimethyl-2-nitroanilino)methylenemalonate was obtained from 4,5-dimethyl-2-nitroaniline and isopropylidene malonate according to a similar manner to that of Example 172-(1).

mp: 242–244° C. NMR (CDCl$_3$, δ): 1.77 (6H, s), 2.36 (3H, s), 2.41 (3H, s), 7.36 (1H, s), 8.07 (1H, s), 8.71 (1H, d, J=10 Hz)

(2) 1,4-Dihydro-5,6-dimethyl-8-nitro-4-oxoquinoline was obtained according to a similar manner to that of Example 172-(2).

mp: 197–227° C.

(3) 4-Chloro-5,6-dimethyl-q-nitrolquinoline was obtained according to a similar manner to that of Preparation 2-(1).

mp: 153–157° C. NMR (CDCl$_3$, δ): 2.55 (3H, s), 2.96 (3H, s), 7.57 (2H, d, J=3 Hz), 7.83 (1H, d), 8.75 (1H, d, J=3 Hz)

(4) 8-Amino-4-chloro-5,6-dimoethylquinoline was obtained according to a similar manner to that of Preparation 2-(3).

mp: 95–97° C. NMR (CDCl$_3$, δ): 2.40 (3H, s), 2.77 (3H, s), 4.85 (2H, s), 6.86 (1H, m), 7.40 (1H, d, J=6 Hz), 8.46 (1H, d, J=4 Hz)

(5) 4-Chloro-8-(2,6-dichl orobenzoylamino)-5,6-dimethyiquinoline was obtained according to a similar manner to that of Example 1.

mp: 190–193° C. NMR (CDCl$_3$, δ): 2.55 (3H, s), 2.88 (3H, s), 7.29–7.44 (3H, m), 7.50 (1H, d, J=4 Hz), 8.47 (1H, d, J=4 Hz), 8.89 (1H, d)

(6) 8-((2,6-Dichlorobenzoylamino)-5,6-dimethyl-4-hydrazinoquinoline was obtained according to a similar manner to that of Example 139-(1).

mp: 190–198° C. NMR (DMSO-d$_6$, δ): 2.41 (3H, s), 2.68 (3H, s), 4.38 (2H, d), 7.17 (1H, d, J=4 Hz), 7.45–7.67 (4H, m), 8.29 (1H, d, J=4 Hz), 8.49 (1H, s)

(7) 4-(2-Acetylhydrazino)-8-(2,6-dichlorobenzoyiamino)-5,6-dimethylquinoline was obtained according to a similar manner to that of Example 86.

mp: >250° C. NMR (DMSO-d$_6$, δ): 1.99 (3H, s), 2.45 (3H, s), 2.75 (3H, s), 6.79 (1H, d, J=4 Hz), 7.45–7.63 (3H, m), 8.33 (1H, d, J=4 Hz), 8.54 (1H, s)

Example 217

8-(2,6-Dichlorobenzoylamino)-5,6-dimethyl-4-(imidazol-1-yl)quinoline was obtained from 4-chloro-8-(2,6-dichlorobenzoylamino)-5,6-dimethylquinoline and imidazole according to a similar manner to that of Example 8.

mp: 200–215° C. NMR (CDCl$_3$, δ): 1.88 (3H, s), 2.52 (3H, s), 7.17 (1H, s), 7.30–7.47 (5H, m), 7.67 (1H, s), 8.24 (1H, d, J=4 Hz), 8.96 (1H, s)

Example 218

(1) 8-(2,6-Dichlorobenzoylamino)-5,6-dimethyl-4-[(2-methylaminoethyl)amino]quinoline was obtained from 4-chloro-8-(2,6-dichlorobenzoylamino)-5,6-dimethylquinoline and N-methylethylenediamine according to a similar manner to that of Example 8.

mp: 162–166° C. NMR (CDCl$_3$, δ): 2.47 (3H, s), 2.50 (3H, s), 2.78 (3H, s), 3.00 (2H, t, J=6 Hz), 3.26 (2H, q, J=6 Hz), 6.35–7.00 (2H, in), 7.25–7.42 (3H, m), 8.26 (1H, d, J=4 Hz), 8.75 (1H, s)

(2) 8-(2,6-Dichlorobenzoylamino)-5,6-dimethyl-4-(3-methyl-2-oxoimidazolidin-1-yl)quinoline was obtained according to a similar manner to that of Example 92-(2).

mp: 213–216° C. NMR (CDCl$_3$, δ): 2.53 (3H, s), 2.65 (3H, s), 2.98 (3H, s), 3.55–3.90 (4H, m), 7.30–7.45 (4H, m), 8.64 (1H, d, J=4 Hz), 8.85 (1H, s)

Example 219

The following compounds were obtained according to a similar manner to that of Example 167.

(1) 8-(2,6-Dichlorobenzoylamino)-4-(3-pyridylmethoxy)quinoline hydrochloride mp: 188–195° C. NMR (DMSO-d$_6$, δ): 5.69 (2H, s), 7.36 (1H, d, J=4 Hz), 7.50–7.63 (3H, m), 7.70 (1H, t, J=8 Hz), 8.03–8.11 (2H, m), 8.71 (1H, d, J=8 Hz), 8.76 (1H, d, J=8 Hz), 8.85 (1H, d, J=4 Hz), 8.95 (1H, d, J=4 Hz), 9.15 (1H, s)

(2) 8-(2,6-Dichlorobenzoylamino)-4-ethoxy-3-methylquinoline mp: 155–157° C. NMR (DMSO-d$_6$, δ): 1.45 (3H, t, J=7.0 Hz), 2.43 (3H, s), 4.18 (2H, q, J=7.0 Hz), 7.47–7.65 (4H, m), 7.85 (1H, d, J=8.0 Hz), 8.15 (1H, d, J=8.0 Hz), 8.73 (1H, s), 10.70 (1H, s)

(3) 4-n-Butoxy-8-(2,6-dichlorobenzoylamino)-3-methylquinoline mp: 136–140° C. NMR (DMSO-d$_6$, δ): 0.98 (3H, t, J=7.0 Hz), 1.56 (2H, m), 1.85 (2H, q, J=7.0 Hz), 2.43 (3H, s), 4.11 (2H, t, J=7.0 Hz), 7.48–7.66 (4H, m), 7.84 (1H, d, J=8.0 Hz), 8.66 (1H, d, J=8.0 Hz), 8.73 (1H, s)

(4) 8-(2,6-Dichlorobenzoylamino)-4-isopropoxy-3-methylquinoline mp: 145–150° C. NMR (DMSO-d$_6$, δ): 1.35 (6H, d, j=6.0 Hz), 2.43 (3H, s), 4.59 (1H, qq, J=6.0, 6.0 Hz), 7.48–7.64 (4H, m), 7.86 (1H, d, J=8.0 Hz), 8.65 (1H, d, J=8.0 Hz), 8.73 (1H, s)

(5) 8-(2,6-Dichlorobenzoylamino)-3-methyl-4-(2-propenyloxy) quinoline mp: 130–133° C. NMR (DMSO-d$_6$, δ): 2.43 (3H, s), 4.67 (2H, d, J=7.0 Hz), 5.30 (1H, dd, J=8.0, 1.0 Hz), 5.50 (1H, dd, J=17.0, 1.0 Hz), 6.18 (1H, tdd, J=17.0, 8.0, 7.0 Hz), 7.48–7.65 (4H, m), 7.85 (1H, d, J=8.0 Hz), 8.65 (1H, d, J=8.0 Hz), 8.76 (1H, s)

(6) 4-Benzyloxy-8-(2,6-dichlorobenzoylamino)-3-methylcquinoline mp: 173–175° C. NMR (DMSO-d$_6$, δ): 2.41 (3H, s), 5.19 (2H, s), 7.39–7.66 (9H, m), 7.84 (1H, d, J=8 Hz), 8.66 (1H, d, J=8 Hz), 8.75 (1H, s), 10.72 (1H, s)

(7) 8-(2,6-Dichlorobenzoylamino)-3-methyl-4-(2-phenoxyethoxy)quinoline mp: 149–150° C. NMR (DMSO-d$_6$, δ): 2.45 (3H, s), 4.38 (2H, m), 4.50 (2H, m), 6.93–7.00 (3H, m), 7.30–7.36 (2H, m), 7.49–7.62 (4H, m), 7.97 (1H, d, J=8.0 Hz), 8.65 (1H, d, J=8.0 Hz), 8.73 (1H, s), 10.70 (1H, s)

(8) 8-(2,6-Dichlorobenzoylamino)-3-methyl-4-[3-(2-pyridyl)propoxy]quinoline mp: 106–107° C. NMR (DMSO-d$_6$, δ): 2.29 (2H, tt, J=7.5, 7 Hz), 2.41 (3H, s), 3.02 (2H, t, J=7.5 Hz), 4.15 (2H, t, J=7 Hz), 7.23 (1H, dd, J=7.5, 5 Hz), 7.35 (1H, d, J=7.5 Hz), 7.48–7.66 (4H, m), 7.72 (1H, dd, J=7.5, 7.5 Hz), 7.87 (1H, d, J=7.5 Hz), 8.51 (1H, d, J=5 Hz), 8.66 (1H, d, J=7.5 Hz), 8.72 (1H, s), 10.69 (1H, s)

Example 220

To a mixture of sodium hydride (60% in oil, 28.9 mg) and N-methylpyrrolidone (3 ml) was added phenol (113 mg) under ice-cooling, and the mixture was stirred for 30 minutes. To the mixture was added 4-chloro-8-(2,6-dichlorobenzoylamino)-3-methylquinoline (200 mg), and the mixture was stirred for 30 minutes at ambient temperature and for 4.5 hours at 120° C. The mixture was extracted with ethyl acetate, and the extract was washed with water, 1N sodium hydroxide solution and brine, dried over magnesium sulfate and concentrated in vacuo. The residue was crystallized from ethanol to give 8-(2,6-dichlorobenzoylamino)-3-methyl-4-phenoxyquinoline (170 mg) as white crystal.

mp: 168–170° C. NMR (DMSO-d$_6$, δ): 2.26 (3H, s), 6.88 (2H, d, J=7.5 Hz), 7.09 (1H, dd, J=7.5, 7.5 Hz), 7.34 (2H, dd, J=7.5, 7.5 Hz), 7.50–7.60 (5H, m), 8.66–8.70 (1H, m), 8.87 (1H, s), 10.84 (1H, s)

Example 221

The following compounds were obtained according to a similar manner to that of Example 220.

(1) 8-(2,6-Dichlorobenzoylamino)-4-(4-methoxyphenoxy)-3-methylquinoline mp: 149–150° C. NMR (DMSO-d$_6$, δ): 2.26 (3H, s), 3.69 (3H, s), 6.81 (2H, d, J=8.0 Hz), 6.90 (2H, d, J=8.0 Hz), 7.50–7.61 (5H, m), 8.65–8.68 (1H, m), 8.85 (1H, s), 10.81 (1H, s)

(2) 8-(2,6-Dichlorobenzoylamino)-3-methyl-4-(pyridin-3-yloxy) quinoline mp: 202–204° C. NMR (DMSO-d$_6$, δ): 2.27 (3H, s), 7.20 (1H, dd, J=8.0, 2.0 Hz), 7.31–7.36 (1H, m), 7.49–7.64 (5H, m), 8.31 (1H, d, J=6.0 Hz), 8.40 (1H, d, J=2.0 Hz), 8.70 (1H, dd, J=7.0, 2.0 Hz), 8.90 (1H, s), 10.88 (1H, s)

(3) 8-(2,6-Dichlorobenzoylamino)-4-[4-(imidazol-1-yl) phenoxy]quinoline mp: 229–232° C. NMR (DMSO-d$_6$, δ): 6.80 (1H, d, J=6 Hz), 7.14 (1H, s), 7.46–7.65 (5H, m), 7.72 (1H, dd, J=8, 8 Hz), 7.79–7.89 (3H, m), 8.10 (1H, d, J=8 Hz), 8.31 (1H, s), 8.71 (1H, d, J=6 Hz), 8.80 (1H, d, J=8 Hz), 10.77 (1H, s)

Example 222

(1) A solution of 4-chloro-8-(2,6-dichlorobenzoylamino)-3-methylquinoline (500 mg) in acetic acid (16 ml) and 6N hydrochloric acid (20 ml) was heated at 130° C. for 5 days. The mixture was concentrated in vacuo and the precipitate was collected and washed with water. The residue was purified by a silica gel column chromatography (methanol:methylene chloride=1:20, V/V) to give a yellow crystal. The solid was treated with hot ethanol (5 ml), allowed to cool to ambient temperature, filtered and washed with water to give 8-(2,6-dichlorobenzoylamino)-1,4-dihydro-3-methyl-4-oxoquinoline (280 mg) as yellow crystal.

mp: >300° C. NMR (DMSO-d$_6$, δ): 2.00 (3H, s), 7.35 (1H, t, J=8.0 Hz), 7.52–7.57 (1H, m), 7.63–7.66 (2H, m), 7.95 (1H, br), 8.04 (1H, d, J=8.0 Hz), 8.12 (1H, br d, J=8.0 Hz), 10.36 (1H, br), 10.52 (1H, br)

(2) To a suspension of 8-(2,6-dichlorobenzoylamino)-1,4-dihydro-3-methyl-4-oxoquinoline (130 mg), potassium carbonate (155 mg) and N-methylpyrrolidone (3 ml) was added cinnamyl bromide (81.2 mg), and the mixture was stirred for 2.5 hours at ambient temperature. The mixture was extracted with ethyl acetate, and the extract was washed with water and brine, dried over magnesium sulfate and concentrated in vacuo. The residue was crystallized from ethanol to give 4-cinnamyloxy-8-(2,6-dichlorobenzoylamino)-3-methylquinoline (125 mg) as white crystal.

mp: 169–171° C. NMR (DMSO-d$_6$, δ): 2.48 (3H, s), 4.85 (2H, d, J=7.0 Hz), 6.67 (1H, td, J=14.5, 7.0 Hz), 7.25–7.38 (3H, m), 7.48–7.67 (6H, m), 7.92 (1H, d, J=8.0 Hz), 8.13 (1H, d, J=8.0 Hz), 8.75 (1H, s), 10.70 (1H, s)

Example 223

8-(2,6-Dichlorobenzoylamino)-3-methyl-4-(phthalimidomethoxy)quinoline was obtained from 8-(2,6-dichlorobenzoylamino)-1,4-dihydro-3-methyl-4-oxoquinoline and 2-bromomethylphthalimide according to a similar manner to that of Example 222-(2).

mp: 217–219° C. NMR (DMSO-d$_6$, δ): 2.42 (3H, s), 5.66 (2H, s), 7.47–7.60 (4H, m), 7.82 (1H, d, J=8.0 Hz), 7.90–7.97 (4H, m), 8.62 (1H, d, J=8.0 Hz), 8.75 (1H, s), 10.73 (1H, s)

Example 224

The following compounds were obtained according to a similar manner to that of Example 25.

(1) 8-(2,6-Dichlorobenzoylamino)-4-(imidazol-2-ylthio)-3-methylquinoline mp: 193–195° C. NMR (DMSO-d$_6$, δ): 2.58 (3H, s), 7.02 (2H, br), 7.48–7.57 (3H, m), 7.65 (1H, dd, J=8.0, 8.0 Hz), 8.22 (1H, d, J=8.0 Hz), 8.63 (1H, d, J=8.0 Hz), 8.82 (1H, S), 10.79 (1H, s)

(2) 8-(2,6-Dichlorobenzoylamino)-3-methyl-4-(1-methylimidazol-2-ylthio)quinoline mp: 244–246° C. NMR (DMSO-d$_6$, δ): 2.52 (3H, s), 3.56 (3H, s), 6.90 (1H, s), 7.26 (1H, s), 7.47–7.58 (3H, m), 7.47–7.58 (3H, m), 7.67 (1H, dd, J=8.0, 8.0 Hz), 8.23 (1H, d, J=8.0 Hz), 8.67 (1H, d, J=8.0 Hz), 8.80 (1H, s)

(3) 8-(2,6-Dichlorobenzoylamino)-3-methyl-4-(pyrimidin-2-ylthio)quinoline mp: 267–270° C. NMR (DMSO-d$_6$, δ): 2.58 (3H, s), 7.24 (1H, dd, J=5.0, 5.0 Hz), 7.49–7.68 (4H, m), 8.06 (1H, d, J=8.0 Hz), 8.54 (2H, d, J=5.0 Hz), 8.66 (1H, d, J=8.0 Hz), 8.97 (1H, s)

Example 225

(1) To a solution of 4-chloro-8-(2,6-dichlorobenzoylamino)quinoline (659 mg) in dimethyl sulfoxide (10 ml) was added sodium azide (487 mg), and the mixture was stirred at 90° C. for 8 hours. The mixture was diluted with water (20 ml), and the precipitate was filtered and washed with water to give 4-azido-8-(2,6-dichlorobenzoylamino)quinoline (560 mg) as white solid.

mp: 188–193° C. NMR (DMSO-$d_6$, δ): 7.48–7.61 (4H, m), 7.67 (1H, dd, J=8, 8 Hz), 7.81 (1H, d, J=8 Hz), 8.36 (1H, d, J=8 Hz), 8.43 (1H, d, J=6 Hz), 10.76 (1H, s)

(2) To a suspension of 4-azido-8-(2,6-dichlorobenzoylamino)quinoline (518 mg) in ethyl acetate (5 ml) was added triphenylphosphine (383 mg), and the mixture was stirred for 3 hours at 45° C. The resulting precipitates were collected by filtration, and the residue was recrystallized from ethanol to give 8-(2,6-dichlorobenzoylamino)-4-[(triphenylphosphoranylidene)amino]quinoline (846 mg) as white crystal.

mp: 276–281° C. NMR (CDCl$_3$, δ): 6.17 (1H, d, J=6 Hz), 7.21–7.39 (3H, m), 7.44–7.64 ((10H, m), 7.75–7.87 (6H, m), 8.05 (1H, d, J=6 Hz), 8.55 (1H, d, J=8 Hz), 8.87 (1H, d, J=8 Hz), 10.14 (1H, br s)

(3) A mixture of 8-(2,6-dichlorobenzoylamino)-4-[(triphenylphosphoranylidene)amino]quinoline (310 mg), 6N hydrochloric acid (5 ml) and acetic acid (5 ml) was heated for 3 hours at 130° C. After cooling, the mixture was neutralized with 6N sodium hydroxide solution, and the insoluble material was collected by filtration. The residue was recrystallized from ethyl acetate to give 4-amino-8-(2,6-dichlorobenzoylamino)quinoline (174 mg).

mp: 265–275° C. NMR (DMSO-$d_6$, δ): 6.87 (1H, d, J=7 Hz), 7.50–7.64 (3H, m), 7.75 (1H, dd, J=8, 8 Hz), 8.34 (1H, d, J=8 Hz), 8.40 (1H, d, J=8 Hz), 8.51 (1H, d, J=7 Hz), 9.07–9.35 (2H, br), 11.07 (1H, s)

(4) A suspension of 4-amino-8-(2,6-dichlorobenzoylamino)quinoline (134 mg) in acetic anhydride (2 ml) was stirred at 120° C. for 2 hours. The mixture was concentrated to dryness and the residue was purified by a silica gel flash chromatography (ethyl acetate:n-hexane=1:1, V/V). Collection of early fractions from the column gave 4-(N,N-diacetylamino)-8-(2,6-dichlorobenzoylamino)quinoline as a white crystal (33 mg). Collection of later fractions gave 4-acetamido-8-(2,6-dichlorobenzoylamino)quinoline as a white crystal (14 mg). 4-(N,N-Diacetylamino)-8-(2,6-dichlorobenzoylamino)quinoline mp: 192–195° C. NMR (DMSO-$d_6$, δ): 2.33 (2×3H, s), 7.32–7.50 (5H, m), 7.60 (1H, dd, J=8, 8 Hz), 8.88 (1H, d, J=6 Hz), 9.04 (1H, d, J=8 Hz), 10.05 (1H, s) 4-Acetamido-8-(2,6-dichlorobenzoylamino)quinoline mp: 286–288° C. (dec.) NMR (DMSO-$d_6$, δ): 2.37 (3H, s), 7.30–7.43 (3H, m), 7.53–7.66 (2H, m), 7.99 (1H, s), 8.38 (1H, d, J=8 Hz), 8.70 (1H, d, J=6 Hz), 8.97 (1H, d, J=8 Hz), 10.18 (1H, s)

Example 226

The following compounds were obtained according to a similar manner to that of Example 8.

(1) 8-(2,6-Dichlorobenzoylamino)-4-phenethylaminoquinoline mp: 220–226° C. NMR (DMSO-$d_6$, δ): 2.99 (2H, t, J=7 Hz), 3.54 (2H, dt, J=7, 5 Hz), 6.63 (1H, d, J=6 Hz), 7.16–7.36 (5H, m), 7.42–7.63 (5H, m), 7.98 (1H, d, J=8 Hz), 8.36 (1H, d, J=6 Hz), 8.63 (1H, d, J=6 Hz), 10.46 (1H, s)

(2) 8-(2,6-Dichlorobenzoylamino)-4-(N-methoxy-N-methylamino)quinoline mp: 155–157° C. NMR (DMSO-$d_6$, δ): 3.18 (3H, s), 3.64 (3H, s), 7.40 (1H, d, J=6.0 Hz), 7.49–7.65 (4H, m), 7.75 (1H, d, J=8.0 Hz), 8.69 (1H, d, J=8.0 Hz), 8.76 (1H, d, J=6.0 Hz)

Example 227

(1) 4-Chloro-8-(2-nitrobenzoylamino)quinoline was obtained from 8-amino-4-chloroquinoline and 2-nitrobenzoyl chloride according to a similar manner to that of Example 1.

mp: 221–223° C. NMR (CDCl$_3$, δ): 7.55 (2H, d, J=4 Hz), 7.65–7.80 (4H, r), 7.99 (1H, d, J=8 Hz), 8.16 (1H, d, J=8 Hz), 8.62 (1H, d, J=4 Hz), 8.97 (1H, d, J=8 Hz)

(2) 4-Hydrazino-8-(2-nitrobenzoylamino)quinoline was obtained according to a similar manner to that of Example 139-(1).

mp: 198–203° C. NMR (DMSO-$d_6$, δ): 4.50 (2H, s), 6.98 (1H, d, J=4 Hz), 7.41 (1H, t, J=8 Hz), 7.76–7.95 (4H, m), 8.15 (1H, d, J=8 Hz), 8.739 (1H, d, J=4 Hz), 8.55 (1H, d, J=8 Hz), 8.68 (1H, s)

(3) 4-(2-Acetylhydrazino)-8-(2-nitrobenzoylamino) quinoline was obtained according to a similar manner to that of Example 86.

mp: 232–235° C. NMR (DMSQ-$d_6$, (5) 3.32 (3H, s), 6.65 (1H, d, J=4 Hz), 7.52 (1H, t, J=8 Hz), 7.75–7.93 (3H, m), 7.99 (4H, d, J=8 Hz), 8.17 (1H, d, J=8 Hz), 8.45 (6H, d, J=4 Hz), 8.60 (1H, d, J=8 Hz), 9.29 (1H, s)

Example 228

4-(Imidazol-1-yl)-8-(2-nitrobenzoylamino)quinoline was obtained from 4-chloro-8-(2-nitrobenzoylamino) quinoline and imidazole according to a similar manner to that of Example 8.

mp: 195–198° C. NMR (DMSO-$d_6$, δ): 7.26 (1H, s), 7.57 (1H, d, J=8 Hz), 7.70–7.95 (6H, m), 8.18 (5H, s), 8.20 (1H, d, J=8 Hz), 8.74 (1H, br d, J=8 Hz), 9.01 (1H, d, J=2 Hz) its hydrochloride mp: 227–235° C. NMR (DMSO-$d_6$, δ): 7.52 (1H, d, J=8 Hz), 7.75–8.03 (6H, m), 8.17–8.24 (2H, m), 8.78 (1H, br d, J=8 Hz), 9.13 (1H, d, J=5 Hz), 9.53 (1H, s)

Example 229

(1) 4-[(2-Methylaminoethyl)amino]-8-(2-nitrobenzoylamino)quinoline was obtained from 4-chloro-8-(2-nitrobenzoylamino)quinoline and N-methylethylenediamine according to a similar manner to that of Example 8.

NMR (DMSO-$d_6$, δ): 2.37 (3H, s), 2.84 (2H, t, J=6 Hz), 3.29–3.48 (2H, m), 6.59 (1H, d, J=6 Hz), 7.30 (1H, t, J=5 Hz), 7.45 (1H, dd, J=8, 8 Hz), 7.75–7.96 (3H, rn), 8.00 (1H, d, J=8 Hz), 8.15 (1H, d, J=8 Hz), 8.37 (1H, d, J=6 Hz), 8.56 (1H, d, J=7.5 Hz), 10.58 (1H, s)

(2) 4-(3-Methyl-2-oxoimidazolidin-1-yl)-8-(2-nitrobenzoylamino)quinoline was obtained according to a similar manner to that of Example 92-(2).

mp: 226–228° C. NMR (DMSO-$d_6$, δ): 2.85 (3H, s), 3.60 (2H, t, J=7.5 Hz), 3.96 (2H, t, J=7.5 Hz), 7.51 (1H, d, j=6 Hz), 7.60 (1H, dd, J=8, 8 Hz), 7.75–7.83 (2H, m), 7.85–7.94 (2H, m), 8.19 (1H, d, J=8 Hz), 8.63 (1H, d, J=7 Hz), 8.84 (1H, d, J=6 Hz), 10.72 (1H, s)

Example 230

(1) 4-Chloro-3-methoxymethyl-8-(2-trifluoromethylbenzoylamino)quinoline was obtained from 8-amino-4-chloro-3-methoxymethylquinoline and 2-trifluoromethylbenzoyl chloride according to a similar manner to that of Example 1.

mp: 121–122° C. NMR (DMSO-$d_6$, δ): 3.40 (3H, s), 4.77 (2H, s), 7.74–7.91 (5H, m), 8.02 (1H, d, J=8.0 Hz), 8.73 (1H, d, J=8.0 Hz), 8.90 (1H, s)

(2) 4-(Imidazol-1-yl)-3-methoxymethyl-8-(2-trifluoromethylbenzoylamino)quinoline was obtained according to a similar manner to that of Example 8.

mp: 126–127° C. NMR (DMSO-d$_6$, δ): 3.26 (3H, s), 4.35 (2H, s), 7.08 (1H, d, J=8.0 Hz), 7.28 (1H, s), 7.56 (1H, s), 1.69–7.92 (5H, m), 7.97 (1H, s), 8.72 (1H, d, J=7.5 Hz), 9.06 (1H, s)

Example 231

(1) 3-Methoxymethyl-4-[(2-methylaminoethyl)amino]-8-(2-trifluoromethylbenzoylamino)quinoline was obtained from 4-chloro-3-methoxymethyl-8-(2-trifluoromethylbenzoylamino)quinoline and N-methylethylenediamine according to a similar manner to that of Example 8.

NMR (DMSO-d$_6$, δ): 2.33 (3H, s), 2.76 (2H, t, J=6 Hz), 3.17 (3H, s), 3.67 (2H, dt, J=6, 5 Hz), 4.53 (2H, s), 6.59 (1H, t, J=5 Hz), 7.47 (1H, dd, J=8, 8 Hz), 7.78 (1H, m), 7.83–7.87 (2H, m), 7.90 (1H, d, J=8 Hz), 7.97 (1H, d, J=8 Hz), 8.32 (1H, s), 8.60 (1H, s), 10.32 (1H, s)

(2) 3-Methoxymethyl-4-(3-methyl-2-oxoimidazolidin-1-yl)-8-(2-trifluoromethylbenzoylamino)quinoline was obtained according to a similar manner to that of Example 92-(2).

mp: 156° C. NMR (DMSO-d$_6$, δ): 2.82 (3H, s), 3.33 (3H, s), 3.59–3.74 (3H, m), 3.85 (1H, m), 4.56 (1H, d, J=12 Hz), 4.61 (1H, d, J=12 Hz), 7.67–7.73 (2H, m), 7.78 (1H, m), 7.83–7.88 (2H, m), 7.90 (1H, d, J=8 Hz), 8.67 (1H, m), 8.93 (1H, s), 10.45 (1H, s)

Example 232

(1) A mixture of 8-amiino-3-bromoquinoline (330 mg), 3-methoxycarbonylbenzoic acid (267 mg), 1-ethyl-3-(3-dimethylaminopropyl)carbodiimide hydrochloride (369 mg) and 1-hydroxybenzotriazole (300 mg) in dimethylformamide (5 ml) was stirred at ambient temperature overnight. To the mixture was added water, and the resulting precipitates were collected by filtration, washed with hot methanol and dried to give 3-bromo-8-[3-(methoxycarbonyl)benzoylamino]quinoline (390 mg) as pale yellow solid.

mp: 157° C. NMR (CDCl$_3$, δ): 3.99 (3H, s), 7.49 (1H, d, J=8 Hz), 7.60–7.70 (2H, m), 8.22–8.30 (2H, m), 8.37 (1H, br s), 8.70 (1H, br s), 8.86 (1H, br s), 8.95 (1H, d, J=8 Hz)

(2) A mixture of 3-bromo-8-[3-(methoxycarbonyl)benzoylamino]quinoline (356 mg) and 1N sodium hydroxide aqueous solution (1.1 ml) in methanol (5 ml) and dioxane (5 ml) was gently refluxed for 2 hours. After cooling, the mixture was neutralized with 1N hydrochloric acid. The solvent was removed in vacuo, and the residue was washed with hot 95% ethanol and collected by filtration to give 3-bromo-8-(3-carboxybenzoylamino)quinoline (397 mg) as pale tan solid.

mp: 275–277° C. NMR (DMSO-d$_6$, δ): 7.65–7.80 (3H, m), 8.14–8.25 (2H, m), 8.54 (1H, m), 8.70 (1H, dd, J=8, 2 Hz), 8.81 (1H, d, J=2 Hz), 9.03 (1H, d, J=2 Hz)

(3) A mixture of 3-bromo-8-(3-carboxybenzoylamino) quinoline (200 mg), dimethylamine hydrochloride (65.9 mg), 1-ethyl-3-(3-dimethylaminopropyl)carbodiimide (100 mg) and 1-hydroxybenzotriazole (109 mg) in dimethylformamide (3 ml) was stirred for 3 hours at ambient temperature. The mixture was diluted with ethyl acetate, washed with water, dried over magnesium sulfate and evaporated in vacuo. The residue was purified by preparative thin layer chromatography (ethyl acetate) and recrystallized from ethanol to give 3-bromo-8-[3-(dimethylcarbamoyl)benzoylamino]quinoline (120 mg) as pale yellow solid.

mp: 157° C. NMR (DMSO-d$_6$, δ): 2.95 (3H, br s), 3.03 (3H, br s), 7.64–7.80 (4H, m), 8.03 (1H, br s), 8.10 (1H, m), 8.68 (1H, d, J=8 Hz), 8.84 (1H, d, J=2 Hz), 9.04 (1H, d, J=2 Hz)

Example 233

(1) 3-Bromo-8-[4-(methoxycarbonyl)benzoylamino] quinoline was obtained from 8-amino-3-bromoquinoline and 4-methoxycarbonylbenzoic acid according to a similar manner to that of Example 232-(1).

mp: 174–176° C. NMR (CDCl$_3$, δ): 3.99 (3H, s), 7.48 (1H, d, J=8 Hz), 7.64 (1H, t, J=8 Hz), 8.10 (2H, d, J=8 Hz), 8.20 (2H, d, J=8 Hz), 8.35 (1H, d, J=3 Hz), 8.84 (1H, d, J=3 Hz), 8.94 (1H, d, J=8 Hz)

(2) 3-Bromo-8-(4-carboxybenzoylamino)quinoline was obtained according to a similar manner to that of Example 232-(2).

mp: >300° C. NMR (DMSO-d$_6$, δ): 7.68–7.79 (2H, m), 8.07 (2H, d, J=9 Hz), 8.11 (2H, d, J=9 Hz), 8.20 (1H, d, J=8 Hz), 8.83 (1H, s), 9.04 (1H, d, J=2 Hz)

(3) 3-Bromo-8-[4-(dimethylcarbamoyl)benzoylamino] quinoline was obtained according to a similar manner to that of Example 232-(3).

mp: 196–198° C. NMR (DMSO-d$_6$, δ): 2.91 (3H, s), 3.02 (3H, s), 7.62 (2H, d, J=9 Hz), 7.69–7.80 (2H, m), 8.08 (2H, d, J=9 Hz), 8.70 (1H, m), 8.84 (1H, d, J=2 Hz), 9.02 (1H, d, J=2 Hz) z

Example 234

(1) 3-Bromo-8-(2,3,4-trimethoxybenzoylamino)quinoline was obtained from 8-amino-3-bromoquinoline and 2,3,4-trimethoxybenzoic acid according to a similar manner to that of Example 232-(1).

mp: 158–161° C. NR (CDCl$_3$, δ): 3.96 (3H×2, s), 4.23 (3H, s), 6.84 (1H, d, J=8 Hz), 7.44 (1H, d, j=8 Hz), 7.60 (1H, d, J=8 Hz), 8.09 (1H, d, J=8 Hz), 8.32 (1H, d, J=2 Hz), 8.89 (1H, d, J=2 Hz), 9.03 (1H, d, J=8 Hz)

(2) To a solution of 3-bromo-8-(2,3,4-trimethoxybenzoylamino)quinoline (700 mg) in dichloromethane (10 ml) was added 1M solution of boron tribromide in dichloromethane (5.5 ml) under ice-cooling, and the mixture was stirred for 2 hours at ambient temperature. To the mixture was added ice-water, and the mixture was stirred for 1.5 hours. The mixture was adjusted to pH 4 with 1N sodium hydroxide solution, and ethyl acetate was added thereto. The mixture was stirred at ambient temperature overnight, and the insoluble material was filtered off. The filtrate was concentrated in vacuo, and the residue was purified by column chromatography (methanol-dichloromethane) to give 3-bromo-8-(2,3,4-trihydroxybenzoylamino)quinoline (110 mg).

mp: 183–193° C. NMR (DMSO-d$_6$, δ): 6.46 (1H, d, J=8 Hz), 7.41 (1H, d, J=8 Hz), 7.60–7.71 (2H, m), 8.77 (1H, d, J=2 Hz), 8.84–8.94 (2H, in)

Example 235

(1) 3-Bromo-8-(2-nitrobenzoylamino)quinoline was obtained from 8-amino-3-bromoquinoline and 2-nitrobenzoyl chloride according to a similar manner to that of Example 1.

mp: 168–171° C. NMR (CDCl$_3$, δ): 7.50 (1H, d, J=8 Hz), 7.59–7.85 (4H, m), 8.15 (1H, d, J=8 Hz), 8.35 (1H, d, J=2 Hz), 8.74 (1H, s), 8.90 (1H, d, J=8 Hz)

(2) To a solution of ammonium chloride (50.9 mg) in water (2 ml) was added ethanol (10 ml), and the mixture was stirred at 50° C. To the mixture were added 3-bromo-8-(2-nitrobenzoylamino)quinoline (590 mg) and iron (531 mg), and the mixture was refluxed for 1 hour. After filtration, the filtrate was concentrated in vacuo, and the residue was suspended in hot 80% ethanol and allowed to cool to ambient temperature. The resulting precipitates were collected by filtration to give 8-(2-aminobenzoylamino)-3-bromoquinoline (470 mg) as pale tan solid.

mp: 147–150° C. NMR (CDCl$_3$, δ): 5.72 (2H, br s), 6.75 (1H, d, J=8 Hz), 6.79 (1H, t, J=8 Hz), 7.29 (1H, t, J=8 Hz), 7.45 (1H, d, J=8 Hz), 7.61 (1H, t, J=8 Hz), 7.73 (1H, d, J=8 Hz), 8.33 (1H, d, J=2 Hz), 8.83 (1H, d, J=2 Hz), 8.87 (1H, d, J=8 Hz)

(3) A mixture of 8-(2-aminobenzoylamino)-3-bromoquinoline (200 mg), acetic anhydride (71.6 mg) and pyridine (139 mg) in ethylene chloride (4 ml) was stirred for 20 hours at ambient temperature. The mixture was diluted with dichloromethane, washed with water, dried over magnesium sulfate and evaporated in vacuo. The residue was suspended in hot ethanol and allowed to cool to ambient temperature. The resulting precipitates were collected by filtration to give 8-(2-acetamidobenzoylamino)-3-bromoquinoline (200 mg) as yellow powder.

mp: 206° C. NMR (DMSO-$d_6$, δ): 2.03 (3H, s), 7.34 (1H, t, J=8 Hz), 7.58 (1H, t, J=8 Hz), 7.67–7.76 (2H, m), 7.84–7.93 (2H, m), 8.70 (1H, d, J=8 Hz), 8.81 (1H, d, J=2 Hz), 8.96 (1H, d, J=2 Hz), 10.46 (2H, br s)

Example 236

(1) 3-Bromo-8-(3-nitrobenzoylamino)quinoline was obtained from 8-amino-3-bromoquinoline and 3-nitrobenzoyl chloride according to a similar manner to that of Example 1.

mp: 258° C. NMR (DMSO-$d_6$, δ): 7.69–7.84 (2H, m), 7.90 (1H, t, J=8 Hz), 8.43–8.52 (2H, m), 8.60 (1H, d, J=6 Hz), 8.76–8.88 (2H, m), 9.03 (1H, d, J=2 Hz)

(2) 8-(3-Aminobenzoylamino)-3-bromoquinoline was obtained according to a similar manner to that of Example 235-(2).

mp: 209–211° C. NMR (DMSO-$d_6$, δ): 5.49 (2H, br s), 6.81 (1H, dd, J=8, 2 Hz), 7.10 (1H, br d, J=8 Hz), 7.18–7.28 (2H, m), 7.67–7.74 (2H, m), 8.24 (1H, m), 8.81 (1H, d, J=2 Hz), 9.01 (1H, d, J=2 Hz)

(3) 8-(3-Acetamidobenzoylamino)-3-bromoquinoline was obtained according to a similar manner to that of Example 235-(3).

mp: 198–202° C. NMR (DMSO-$d_6$, δ): 2.09 (3H, s), 7.54 (1H, t, J=8 Hz), 7.63–7.78 (3H, m), 7.86 (1H, br d, J=8 Hz), 8.24 (1H, s), 8.72 (1H, m), 8.81 (1H, s), 9.00 (1H, d, J=2 Hz)

Example 237

3-Bromo-8-(3-methyl-2-nitrobenzoylamino)quinoline was obtained from 2-amino-3-bromoquinoline and 3-methyl-2-nitrobenzoic acid according to a similar manner to that of Example 232-(1).

mp: 203–209° C. NMR (DMSO-$d_6$, δ): 2.37 (3H, s), 7.65–7.80 (4H, m), 7.82–7.93 (1H, m), 8.52 (1H, d, J=8 Hz), 8.83 (1H, d, J=2 Hz), 8.99 (1H, d, J=2 Hz)

Example 238

3-Bromo-8-(2-trifluoromethylbenzoylamino)quinoline was obtained from 2-amino-3-bromoquinoline and 2-trifluoromethylbenzoyl chloride according to a similar manner to that of Example 1.

mp: 138–141° C. NMR (CDCl$_3$, δ): 7.50 (1H, d, J=8 Hz), 7.60–7.84 (4H, m), 8.35 (1H, s), 8.75 (1H, s), 8.94 (1H, d, J=8 Hz)

Example 239

3-Bromo-8-[(2-chloropyridin-3-ylcarbonyl)amino]quinoline was obtained from 2-amino-3-bromoquinoline and 2-chloro-3-pyridinecarboxylic acid according to a similar manner to that of Example 232-(1).

mp: 164–168° C. NMR (DMSO-$d_6$, δ): 7.50–7.63 (1.2H, m), 7.66–7.80 (2.1H, m), 8.00 (0.4H, d, J=8 Hz), 8.11–8.28 (1.2H, m), 8.52–8.60 (0.8H, m), 8.67–8.76 (0.8H, m), 8.80 (0.7H, br s), 8.87 (0.3H, t, J=6 Hz), 8.95 (0.5H, m)

Example 240

(1) 8-(2,6-Dichlorobenzoylamino)-3,5-dimethyl-4-hydrazinoquinoline was obtained from 4-chloro-8-(2,6-dichlorobenzoylamino)-3,5-dimethylquinoline and hydrazine monohydrate according to a similar manner to that of Example 139-(1).

NMR (DMSO-$d_6$, δ): 1.84 (3H, s), 1.93 (3H, s), 4.15–4.33 (2H, m), 6.60 (1H, d, J=8 Hz), 7.16–7.33 (1H, m), 7.40–7.71 (4H, m), 10.01 (1H, s)

(2) 4-(2-Acetylhydrazino)-8-(2,6-dichlorobenzoylamino)-3,5-dimethyiquinoline was obtained according to a similar manner to that of Example 86.

mp: 234–238° C. NMR (DMSO-$d_6$, δ): 1.76 (2×3H, s), 2.03 (3H, s), 7.23–7.73 (6H, m), 8.80 (1H, s), 9.45 (1H, br), 9.73 (1H, br)

Example 241

(1) 8-(2,6-Dichlorobenzoylamino)-3,5-dimethyl-4-[(2-methylaminoethyl)amino]quinoline was obtained from 4-chloro-8-(2,6-dichlorobenzoylamino)-3,5-dimethylquinoline and N-methylethylenediamine according to a similar manner to that of Example 8.

mp: 151–152° C. NMR (DMSO-$d_6$, δ): 2.26 (3H, s), 2.37 (3H, s), 2.58 (2H, t, J=6 Hz), 2.86 (3H, s), 3.25 (2H, dt, J=6, 5 Hz), 5.56 (1H, t, J=5 Hz), 7.24 (1H, d, J=7.5 Hz), 7.48–7.63 (3H, m), 8.34 (1H, s), 8.43 (1H, d, J=7.5 Hz), 10.41 (1H, s)

(2) 8-(2,6-Dichlorobenzoylamino)-3,5-dimethyl-4-(3-methyl-2-oxoimidazolidin-1-yl)quinoline was obtained according to a similar manner to that of Example 92-(2).

mp: >300° C. NMR (DMSO-$d_6$, δ): 2.34 (3H, s), 2.68 (3H, s), 2.80 (3H, s), 3.52–3.74 (4H, m), 7.45 (1H, d, J=8 Hz), 7.48–7.62 (3H, m), 8.53 (1H, d, J=8 Hz), 8.83 (1H, s), 10.66 (1H, s)

Example 242

8-(2,6-Dichlorobenzoylamino)-3,5-dimethyl-4-(3-methyl-2-thioxoimidazolidin-1-yl)quinoline was obtained from 8-(2,6-dichlorobenzoylamino)-3,5-dimethyl-4-[(2-methylaminoethyl)amino]quinoline and 1,1'-thiocarbonyldiimidazole according to a similar manner to that of Example 92-(2).

mp: 275–278° C. NMR (DMSO-$d_6$, δ): 2.35 (3H, s), 2.67 (3H, s), 3.15 (3H, s), 3.78–4.03 (4H, m), 7.45 (1H, d, J=8 Hz), 7.48–7.63 (3H, m), 8.54 (1H, d, J=8 Hz), 8.85 (1H, s), 10.68 (1H, s)

Example 243

8-(2,6-Dichlorobenzoylamino)-3,5-dimethyl-4-(pyridin-3-yloxy)quinoline was obtained from 4-chloro-8-(2,6-dichlorobenzoylamino)-3,5-dimethylquinoline and 3-hydroxypyridine according to a similar manner to that of Example 220.

mp: 234–237° C. NMR (DMSO-$d_6$, δ): 2.16 (3H, s), 2.57 (3H, s), 7.12 (1H, dd, J=9.0, 2.0 Hz), 7.32 (1H, dd, J=9.0, 4.0 Hz), 7.43 (1H, d, J=8.0 Hz), 7.48–7.60 (3H, m), 8.30–8.35 (2H, m), 8.59 (1H, d, J=8.0 Hz), 8.85 (1H, s)

Example 244

8-(2,6-Dichlorobenzoylamino)-3,5-dimethyl-4-(imidazol-2-ylthio)quinoline was obtained from 4-chloro-8-(2,6-dichlorobenzoylamino)-3,5-dimethylquinoline and 2-mercaptoimidazole according to a similar manner to that of Example 25.

mp: 263–266° C. NMR (DMSO-$d_6$, δ): 2.43 (3H, s), 3.03 (3H, s), 6.85 (1H, s), 7.11 (1H, s), 7.48–7.59 (4H, m), 8.54 (1H, d, J=8.0 Hz), 8.75 (1H, s), 10.67 (1H, s)

Example 245

(1) 5-Chloro-1,4-dihydro-3-hydroxymethyl-8-nitro-4-oxoquinoline was obtained from 5-chloro-1,4-dihydro-8- nitro-4-oxoquinoline according to a similar manner to that of Example 172-(3).

mp: >250° C. NMR (DMSO-$d_6$, δ): 4.37 (2H, s), 7.45 (1H, d, J=8 Hz), 7.93 (1H, d, J=4 Hz), 8.52 (1H, d, J=8 Hz)

(2) 5-Chloro-1,4-dihydro-3-methyl-8-nitro-4-oxoquinoline was obtained according to a similar manner to that of Example 104-(2).

mp: >250° C. NMR (DMSO-$d_6$, δ): 1.97 (3H, s), 7.42 (1H, d, J=8 Hz), 7.87 (1H, d, J=6 Hz), 8.49 (1H, d, J=8) z)

(3) 4,5-Dichloro-3-methyl-8-nitroquinoline was obtained according to a similar manner to that of Preparation 2-(3).

mp: 136–138° C. NMR (CDCl$_3$, δ): 2.61 (3H, s), 7.73 (2H, d, J=8 Hz), 7.80 (1H, d, J=8 Hz), 8.84 (1H, s)

(4) 8-Amino-4,5-dichloro-3-methylquinoline was obtained according to a similar manner to that of Preparation 2-(3)

mp: 128–230° C. NMR (CDCl$_3$, δ): 2.53 (3H, s), 5.07 (2H, s), 6.79 (7H, d, J=8 Hz), 7.42 (1H, d, J=8 Hz), 8.55 (1H, s)

(5) 4,5-Dichloro-8-(2,6-d ichlorobenzoylamino)-3-methylquinoline was obtained according to a similar manner to that of Example 1.

mp: 222–233° C. NMR (CDCl$_3$, δ): 2.56 (3H, s), 7.30–7.44 (3H, s), 7.71 (1H, d, J=7 Hz), 8.58 (3H, m), 8.83 (2H, d, J=8 Hz)

(6) 5-Chloro-1-(2,6-didchlorobenzoylamino)-4-(imidazol-1-yl)-3-methylquinoline was obtained according to a similar manner to that of Example 8.

mp: 260–262° C. NMR (DMSO-$d_6$, δ): 2.14 (3H, s), 7.19 (1H, d), 7.40 (1H, s), 7.50–7.60 (3H, m), 7.79 (2H, d, J=8 Hz), 7.83 (1H, d), 8.69 (1H, d, J=8 Hz), 9.04 (1H, s)

Example 246

5-Chloro-8-(2,6-dichlorobenzoylamino)-3-methyl-4-(pyridin-3-yloxy)quinoline was obtained from 4,5-dichloro-8-(2,6-dichlorobenzoylamino)-3-methylquinoline and 3-hydroxypyridine according to a similar manner to that of Example 220.

mp: 232–236° C. NMR (CDCl$_3$, δ): 2.28 (3H, s), 6.96 (1H, dd, J=8, 2 Hz), 7.21 (1H, dd, J=8, 5 Hz), 7.31–7.45 (3H, m), 7.60 (1H, d, J=8 Hz), 8.25 (1H, d, J=2 Hz), 8.34 (1H, d, J=5 Hz), 8.70 (1H, s), 8.87 (1H, d, J=8 Hz)

Example 247

5-Chloro-8-(2,6-dichlorobenzoylamino)-4-(imidazol-2-ylthio)-3-methylquinoline was obtained from 4,5-dichloro-8-(2,6-dichlorobenzoylamino)-3-methylquinoline and 2-mercaptoimidazole according to a similar manner to that of Example 25.

mp: >288° C. (dec.) NMR (CDCl$_3$, δ): 2.40 (3H, s), 7.30–7.49 (5H, m), 7.76 (1H, s), 8.47 (1H, s), 8.98 (1H, d, J=8 Hz)

Example 248

(1) 8-Amino-1,4-dihydro-3-methoxymethyl-4-oxoquinoline was obtained from 1,4-dihydro-3-methoxymethyl-8-nitro-4-oxoquinoline according to a similar manner to that of Preparation 2-(3).

mp: >300° C. NMR (DMSO-$d_6$, δ): 3.30 (3H, s)r 4.30 (2H, s), 5.45 (2H, S), 6.90 (1H, d, J=8 Hz), 7.04 (1H, dd, J=8, 8 Hz), 7.39 (1H, d, J=8 Hz), 7.85 (1H, s)

(2) 8-(2,6-Dichlorobenzoylamino)-4-(2,6-dichlorobenzoyloxy)-3-methoxymethylquinoline was obtained from 8-amino-1,4-dihydro-3-methoxymethyl-4-oxoquinoline and 2,6-dichlorobenzoyl chloride according to a similar manner to that of Example 1.

mp: 241–243° C. NMR (DMSO-$d_6$, δ): 3.36 (3H, s), 4.80 (2H, s), 7.46–7.62 (3H, m), 7.72 (1H, m), 7.79–7.87 (3H, m), 8.01 (1H, d, J=8 Hz), 8.81 (1H, d, J=8 Hz), 9.07 (1H, s), 11.01 (1H, s)

(3) A suspension of 8-(2,6-dichlorobenzoylamino)-4-(2,6-dichlorobenzoyloxy)-3-methoxymethylquinoline (4.88 g) in ethanol (100 ml) and 1N sodium hydroxide solution (30 ml) was stirred for 2 hours at 90° C. After evaporation, the residue was diluted with water, and the solution was neutralized with 1N hydrochloric acid. The resulting precipitates were collected by filtration and washed with water and diethyl ether to give 8-(2,6-dichlorobenzoylamino)-1,4-dihydro-3-methoxymethyl-4-oxoquinoline (3.41 g) as white powder.

mp: 290° C. (dec.) NMR (DMSO-$d_6$, δ): 3.32 (3H, s), 4.32 (2H, s), 7.40 (1H, dd, J=8, 8 Hz), 7.52–7.68 (3H, m), 8.01 (1H, d, J=7 Hz), 8.05 (1H, d, J=8 Hz), 8.10 (1H, d, J=8 Hz), 10.45 (1H, s), 10.66 (1H, d, J=7 Hz)

(4) To a solution of 8-(2,6-dichlorobenzoylamino)-1,4-dihydro-3-methoxymethyl-4-oxoquinoline (209 mg) in N-methylpyrrolidone (4 ml) were added 3-chloromethylpyridine hydrochloride (109 mg), potassium carbonate (153 mg) and sodium iodide (20 mg), and the mixture was stirred for 4 hours at 80° C. The mixture was partitioned between ethyl acetate and water, and the separated organic layer was washed with brine, dried over magnesium sulfate and evaporated in vacuo. The residue was crystallized from ethanol to give 8-(2,6-dichlorobenzoylamino)-3-methoxymethyl-4-(pyridin-3-ylmethoxy)quinoline (170 mg) as white crystal.

mp: 174–176° C. NMR (DMSO-$d_6$, δ): 3.33 (3H, s), 4.65 (2H, s), 5.32 (2H, s), 7.46–7.61 (4H, m), 7.67 (1H, dd, J=8, 8 Hz), 7.90 (1H, d, J=8 Hz), 8.00 (1H, m), 8.61 (1H, d, J=5 Hz), 8.70–8.77 (2H, m), 8.85 (1H, s), 10.80 (1H, s)

(5) 8-(2,6-Dichlorobenzoylamino)-3-methoxymethyl-4-(pyridin-2-ylmethoxy)quinoline was obtained from 8-(2,6-dichlorobenzoylamino)-1,4-dihydro-3-methoxymethyl-4-oxoquinoline and 2-chloromethylpyridine according to a similar manner to that of Example 248-(4).

mp: 112–113° C. NMR (DMSO-$d_6$, δ): 2.50 (3H, s), 4.66 (2H, s), 5.33 (2H, s), 7.40–7.44 (1H, m), 7.48–7.73 (5H, m), 7.90–7.98 (2H, m), 8.62 (1H, d, J=4.0 Hz), 8.73 (1H, d, J=8.0 Hz), 8.85 (1H, s), 10.80 (1H, s)

Example 249

The following compounds were obtained according to a similar manner to that of Example 220.

(1) 8-(2,6-Dichlorobenzoylamino)-4-(3-methoxyphenoxy)-3-methylquinoline mp: 168–170° C. NMR (DMSO-$d_6$, δ): 2.27 (3H, s), 3.73 (3H, s), 6.31 (1H, dd, J=7.5, 2.0 Hz), 6.56 (1H, m), 6.67 (1H, dd, J=7.5, 2.0 Hz), 7.20 (1H, dd, J=7.5, 7.5 Hz), 7.50–7.60 (5H, m), 8.67–8.70 (1H, m), 8.88 (1H, s), 10.85 (1H, s)

(2) 8-(2,6-Dichlorobenzoylamino)-3-methyl-4-(pyridin-2-yloxy) quinoline mp: 185–186° C. NMR (DMSO-$d_6$, δ): 2.25 (3H, s), 7.11–7.16 (1H, m), 7.33 (1H, d, J=7.5 Hz), 7.48–7.60 (5H, m), 7.93–8.00 (2H, m), 8.65 (1H, d, j=7.5 Hz), 8.85 (1H, s)

(3) 4-(2-Chloropyridin-3-yloxy)-8-(2,6-dichlorobenzoylamino)-3-methylquinoline mp: 186–187° C. NMR (DMSO-$d_6$, δ): 2.28 (3H, s), 7.00 (1H, d, J=8.0 Hz), 7.22–7.27 (1H, m), 7.49–7.67 (5H, m), 8.16 (1H, d, J=2.0 Hz), 8.22 (1H, d, J=8.0 Hz), 8.93 (1H, s), 10.91 (1H, s)

(4) 4-(5-Chloropyridin-3-yloxy)-8-(2,6-dichlorobenzoylamino)-3-methylquinoline mp: 163–165° C. NMR (DMSO-$d_6$, δ): 2.30 (3H, s), 7.49–7.66 (6H, m), 8.35 (1H, d, J=2.0 Hz), 8.41 (1H, d, J=1.0 Hz), 8.72 (1H, d, J=8.0 Hz), 8.90 (1H, s), 10.90 (1H, s)

(5) 8-(2,6-Dichlorobenzoylamino)-3-methyl-4-(2-methylpyridin-3-yloxy)quinoline mp: 159–160° C. NMR (DMSO-d$_6$, δ): 2.25 (3H, s), 2.73 (3H, s), 6.65 (1H, d, J=8.0 Hz), 7.01–7.05 (1H, m), 7.49–7.65 (5H, m), 8.16 (1H, d, J=4.0 Hz), 8.70 (1H, d, J=8.0 Hz), 8.90 (1H, s), 10.89 (1H, s)

(6) 8-(2,6-Dichlorobenzoylamino)-3-methyl-4-(6-methylpyridin-3-yloxy)quinoline NMR (DMSO-d$_6$, δ): 2.27 (3H, s), 2.43 (3H, s), 7.10 (1H, dd, J=9.0, 2.0 Hz), 7.15 (1H, d, J=7.5 Hz), 7.50–7.66 (5H, m), 8.23 (1H, d, J=2.0 Hz), 8.70 (1H, dd, J=9.0, 2.0 Hz), 8.88 (1H, s), 10.85 (1H, s)

(7) 8-(2,6-Dichlorobenzoylamino)-4-[2-(dimethylaminomethyl)pyridin-3-yloxy]-3-methylquinoline NMR (DMSO-d$_6$, δ): 2.26 (3H, s), 2.35 (6H, s), 6.70 (1H, d, J=8.0 Hz), 7.10–7.15 (1H, m), 7.50–7.70 (5H, m), 8.22 (1H, d, J=4.0 Hz), 8.70 (1H, d, J=8.0 Hz), 8.90 (1H, s)

(8) 4-(1H-Benzimidazol-2-yloxy)-8-(2,6-dichlorobenzoylamino)-3-methylquinoline mp: 106–110° C. NMR (DMSO-d$_6$, δ): 2.36 (5/9×3H, s), 2.55 (4/9×3H, s), 6.50 (5/9H, d, J=7.5 Hz), 6.86–7.00 (2H, in), 7.11 (5/9H, dd, J=7.5, 7.5 Hz), 7.16–7.23 ((1+4/9H, m), 7.49–7.90 ((4+4/9H, m), 8.41 (4/9H, d, J=7.5 Hz), 8.70 (5/9H, d, J=7.5 Hz), 8.77 (4/9H, s), 9.04 (5/9H, s), 10.34 (4/9H, s), 10.95 (5/9H, s), 11.00 (4/9H, br s), 11.40 (5/9H, br s)

(9) 8-(2,6-Dichlorobenzoylamino)-4-(2-methoxyphenoxy)-3-methylquinoline mp: 189–190° C. NMR (DMSO-d$_6$, δ): 2.23 (3H, s), 3.93 (3H, s), 6.38 (1H, d, J=7.5 Hz), 6.75 (1H, dd, J=7.5, 7.5 Hz), 7.05 (1H, dd, J=7.5, 7.5 Hz), 7.21 (1H, d, J=7.5 Hz), 7.50–7.60 (5H, m), 8.64–8.67 (1H, m), 8.84 (1H, s), 10.83 (1H, s)

Example 250

To a solution of 4-hydroxypyridine (114 mg) in N-methylpyrrolidone (3 ml) was added sodium hydride (60% in oil, 28.9 mg) under ice-cooling, and the mixture was stirred for 30 minutes. To the mixture was added 4-chloro-8-(2,6-dichlorobenzoylamino)-3-methylquinoline (200 mg), and the mixture was stirred for 1.5 hours at 120° C. The mixture was extracted with ethyl acetate, and the extract was washed with water and brine, dried over magnesium sulfate and concentrated in vacuo. The residue was purified by flash chromatography (ethyl acetate-methanol-dichloromethane) and crystallized from diethyl ether to give 8-(2,6-dichlorobenzoylamino)-3-methyl-4-(1,4-dihydro-4-oxopyridin-1-yl)quinoline (185 mg) as white crystal.

mp: 280–282° C. NMR (DMSO-d$_6$, δ): 2.35 (3H, s), 6.34 (2H, d, J=7.0 Hz), 7.22 (1H, d, J=8.0 Hz), 7.50–7.60 (3H, m), 7.75 (1H, dd, J=8.0, 8.0 Hz), 7.82 (2H, d, J=7.0 Hz), 8.74 (1H, d, J=8.0 Hz), 9.01 (1H, s), 10.98 (1H, s)

Example 251

The following compounds were obtained according to a similar manner to that of Example 25.

(1) 8-(2,6-Dichlorobenzoylamino)-3-methyl-4-(thiazolin-2-ylthio)quinoline mp: 206–209° C. NMR (DMSO-d$_6$, δ): 2.68 (3H, s), 3.18–3.25 (2H, m), 3.75 (1H, dd, J=8.0, 8.0 Hz), 4.05 (1H, dd, J=8.0, 8.0 Hz), 7.48–7.61 (3H, m), 7.74 (1H, dd, J=8.0, 8.0 Hz), 8.25 (1H, d, J=8.0 Hz), 8.70 (1H, d, J=8.0 Hz), 8.72 (1H, s), 10.80 (1H, s)

(2) 8-(2,6-Dichlorobenzoylamino)-3-methyl-4-(5-methyl-1,3,4-thiadiazol-2-ylthio)quinoline mp: 186–187° C. NMR (DMSO-d$_6$, δ): 2.57 (3H, s), 2.70 (3H, s), 7.50–7.59 (3H, m), 7.76 (1H, dd, J=8.0, 8.0 Hz), 8.13 (1H, d, J=8.0 Hz), 8.22 (1H, d, J=8.0 Hz), 9.00 (1H, s), 10.94 (1H, s)

(3) 8-(2,6-Dichlorobenzoylamino)-3-methyl-4-(pyridin-4-ylthio)quinoline mp: 202–203° C. NMR (DMSO-d$_6$, δ): 2.60 (3H, s), 6.95 (2H, d, J=6.0 Hz), 7.49–7.60 (3H, s), 7.70 (1H, dd, J=8.0, 8.0 Hz), 8.01 (1H, d, J=8.0 Hz), 8.32 (1H, d, J=6.0 Hz), 8.72 (1H, d, J=8.0 Hz), 9.01 (1H, s), 10.95 (1H, s)

(4) 4-(1H-Benzimidazol-2-ylthio)-8-(2,6-dichlorobenzoylamino)-3-methylquinoline mp: 162–164-C NMR (DMSO-d$_6$, δ): 2.60 (3H, s), 7.08–7.12 (2H, m), 7.35–7.39 (2H, m), 7.50–7.61 (3H, m), 7.68 (1H, dd, J=8.0, 8.0 Hz), 8.11 (1H, d, J=8.0 Hz), 8.69 (1H, d, J=8.0 Hz), 8.95 (1H, s), 10.90 (1H, s)

(5) 8-(2,6-Dichlorobenzoylamino)-3-methyl-4-(1-methyltetrazol-5-ylthio)quinoline mp: 194–203° C. NMR (CDCl$_3$, δ): 2.66 (3H, s), 4.05 (3H, s), 7.30–7.45 (3H, m), 7.69 (1H, t, J=8 Hz), 8.03 (1H, d, J=8 Hz), 8.76 (1H, s), 8.97 (1H, d, J=8 Hz)

(6) 8-(2,6-Dichlorobenzoylamino)-3-methyl-4-(4-methyl-4H-1,2,4-triazol-3-ylthio)quinoline mp: 234–235° C. NMR (DMSO-d$_6$, δ): 2.62 (3H, s), 3.59 (3H, s), 7.47–7.59 (3H, m), 7.71 (1H, dd, J=8.0, 8.0 Hz), 8.20 (1H, d, J=8.0 Hz), 8.58 (1H, s), 8.69 (1H, d, J=8.0 Hz), 8.90 (1H, s), 10.85 (1H, s)

Example 252

(1) 4-Chloro-3-methyl-8-(2-nitrobenzoylamino)quinoline was obtained from 8-amino-4-chloro-3-methylquinoline and 2-nitrobenzoyl chloride according to a similar manner to that of Example 1.

mp: 178–182° C. NMR (CDCl$_3$, δ): 2.57 (3H, s), 7.60–7.70 (2H, m), 7.71–7.80 (2H, m), 7.96 (1H, d, J=8 Hz), 8.14 (1H, d, J=8 Hz), 8.55 (1H, s), 8.86 (1H, d, J=8 Hz)

(2) 4-(Imidazol-1-yl)-3-methyl-8-(2-nitrobenzoylamino)quinoline was obtained according to a similar manner to that of Example 8.

mp: 199–204° C. NMR (DMSO-d$_6$, δ): 2.25 (3H, s), 7.01 (1H, d, J=8 Hz), 7.30 (1H, s), 7.54 (1H, d, J=2 Hz), 7.67 (1H, t, J=8 Hz), 7.77–7.96 (4H, m), 7.99 (1H, s), 8.20 (1H, d, J=8 Hz), 8.64 (1H, br d, J=9 Hz), 8.98 (1H, s)

Example 253

(1) 4-Chloro-8-(2-nitrobenzoylamino)-3,5-dimethylquinoline was obtained 8-amino-4-chloro-3,5-dimethylquinoline and 2-nitrobenzoyl chloride according to a similar manner to that of Example 1.

mp: 165–166° C. NMR (DMSO-d$_6$, δ): 2.51 (3H, s), 2.98 (3H, s), 7.53 (1H, d, J=8 Hz), 7.77 (1H, ddd, J=8, 8, 2 Hz), 7.82–7.93 (2H, m), 8.17 (1H, d, J=8 Hz), 8.50 (1H, d, J=8 Hz), 8.77 (1H, s), 10.66 (1H, s)

(2) 3,5-Dimethyl-4-(imidazol-1-yl)-8-(2-nitrobenzoylamino)quinoline was obtained according to a similar manner to that of Example 8.

mp: 231–233° C. NMR (DMSO-d$_6$, δ): 1.92 (3H, s), 2.08 (3H, s), 7.23 (1H, s), 7.43–7.50 (2H, m), 7.75–7.95 (4H, m), 8.08 (1H, d, J=8 Hz), 8.53 (1H, d, J=8 Hz), 8.93 (1H, s), 10.75 (1H, s)

Example 254

(1) 4-Chloro-3-methoxymethyl-8-(2-nitrobenzoylamino)quinoline was obtained from 8-amino-4-chloro-3-methoxymethylquinoline and 2-nitrobenzoyl chloride according to a similar manner to that of Example 1.

mp 174–175° C. NMR (DMSO-d$_6$, δ): 3.40 (3H, s), 4.78 (2H, s), 7.75–7.91 (4H, m), 8.02 (1H, d, J=8.0 Hz), 8.20 (1H, d, J=8.0 Hz), 8.73 (1H, br d, J=8.0 Hz), 8.90 (1H, s)

(2) 4-(Imidazol-1-yl)-3-methoxymethyl-8-(2-nitrobenzoylamino)quinoline hydrochloride was obtained according to a similar manner to that of Example 8.

mp: 175–185° C. NMR (DMSO-d$_6$, δ): 3.23 (3H, s), 4.49 (2H, s), 7.20 (1H, d, J=8 Hz), 7.75–7.97 (4H, m), 8.00 (1H, d, J=0.5 Hz), 8.07 (1H, d, J=0.5 Hz), 8.21 (1H, d, J=8 Hz), 8.77 (1H, d, J=7 Hz), 9.14 (1H, s), 9.35 (1H, s), 11.00 (1H, s)

Example 255

(1) 3-Methoxymethyl-4-[(2-methylaminoethyl)amino]-8-(2-nitrobenzoylamino)quinoline was obtained from 4-chloro-3-methoxymethyl-8-(2-nitrobenzoylamino) quinoline and N-methylethylenediamine according to a similar manner to that of Example 8.

NMR (CDCl$_3$, δ): 2.48 (3H, s), 2.88 (2H, m), 3.37 (3H, s), 3.76 (2H, m), 4.59 (2H, s), 6.11 (1H, m), 7.43 (1H, t, J=8 Hz), 7.63 (1H, dd, J=8, 2 Hz), 7.70–7.84 (4H, m), 8.11 (1H, d, J=8 Hz), 8.26 (1H, s), 8.79 (1H, d, J=8 Hz)

(2) 3-Methoxymethyl-4-(3-methyl-2-oxoimidazolidin-1-yl)-8-(2-nitrobenzoylamino)quinoline was obtained according to a similar manner to that of Example 92-(2).

mp: 156–159° C. NMR (CDCl$_3$, δ): 2.98 (3H, s), 3.41 (3H, s), 3.59–3.79 (3H, m), 3.85–3.98 (1H, m), 4.54 (1H, d, J=9 Hz), 4.70 (1H, d, J=9 Hz), 7.58–7.70 (3H, m), 7.71–7.81 (2H, m), 8.13 (1H, d, J=8 Hz), 8.82 (1H, s), 8.88 (1H, t, J=5 Hz)

Example 256

4-(Imidazol-2-ylthio)-3-methoxymethyl-8-(2-nitrobenzoylamino)quinoline was obtained from 4-chloro-3-methoxymethyl-8-(2-nitrobenzoylamino)quinoline and 2-mercaptoimidazole according to a similar manner to that of Example 25.

mp: 196–203° C. NMR (DMSO-d$_6$, δ): 3.38 (3H, s), 4.90 (2H, s), 6.92 (1H, s), 7.16 (1H, s), 7.67 (1H, t, J=8 Hz), 7.75–7.95 (3H, m), 8.16–8.20 (2H, m), 8.63 (1H, d, J=8 Hz), 8.94 (1H, s)

Example 257

3-Methoxymethyl-8-(2-nitrobenzoylamino)-4-(pyridin-3-yloxy)quinoline was obtained from 4-chloro-3-methoxymethyl-8-(2-nitrobenzoylamino)quinoline and 3-hydroxypyridine according to a similar manner to that of Example 220.

NMR (DMSO-d$_6$, δ): 3.23 (3H, s), 4.53 (2H, s), 7.22 (1H, dd, J=8.0, 3.0 Hz), 7.31–7.36 (1H, m), 7.56–7.67 (2H, m), 7.76–7.95 (3H, m), 8.20 (1H, d, J=7.5 Hz), 8.33 (1H, d, J=3.0 Hz), 8.41 (1H, d, J=2.0 Hz), 8.70 (1H, d, J=7.5 Hz), 8.98 (1H, s), 10.85 (1H, s)

Example 258

(1) 4-Chloro-3-methyl-8-(2-trifluoromethylbenzoylamino) quinoline was obtained from 8-amino-4-chloro-3-methylquinoline and 2-trifluoromethylbenzoyl chloride according to a similar manner to that of Example 1.

mp: 169–173° C. NMR (CDCl$_3$, δ): 2.57 (3H, s), 7.58–7.86 (5H, m), 7.95 (1H, d, J=8 Hz), 8.55 (1H, s), 8.90 (1H, d, J=8 Hz)

(2) 4-(Imidazol-1-yl)-3-methyl-8-(2-trifluoromethylbenzoylamino)quinoline was obtained according to a similar manner to that of Example 8.

NMR (CDCl$_3$, δ): 2.30 (3H, s), 7.09 (1H, d, J=9 Hz), 7.11 (1H, s), 7.40 (1H, s), 7.56–7.85 (6H, m), 8.25 (1H, s), 8.94 (1H, d, J=9 Hz)

its hydrochloride mp: 189–196° C. NMR (DMSO-d$_6$, δ): 2.31 (3H, s), 7.13 (1H, d, J=8 Hz), 7.69–7.94 (5H, m), 8.04–8.13 (2H, m), 8.70 (1H, d, J=9 Hz), 9.07 (1H, s), 9.47 (1H, s)

Example 259

(1) 3-Methyl-4-[(2-methylaminoethyl)amino]-8-(2-trifluoromethylbenzoylamino)quinoline was obtained from 4-chloro-3-methyl-8-(2-trifluoromethylbenzoylamino) quinoline and N-methylethylenediamine according to a similar manner to that of Example 8.

NMR (CDCl$_3$, δ): 2.40 (3H, s), 2.50 (3H, s), 2.88 (2H, t, J=6 Hz), 3.62 (2H, q, J=6 Hz), 5.30 (1H, s), 7.48 (1H, t, J=8 Hz), 7.55–7.85 (5H, m), 8.30 (1H, s), 8.80 (1H, d, J=8 Hz)

(2) 3-Methyl-4-(3-methyl-2-oxoimidazolidin-1-yl)-8-(2-trifluoromethylbenzoylamino)quinoline was obtained according to a similar manner to that of Example 92-(2).

mp: 182–191° C. NMR (CDCl$_3$, δ): 2.45 (3H, s), 2.99 (3H, s), 3.63–3.93 (4H, m), 7.55–7.85 (6H, m), 8.68 (1H, s), 8.87 (1H, dd, J=8, 2 Hz)

Example 260

(1) 4-Hydrazino-3-methyl-8-(2-trifluoromethylbenzoylamino)quinoline was obtained from 4-chloro-3-methyl-8-(2-trifluoromethylbenzoylamino) quinoline and hydrazine monohydrate according to a similar manner to that of Example 139-(1).

mp: 160–167° C. NMR (DMSO-d$_6$, δ): 2.40 (3H, s), 4.70 (2H, s), 7.33 (1H, t, J=8 Hz), 7.70–7.88 (4H, m), 7.91 (1H, d, J=8 Hz), 8.18 (1H, s), 8.51 (1H, d, J=8 Hz), 8.64 (1H, d, J=8 Hz)

(2) 4-(2-Acetylhydrazino)-3-methyl-8-(2-trifluoromethylbenzoylamino)quinoline was obtained according to a similar manner to that of Example 86.

mp: 209–211° C. 9 NMR (DMSO-d$_6$, δ): 1.88 (3H, s), 2.35 (3H, s), 7.48 (1H, t, J=8 Hz), 7.70–7.88 (3H, m), 7.90 (1H, d, J=8 Hz), 8.11 (1H, d, J=8 Hz), 8.28 (1H, d, J=2 Hz), 8.33 (1H, s), 8.56 (1H, d, J=8 Hz)

Example 261

3-Methyl-4-(pyridin-3-yloxy)-8-(2-trifluoromethylbenzoylamino)quinoline was obtained from 4-chloro-3-methyl-8-(2-trifluoromethylbenzoylamino) quinoline and 3-hydroxypyridine according to a similar manner to that of Example 220.

mp: 102–108° C. NMR (CDCl$_3$, δ): 2.29 (3H, s), 6.98 (1H, dd, J=8, 3 Hz), 7.15–7.29 (2H, m), 7.48–7.85 (6H, m), 8.30–8.40 (2H, m), 8.67 (1H, s), 8.88 (1H, d, J=8 Hz)

Example 262

4-(Imidazol-2-ylthio)-3-methyl-8-(2-trifluoromethylbenzoylamino)quinoline was obtained from 4-chloro-3-methyl-8-(2-trifluoromethylbenzoylamino) quinoline and 2-mercaptoimidazole according to a similar manner to that of Example 25.

mp: 216–220° C. NMR (CDCl$_3$, δ): 2.59 (3H, s), 6.97 (2H, br s), 7.55–7.83 (5H, m), 8.22 (1H, d, J=8 Hz), 8.60 (1H, s), 8.80 (1H, d, J=8 Hz)

Example 263

8-(2,6-Dichlorobenzoylamino)-4-(4-hydroxyindol-1-yl) quinoline was obtained from 4-chloro-8-(2,6-dichlorobenzoylamino)quinoline and 4-hydroxyindole according to a similar manner to that of Example 8.

mp: 289–290° C. NMR (DMSO-d$_6$, δ): 6.12 (1H, br s), 6.58 (1H, d, J=5.5 Hz), 6.94 (1H, d, J=7.5 Hz), 7.22 (1H, t, J=7.5 Hz), 7.35 (1H, t, J=4.0 Hz), 7.43 (1H, d, J=7.5 Hz), 7.51–7.60 (3H, m), 7.74 (1H, dd, J=8.0, 8.0 Hz), 8.20 (1H, d, J=8.0 Hz), 8.62 (1H, d, J=5.5 Hz), 8.82 (1H, d, J=8.0 Hz), 10.73 (1H, s), 11.45 (1H, br s)

Example 264

(1) 5-Chloro-8-(2,6-dichlorobenzoylamino)-3-methyl-4-[(2-methylaminoethyl)amino]quinoline was obtained from 4,5-dichloro-8-(2,6-dichlorobenzoylamino)-3-methylquinoline and N-methylethylenediamine according to a similar manner to that of Example 8.

mp: 127–129° C. NMR (DMSO-$d_6$, δ): 2.40 (3H, s), 2.47 (3H, s), 2.84 (2H, t, J=6 Hz), 3.23 (2H, dt, J=6, 5 Hz), 6.56 (1H, br t, J=5 Hz), 7.27–7.40 (3H, m), 7.45 (1H, d, J=8 Hz), 8.30 (1H, s), 8.71 (1H, d, J=8 Hz), 10.23 (1H, s)

(2) 5-Chloro-8-(2,6-dichlorobenzoylamino)-3-methyl-4-(3-methyl-2-oxoimidazolidin-1-yl)quinoline was obtained according to a similar manner to that of Example 92-(2).

mp: 280–292° C. (dec.) NMR (DMSO-$d_6$, δ): 2.38 (3H, s), 2.78 (3H, s), 3.56–3.66 (2H, m), 3.70–3.80 (2H, m), 7.47–7.63 (3H, m), 7.77 (1H, d, J=8 Hz), 8.63 (1H, d, J=8 Hz), 8.93 (1H, s), 10.89 (1H, s)

We claim:

1. A compound of the formula:

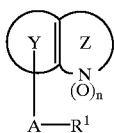

herein

R$^1$ is pyridyl or aryl, each of which is substituted with substituent(s) selected from the group consisting of halogen, nitro, lower alkyl, lower alkoxy, hydroxy, halo(lower)alkyl, amino, lower alkanoylamino, carboxy, lower alkoxycarbonyl and lower alkylcarbamoyl, A is —COHN— or —NHCO—, n is an integer of 0 or 1,

is a group of the formula:

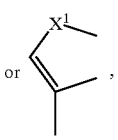

in which

R$^2$ is hydrogen, halogen, lower alkyl, lower alkoxy or halo(lower)alkyl,

R$^3$ is hydrogen, halogen, lower alkyl, lower alkoxy or halo(lower)alkyl, a

R$^4$ is hydrogen, halogen, lower alkyl, lower alkoxy or halo(lower)alkyl,

is a group of the formula:

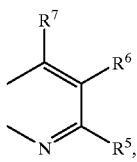

in which

R$^5$ is hydrogen or lower alkyl,

R$^6$ is hydrogen, halogen, cyano, amino, lower alkyl, substituted lower alkyl, lower alkenyl, substituted lower alkenyl, lower alkynyl, substituted lower alkynyl, lower alkylthio, lower alkylsulfinyl, lower alkylsulfonyl, a heterocyclicthio group, acyl, acylamino, aryl, substituted aryl or a heterocyclic group, and R$^7$ is hydrogen, halogen, lower alkyl, substituted lower alkyl, lower alkenyl, substituted lower alkenyl, azido, amino, substituted amino, hydrazino, substituted hydrazino, semicarbazido, substituted semicarbazido, thiosemicarbazido, substituted thiosemicarbazido, hydroxy, substituted hydroxy, mercapto, substituted mercapto, acyl or a substituted or unsubstituted heterocyclic group, provided that R$^1$ is 2,6-dichlorophenyl when R$^6$ and R$^7$ are each hydrogen, and pharmaceutically acceptable salts thereof.

2. A compound of claim 1, wherein

R$^6$ is hydrogen; halogen; cyano; amino; lower alkyl optionally substituted with substituent(s) selected from the group consisting of phenyl, nitro, halogen, hydroxy, lower alkoxy, lower alkylthio, phenyloxy, lower alkanoyloxy, lower alkylcarbamoyloxy, carboxy, lower alkoxycarbonyl, carbamoyl, lower alkylcarbamoyl, hydroxyimino, imidazolyl, benzimidazolyl, morpholinyl, imidazolylthio and pyridylthio; lower alkenyl optionally substituted with substituent(s) selected from the group consisting of carboxy, lower alkoxycarbonyl, carbamoyl and lower alkylcarbamoyl; lower alkynyl optionally substituted with substituent(s) selected from the group consisting of lower alkyl, hydroxy and pyridyl; lower alkylthio; lower alkylsulfinyl; lower alkylsulfonyl; pyridylthio; lower alkanoyl; carboxy; lower alkoxycarbonyl; carbamoyl; lower alkylcarbamoyl; N-(lower alkoxy)-N-(lower alkyl) carbamoyl; morpholinocarbonyl; piperidinocarbonyl; lower alkanoylamino; lower alkoxycarbonylamino; phenyl optionally substituted with amino; or pyridyl; and R$^7$ is hydrogen; halogen; lower alkyl optionally substituted with substituent(s) selected from the group consisting of halogen, cyano, hydroxy, lower alkoxy, lower alkanoyloxy, carboxy, lower alkoxycarbonyl, carbamoyl, lower alkylcarbamoyl, pyridyl(lower)alkylcarbamoyl, hydroxy(lower)alkylcarbamoyl, N-[lower alkoxy(lower)alkyl]-N-(lower alkyl) carbamoyl, phenylcarbamoyl, halo(lower) alkylphenylcarbamoyl, morpholinocarbonyl, piperidinocarbonyl, lower alkyl piperazinylcarbonyl, amino, lower alkylamino, N-[lower alkoxy(lower) alkyl]-N-(lower alkyl)amino, N-[hydroxy(lower) alkyl]-N-(lower alkyl)amino, imidazolyl optionally substituted with lower alkyl, lower alkylthio or phenyl, benzimidazolyl, morpholinyl, pyridyl, imidazolinyl optionally substituted with lower alkyl, imidazolidinyl optionally substituted with lower alkyl and/or oxo, imidazolylthio and pyridylthio; lower alkenyl optionally substituted with substituent(s) selected from the group consisting of carboxy, lower alkoxycarbonyl, carbamoyl and lower alkylcarbamoyl; azido; amino optionally substituted with substituent(s) selected from the group consisting of lower alkyl, lower alkoxy, lower alkoxy(lower)alkyl, hydroxy(lower)alkyl, phenyl(lower)alkyl, amino(lower)alkyl, lower alkylamino(lower)alkyl, pyridyl(lower)alkyl, phenyl, tolyl, phenyl substituted with amino, phenyl substituted with pyridylcarbonylamino, N-pyridylcarbonyl-N-(lower alkyl) amino (lower)alkyl, N-imidazolylcarbonyl-N-(lower alkyl)amino(lower) alkyl, N-pyridylcarbamoyl-N-(lower alkyl)amino (lower)alkyl, lower alkanoyl, pyrazolyl, imidazolyl, triazolyl, morpholino, piperazinyl optionally substituted with lower alkyl, oxazolidinyl optionally substituted with oxo, and pyrrolidinyl optionally substituted with oxo; hydrazino optionally substituted with substituent(s) selected from the group consisting of lower alkyl, lower alkylidene, hydroxy(lower)alkyl, lower alkoxy(lower)alkyl, lower alkanoyl, halo (lower) alkanoyl, cyclo(lower)alkylcarbonyl, carboxy, lower alkoxycarbonyl, carboxy(lower)alkanoyl, hydroxy (lower)alkanoyl, lower alkanoyloxy(lower)alkanoyl, lower alkoxy(lower)alkanoyl, lower alkanoylamino (lower)alkanoyl, lower alkylamino(lower)alkanoyl, oxamoyl, lower alkenoyl, lower alkylsulfonyl, phenylsulfonyl, tolylsulfonyl, thienylsulfonyl, thiazolylsulfonyl optionally substituted with lower alkyl and/or lower alkanoylamino, phenyl(lower) alkylsulfonyl, phenyl(lower)alkenylsulfonyl, benzoyl optionally substituted with lower alkoxy or halo(lower) alkyl, phenyl(lower)alkenoyl, thienyl(lower)alkanoyl, imidazolyl(lower)alkanoyl, pyridyl(lower)alkanoyl, thienylcarbonyl, furoyl, imidazolylcarbonyl optionally substituted with lower alkyl, and pyridylcarbonyl; semicarbazido optionally substituted with lower alkyl or phenyl; thiosemicarbazido optionally substituted with lower alkyl or phenyl; hydroxy optionally substituted with a substituent selected from the group consisting of lower alkyl, lower alkoxy(lower)alkyl, phenyl(lower)alkyl, furyl(lower)alkyl, pyridyl(lower) alkyl, benzimidazolyl(lower)alkyl, carboxy(lower) alkyl, lower alkoxycarbonyl(lower)alkyl, carbamoyl (lower)alkyl, lower alkylcarbamoyl(lower)alkyl, lower alkenyl, phenyl, phenyl substituted with lower alkoxy, phenyl substituted with imidazolyl, dichlorobenzoyl, phenyl(lower)alkenyl, pyridyl, benzimidazolyl, pyridyl substituted with halogen, pyridyl substituted with lower alkyl, pyridyl substituted with lower alkylamino(lower) alkyl, phenyloxy(lower)alkyl and phthalimido(lower) alkyl; mercapto optionally substituted with a substituent selected from the group consisting of carboxy (lower)alkyl, lower alkoxycarbonyl(lower)alkyl, carbamoyl(lower)alkyl, lower alkylcarbamoyl(lower) alkyl, pyridyl(lower)alkylcarbamoyl(lower)alkyl, imidazolyl, pyridyl, lower alkylimidazolyl, imidazo[4, 5-b]pyridyl, pyrimidinyl, benzimidazolyl, thiazolyl, thiazolinyl, thiadiazolyl optionally substituted with lower alkyl, tetrazolyl optionally substituted with lower alkyl and triazolyl optionally substituted with lower alkyl; lower alkanoyl; carboxy; lower alkoxycarbonyl; carbamoyl; lower alkylcarbamoyl; imidazolyl optionally substituted with lower alkyl or lower alkylcarbamoyl; benzimidazolyl optionally substituted with pyridyl; dihydropyridyl optionally substituted with oxo; morpholino; piperidino; piperazinyl optionally substituted with lower alkyl; pyrazolyl optionally substituted with hydroxy; indolyl optionally substituted with hydroxy; triazolyl; imidazolidinyl optionally substituted with lower alkyl, phenyl(lower)alkyl, oxo and/ or thioxo; hexahydropyrimidinyl optionally substituted with lower alkyl, phenyl(lower)alkyl, oxo and/or thioxo; benzimidazolidinyl optionally substituted with lower alkyl, phenyl(lower)alkyl, oxo and/or thioxo; or pyrazolidinyl optionally substituted with lower alkyl, phenyl(lower)alkyl, oxo and/or thioxo.

3. A compound of claim 2, wherein $R^6$ is hydrogen; halogen; cyano; phenyl; lower alkyl optionally substituted with substituent(s) selected from the group consisting of hydroxy, nitro, lower alkoxy, lower alkylthio, lower alkanoyloxy and lower alkoxycarbonyl; lower alkenyl optionally substituted with lower alkoxycarbonyl; lower alkynyl; lower alkylthio; lower alkylsulfonyl; lower alkanoyl; or lower alkoxycarbonyl; and $R^7$ is lower alkyl optionally substituted with substituent(s) selected from the group consisting of hydroxy, cyano, lower alkoxy, lower alkanoyloxy, carboxy, lower alkoxycarbonyl, carbamoyl, lower alkylcarbamoyl, pyridyl(lower)alkylcarbamoyl, hydroxy(lower) alkylcarbamoyl, N-[lower alkoxy(lower)alkyl]-N-(lower alkyl)carbamoyl, halo(lower) alkylphenylcarbamoyl, morpholinocarbonyl, piperidinocarbonyl, lower alkylpiperazinylcarbonyl, lower alkylamino, N-[hydroxy(lower)alkyl]-N-(lower alkyl)amino, imidazolyl optionally substituted with lower alkyl or lower alkylthio, benzimidazolyl, imidazolylthio and pyridylthio; lower alkenyl optionally substituted with carbamoyl; amino substituted with lower alkyl or triazolyl; hydrazino optionally substituted with substituent(s) selected from the group consisting of lower alkyl, lower alkanoyl, lower alkylsulfonyl, phenylsulfonyl, tolylsulfonyl, thienylsulfonyl, phenyl (lower)alkylsulfonyl, benzoyl optionally substituted with lower alkoxy, phenyl(lower)alkenoyl and thienyl (lower)alkanoyl; thiosemicarbazido optionally substituted with lower alkyl; hydroxy substituted with a substituent selected from the group consisting of lower alkyl, lower alkoxy(lower)alkyl, phenyl(lower)alkyl, furyl(lower)alkyl, lower alkenyl, phenyl(lower) alkenyl, phenyl and phenyloxy(lower)alkyl; mercapto substituted with a substituent selected from the group consisting of imidazolyl, pyridyl, lower alkylimidazolyl and imidazo[4,5-b]pyridyl; lower alkanoyl; carbamoyl; imidazolyl optionally substituted with lower alkyl; morpholino; piperidino; piperazinyl optionally substituted with lower alkyl; pyrazolyl; triazolyl; imidazolidinyl optionally substituted with lower alkyl, phenyl(lower)alkyl, oxo and/or thioxo; or hexahydropyrimidinyl optionally substituted with lower alkyl, phenyl(lower)alkyl, oxo and/or thioxo.

4. A compound of claim 2, wherein $R^6$ is halogen; cyano; phenyl; lower alkyl optionally substituted with substituent(s) selected from the group consisting of hydroxy, nitro, lower alkoxy, lower alkylthio, lower alkanoyloxy and lower alkoxycarbonyl; lower alkenyl optionally substituted with lower alkoxycarbonyl; lower alkynyl; lower alkylthio; lower alkylsulfonyl; lower alkanoyl; or lower alkoxycarbonyl; and $R^7$ is hydrogen.

5. A compound of claim 2, wherein
$R^1$ is phenyl substituted with one or two halogen(s), phenyl substituted with nitro, or phenyl substituted with trifluoromethyl, and
$R^5$ is hydrogen.

6. A compound according to claim 1, which is 8-(2,6-dichlorobenzoylamino)-3-methyl-4-(3-methyl-2-oxoimidazolidin-1-yl) quinoline.

7. A process for preparing a compound of claim 1, comprising reacting a compound of the formula:

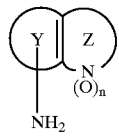

wherein n,

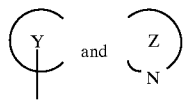

are each as defined in claim 1 or its reactive derivative at the amino group or a salt thereof with a compound of the formula:

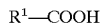

wherein $R^1$ is as defined in claim 1, or its reactive derivative at the carboxy group or a salt thereof to give a compound of the formula:

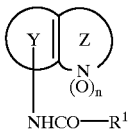

wherein $R^1$, n,

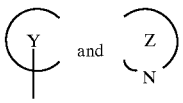

are each as defined in claim 1 or its salt.

8. A pharmaceutical composition comprising a pharmaceutically effective amount of a compound of claim 1, as an active ingredient, in association with a pharmaceutically acceptable, substantially nontoxic carrier or excipient.

9. A method for the prevention and/or the treatment of bone diseases caused by abnormal bone metabolism which comprises administering an effective amount therefore of a compound of claim 1 to human being or animals.

* * * * *